United States Patent
Mautino et al.

(10) Patent No.: US 8,748,469 B2
(45) Date of Patent: *Jun. 10, 2014

(54) IDO INHIBITORS

(75) Inventors: Mario R. Mautino, Ankeny, IA (US); Sanjeev Kumar, Ames, IA (US); Firoz Jaipuri, Ames, IA (US); Jesse Waldo, Ames, IA (US); Tanay Kesharwani, Lake Katrine, NY (US); Nicholas N. Vahanian, Polk City, IA (US); Charles J. Link, Clive, IA (US)

(73) Assignees: NewLink Genetics Corporation, Ames, IA (US); Lankeanau Institute for Medical Research, Wynnewood, PA (US)

( * ) Notice: Subject to any disclaimer, the term of this patent is extended or adjusted under 35 U.S.C. 154(b) by 479 days.

This patent is subject to a terminal disclaimer.

(21) Appl. No.: 12/988,391

(22) PCT Filed: Apr. 24, 2009

(86) PCT No.: PCT/US2009/041609
§ 371 (c)(1),
(2), (4) Date: Dec. 10, 2010

(87) PCT Pub. No.: WO2009/132238
PCT Pub. Date: Oct. 29, 2009

(65) Prior Publication Data
US 2011/0136796 A1 Jun. 9, 2011

Related U.S. Application Data

(60) Provisional application No. 61/047,579, filed on Apr. 24, 2008.

(51) Int. Cl.
*A61K 31/4174* (2006.01)
(52) U.S. Cl.
USPC ........................................ 514/399; 548/341.1
(58) Field of Classification Search
USPC ........................................ 548/341.1; 514/399
See application file for complete search history.

(56) References Cited

U.S. PATENT DOCUMENTS

| | | | |
|---|---|---|---|
| 5,428,173 A | 6/1995 | Kanai et al. | |
| 5,583,130 A | 12/1996 | Bochis et al. | |
| 5,859,035 A | 1/1999 | Anthony et al. | |
| 6,043,254 A | 3/2000 | Grell et al. | |
| 6,417,185 B1 | 7/2002 | Goff et al. | |
| 6,465,486 B1 | 10/2002 | Baxter et al. | |
| 6,878,714 B2 | 4/2005 | Askew et al. | |
| 2002/0026052 A1 | 2/2002 | Boschelli et al. | |
| 2002/0137054 A1 | 9/2002 | Aubart et al. | |
| 2002/0156087 A1 | 10/2002 | Nuss et al. | |
| 2003/0125339 A1 | 7/2003 | Chen et al. | |
| 2006/0258666 A1 | 11/2006 | Player et al. | |

FOREIGN PATENT DOCUMENTS

| | | |
|---|---|---|
| DE | 195 36 811 A1 | 2/1995 |
| EP | 0 915 086 A1 | 5/1999 |
| EP | 1 798 229 A1 | 6/2007 |
| JP | WO 94/17059 A1 | 4/1994 |
| WO | WO 96/34866 A1 | 4/1996 |
| WO | WO 02/62795 A2 | 2/2002 |
| WO | WO 02/24650 A2 | 3/2002 |
| WO | 2005/019184 A1 | 3/2005 |
| WO | WO 2005/054188 A1 | 6/2005 |
| WO | WO 2007/140222 A2 | 5/2007 |

OTHER PUBLICATIONS

Yamada et al, "Synthesis and Bleaching Activity of 1,5-Disubstituted Imidazoles," Biosci. Biotech. Biochem., 56(12), 1992, 1943-48.*
Copending U.S. Appl. No. 13/501,633, commonly assigned.*
Bellina et al, J.O.C. 2007, (72) pp. 8543-8546.*
Starcevic, et al., "Synthesis, antiviral and antitumor activity of 2-substituted-5-amidino-benzimidazoles", Bioorganic & Medicinal Chemistry, 15(13), 4419-4426 CODEN:BMECEP; ISSN:0968-0896, 2007.
Darvas, et al., "Cytochrome P-450 inducers and inhibitors interfering with ecdysone 20-monooxygenases and their activities during postembryonic development of *Neobellieria bullata* Parker", Pesticide Science, 36(2), 135-42 CODEN: PSSCBG; ISSN:0031-613X, 1992.
Yamada, et al., "Synthesis and bleaching activity of 1,5-disubstituted imidazoles", Bioscience, Biotechnology, and Biochemistry, 56(12), 1943-8 CODEN:BBBIEJ; ISSN:0916-8451, 1992.
Korth, et al., "A DFT Study on Intramolecular Hydrogen Bonding in 2-Substituted Phenols: Conformations, Enthalpies, and Correlation with Solute Parameters", Journal of Physical Chemistry A, 106(37), 8779-8789 CODEN: JPCAFH; ISSN:1089-5639, 2002.

(Continued)

Primary Examiner — Kamal Saeed
Assistant Examiner — Janet L Coppins
(74) Attorney, Agent, or Firm — McDonnell Boehnen Hulbert & Berghoff LLP

(57) ABSTRACT

Presently provided are compounds according to the formula (I) or (II), and pharmaceutical compositions comprising the compounds, wherein $R^1$, $R^4$, and $R^5$ are defined herein. Such compounds and compositions are useful for modulating an activity of indoleamine 2,3-dioxygenase; treating indoleamine 2,3-dioxygenase (IDO) mediated immunosuppression; treating a medical conditions that benefit from the inhibition of enzymatic activity of indoleamine -2,3-dioxygenase; enhancing the effectiveness of an anti-cancer treatment comprising administering an anti-cancer agent; treating tumor-specific immunosuppression associated with cancer; and treating immunosupression associated with an infectious disease.

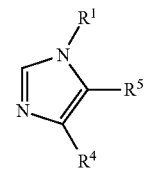

(I)

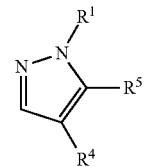

(II)

7 Claims, No Drawings

(56) References Cited

OTHER PUBLICATIONS

Ho, et al., "Imidazolylpyrimidine based CXCR2 chemokine receptor antagonists", Bioorganic & medicinal Chemistry Letters, 16(10), 2724-2728 CODEN:BMCLE8; ISSN:0960-894X, 2006.
Pratt, et al., "Structure/activity studies on 1,5-disubstituted imidazoles as inhibitors of juvenile hormone biosynthesis in isolated corpora allata of the cockroach Diploptera punctata" Pesticide Biochem. & Physiology, vol. 38, pp. 223-230, 1990.
Primas et al., "A new boronic-acid based strategy to synthesize 4(5)-(het)aryl-1H-imidazoles", Tetrahedron, 2008, 64 (20), 4596-4601.
Bellina et al., "Efficient and Practical Synthesis of 4(5)-Aryl-1H-imidazoles and 2,4(5)-Diaryl-1H-imidazoles via Highly Selective Palladium-Catalyzed Arylation Reactions", Journal of Organic Chemistry, 2007, 72(22), 8543-8546.
Ho et al., "Imidazolylpyrimidine based CXCR2 chemokine receptor antagonists", Bioorganic & Medicinal Chemistry Letters, 2006, 16(10), 2724-2728.
Young et al., "Discovery and Evaluation of Potent P1 Aryl Heterocycle-Based Thrombin Inhibitors", Journal of Medicinal Chemistry, 2004, 47(12), 2995-3008.
Medebielle et al., "A convenient synthesis of perfluoroalkylated and fluorinated-aryl nitrogen bases by electrochemically induced SRN1 substitution", Journal of Organic Chemistry, 1996, 61(4), 1331-1340.
Ishida et al., "Molecular Conformations of Aminophenylimidazoles Exhibiting Antiulcer Activities", Chemical & Pharmaceutical Bulletin, 1990, 38(7), 1803-1809.
Savola et al., "Cardiovascular and Sedative α-Adrenoreceptor Effects of Detomodine-like Arylalkyl Imidazoles and Associated Derivatives", Arzneimittel Forschung, 1988, 38(1), 29-35.
Overberger et al., "Intramolecular Base-Catalyzed Imidazole Catalysis", Journal of the American Chemical Society, 1971, 93(25), 6992-6998.
Benkovic et al., "Photolysis of Diazomethane in Tetrachloromethane. An Abstraction Reaction of Singlet Methylene", Journal of the American Chemical Society, 1971, vol. 93, p. 1526-1527.
Benkovic et al., "Intramolecular Catalysis of Sulfate Ester Hydrolysis. A Model for Aryl Sulfate Sulfohydrolase", Biochemistry, 1970, vol. 9, 1390-1397.
Felton et al., "Intramolecular General-Base-Catalyzed Hydrolysis and Aminolysis of the Ester Bond by Imidazole and Quinoline Bases", Journal of the American Chemical Society, 1969, vol. 91, p. 6721-6732.
Felton et al., "Mechanism of the Solvolysis of 4-(2'-Acetoxyphenyl)imidazole", Chemical Communications (London), 1968, 907-908.
Ellis et al., "Antifungal activity of some imidazole derivatives", Journal of Pharmacy and Pharmacology, 1964, vol. 16, 400-407.
Pandit et al., "Imidazole Catalysis. VII. The Dependence of Imidazole Catalysis of Ester Hydrolysis on the Nature of the Acyl Group", Journal of the American Chemical Society, 1960, vol. 82, 3386-3390.
Schmir et al., "Imidazole Catalysis. III. The Solvolysis of 4-(2'-Acetoxyphenyl)-imidazole", Journal of the American Chemical Society, 1958, Vol. 80, p. 1173-1177.
Balaban et al., "CCCLXX. Trypanocidal Action and Chemical Constitution. Part III. Arsinic Acids Containing the Glyoxaline Nucleus", Journal of the Chemical Society, 1925, vol. 127, p. 2701-2714.
Starcevic, K. et al., "Synthesis, antiviral and antitumor activity of 2-substituted-5-amidio-benzimidazoles", Bioorganic & Medicinal Chemistry Letters, 2007, 15, 4419-4426.
Kikuchi, M. et al., "Synthesis and Plant Growth Regulatory Activity of 1,5-disubstituted Imidazoles", J. Fac. Agr., Kyushu Univ., 1990, 34(4), 397-404.
Sonoda, M. et al., "Precocious Metamorphosis Induced by 1,5-Disubstituted Imidazoles in Counteracted by Tebufenozide (RH-5992), an Ecdysteroid Agonist" J. Pesticide Sci., 1995, 20(3), 325-327.
Kuwano, S. et al., "Insect Growth Regulating Activity of 1,5-Disubstituted Imidazoles Against *Bombyx mori* and *Oncopeltus fasciatus*", Pestic.Sci., 1992, 34(3), 263-268.
Lyga, J. W. et al., "N-difluoromethylation of phenylazoles", Journal of Fluorine Chemistry, 1998, 92, 141-145.
Collman, J. P., "Imidazole Acid Chlorides: Preparation and Application in the Syntheses of Biomimetic Heme Models", J. Org. Chem., 1998, 63(23), 8084-8085.
Horvath, A., "Catalysis and Regioselectivity in the Michael Addition of Azoles. Kinetic vs. Thermodynamic Control", Tetrahedron Letters, 1996, 37(25), 4423-4426.
Horvath, A., "Michael Adducts in the Regioselective Synthesis of N-Substituted Azoles", Synthesis, 1995, (9), 1183-1189.
Carroll, W. A., "Novel and Potent 3-(2,3-dichlorophenyl)-4-(benzyl)-4H-1,2,4-triazole P2X7 Antagonists", Bioorganic & Medicinal Chemistry Letters, 2007, 17, 4044-4048.

* cited by examiner

IDO INHIBITORS

CROSS-REFERENCE TO RELATED APPLICATIONS

This application claims the benefit of the filing date of U.S. Provisional Application Ser. No. 61/047,579 filed 24 Apr. 2008, which is hereby incorporated by reference in its entirety.

STATEMENT OF GOVERNMENT INTEREST

The invention described herein was made in part with government support under Grant No. R01-CA109542, awarded by the National Institutes of Health. The United States Government has certain rights in the invention.

BACKGROUND OF THE INVENTION

1. Field of the Invention

The present disclosure relates to compounds and methods for inhibition of indoleamine 2,3-dioxygenase; further the disclosure relates to method of treatment of diseases and disorders mediated by indoleamine 2,3-dioxygenase.

2. Summary of the Related Art

Tryptophan (Trp) is an essential amino acid required for the biosynthesis of proteins, niacin and the neurotransmitter 5-hydroxytryptamine (serotonin). The enzyme indoleamine 2,3-dioxygenase (also known as INDO or IDO) catalyzes the first and rate limiting step in the degradation of L-tryptophan to N-formyl-kynurenine. In human cells, IFN-y stimulation induces activation of IDO, which leads to a depletion of Trp, thereby arresting the growth of Trp-dependent intracellular pathogens such as *Toxoplasma gondii* and *Chlamydia trachomatis*. IDO activity also has an antiproliferative effect on many tumor cells, and IDO induction has been observed in vivo during rejection of allogeneic tumors, indicating a possible role for this enzyme in the tumor rejection process.

It has been observed that HeLa cells co-cultured with peripheral blood lymphocytes (PBLs) acquire an immunoinhibitory phenotype through up-regulation of IDO activity. A reduction in PBL proliferation upon treatment with interleukin-2 (IL-2) was believed to result from IDO released by the tumor cells in response to IFN-y secretion by the PBLs. This effect was reversed by treatment with 1-methyl-tryptophan (1MT), a specific IDO inhibitor. It was proposed that IDO activity in tumor cells may serve to impair antitumor responses (Logan, et al., 2002, Immunology, 105: 478-87).

Several lines of evidence suggest that IDO is involved in induction of immune tolerance. Studies of mammalian pregnancy, tumor resistance, chronic infections and autoimmune diseases have shown that cells expressing IDO can suppress T-cell responses and promote tolerance. Accelerated Trp catabolism has been observed in diseases and disorders associated with cellular immune activation, such as infection, malignancy, autoimmune diseases and AIDS, as well as during pregnancy. It was proposed that IDO is induced chronically by HIV infection, and is further increased by opportunistic infections, and that the chronic loss of Trp initiates mechanisms responsible for cachexia, dementia and diarrhea and possibly immunosuppression of AIDS patients (Brown, et al., 1991, Adv. Exp. Med. Biol., 294: 425-35). To this end, it has recently been shown that IDO inhibition can enhance the levels of virus-specific T cells and, concomitantly, reduce the number of virally infected macrophages in a mouse model of HIV (Portula et al., 2005, Blood, 106:2382-90).

IDO is believed to play a role in the immunosuppressive processes that prevent fetal rejection in utero. More than 40 years ago, it was observed that, during pregnancy, the genetically disparate mammalian conceptus survives in spite of what would be predicted by tissue transplantation immunology (Medawar, 1953, Symp. Soc. Exp. Biol. 7: 320-38). Anatomic separation of mother and fetus and antigenic immaturity of the fetus cannot fully explain fetal allograft survival. Recent attention has focused on immunologic tolerance of the mother. Because IDO is expressed by human syncytiotrophoblast cells and systemic tryptophan concentration falls during normal pregnancy, it was hypothesized that IDO expression at the maternal-fetal interface is necessary to prevent immunologic rejection of the fetal allografts. To test this hypothesis, pregnant mice (carrying syngeneic or allogeneic fetuses) were exposed to 1MT, and a rapid, T cell-induced rejection of all allogeneic concepti was observed. Thus, by catabolizing tryptophan, the mammalian conceptus appears to suppress T-cell activity and defends itself against rejection, and blocking tryptophan catabolism during murine pregnancy allows maternal T cells to provoke fetal allograft rejection (Munn, et al., 1998, Science 281: 1191-3).

Further evidence for a tumoral immune resistance mechanism based on tryptophan degradation by IDO comes from the observation that most human tumors constitutively express IDO, and that expression of IDO by immunogenic mouse tumor cells prevents their rejection by preimmunized mice. This effect is accompanied by a lack of accumulation of specific T cells at the tumor site and can be partly reverted by systemic treatment of mice with an inhibitor of IDO, in the absence of noticeable toxicity. Thus, it was suggested that the efficacy of therapeutic vaccination of cancer patients might be improved by concomitant administration of an IDO inhibitor (Uyttenhove et al., 2003, Nature Med., 9: 1269-74). It has also been shown that the IDO inhibitor, 1-MT, can synergize with chemotherapeutic agents to reduce tumor growth in mice, suggesting that IDO inhibition may also enhance the anti-tumor activity of conventional cytotoxic therapies (Muller et al., 2005, Nature Med., 11:312-9).

One mechanism contributing to immunologic unresponsiveness toward tumors may be presentation of tumor antigens by tolerogenic host APCs. A subset of human IDO-expressing antigen-presenting cells (APCs) that coexpressed CD123 (IL3RA) and CCR6 and inhibited T-cell proliferation have also been described. Both mature and immature CD123-positive dendritic cells suppressed T-cell activity, and this IDO suppressive activity was blocked by 1MT (Munn, et al., 2002, Science 297: 1867-70). It has also been demonstrated that mouse tumor-draining lymph nodes (TDLNs) contain a subset of plasmacytoid dendritic cells (pDCs) that constitutively express immunosuppressive levels of IDO. Despite comprising only 0.5% of lymph node cells, in vitro, these pDCs potently suppressed T cell responses to antigens presented by the pDCs themselves and also, in a dominant fashion, suppressed T cell responses to third-party antigens presented by nonsuppressive APCs. Within the population of pDCs, the majority of the functional IDO-mediated suppressor activity segregated with a novel subset of pDCs coexpressing the B-lineage marker CD19. Thus, it was hypothesized that IDO-mediated suppression by pDCs in TDLNs creates a local microenvironment that is potently suppressive of host antitumor T cell responses (Munn, et al., 2004, J. Clin. Invest., 114(2): 280-90).

IDO degrades the indole moiety of tryptophan, serotonin and melatonin, and initiates the production of neuroactive and immunoregulatory metabolites, collectively known as kynurenines. By locally depleting tryptophan and increasing proapoptotic kynurenines, IDO expressed by dendritic cells (DCs) can greatly affect T-cell proliferation and survival. IDO induction in DCs could be a common mechanism of deletional tolerance driven by regulatory T cells. Because such tolerogenic responses can be expected to operate in a variety of physiopathological conditions, tryptophan metabolism and kynurenine production might represent a crucial interface between the immune and nervous systems (Grohmann, et al., 2003, Trends Immunol., 24: 242-8).

Small molecule inhibitors of IDO are being developed to treat or prevent IDO-related diseases such as those described above. For example, PCT Publication WO 99/29310 reports methods for altering T cell-mediated immunity comprising altering local extracellular concentrations of tryptophan and tryptophan metabolites, using an inhibitor of IDO such as 1-methyl-DL-tryptophan, p-(3-benzofuranyl)-DL-alanine, p-[3-benzo(b)thienyl]-DL-alanine, and 6-nitro-L-tryptophan) (Munn, 1999). Reported in WO 03/087347, also published as European Patent 1501918, are methods of making antigen-presenting cells for enhancing or reducing T cell tolerance (Munn, 2003). Compounds having indoleamine-2,3-dioxygenase (IDO) inhibitory activity are further reported in WO 2004/094409; and U.S. Patent Application Publication No. 2004/0234623 is directed to methods of treating a subject with a cancer or an infection by the administration of an inhibitor of indoleamine-2,3-dioxygenase in combination with other therapeutic modalities.

In light of the experimental data indicating a role for IDO in immunosuppression, tumor resistance and/or rejection, chronic infections, HIV-infection, AIDS (including its manifestations such as cachexia, dementia and diarrhea), autoimmune diseases or disorders (such as rheumatoid arthritis), and immunologic tolerance and prevention of fetal rejection in utero, therapeutic agents aimed at suppression of tryptophan degradation by inhibiting IDO activity are desirable. Inhibitors of IDO can be used to activate T cells and therefore enhance T cell activation when the T cells are suppressed by pregnancy, malignancy or a virus such as HIV. Inhibition of IDO may also be an important treatment strategy for patients with neurological or neuropsychiatric diseases or disorders such as depression. The compounds, compositions and methods herein help meet the current need for IDO modulators.

SUMMARY OF THE INVENTION

In one aspect, the invention comprises compounds and pharmaceutical compositions containing them together with a pharmaceutically acceptable excipient, diluent, or carrier, where the compounds are of formula (I) or (II),

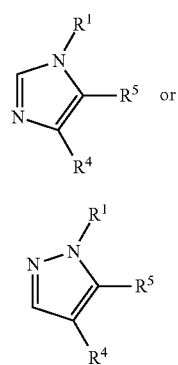

a tautomer thereof, or a pharmaceutically acceptable salt thereof, wherein $R^1$, $R^4$, and $R^5$ are defined herein.

In a second aspect, the invention comprises compounds and pharmaceutical compositions containing them together with a pharmaceutically acceptable excipient, diluent, or carrier, are provided where the compounds are according to formula (III),

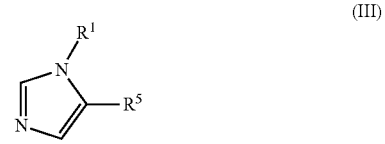

or a pharmaceutically acceptable salt thereof, wherein $R^1$ and $R^5$ are defined herein.

In a third aspect, the invention comprises compounds and pharmaceutical compositions containing them together with a pharmaceutically acceptable excipient, diluent, or carrier, are provided where the compounds are according to formula (IV) or its tautomer (V),

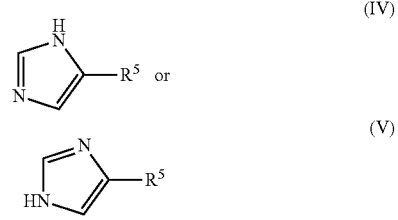

or a pharmaceutically acceptable salt thereof, wherein $R^5$ is defined herein.

In a fourth aspect, the invention comprises compounds and pharmaceutical compositions containing them together with a pharmaceutically acceptable excipient, diluent, or carrier, are provided where the compounds are according to formula (VI) or its tautomer (VII),

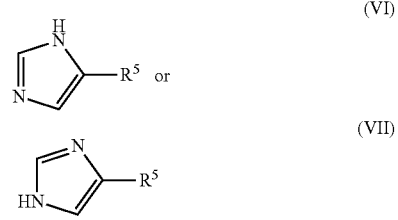

or a pharmaceutically acceptable salt thereof, wherein $R^5$ is

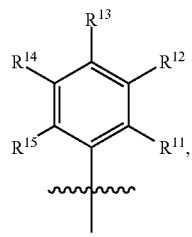

wherein $R^{11}$, $R^{12}$, $R^{13}$, $R^{14}$, and $R^{15}$ are defined herein.

In a fifth aspect, the invention comprises compounds and pharmaceutical compositions containing them together with a pharmaceutically acceptable excipient, diluent, or carrier, are provided where the compounds are according to the formula,

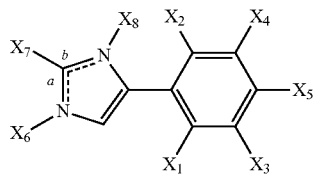

(VIII)

wherein $X_1$-$X_8$ are defined here.

In another aspect methods are provided for (a) modulating an activity of indoleamine 2,3-dioxygenase comprising contacting an indoleamine 2,3-dioxygenase with a modulation effective amount of a compound according to any one of formulae (I)-(XVII), as described herein, or a pharmaceutical composition of any one of the first through fifth aspects; (b) treating indoleamine 2,3-dioxygenase (IDO) mediated immunosuppression in a subject in need thereof, comprising administering an effective indoleamine 2,3-dioxygenase inhibiting amount of a compound according to any one of formulae (I)-(XVII), as described herein, or a pharmaceutical composition of any one of the first through fifth aspects; (c) treating a medical conditions that benefit from the inhibition of enzymatic activity of indoleamine-2,3-dioxygenase comprising administering an effective indoleamine 2,3-dioxygenase inhibiting amount of a compound according to any one of formulae (I)-(XVII), as described herein, or a pharmaceutical composition of any one of the first through fifth aspects; (d) enhancing the effectiveness of an anti-cancer treatment comprising administering an anti-cancer agent and a compound according to any one of formulae (I)-(XVII), as described herein, or a pharmaceutical composition of any one of the first through fifth aspects; (e) treating tumor-specific immunosuppression associated with cancer comprising administering an effective indoleamine 2,3-dioxygenase inhibiting amount of a compound according to any one of formulae (I)-(XVII), as described herein, or a pharmaceutical composition of any one of the first through fifth aspects; and (f) treating immunosupression associated with an infectious disease, e.g., HIV-1 infection, comprising administering an effective indoleamine 2,3-dioxygenase inhibiting amount of a compound according to any one of formulae (I)-(XVII), as described herein, or a pharmaceutical composition of any one of the first through fifth aspects.

In another aspect, the invention provides compounds according to formula (XX),

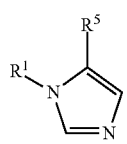

(XX)

a tautomer thereof, or a pharmaceutically acceptable salt thereof, wherein $R^1$ and $R^5$ are defined herein.

DETAILED DESCRIPTION OF THE INVENTION

In embodiment (1) of the first aspect, the instant disclosure provides compounds and pharmaceutical compositions comprising the compounds together with a pharmaceutically acceptable excipient, diluent, or carrier, wherein the compounds are according to formula (I) or (II),

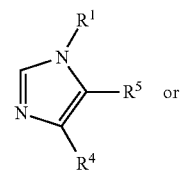

(I)

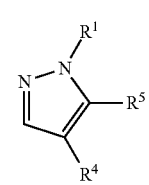

(II)

a tautomer thereof, or a pharmaceutically acceptable salt thereof, wherein $R^1$ and $R^4$ are each independently hydrogen, $C_1$-$C_6$ alkyl, $C_1$-$C_6$ haloalkyl, —$(C_1$-$C_6)$alkyl-$R^{B1}$, —$(C_1$-$C_6)$alkyl-Z—$(C_1$-$C_6)$alkyl-$R^{B1}$, or —$(C_1$-$C_6)$alkyl-Z—$(C_1$-$C_6)$alkyl-Z—$R^{B1}$, provided that at least one of $R^1$ and $R^4$ is hydrogen, wherein each Z is independently —O—, —N($R^Z$)—, —S—, —S(O)—, or —S(O)$_2$—, wherein $R^Z$ is hydrogen or $C_1$-$C_6$alkyl; and $R^{B1}$ is $R^{B2}$, $C_3$-$C_8$cycloalkyl, heterocyclyl, aryl, or heteroaryl, wherein the cycloalkyl, heterocyclyl, aryl, and heteroaryl groups are optionally substituted by 1, 2, 3, or 4 $R^{B2}$ groups, wherein each $R^{B2}$ is independently halogen, cyano, nitro, $C_1$-$C_6$ alkyl, $C_1$-$C_6$ haloalkyl, —OR, —SR, —NR$_2$, —C(O)R, —C(O)OR, —C(O)NR$_2$, —S(O)R, —S(O)$_2$R, —S(O)OR, —S(O)$_2$OR, —S(O)NR$_2$, —S(O)$_2$NR$_2$, —OC(O)R, —OC(O)OR, —OC(O)NR$_2$, —N(R)C(O)R, —N(R)C(O)OR, —N(R)C(O)NR$_2$, —N(R)S(O)R, or —N(R)S(O)$_2$R; and $R^5$ is (i)

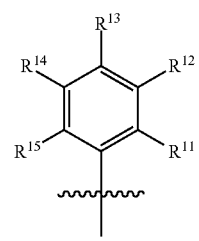

wherein $R^{13}$ is hydrogen or —SH; and $R^{11}$, $R^{12}$, $R^{14}$, and $R^{15}$ are each independently hydrogen or $R^{20}$, or one of $R^{11}$ and $R^{12}$ or $R^{14}$ and $R^{15}$ taken together with the carbon atoms to which they are attached form a fused phenyl, fused 5 or 6 membered monocyclic heteroaryl, fused 5 or 6 membered monocyclic cycloalkyl, fused 5 or 6 membered monocyclic cycloalkenyl, or fused monocyclic 5 or 6 membered heterocyclyl, each fused ring optionally substituted with 1, 2, 3, or 4 $R^{20}$ groups;

or (ii) $R^5$ is heteroaryl optionally substituted with 1, 2, 3, or 4 groups which are each independently $R^{20}$, wherein each $R^{20}$ is independently halogen, cyano, —OR, —SR, —NR$_2$, —C(O)OR, —C(O)NR$_2$, —N(R)S(O)$_2$R, —C(O)R$^2$, —S(O)R, —S(O)$_2$R, —S(O)OR, —S(O)$_2$OR, —S(O)NR$_2$, —S(O)$_2$NR$_2$, —OC(O)R, —OC(O)OR, —OC(O)NR$_2$, —N(R)C(O)R, —N(R)C(O)OR, —N(R)C(O)NR$_2$, —N(R)S(O)R, $C_1$-$C_6$alkyl, $C_2$-$C_6$alkenyl, $C_2$-$C_6$alkynyl, $C_1$-$C_6$haloalkyl, $C_3$-$C_8$cycloalkyl, heterocyclyl, aryl, heteroaryl, $C_3$-$C_8$cycloalkyl($C_1$-$C_6$)alkyl, heterocyclyl($C_1$-$C_6$)alkyl, aryl($C_1$-$C_6$)alkyl, heteroaryl($C_1$-$C_6$)alkyl, —$C_1$-$C_6$alkyl-$R^{41}$, -Q-$C_1$-$C_6$alkyl-$R^{41}$, —$C_1$-$C_6$alkyl-Q-$R^{41}$, -Q-$C_1$-$C_6$alkyl-Q-$R^{41}$, —$C_1$-$C_6$alkyl-Q-($C_1$-$C_6$)alkyl-$R^{41}$, -Q($C_1$-$C_6$)alkyl-Q-($C_1$-$C_6$)alkyl-$R^{41}$, or -Q($C_1$-$C_6$)alkyl-Q-($C_1$-$C_6$)alkyl-Q$R^{41}$, wherein each Q is independently —C($R^{42}$)$_2$—, —O—, —N($R^{42}$)—, —S—, —C(O)—, —S(O)—, —S(O)$_2$—, —C(O)N($R^{42}$)—, —N($R^{42}$)C(O)—, —C(O)O—, or —OC(O)—, wherein each $R^{42}$ is independently hydrogen, $C_1$-$C_6$alkyl, or $C_1$-$C_6$haloalkyl;

$R^{41}$ is $R^{43}$, $C_1$-$C_6$ alkyl, —$C_1$-$C_6$ alkyl-$R^{43}$, $C_1$-$C_6$ haloalkyl, $C_3$-$C_8$cycloalkyl, heterocyclyl, aryl, or heteroaryl, wherein the cycloalkyl, heterocyclyl, aryl, and heteroaryl groups are optionally substituted by 1, 2, 3, or 4 $R^{43}$ groups, wherein each $R^{43}$ is independently halogen, cyano, nitro, —OR, —SR, —NR$_2$, —C(O)R, —C(O)OR, —C(O)NR$_2$, —S(O)R, —S(O)$_2$R, —S(O)OR, —S(O)$_2$OR, —S(O)NR$_2$, —S(O)$_2$NR$_2$, —OC(O)R, —OC(O)OR, —OC(O)NR$_2$, —N(R)C(O)R, —N(R)C(O)OR, —N(R)C(O)NR$_2$, —N(R)S(O)R, —N(R)S(O)$_2$R, $C_1$-$C_6$ alkyl, $C_1$-$C_6$ haloalkyl, $C_2$-$C_6$ alkenyl, $C_2$-$C_6$ alkynyl, $C_3$-$C_8$cycloalkyl, heterocyclyl, aryl, or heteroaryl, wherein the cycloalkyl, heterocyclyl, aryl, heteroaryl, are each optionally substituted with 1, 2, 3, or 4 groups which are each independently $R^{30}$ or —$C_1$-$C_6$ alkyl-$R^{30}$, wherein $R^{30}$ is halogen, cyano, nitro, —OR$^{411}$, —SR$^{411}$, —N($R^{411}$)$_2$, —C(O)OR$^{411}$, —C(O)N($R^{411}$)$_2$, —C(O)R$^{411}$, —S(O)R$^{411}$, —S(O)$_2$R$^{411}$, —S(O)OR$^{411}$, —S(O)$_2$OR$^{411}$, —S(O)N($R^{411}$)$_2$, —S(O)$_2$N($R^{411}$)$_2$, —OC(O)R$^{411}$, —OC(O)OR$^{411}$, —OC(O)N($R^{411}$)$_2$, —N($R^{411}$)C(O)R$^{411}$, —N($R^{411}$)C(O)OR$^{411}$, —N($R^{411}$)C(O)N($R^{411}$)$_2$, —N($R^{411}$)S(O)R$^{411}$, —N($R^{411}$)S(O)$_2$R$^{411}$, $C_1$-$C_6$ alkyl, or $C_1$-$C_6$ haloalkyl, wherein each $R^{411}$ is independently hydrogen, $C_1$-$C_6$ alkyl, $C_2$-$C_6$ alkenyl, $C_2$-$C_6$ alkynyl, $C_1$-$C_6$ haloalkyl, $C_3$-$C_8$cycloalkyl, heterocyclyl, aryl, heteroaryl, $C_3$-$C_8$cycloalkyl($C_1$-$C_6$)alkyl, heterocyclyl($C_1$-$C_6$)alkyl, aryl($C_1$-$C_6$)alkyl, or heteroaryl($C_1$-$C_6$)alkyl, or $R^{41}$ and $R^{42}$ taken together, when attached to the same carbon atom, form =$C_3$-$C_8$cycloalkyl, or =heterocyclyl, wherein the cycloalkyl and heterocyclyl are optionally substituted with 1, 2, 3, or 4 groups which are each independently halogen, cyano, nitro, —OR, —SR, —NR$_2$, —C(O)OR, —C(O)NR$_2$, —C(O)R, —S(O)R, —S(O)$_2$R, —S(O)OR, —S(O)$_2$OR, —S(O)NR$_2$, —S(O)$_2$NR$_2$, —OC(O)R, —OC(O)OR, —OC(O)NR$_2$, —N(R)C(O)R, —N(R)C(O)OR, —N(R)C(O)NR$_2$, —N(R)S(O)R, —N(R)S(O)$_2$R, $C_1$-$C_6$ alkyl, or $C_1$-$C_6$ haloalkyl;

or $R^{20}$ and $R^1$ taken together form —CH$_2$CH$_2$W—, —CH$_2$WCH$_2$—, —WCH$_2$CH$_2$—, —C(H)=C(H)—, —C(H)=C(H)W—, or —WC(H)=C(H)—, wherein W is —O—, —S—, —S(O)—, —S(O)$_2$—, or —NH—; and each R is independently hydrogen or $R^2$, wherein $R^2$ is $C_1$-$C_6$ alkyl, $C_2$-$C_6$ alkenyl, $C_2$-$C_6$ alkynyl, $C_1$-$C_6$ haloalkyl, $C_3$-$C_8$cycloalkyl, heterocyclyl, aryl, heteroaryl, $C_3$-$C_8$cycloalkyl($C_1$-$C_6$)alkyl, heterocyclyl($C_1$-$C_6$)alkyl, aryl($C_1$-$C_6$)alkyl, or heteroaryl($C_1$-$C_6$)alkyl, wherein the alkyl, cycloalkyl, heterocyclyl, aryl, heteroaryl, cycloalkylalkyl, heterocyclylalkyl, arylalkyl, and heteroarylalkyl are each optionally substituted with 1, 2, 3, or 4 groups which are each independently halogen, cyano, nitro, —OR$^{10}$, —SR$^{10}$, —N($R^{10}$)$_2$, —C(O)OR$^{10}$, —C(O)N($R^{10}$)$_2$, —C(O)R$^{10}$, —S(O)R$^{10}$, —S(O)$_2$R$^{10}$, —S(O)OR$^{10}$, —S(O)$_2$OR$^{10}$, —S(O)N($R^{10}$)$_2$, —S(O)$_2$N($R^{10}$)$_2$, —OC(O)R$^{10}$, —OC(O)OR$^{10}$, —OC(O)N($R^{10}$)$_2$, —N($R^{10}$)C(O)$_R^{10}$, —N($R^{10}$)C(O)OR$^{10}$, —N($R^{10}$)C(O)N($R^{10}$)$_2$, —N($R^{10}$)S(O)R$^{10}$, —N($R^{10}$)S(O)$_2$R$^{10}$, $C_1$-$C_6$ alkyl, $C_2$-$C_6$ alkenyl, $C_2$-$C_6$ alkynyl, $C_1$-$C_6$ haloalkyl, $C_3$-$C_8$cycloalkyl, heterocyclyl, aryl, or heteroaryl, wherein each $R^{10}$ is independently hydrogen, $C_1$-$C_6$ alkyl, $C_2$-$C_6$ alkenyl, $C_2$-$C_6$ alkynyl, $C_1$-$C_6$ haloalkyl, $C_3$-$C_8$cycloalkyl, heterocyclyl, aryl, heteroaryl, $C_3$-$C_8$cycloalkyl($C_1$-$C_6$)alkyl, heterocyclyl($C_1$-$C_6$)alkyl, aryl($C_1$-$C_6$)alkyl, or heteroaryl($C_1$-$C_6$)alkyl, provided that (i) $R^1$ is not —(CH$_2$)$_{3-4}$—NH$_2$, —(CH$_2$)$_{1-2}$—C(O)NH$_2$, —(CH$_2$)$_{2-3}$—C(O)N(H)CH$_3$, —(CH$_2$)$_{1-2}$N(H)C(O)CH$_3$, —(CH$_2$)$_2$—OH, or —(CH$_2$)$_3$-thiomorpholinyl; and (ii) the compound is not 4-phenyl-1H-imidazole;
4-(4-methoxycarbonylphenyl)-1H-imidazole;
4-(4-carboxyphenyl)1H-imidazole;
1-(2-phenylethyl)-5-phenyl-1H-imidazole;
1-(2-aminoethyl)-5-phenyl-1H-imidazole;
1-(2-ethoxycarbonylethyl)-5-phenyl-1H-imidazole;
4-benzyl-5-phenyl-1H-imidazole;
4-(2-phenylethyl)-5-phenyl-1H-imidazole;
4-(4-cyanophenyl)-1H-imidazole;
2-(2-(1H-imidazol-5-yl)phenoxy)ethanamine);
4-methyl-5-phenyl-1H-imidazole;
imidazo[5,1-a]isoquinoline;
4-phenyl-1H-pyrazole;
(3S-trans)-N-(6-cyano-3,4-dihydro-3-hydroxy-2,2-dimethyl-2H-1-benzopyran-4-yl)-N'-[3-(5-imidazolyl)phenyl]urea;
1H,1'H-[2,4]biimidazolyl-4-carbonitrile;
2-(1H-imidazol-4-yl)-phenylamine;
2-(3-chloroanilino)-4-(imidazol-5-yl)pyrimidine;
2,6-dichloro-3-(1H-imidazol-5-yl)-4-phenylquinoline;
2-chloro-3-(1H-imidazol-5-yl)-4-phenylquinoline-6-carbonitrile;
3-(1H-imidazol-4-yl)-4-(phenylsulfonyl)-1,2,5-oxadiazole;
3-(4-(1H-imidazol-4-yl)-1,2,5-oxadiazol-3-yloxy)-N,N-dimethylpropan-1-amine;
3-amino-4-[3-(4-imidazolyl)anilino]-3-cyclobutene-1,2-dione;
3-amino-4-ethoxy-7-(1H-imidazol-4-yl)-benzo[b]thiophene-2-carboxylic acid amide;
4-((3-(1-methyl-1H-imidazol-5-yl)-5-(trifluoromethyl)benzyloxy)methyl)-4-phenylpiperidine;
4-(1H-imidazol-4-yl)-pyridine;
4-(2-isopropoxyphenyl)-1H-imidazole;
4-(2-isopropoxy-phenyl)-1H-imidazole;
4-(3-aminophenyl)imidazole;
4-(3-cyanophenyl)imidazole;
4-(3-hydroxy-phenyl)-1H-imidazole;
4-(3-pyridinyl)-1H-imidazole;
4-(3-trifluoromethyl-phenyl)-1H-imidazole;
4-[(pyridin-2-yl)methylphenyl]-1H-imidazole;
4-benzo[b]thiophen-4-yl-1H-imidazole;
4-trifluoromethyl-1H,1'H-[2,4]biimidazolyl;
5-(2-chlorophenyl)-imidazole;

5-(4,5-dihydro-1H-imidazol-2-yl)-2-(1H-imidazol-5-yl)-1H-benzimidazole;

6-(1H-imidazol-4-yl)-5-methoxy-pyridine-2-carboxylic acid;

6-(1H-imidazol-4-yl)-5-methoxy-pyridine-2-carboxylic acid methyl ester;

6-chloro-3-(1H-imidazol-5-yl)-4-phenylquinolin-2(1H)-one;

ethyl-[4-(1H-imidazol-4-yl)-pyridin-2-yl]-amine;

methyl [3-(1H-imidazol-4-yl)-phenoxy]-acetate;

N-(2-(1H-imidazol-4-yl)phenyl)-2-(pyridin-4-ylmethylamino)nicotinamide;

ethyl-3-[7-(3-methyl-3H-imidazol-4-yl)-5-pyridin-3-yl-benzothiazol-2-yl]urea;

[5-(3-Methyl-3H-imidazol-4-yl)-benzofuran-7ylmethyl]-(2S-phenyl-piperidin-3S-yl)-amine;

(4-Benzyloxy-phenyl)-(6-(3-methyl-3H-imidazol-4-yl)-quinazolin-4-yl)-amine;

5-(1H-imidazol-4-yl)-1H-indazol-3-amine; and (4-bromo-2-chloro-phenyl)-[4-fluoro-6-(3H-imidazol-4-yl)-1H-benzoimidazol-5-yl]-amine.

The invention further comprises subgenera of embodiment (1) in which the substituents are selected as any and all combinations of structural formula (I) or (II), $R^1$, $R^4$, and $R^5$ as defined herein, including without limitation, the following:

Structural Formula I is one of formulae (I)-(If):

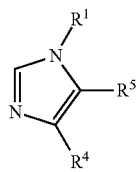
(I)

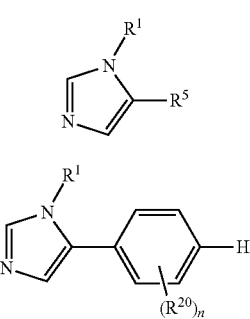
(Ia)

(Ib)

(Ic)

(Ic')

(Id)

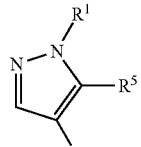
(Id')

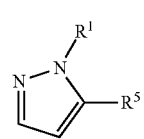
(Ie)

(Ie')

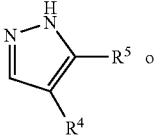
(If)

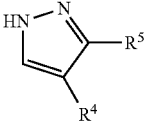
(If')

wherein n is 0, 1, 2, 3, or 4; or n is 0, 1, or 2 (i.e., in formulae (Ib), (Id), (Id'), (If), and (If'), the para-position on the phenyl with respect to the imidazole cannot be substituted with $R^{20}$).

Structural Formula (II) is one of formulae (II)-(IIe):

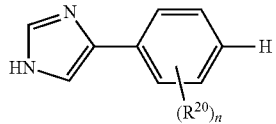
(II)

(IIa)

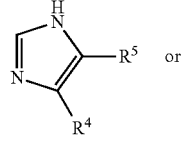
(IIb)

(IIb')

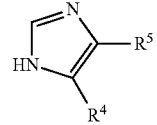
(IIc)

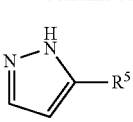
(IIc')

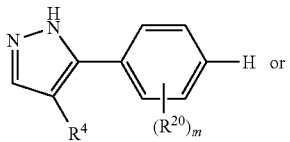
(IId)

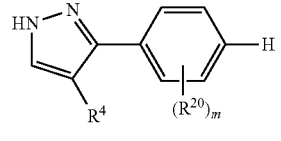
(IId')

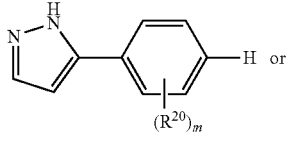
(IIe)

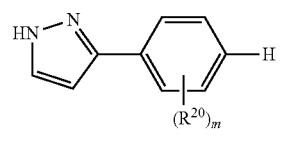
(IIe')

wherein m is 0, 1, 2, 3, or 4; or m is 0, 1, or 2. (i.e., in formulae (IId), (IId'), (IIe), and (IIe'), the para-position on the phenyl with respect to the pyazole cannot be substituted with $R^{20}$ $R^5$ is one of the following groups (a)-(oo):

(a) $R^5$ is

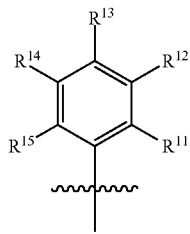

wherein $R^{11}$, $R^{12}$, $R^{14}$, and $R^{15}$ are each independently hydrogen or $R^{20}$, or one of $R^{11}$ and $R^{12}$ or $R^{14}$ and $R^{15}$ taken together with the carbon atoms to which they are attached form a fused phenyl, fused 5 or 6 membered monocyclic heteroaryl, fused 5 or 6 membered monocyclic cycloalkyl, fused 5 or 6 membered monocyclic cycloalkenyl, or fused monocyclic 5 or 6 membered heterocyclyl, each fused ring optionally substituted with 1, 2, 3, or 4 $R^{20}$ groups; and $R^{13}$ is hydrogen or —SH; provided at least one of $R^{11}$, $R^{12}$, $R^{13}$, $R^{14}$, and $R^{15}$ is not hydrogen.

(b) $R^5$ is according to group (a), wherein one of $R^{11}$, $R^{12}$, $R^{14}$, and $R^{15}$ is halogen, cyano, —OR, —SR, —NR$_2$, —C(O)OR, —C(O)NR$_2$, —N(R)S(O)$_2$R, —C$_1$-C$_6$alkyl-R$^{41}$, -Q-(C$_1$-C$_6$)alkyl-R$^{41}$, —C$_1$-C$_6$alkyl-Q-R$^{41}$, -Q-(C$_1$-C$_6$)alkyl-Q-R$^{41}$, —C$_1$-C$_6$alkyl-Q-(C$_1$-C$_6$)alkyl-R$^{41}$, -Q(C$_1$-C$_6$)alkyl-Q-(C$_1$-C$_6$)alkyl-R$^{41}$, or -Q(C$_1$-C$_6$)alkyl-Q-(C$_1$-C$_6$)alkyl-QR$^{41}$, and $R^{13}$ is hydrogen or —SH.

(c) $R^5$ is according to group (a), wherein $R^{11}$ is —OR, —SR, —NR$_2$, —C$_1$-C$_6$alkyl-R$^{41}$, -Q-(C$_1$-C$_6$)alkyl-R$^{41}$, —C$_1$-C$_6$alkyl-Q-R$^{41}$, -Q-(C$_1$-C$_6$)alkyl-Q-R$^{41}$, —C$_1$-C$_6$alkyl-Q-(C$_1$-C$_6$)alkyl-R$^{41}$, -Q(C$_1$-C$_6$)alkyl-Q-(C$_1$-C$_6$)alkyl-R$^{41}$, or -Q(C$_1$-C$_6$)alkyl-Q-(C$_1$-C$_6$)alkyl-QR$^{41}$.

(d) $R^5$ is according to group (a), wherein $R^{12}$, $R^{14}$, and $R^{15}$ are each independently hydrogen, halogen, cyano, C$_1$-C$_6$alkyl, C$_1$-C$_6$haloalkyl, —OR, —SR, —NR$_2$, —C(O)OR, —C(O)NR$_2$, —N(R)S(O)$_2$R, $R^{13}$ is hydrogen or —SH, and $R^{11}$ is —OR, —SR, —NR$_2$, —C$_1$-C$_6$alkyl-R$^{41}$, -Q-(C$_1$-C$_6$)alkyl-R$^{41}$, —C$_1$-C$_6$alkyl-Q-R$^{41}$, -Q-(C$_1$-C$_6$)alkyl-Q-R$^{41}$, —C$_1$-C$_6$alkyl-Q-(C$_1$-C$_6$)alkyl-R$^{41}$, -Q(C$_1$-C$_6$)alkyl-Q-(C$_1$-C$_6$)alkyl-R$^{41}$, or -Q(C$_1$-C$_6$)alkyl-Q-(C$_1$-C$_6$)alkyl-QR$^{41}$.

(e) $R^5$ is according to group (a), wherein $R^{12}$, $R^{14}$, and $R^{15}$ are each independently hydrogen, fluoro, chloro, bromo, methyl, or ethyl, $R^{13}$ is hydrogen or —SH, and $R^{11}$ is —OR, —SR, —NR$_2$, —C$_1$-C$_6$alkyl-R$^{41}$, -Q-(C$_1$-C$_6$)alkyl-R$^{41}$, —C$_1$-C$_6$alkyl-Q-R$^{41}$, -Q-(C$_1$-C$_6$)alkyl-Q-R$^{41}$, —C$_1$-C$_6$alkyl-Q-(C$_1$-C$_6$)alkyl-R$^{41}$, -Q(C$_1$-C$_6$)alkyl-Q-(C$_1$-C$_6$)alkyl-R$^{41}$, or -Q(C$_1$-C$_6$)alkyl-Q-(C$_1$-C$_6$)alkyl-QR$^{41}$.

(f) $R^5$ is

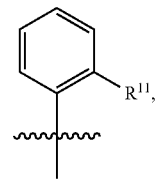

wherein $R^{11}$ is —OR, —SR, —NR$_2$, —C$_1$-C$_6$alkyl-R$^{41}$, -Q-(C$_1$-C$_6$)alkyl-R$^{41}$, —C$_1$-C$_6$alkyl-Q-R$^{41}$, -Q-(C$_1$-C$_6$)alkyl-Q-R$^{41}$, —C$_1$-C$_6$alkyl-Q-(C$_1$-C$_6$)alkyl-R$^{41}$, -Q(C$_1$-C$_6$)alkyl-Q-(C$_1$-C$_6$)alkyl-R$^{41}$, or -Q(C$_1$-C$_6$)alkyl-Q-(C$_1$-C$_6$)alkyl-QR$^{41}$.

(g) $R^5$ is according to group (a), wherein $R^{11}$ is —OR or —SR.

(h) $R^5$ is according to group (a), wherein $R^{11}$ is —OR$^{21}$ or —SR$^{21}$, wherein $R^{21}$ is hydrogen, C$_1$-C$_6$ alkyl, C$_2$-C$_6$ alkenyl, C$_3$-C$_8$cycloalkyl(C$_1$-C$_6$)alkyl, heterocyclyl(C$_1$-C$_6$)alkyl, aryl(C$_1$-C$_6$)alkyl, or heteroaryl(C$_1$-C$_6$)alkyl, wherein the cycloalkylalkyl, heterocyclylalkyl, arylalkyl, and heteroarylalkyl are each optionally substituted with 1, 2, 3, or 4 groups (e.g., 1 or 2 groups) which are each independently halogen, cyano, nitro, C$_1$-C$_6$ alkyl, C$_1$-C$_6$ haloalkyl, —OR$^{10}$, —SR$^{10}$, —N(R$^{10}$)$_2$, —C(O)OR$^{10}$, —C(O)N(R$^{10}$)$_2$, —C(O)R$^{10}$, —S(O)$_2$R$^{10}$, —S(O)$_2$OR$^{10}$, —S(O)$_2$N(R$^{10}$)$_2$, —OC(O)R$^{10}$, —OC(O)OR$^{10}$, —OC(O)N(R$^{10}$)$_2$, —N(R$^{10}$)C(O)OR$^{10}$, —N(R$^{10}$)C(O)OR$^{10}$, —N(R$^{10}$)C(O)N(R$^{10}$)$_2$, —N(R$^{10}$)S(O)$_2$R$^{10}$, wherein each $R^{10}$ is independently hydrogen, C$_1$-C$_6$ alkyl, or C$_1$-C$_6$ haloalkyl.

(i) $R^5$ is according to group (a), wherein $R^{11}$ is —OR$^{21}$ or —SR$^{21}$, wherein $R^{21}$ is hydrogen, C$_1$-C$_6$ alkyl, C$_2$-C$_6$ alkenyl, C$_3$-C$_8$cycloalkyl(C$_1$-C$_6$)alkyl, heterocyclyl(C$_1$-C$_6$)alkyl, aryl(C$_1$-C$_6$)alkyl, or heteroaryl(C$_1$-C$_6$)alkyl.

(j) $R^5$ is according to group (a), wherein $R^{12}$, $R^{14}$, and $R^{15}$ are each independently hydrogen, halogen, cyano, C$_1$-C$_6$alkyl, C$_1$-C$_6$haloalkyl, —OR, —SR, —NR$_2$, —C(O)OR, —C(O)NR$_2$, —N(R)S(O)$_2$R, $R^{13}$ is hydrogen or —SH, and $R^{11}$ is —OR or —SR.

(k) $R^5$ is according to group (a), wherein $R^{12}$, $R^{14}$, and $R^{15}$ are each independently hydrogen, halogen, cyano, C$_1$-C$_6$alkyl, C$_1$-C$_6$haloalkyl, —OR, —SR, —NR$_2$, —C(O)OR, —C(O)NR$_2$, —N(R)S(O)$_2$R, $R^{13}$ is hydrogen or —SH, and $R^{11}$ is $-OR^{21}$ or $-SR^{21}$, wherein $R^{21}$ is hydrogen, $C_1$-$C_6$ alkyl, $C_2$-$C_6$ alkenyl, $C_3$-$C_8$cycloalkyl($C_1$-$C_6$)alkyl, heterocyclyl($C_1$-$C_6$)alkyl, aryl($C_1$-$C_6$)alkyl, or heteroaryl ($C_1$-$C_6$)alkyl, wherein the cycloalkylalkyl, heterocyclylalkyl, arylalkyl, and heteroarylalkyl are each optionally substituted with 1, 2, 3, or 4 groups (e.g., 1 or 2 groups) which are each independently halogen, cyano, nitro, $C_1$-$C_6$ alkyl, $C_1$-$C_6$ haloalkyl, $-OR^{10}$, $-SR^{10}$, $-N(R^{10})_2$, $-C(O)OR^{10}$, $-C(O)N(R^{10})_2$, $-C(O)R^{10}$, $-S(O)_2R^{10}$, $-S(O)_2OR^{10}$, $-S(O)_2N(R^{10})_2$, $-OC(O)R^{10}$, $-OC(O)OR^{10}$, $-OC(O)N(R^{10})_2$, $-N(R^{10})C(O)R^{10}$, $-N(R^{10})C(O)OR^{10}$, $-N(R^{10})C(O)N(R^{10})_2$, $-N(R^{10})S(O)_2R^{10}$, wherein each $R^{10}$ is independently hydrogen, $C_1$-$C_6$ alkyl, or $C_1$-$C_6$ haloalkyl.

(l) $R^5$ is according to group (a), wherein $R^{12}$, $R^{14}$, and $R^{15}$ are each independently hydrogen, halogen, cyano, $C_1$-$C_6$alkyl, $C_1$-$C_6$haloalkyl, $-OR$, $-SR$, $-NR_2$, $-C(O)OR$, $-C(O)NR_2$, $-N(R)S(O)_2R$, $R^{13}$ is hydrogen or $-SH$, and $R^{11}$ is $-OR^{21}$ or $-SR^{21}$, wherein $R^{21}$ is hydrogen, $C_1$-$C_6$ alkyl, $C_2$-$C_6$ alkenyl, $C_3$-$C_8$cycloalkyl($C_1$-$C_6$)alkyl, heterocyclyl($C_1$-$C_6$)alkyl, aryl($C_1$-$C_6$)alkyl, or heteroaryl ($C_1$-$C_6$)alkyl.

(m) $R^5$ is according to group (a), wherein $R^{12}$, $R^{14}$, and $R^{15}$ are each independently hydrogen, fluoro, chloro, bromo, methyl, or ethyl, $R^{13}$ is hydrogen or $-SH$, and $R^{11}$ is $-OR$ or $-SR$.

(n) $R^5$ is according to group (a), wherein $R^{12}$, $R^{14}$, and $R^{15}$ are each independently hydrogen, fluoro, chloro, bromo, methyl, or ethyl, $R^{13}$ is hydrogen or $-SH$, and $R^{11}$ is $-OR^{21}$ or $-SR^{21}$, wherein $R^{21}$ is hydrogen, $C_1$-$C_6$ alkyl, $C_2$-$C_6$ alkenyl, $C_3$-$C_8$cycloalkyl($C_1$-$C_6$)alkyl, heterocyclyl($C_1$-$C_6$)alkyl, aryl($C_1$-$C_6$)alkyl, or heteroaryl($C_1$-$C_6$)alkyl.

(o) $R^5$ is

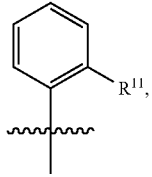

wherein $R^{11}$ is $-OR$ or $-SR$.

(p) $R^5$ is

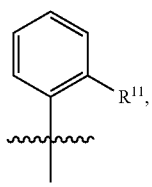

wherein $R^{11}$ is $-OR^{21}$ or $-SR^{21}$, wherein $R^{21}$ is hydrogen, $C_1$-$C_6$ alkyl, $C_2$-$C_6$ alkenyl, $C_3$-$C_8$cycloalkyl($C_1$-$C_6$) alkyl, heterocyclyl($C_1$-$C_6$)alkyl, aryl($C_1$-$C_6$)alkyl, or heteroaryl($C_1$-$C_6$)alkyl, wherein the cycloalkylalkyl, heterocyclylalkyl, arylalkyl, and heteroarylalkyl are each optionally substituted with 1, 2, 3, or 4 groups (e.g., 1 or 2 groups) which are each independently halogen, cyano, nitro, $C_1$-$C_6$ alkyl, $C_1$-$C_6$ haloalkyl, $-OR^{10}$, $-SR^{10}$, $-N(R^{10})_2$, $-C(O)OR^{10}$, $-C(O)N(R^{10})_2$, $-C(O)R^{10}$, $-S(O)_2R^{10}$, $-S(O)_2OR^{10}$, $-S(O)_2N(R^{10})_2$, $-OC(O)R^{10}$, $-OC(O)OR^{10}$, $-OC(O)N(R^{10})_2$, $-N(R^{10})C(O)R^{10}$, $-N(R^{10})C(O)OR^{10}$, $-N(R^{10})C(O)N(R^{10})_2$, $-N(R^{10})S(O)_2R^{10}$, wherein each $R^{10}$ is independently hydrogen, $C_1$-$C_6$ alkyl, or $C_1$-$C_6$ haloalkyl.

(q) $R^5$ is

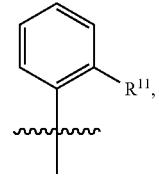

wherein $R^{11}$ is $-OR^{21}$ or $-SR^{21}$, wherein $R^{21}$ is hydrogen, $C_1$-$C_6$ alkyl, $C_2$-$C_6$ alkenyl, $C_3$-$C_8$cycloalkyl($C_1$-$C_6$) alkyl, heterocyclyl($C_1$-$C_6$)alkyl, aryl($C_1$-$C_6$)alkyl, or heteroaryl($C_1$-$C_6$)alkyl.

(r) $R^5$ is according to group (a), wherein $R^{11}$ is $-C_1$-$C_6$alkyl-$R^{A1}$, -Q-($C_1$-$C_6$)alkyl-$R^{A1}$, $-C_1$-$C_6$alkyl-Q-$R^{A1}$, -Q-($C_1$-$C_6$)alkyl-C($R^{A2}$)$_2$—$R^{A1}$, or $-(C_1$-$C_6$)alkyl-Q-$C_1$-$C_6$ alkyl-$R^{A1}$, or -Q($C_1$-$C_6$)alkyl-C($R^{A2}$)$_2$—($C_1$-$C_6$)alkyl-Q$R^{A1}$, wherein each is Q is independently $-O-$, $-N(R^{A2})-$, or $-S-$.

(s) $R^5$ is according to group (a), wherein $R^{12}$, $R^{14}$, and $R^{15}$ are each independently hydrogen, halogen, cyano, $C_1$-$C_6$alkyl, $C_1$-$C_6$haloalkyl, $-OR$, $-SR$, $-NR_2$, $-C(O)OR$, $-C(O)NR_2$, $-N(R)S(O)_2R$, $R^{13}$ is hydrogen or $-SH$, and $R^{11}$ is $-C_1$-$C_6$alkyl-$R^{A1}$, -Q-($C_1$-$C_6$)alkyl-$R^{A1}$, $-C_1$-$C_6$alkyl-Q-$R^{A1}$, -Q-($C_1$-$C_6$)alkyl-C($R^{A2}$)$_2$—$R^{A1}$, or $-(C_1$-$C_6$)alkyl-Q-$C_1$-$C_6$ alkyl-$R^{A1}$, or -Q($C_1$-$C_6$)alkyl-C($R^{A2}$)$_2$—($C_1$-$C_6$)alkyl-Q$R^{A1}$, wherein each is Q is independently $-O-$, $-N(R^{A2})-$, or $-S-$.

(t) $R^5$ is according to group (a), wherein $R^{12}$, $R^{14}$, and $R^{15}$ are each independently hydrogen, fluoro, chloro, bromo, methyl, or ethyl, $R^{13}$ is hydrogen or $-SH$, and $R^{11}$ is $-C_1$-$C_6$alkyl-$R^{A1}$, -Q-($C_1$-$C_6$)alkyl-$R^{A1}$, $-C_1$-$C_6$alkyl-Q-$R^{A1}$, -Q-($C_1$-$C_6$)alkyl-C($R^{A2}$)$_2$—$R^{A1}$, or $-(C_1$-$C_6$) alkyl-Q-$C_1$-$C_6$ alkyl-$R^{A1}$, or -Q($C_1$-$C_6$)alkyl-C($R^{A2}$)$_2$—($C_1$-$C_6$)alkyl-Q$R^{A1}$, wherein each is Q is independently $-O-$, $-N(R^{A2})-$, or $-S-$.

(u) $R^5$ is

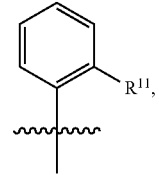

wherein $R^{11}$ is $-C_1$-$C_6$alkyl-$R^{A1}$, -Q-($C_1$-$C_6$)alkyl-$R^{A1}$, $-C_1$-$C_6$alkyl-Q-$R^{A1}$, -Q-($C_1$-$C_6$)alkyl-C($R^{A2}$)$_2$—$R^{A1}$, or $-(C_1$-$C_6$)alkyl-Q-$C_1$-$C_6$ alkyl-$R^{A1}$, or -Q($C_1$-$C_6$)alkyl-C($R^{A2}$)$_2$—($C_1$-$C_6$)alkyl-Q$R^{A1}$, wherein each is Q is independently $-O-$, $-N(R^{A2})-$, or $-S-$.

(v) $R^5$ is according to group (a), wherein $R^{11}$ is $-C_1$-$C_6$alkyl-$R^{A1}$, $-O(C_1$-$C_6)$alkyl-$R^{A1}$, $-C_1$-$C_6$alkylO$R^{A1}$, $-C_1$-$C_6$alkyl-C($R^{A2}$)$_2$—$R^{A1}$, $-O(C_1$-$C_6)$alkyl-C($R^{A2}$)$_2$—$R^{A1}$, $-C_1$-$C_6$alkyl-O($C_1$-$C_6$)alkyl-$R^{A1}$, or $-O(C_1$-$C_6)$alkyl-C($R^{A2}$)$_2$—($C_1$-$C_6$)alkyl-O$R^{A1}$.

(w) $R^5$ is according to group (a), wherein $R^{12}$, $R^{14}$, and $R^{15}$ are each independently hydrogen, halogen, cyano, $C_1$-$C_6$alkyl, $C_1$-$C_6$haloalkyl, $-OR$, $-SR$, $-NR_2$, $-C(O)OR$, $-C(O)NR_2$, $-N(R)S(O)_2R$, $R^{13}$ is hydrogen or $-SH$, and $R^{11}$ is —$C_1$-$C_6$alkyl-$R^{A1}$, —$O(C_1$-$C_6)$alkyl-$R^{A1}$, —$C_1$-$C_6$alkyl$OR^{A1}$, —$C_1$-$C_6$alkyl-$C(R^{A2})_2$—$R^{A1}$, —$O(C_1$-$C_6)$alkyl-$C(R^{A2})_2$—$R^{A1}$, —$C_1$-$C_6$alkyl-$O(C_1$-$C_6)$alkyl-$R^{A1}$, or —$O(C_1$-$C_6)$alkyl-$C(R^{A2})_2$—$(C_1$-$C_6)$alkyl-$OR^{A1}$.

(x) $R^5$ is according to group (a), wherein $R^{12}$, $R^{14}$, and $R^{15}$ are each independently hydrogen, fluoro, chloro, bromo, methyl, or ethyl, $R^{13}$ is hydrogen or —SH, and $R^{11}$ is —$C_1$-$C_6$alkyl-$R^{A1}$, —$O(C_1$-$C_6)$alkyl-$R^{A1}$, —$C_1$-$C_6$alkyl$OR^{A1}$, —$C_1$-$C_6$alkyl-$C(R^{A2})_2$—$R^{A1}$, —$O(C_1$-$C_6)$alkyl-$C(R^{A2})_2$—$R^{A1}$, —$C_1$-$C_6$alkyl-$O(C_1$-$C_6)$alkyl-$R^{A1}$, or —$O(C_1$-$C_6)$alkyl-$C(R^{A2})_2$—$(C_1$-$C_6)$alkyl-$OR^{A1}$.

(y) $R^5$ is

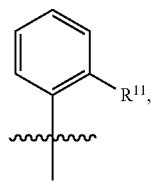

wherein $R^{11}$ is —$C_1$-$C_6$alkyl-$R^{A1}$, —$O(C_1$-$C_6)$alkyl-$R^{A1}$, —$C_1$-$C_6$alkyl$OR^{A1}$, —$C_1$-$C_6$alkyl-$C(R^{A2})_2$—$R^{A1}$, —$O(C_1$-$C_6)$alkyl-$C(R^{A2})_2$—$R^{A1}$, —$C_1$-$C_6$alkyl-$O(C_1$-$C_6)$alkyl-$R^{A1}$, or —$O(C_1$-$C_6)$alkyl-$C(R^{A2})_2$—$(C_1$-$C_6)$alkyl-$OR^{A1}$.

(z) $R^5$ is according to group (a), wherein $R^{11}$ is —$O(C_1$-$C_6)$alkyl-$R^{A1}$, —$C_1$-$C_6$alkyl$OR^{A1}$, —$C_1$-$C_6$alkyl-$C(CH_3)_2$—$R^{A1}$, —$O(C_1$-$C_6)$alkyl-$C(CH_3)_2$—$R^{A1}$, —$C_1$-$C_6$alkyl-$O(C_1$-$C_6)$alkyl-$R^{A1}$, or —$O(C_1$-$C_6)$alkyl-$C(CH_3)_2$—$(C_1$-$C_6)$alkyl-$OR^{A1}$, (aa) $R^5$ is according to group (a), wherein $R^{12}$, $R^{14}$, and $R^{15}$ are each independently hydrogen, halogen, cyano, $C_1$-$C_6$alkyl, $C_1$-$C_6$haloalkyl, —OR, —SR, —$NR_2$, —C(O)OR, —C(O)$NR_2$, —N(R)S(O)$_2$R, $R^{13}$ is hydrogen or —SH, and $R^{11}$ is —$O(C_1$-$C_6)$alkyl-$R^{A1}$, —$C_1$-$C_6$alkyl$OR^{A1}$, —$C_1$-$C_6$alkyl-$C(CH_3)_2$—$R^{A1}$, —$O(C_1$-$C_6)$alkyl-$C(CH_3)_2$—$R^{A1}$, —$C_1$-$C_6$alkyl-$O(C_1$-$C_6)$alkyl-$R^{A1}$, or —$O(C_1$-$C_6)$alkyl-$C(CH_3)_2$—$(C_1$-$C_6)$alkyl-$OR^{A1}$.

(bb) $R^5$ is according to group (a), wherein $R^{12}$, $R^{14}$, and $R^{15}$ are each independently hydrogen, fluoro, chloro, bromo, methyl, or ethyl, $R^{13}$ is hydrogen or —SH, and $R^{11}$ is —$O(C_1$-$C_6)$alkyl-$R^{A1}$, —$C_1$-$C_6$alkyl$OR^{A1}$, —$C_1$-$C_6$alkyl-$C(CH_3)_2$—$R^{A1}$, —$O(C_1$-$C_6)$alkyl-$C(CH_3)_2$—$R^{A1}$, —$C_1$-$C_6$alkyl-$O(C_1$-$C_6)$alkyl-$R^{A1}$, or —$O(C_1$-$C_6)$alkyl-$C(CH_3)_2$—$(C_1$-$C_6)$alkyl-$OR^{A1}$.

(cc) $R^5$ is

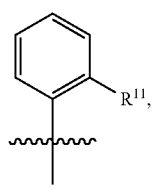

wherein $R^{11}$ is —$O(C_1$-$C_6)$alkyl-$R^{A1}$, —$C_1$-$C_6$alkyl$OR^{A1}$, —$C_1$-$C_6$alkyl-$C(CH_3)_2$—$R^{A1}$, —$O(C_1$-$C_6)$alkyl-$C(CH_3)_2$—$R^{A1}$, —$C_1$-$C_6$alkyl-$O(C_1$-$C_6)$alkyl-$R^{A1}$, or —$O(C_1$-$C_6)$alkyl-$C(CH_3)_2$—$(C_1$-$C_6)$alkyl-$OR^{A1}$.

(dd) $R^5$ is according to group (a), wherein $R^{11}$, $R^{12}$, $R^{14}$, and $R^{15}$ are independently hydrogen, halogen, cyano, $C_1$-$C_6$alkyl, $C_1$-$C_6$haloalkyl, —OR, —SR, —$NR_2$, —C(O)OR, —C(O)$NR_2$, —N(R)S(O)$_2$R, and $R^{13}$ is hydrogen or —SH.

(ee) $R^5$ is according to group (a), wherein $R^{12}$, $R^{14}$, and $R^{15}$ are each independently hydrogen or $R^{20}$, wherein at least one of $R^{12}$, $R^{14}$, and $R^{15}$ is fluoro, chloro, bromo, methyl, or ethyl, $R^{13}$ is hydrogen or —SH, and $R^{11}$ is —OH, —$OCH_3$, or —SH.

(ff) $R^5$ is according to group (a), wherein $R^{12}$, $R^{14}$, and $R^{15}$ are each independently hydrogen, fluoro, chloro, bromo, methyl, or ethyl, $R^{13}$ is hydrogen or —SH, and $R^{11}$ is —OH, —$OCH_3$, or —SH.

(gg) $R^5$ is

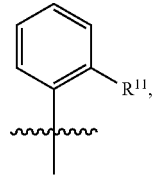

wherein $R^{11}$ is —OH, —$OCH_3$, or —SH.

(hh) $R^5$ is heteroaryl optionally substituted with 1, 2, 3, or 4 groups (e.g., 1 or 2 groups) which are each independently $R^{20}$.

(ii) $R^5$ is a 6-membered heteroaryl optionally substituted with 1, 2, 3, or 4 groups (e.g., 1 or 2 groups) which are each independently $R^{20}$.

(jj) $R^5$ is a 6-membered heteroaryl optionally substituted with 1, 2, 3, or 4 groups (e.g., 1 or 2 groups) which are each independently $R^{20}$, wherein the para-position of $R^5$ with respect to the bond between $R^5$ and the parent imidazole or pyrazole ring is unsubstituted.

(kk) $R^5$ is benzothiophenyl, pyrrolopyridinyl, imidazopyridinyl, quinolinyl, isoquinolinyl, naphthyridinyl, indolyl, indolinyl, benzothiadiazolyl, dihydrobenzodioxinyl, tetrahydropyrimidinyl, pyridinyl, pyrimidinyl, thienyl, or isoxazolyl, each optionally with 1, 2, 3, or 4 groups (e.g., 1 or 2 groups) which are each independently $R^{20}$.

(ll) $R^5$ is benzo[b]thiophen-3-yl, 1H-pyrrolo[2,3-b]pyridin-3-yl, 1H-pyrrolo[2,3-b]pyridin-5-yl, 7-methylimidazo[1,2-a]pyridin-6-yl, quinolin-8-yl, 7-chloroquinolin-4-yl, 2,8-bis(trifluoromethyl)quinolin-4-yl, 5-chloro-8-hydroxyquinolin-7-yl, isoquinolin-4-yl, isoquinolin-5-yl, 2-carboxy-1,6-naphthyridin-8-yl, 1H-indol-7-yl, 1H-indol-6-yl, 1H-indol-5-yl, 9H-purin-6-yl,2-oxo-2,3-dihydro-1H-imidazo[4,5-b]pyridin-6-yl, 2,3-dioxoindolin-5-yl, 2,3-dioxoindolin-7-yl, benzo[c][1,2,5]thiadiazol-4-yl, 2,3-dihydrobenzo[b][1,4]dioxin-6-yl, 1,3-dimethyl-2,4-dioxo-1,2,3,4-tetrahydropyrimidin-5-yl, 2-morpholinopyridin-3-yl, 4-hydroxybiphenyl-3-yl, 2-hydroxypyridin-3-yl, 2,5-dichlorothiophen-3-yl or 3,5-dimethylisoxazol-4-yl.

(mm) $R^5$ is according to group (a), wherein $R^{11}$ and $R^1$ taken together form —$CH_2CH_2$W—, —$CH_2WCH_2$—, —$WCH_2CH_2$—, —C(H)=C(H)—, —C(H)=C(H)W—, or —WC(H)=C(H)—, wherein W is —O—, —S—, —S(O)—, —S(O)$_2$—, or —NH—.

(nn) $R^5$ is according to group (a), wherein $R^{12}$, $R^{14}$, and $R^{15}$ are each independently hydrogen, halogen, cyano, $C_1$-$C_6$alkyl, $C_1$-$C_6$haloalkyl, —OR, —SR, —$NR_2$, —C(O)OR, —C(O)$NR_2$, —N(R)S(O)$_2$R, $R^{13}$ is hydrogen or —SH, and $R^{11}$ and $R^1$ taken together form —$CH_2CH_2$W—, —$CH_2WCH_2$—, —$WCH_2CH_2$—, —C(H)═C(H)—, —C(H)═C(H)W—, or —WC(H)═C(H)—, wherein W is —O—, —S—, —S(O)—, —S(O)$_2$—, or —NH—.

(oo) $R^5$ is according to group (a), wherein $R^{12}$, $R^{14}$, and $R^{15}$ are each independently hydrogen, fluoro, chloro, bromo, methyl, or ethyl, $R^{13}$ is hydrogen or —SH, and $R^{11}$ and $R^1$ taken together form —CH$_2$CH$_2$W—, —CH$_2$WCH$_2$—, —WCH$_2$CH$_2$—, —C(H)═C(H)—, —C(H)═C(H)W—, or —WC(H)═C(H)—, wherein W is —O—, —S—, —S(O)—, —S(O)$_2$—, or —NH—.

$R^4$ is hydrogen and $R^1$ is one of the following groups (pp)-(kkk):

(pp) $R^1$ is hydrogen, C$_1$-C$_6$alkyl, or —(C$_1$-C$_6$)alkyl-R$^{B1}$ wherein R$^{B1}$ is R$^{B2}$, C$_3$-C$_8$cycloalkyl, heterocyclyl, aryl, or heteroaryl, wherein the cycloalkyl, heterocyclyl, aryl, and heteroaryl groups are optionally substituted by 1, 2, 3, or 4 R$^{B2}$ groups (e.g., 1 or 2 groups).

(qq) $R^1$ is hydrogen or C$_1$-C$_6$alkyl.

(rr) $R^1$ is neohexyl.

(ss) $R^1$ is —(C$_1$-C$_6$)alkyl-R$^{B2}$.

(tt) $R^1$ is —(C$_1$-C$_6$)alkyl-R$^{B2}$, wherein R$^{B2}$ is —OR, —SR, —NR$_2$, —C(O)R, —C(O)OR, —C(O)NR$_2$, —OC(O)R, —OC(O)OR, —OC(O)NR$_2$, —N(R)C(O)R, —N(R)C(O)OR, or —N(R)C(O)NR$_2$.

(uu) $R^1$ is —(C$_1$-C$_6$)alkyl-R$^{B2}$, wherein R$^{B2}$ is —OR$^{22}$, —SR$^{22}$, —N(R$^{22}$)$_2$, —C(O)R$^{22}$, —C(O)OR$^{22}$, —C(O)N(R$^{22}$)$_2$, —OC(O)R$^{22}$, —OC(O)OR$^{22}$, —OC(O)N(R$^{22}$)$_2$, —N(R$^{22}$)C(O)R$^{22}$, —N(R$^{22}$)C(O)OR$^{22}$, or —N(R$^{22}$)C(O)N(R$^{22}$)$_2$, wherein each R$^{22}$ is independently hydrogen or C$_1$-C$_6$ alkyl.

(vv) $R^1$ is —(C$_1$-C$_6$)alkyl-R$^{B1}$ wherein R$^{B1}$ is C$_3$-C$_8$cycloalkyl, heterocyclyl, aryl, or heteroaryl, wherein the cycloalkyl, heterocyclyl, aryl, and heteroaryl groups are optionally substituted by 1, 2, 3, or 4 R$^{B2}$ groups (e.g., 1 or 2 R$^{B2}$ groups).

(ww) $R^1$ is —(C$_1$-C$_4$)alkyl-R$^{B1}$ wherein R$^{B1}$ is C$_3$-C$_8$cycloalkyl, heterocyclyl, aryl, or heteroaryl, wherein the cycloalkyl, heterocyclyl, aryl, and heteroaryl groups are optionally substituted by 1, 2, 3, or 4 R$^{B2}$ groups (e.g., 1 or 2 R$^{B2}$ groups).

(xx) $R^1$ is —(C$_1$-C$_6$)alkyl-R$^{B1}$ wherein R$^{B1}$ is phenyl optionally substituted by 1, 2, 3, or 4 R$^{B2}$ groups (e.g., 1 or 2 R$^{B2}$ groups).

(yy) $R^1$ is —(C$_1$-C$_4$)alkyl-R$^{B1}$ wherein R$^{B1}$ is phenyl optionally substituted by 1, 2, 3, or 4 R$^{B2}$ groups (e.g., 1 or 2 R$^{B2}$ groups).

(zz) $R^1$ is —(C$_1$-C$_2$)alkyl-R$^{B1}$ wherein R$^{B1}$ is phenyl optionally substituted by 1, 2, 3, or 4 R$^{B2}$ groups (e.g., 1 or 2 R$^{B2}$ groups).

(aaa) $R^1$ is —CH$_2$—R$^{B1}$ wherein R$^{B1}$ is phenyl optionally substituted by 1, 2, 3, or 4 R$^{B2}$ groups (e.g., 1 or 2 R$^{B2}$ groups).

(bbb) $R^1$ is —CH$_2$—R$^{B1}$ wherein R$^{B1}$ is phenyl optionally substituted by one R$^{B2}$ group.

(ccc) $R^1$ is —(C$_1$-C$_6$)alkyl-R$^{B1}$ wherein R$^{B1}$ is phenyl optionally substituted by 1, 2, 3, or 4 R$^{B2}$ groups (e.g., 1 or 2 R$^{B2}$ groups), wherein each R$^{B2}$ is independently halogen, cyano, nitro, —OR$^{B20}$, —SR$^{B20}$, —N(R$^{B20}$)$_2$, C$_1$-C$_6$ alkyl, or C$_1$-C$_6$ haloalkyl, wherein R$^{B20}$ is hydrogen or C$_1$-C$_6$ alkyl.

(ddd) $R^1$ is —(C$_1$-C$_6$)alkyl-R$^{B1}$ wherein R$^{B1}$ is phenyl optionally substituted by one R$^{B2}$ group, wherein R$^{B2}$ is halogen, cyano, nitro, —OR$^{B20}$, —SR$^{B20}$, —N(R$^{B20}$)$_2$, C$_1$-C$_6$ alkyl, or C$_1$-C$_6$ haloalkyl, wherein R$^{B20}$ is hydrogen or C$_1$-C$_6$ alkyl.

(eee) $R^1$ is —(C$_1$-C$_4$)alkyl-R$^{B1}$ wherein R$^{B1}$ is phenyl optionally substituted by one R$^{B2}$ groups (e.g., 1 or 2 R$^{B2}$ groups), wherein each R$^{B2}$ is independently halogen, cyano, nitro, —OR$^{B20}$, —SR$^{B20}$, —N(R$^{B20}$)$_2$, C$_1$-C$_6$ alkyl, or C$_1$-C$_6$ haloalkyl, wherein R$^{B20}$ is hydrogen or C$_1$-C$_6$ alkyl.

(fff) $R^1$ is —(C$_1$-C$_4$)alkyl-R$^{B1}$ wherein R$^{B1}$ is phenyl optionally substituted by one R$^{B2}$ group, wherein R$^{B2}$ is halogen, cyano, nitro, —OR$^{B20}$, —SR$^{B20}$, —N(R$^{B20}$)$_2$, C$_1$-C$_6$alkyl, or C$_1$-C$_6$ haloalkyl, wherein R$^{B20}$ is hydrogen or C$_1$-C$_6$ alkyl.

(ggg) $R^1$ is —(C$_1$-C$_2$)alkyl-R$^{B1}$ wherein R$^{B1}$ is phenyl optionally substituted by 1, 2, 3, or 4 R$^{B2}$ groups (e.g., 1 or 2 R$^{B2}$ groups), wherein each R$^{B2}$ is independently halogen, cyano, nitro, —OR$^{B20}$, —SR$^{B20}$, —N(R$^{B20}$)$_2$, C$_1$-C$_6$alkyl, or C$_1$-C$_6$ haloalkyl, wherein R$^{B20}$ is hydrogen or C$_1$-C$_6$ alkyl.

(hhh) $R^1$ is —(C$_1$-C$_2$)alkyl-R$^{B1}$ wherein R$^{B1}$ is phenyl optionally substituted by one R$^{B2}$ group, wherein R$^{B2}$ is halogen, cyano, nitro, —OR$^{B20}$, —SR$^{B20}$, —N(R$^{B20}$)$_2$, C$_1$-C$_6$alkyl, or C$_1$-C$_6$ haloalkyl, wherein R$^{B20}$ is hydrogen or C$_1$-C$_6$ alkyl.

(iii) $R^1$ is —(CH$_2$)—R$^{B1}$ wherein R$^{B1}$ is phenyl optionally substituted by 1, 2, 3, or 4 R$^{B2}$ groups (e.g., 1 or 2 R$^{B2}$ groups), wherein each R$^{B2}$ is independently halogen, cyano, nitro, —OR$^{B20}$, —SR$^{B20}$, —N(R$^{B20}$)$_2$, C$_1$-C$_6$alkyl, or C$_1$-C$_6$ haloalkyl, wherein R$^{B20}$ is hydrogen or C$_1$-C$_6$ alkyl.

(jjj) $R^1$ is —(CH$_2$)—R$^{B1}$ wherein R$^{B1}$ is phenyl optionally substituted by one R$^{B2}$ group, wherein R$^{B2}$ is halogen, cyano, nitro, —OR$^{B20}$, —SR$^{B20}$, —N(R$_{B20}$)$_2$, C$_1$-C$_6$ alkyl, or C$_1$-C$_6$ haloalkyl, wherein R$^{B20}$ is hydrogen or C$_1$-C$_6$ alkyl.

(kkk) $R^{20}$ and $R^1$ taken together form —CH$_2$CH$_2$W—, —CH$_2$WCH$_2$—, —WCH$_2$CH$_2$—, —C(H)═C(H)—, —C(H)═C(H)W—, or —WC(H)═C(H)—, wherein W is —O—, —S—, —S(O)—, —S(O)$_2$—, or —NH—.

$R^1$ is hydrogen and $R^4$ is one of the following groups (lll)-(ffff):

(lll) $R^4$ is hydrogen, C$_1$-C$_6$alkyl, or —(C$_1$-C$_6$)alkyl-R$^{B1}$ wherein R$^{B1}$ is R$^{B2}$, C$_3$-C$_8$cycloalkyl, heterocyclyl, aryl, or heteroaryl, wherein the cycloalkyl, heterocyclyl, aryl, and heteroaryl groups are optionally substituted by 1, 2, 3, or 4 R$^{B2}$ groups (e.g., 1 or 2 groups).

(mmm) $R^4$ is hydrogen or C$_1$-C$_6$alkyl.

(nnn) $R^4$ is neohexyl.

(ooo) $R^4$ is —(C$_1$-C$_6$)alkyl-R$^{B2}$.

(ppp) $R^4$ is —(C$_1$-C$_6$)alkyl-R$^{B2}$, wherein R$^{B2}$ is —OR, —SR, —NR$_2$, —C(O)R, —C(O)OR, —C(O)NR$_2$, —OC(O)R, —OC(O)OR, —OC(O)NR$_2$, —N(R)C(O)R, —N(R)C(O)OR, or —N(R)C(O)NR$_2$.

(qqq) $R^4$ is —(C$_1$-C$_6$)alkyl-R$^{B2}$, wherein R$^{B2}$ is —OR$^{22}$, —SR$^{22}$, —N(R$^{22}$)$_2$, —C(O)R$^{22}$, —C(O)OR$^{22}$, —C(O)N(R$^{22}$)$_2$, —OC(O)R$^{22}$, —OC(O)OR$^{22}$, —OC(O)N(R$^{22}$)$_2$, —N(R$^{22}$)C(O)R$^{22}$, —N(R$^{22}$)C(O)OR$^{22}$, or —N(R$^{22}$)C(O)N(R$^{22}$)$_2$, wherein each R$^{22}$ is independently hydrogen or C$_1$-C$_6$ alkyl.

(rrr) $R^4$ is —(C$_1$-C$_6$)alkyl-R$^{B1}$ wherein R$^{B1}$ is C$_3$-C$_8$cycloalkyl, heterocyclyl, aryl, or heteroaryl, wherein the cycloalkyl, heterocyclyl, aryl, and heteroaryl groups are optionally substituted by 1, 2, 3, or 4 R$^{B2}$ groups (e.g., 1 or 2 R$^{B2}$ groups).

(sss) $R^1$ is —(C$_1$-C$_4$)alkyl-R$^{B1}$ wherein R$^{B1}$ is C$_3$-C$_8$cycloalkyl, heterocyclyl, aryl, or heteroaryl, wherein the cycloalkyl, heterocyclyl, aryl, and heteroaryl groups are optionally substituted by 1, 2, 3, or 4 R$^{B2}$ groups (e.g., 1 or 2 R$^{B2}$ groups).

(ttt) $R^4$ is —$(C_1$-$C_6)$alkyl-$R^{B1}$ wherein $R^{B1}$ is phenyl optionally substituted by 1, 2, 3, or 4 $R^{B2}$ groups (e.g., 1 or 2 $R^{B2}$ groups).

(uuu) $R^4$ is —$(C_1$-$C_4)$alkyl-$R^{B1}$ wherein $R^{B1}$ is phenyl optionally substituted by 1, 2, 3, or 4 $R^{B2}$ groups (e.g., 1 or 2 $R^{B2}$ groups).

(vvv) $R^4$ is —$(C_1$-$C_2)$alkyl-$R^{B1}$ wherein $R^{B1}$ is phenyl optionally substituted by 1, 2, 3, or 4 $R^{B2}$ groups (e.g., 1 or 2 $R^{B2}$ groups).

(www) $R^4$ is —$CH_2$—$R^{B1}$ wherein $R^{B1}$ is phenyl optionally substituted by 1, 2, 3, or 4 $R^{B2}$ groups (e.g., 1 or 2 $R^{B2}$ groups).

(xxx) $R^4$ is —$CH_2$—$R^{B1}$ wherein $R^{B1}$ is phenyl optionally substituted by one $R^{B2}$ group.

(yyy) $R^4$ is —$(C_1$-$C_6)$alkyl-$R^{B1}$ wherein $R^{B1}$ is phenyl optionally substituted by 1, 2, 3, or 4 $R^{B2}$ groups (e.g., 1 or 2 $R^{B2}$ groups), wherein each $R^{B2}$ is independently halogen, cyano, nitro, —$OR^{B20}$, —$SR^{B20}$, —$N(R^{B20})_2$, $C_1$-$C_6$ alkyl, or $C_1$-$C_6$ haloalkyl, wherein $R^{B20}$ is hydrogen or $C_1$-$C_6$ alkyl.

(zzz) $R^4$ is —$(C_1$-$C_6)$alkyl-$R^{B1}$ wherein $R^{B1}$ is phenyl optionally substituted by one $R^{B2}$ group, wherein $R^{B2}$ is halogen, cyano, nitro, —$OR^{B20}$, —$SR^{B20}$, —$N(R^{B20})_2$, $C_1$-$C_6$ alkyl, or $C_1$-$C_6$ haloalkyl, wherein $R^{B20}$ is hydrogen or $C_1$-$C_6$ alkyl.

(aaaa) $R^4$ is —$(C_1$-$C_4)$alkyl-$R^{B1}$ wherein $R^{B1}$ is phenyl optionally substituted by one $R^{B2}$ groups (e.g., 1 or 2 $R^{B2}$ groups), wherein each $R^{B2}$ is independently halogen, cyano, nitro, —$OR^{B20}$, —$SR^{B20}$, —$N(R^{B20})_2$, $C_1$-$C_6$ alkyl, or $C_1$-$C_6$ haloalkyl, wherein $R^{B20}$ is hydrogen or $C_1$-$C_6$ alkyl.

(bbbb) $R^4$ is —$(C_1$-$C_4)$alkyl-$R^{B1}$ wherein $R^{B1}$ is phenyl optionally substituted by one $R^{B2}$ group, wherein $R^{B2}$ is halogen, cyano, nitro, —$OR^{B20}$, —$SR^{B20}$, —$N(R^{B20})_2$, $C_1$-$C_6$ alkyl, or $C_1$-$C_6$ haloalkyl, wherein $R^{B20}$ is hydrogen or $C_1$-$C_6$ alkyl.

(cccc) $R^4$ is —$(C_1$-$C_2)$alkyl-$R^{B1}$ wherein $R^{B1}$ is phenyl optionally substituted by 1, 2, 3, or 4 $R^{B2}$ groups (e.g., 1 or 2 $R^{B2}$ groups), wherein each $R^{B2}$ is independently halogen, cyano, nitro, —$OR^{B20}$, —$SR^{B20}$, —$N(R^{B20})_2$, $C_1$-$C_6$ alkyl, or $C_1$-$C_6$ haloalkyl, wherein $R^{B20}$ is hydrogen or $C_1$-$C_6$ alkyl.

(dddd) $R^4$ is —$(C_1$-$C_2)$alkyl-$R^{B1}$ wherein $R^{B1}$ is phenyl optionally substituted by one $R^{B2}$ group, wherein $R^{B2}$ is halogen, cyano, nitro, —$OR^{B20}$, —$SR^{B20}$, —$N(R^{B20})_2$, $C_1$-$C_6$ alkyl, or $C_1$-$C_6$ haloalkyl, wherein $R^{B20}$ is hydrogen or $C_1$-$C_6$ alkyl.

(eeee) $R^4$ is —$(CH_2)$—$R^{B1}$ wherein $R^{B1}$ is phenyl optionally substituted by 1, 2, 3, or 4 $R^{B2}$ groups (e.g., 1 or 2 $R^{B2}$ groups), wherein each $R^{B2}$ is independently halogen, cyano, nitro, —$OR^{B20}$, —$SR^{B20}$, —$N(R^{B20})_2$, $C_1$-$C_6$ alkyl, or $C_1$-$C_6$ haloalkyl, wherein $R^{B20}$ is hydrogen or $C_1$-$C_6$ alkyl.

(ffff) $R^4$ is —$(CH_2)$—$R^{B1}$ wherein $R^{B1}$ is phenyl optionally substituted by one $R^{B2}$ group, wherein $R^{B2}$ is halogen, cyano, nitro, —$OR^{B20}$, —$SR^{B20}$, —$N(R^{B20})_2$, $C_1$-$C_6$ alkyl, or $C_1$-$C_6$ haloalkyl, wherein $R^{B20}$ is hydrogen or $C_1$-$C_6$ alkyl.

So, for example, the invention also comprises each of the following embodiments:

(2) embodiment (1), wherein the compound is of the formula,

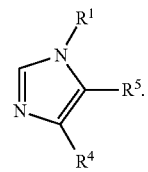

(3) embodiment (1), wherein the compound is of the formula,

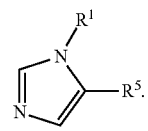

(4) embodiment (1), wherein the compound is of the formula,

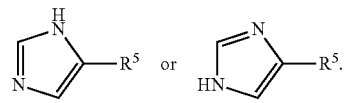

(5) embodiment (1), wherein the compound is of the formula,

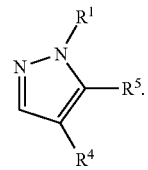

(6) embodiment (1), wherein the compound is of the formula,

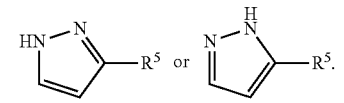

(7) any one of embodiments (1)-(6), wherein $R^5$ is

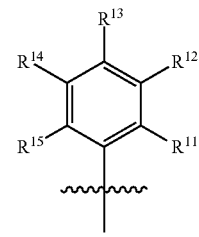

wherein $R^{11}$, $R^{12}$, $R^{14}$, and $R^{15}$ are each independently hydrogen or $R^{20}$, or one of $R^{11}$ and $R^{12}$ or $R^{14}$ and $R^{15}$ taken together with the carbon atoms to which they are attached form a fused phenyl, fused 5 or 6 membered monocyclic heteroaryl, fused 5 or 6 membered monocyclic cycloalkyl, fused 5 or 6 membered monocyclic cycloalkenyl, or fused monocyclic 5 or 6 membered heterocyclyl, each fused ring optionally substituted with 1, 2, 3, or 4 $R^{20}$ groups; and $R^{13}$ is hydrogen or —SH; provided at least one of $R^{11}$, $R^{12}$, $R^{13}$, $R_{14}$, and $R^{15}$ is not hydrogen.

(8) embodiment (7), wherein one of $R^{11}$, $R^{12}$, $R^{14}$, and $R^{15}$ is halogen, cyano, —OR, —SR, —NR$_2$, —C(O)OR, —C(O)NR$_2$, —N(R)S(O)$_2$R, —C$_1$-C$_6$alkyl-R$^{A1}$, -Q-(C$_1$-C$_6$)alkyl-R$^{A1}$, —C$_1$-C$_6$alkyl-Q-R$^{A1}$, -Q-(C$_1$-C$_6$)alkyl-Q-R$^{A1}$, —C$_1$-C$_6$alkyl-Q-(C$_1$-C$_6$)alkyl-R$^{A1}$, -Q(C$_1$-C$_6$)alkyl-Q-(C$_1$-C$_6$)alkyl-R$^{A1}$, or -Q(C$_1$-C$_6$)alkyl-Q-(C$_1$-C$_6$)alkyl-QR$^{A1}$, and $R^{13}$ is hydrogen or —SH.

(9) embodiment (7), wherein $R^{11}$ is —OR, —SR, —NR$_2$, —C$_1$-C$_6$alkyl-R$^{A1}$, -Q-(C$_1$-C$_6$)alkyl-R$^{A1}$, —C$_1$-C$_6$alkyl-Q-R$^{A1}$, -Q-(C$_1$-C$_6$)alkyl-Q-R$^{A1}$, —C$_1$-C$_6$alkyl-Q-(C$_1$-C$_6$)alkyl-R$^{A1}$, -Q(C$_1$-C$_6$)alkyl-Q-(C$_1$-C$_6$)alkyl-R$^{A1}$, or -Q(C$_1$-C$_6$)alkyl-Q-(C$_1$-C$_6$)alkyl-QR$^{A1}$.

(10) embodiment (7), wherein $R^{11}$ is —OR or —SR.

(11) embodiment (7), wherein $R^{11}$ is —C$_1$-C$_6$alkyl-R$^{A1}$, -Q-(C$_1$-C$_6$)alkyl-R$^{A1}$, —C$_1$-C$_6$alkyl-Q-R$^{A1}$, -Q-(C$_1$-C$_6$)alkyl-C(R$^{A2}$)$_2$—R$^{A1}$, or —(C$_1$-C$_6$)alkyl-Q-C$_1$-C$_6$ alkyl-R$^{A1}$, or -Q(C$_1$-C$_6$)alkyl-C(R$^{A2}$)$_2$—(C$_1$-C$_6$)alkyl-QR$^{A1}$, wherein each is Q is independently —O—, —N(R$^{A2}$)—, or —S—.

(12) embodiment (7), wherein $R^{11}$ is -C$_1$-C$_6$alkyl-R$^{A1}$, -O(C$_1$-C$_6$)alkyl-R$^{A1}$, —C$_1$-C$_6$alkylOR$^{A1}$, —C$_1$-C$_6$alkyl-C(R$^{A2}$)$_2$—R$^{A1}$, —O(C$_1$-C$_6$)alkyl-C(R$^{A2}$)$_2$—R$^{A1}$, —C$_1$-C$_6$alkyl-O(C$_1$-C$_6$)alkyl-R$^{A1}$, or —O(C$_1$-C$_6$)alkyl-C(R$^{A2}$)$_2$—(C$_1$-C$_6$)alkyl-OR$^{A1}$.

(13) embodiment (7), wherein $R^{11}$ is —O(C$_1$-C$_6$)alkyl-R$^{A1}$, —C$_1$-C$_6$alkylOR$^{A1}$, —C$_1$-C$_6$alkyl-C(CH$_3$)$_2$—R$^{A1}$, —O(C$_1$-C$_6$)alkyl-C(CH$_3$)$_2$—R$^{A1}$, —C$_1$-C$_6$alkyl-O(C$_1$-C$_6$)alkyl-R$^{A1}$, or —O(C$_1$-C$_6$)alkyl-C(CH$_3$)$_2$—(C$_1$-C$_6$)alkyl-OR$^{A1}$,

(14) embodiment (7), wherein $R^{11}$, $R^{12}$, $R^{14}$, and $R^{15}$ are independently hydrogen, halogen, cyano, C$_1$-C$_6$alkyl, C$_1$-C$_6$haloalkyl, —OR, —SR, —NR$_2$, —C(O)OR, —C(O)NR$_2$, —N(R)S(O)$_2$R, and $R^{13}$ is hydrogen or —SH.

(15) embodiment (7), wherein $R^{11}$ is —OH, —OCH$_3$, or —SH, $R^{13}$ is hydrogen or —SH, and at least one of $R^{12}$, $R^{14}$, and $R^{15}$ is fluoro, chloro, bromo, methyl, or ethyl.

(16) any one of embodiments (1)-(6), wherein $R^5$ is heteroaryl optionally substituted with 1, 2, 3, or 4 groups (e.g., 1 or 2 groups) which are each independently $R^{20}$.

(17) any one of embodiments (1)-(6), $R^5$ is benzothiophenyl, pyrrolopyridinyl, imidazopyridinyl, quinolinyl, isoquinolinyl, naphthyridinyl, indolyl, indolinyl, benzothiadiazolyl, dihydrobenzodioxinyl, tetrahydropyrimidinyl, pyridinyl, pyrimidinyl, thienyl, or isoxazolyl, each optionally with 1, 2, 3, or 4 groups (e.g., 1 or 2 groups) which are each independently $R^{20}$.

(18) any one of embodiments (1)-(6), $R^5$ is benzo[b]thiophen-3-yl, 1H-pyrrolo[2,3-b]pyridin-3-yl, 1H-pyrrolo[2,3-b]pyridin-5-yl, 7-methylimidazo[1,2-a]pyridin-6-yl, quinolin-8-yl, 7-chloroquinolin-4-yl, 2,8-bis(trifluoromethyl)quinolin-4-yl, 5-chloro-8-hydroxyquinolin-7-yl, isoquinolin-4-yl, isoquinolin-5-yl, 2-carboxy-1,6-naphthyridin-8-yl, 1H-indol-7-yl, 1H-indol-6-yl, 1H-indol-5-yl, 9H-purin-6-yl,2-oxo-2,3-dihydro-1H-imidazo[4,5-b]pyridin-6-yl, 2,3-dioxoindolin-5-yl, 2,3-dioxoindolin-7-yl, benzo[c][1,2,5]thiadiazol-4-yl, 2,3-dihydrobenzo[b][1,4]dioxin-6-yl, 1,3-dimethyl-2,4-dioxo-1,2,3,4,-tetrahydropyrimidin-5-yl, 2-morpholinopyridin-3-yl, 4-hydroxybiphenyl-3-yl, 2-hydroxypyridin-3-yl, 2,5-dichlorothiophen-3-yl or 3,5-dimethylisoxazol-4-yl.

(19) any one of embodiments (1)-(18), wherein $R^1$ is hydrogen, C$_1$-C$_6$alkyl, or —(C$_1$-C$_6$)alkyl-R$^{B1}$ wherein $R^{B1}$ is $R^{B2}$, C$_3$-C$_8$cycloalkyl, heterocyclyl, aryl, or heteroaryl, wherein the cycloalkyl, heterocyclyl, aryl, and heteroaryl groups are optionally substituted by 1, 2, 3, or 4 $R^{B2}$ groups (e.g., 1 or 2 groups).

(20) any one of embodiments (1)-(18), wherein $R^1$ is —(C$_1$-C$_6$)alkyl-R$^{B2}$.

(21) embodiment (19) or (20), wherein $R^{B2}$ is —OR, —SR, —NR$_2$, —C(O)R, —C(O)OR, —C(O)NR$_2$, —OC(O)R, —OC(O)OR, —OC(O)NR$_2$, —N(R)C(O)R, —N(R)C(O)OR, or —N(R)C(O)NR$_2$.

(22) any one of embodiments (1)-(18), wherein $R^1$ is —(C$_1$-C$_6$)alkyl-R$^{B1}$ wherein $R^{B1}$ is C$_3$-C$_8$cycloalkyl, heterocyclyl, aryl, or heteroaryl, wherein the cycloalkyl, heterocyclyl, aryl, and heteroaryl groups are optionally substituted by 1, 2, 3, or 4 $R^{B2}$ groups(e.g., 1 or 2 groups).

(23) embodiment (22), wherein $R^{B1}$ is phenyl optionally substituted by 1, 2, 3, or 4 $R^{B2}$ groups (e.g., 1 or 2 groups).

(24) embodiment (23), wherein each $R^{B2}$ is independently halogen, cyano, nitro, —OR$^{B20}$, —SR$^{B20}$, —N(R$^{B20}$)$_2$, C$_1$-C$_6$ alkyl, or C$_1$-C$_6$ haloalkyl, wherein R$^{B20}$ is hydrogen or C$_1$-C$_6$ alkyl.

(25) embodiment (1), wherein the compound is of the formula,

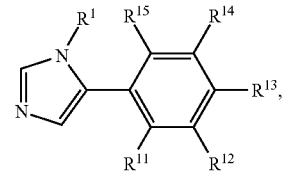

wherein $R^{11}$ is —OR, —SR, —NR$_2$, —C$_1$-C$_6$alkyl-R$^{A1}$, -Q-(C$_1$-C$_6$)alkyl-R$^{A1}$, —C$_1$-C$_6$alkyl-Q-R$^{A1}$, -Q-(C$_1$-C$_6$)alkyl-Q-R$^{A1}$, —C$_1$-C$_6$alkyl-Q-(C$_1$-C$_6$)alkyl-R$^{A1}$, -Q(C$_1$-C$_6$)alkyl-Q-(C$_1$-C$_6$)alkyl-R$^{A1}$, or -Q(C$_1$-C$_6$)alkyl-Q-(C$_1$-C$_6$)alkyl-QR$^{A1}$; $R^{13}$ is hydrogen or —SH, and $R^{12}$, $R^{14}$, and $R^{15}$ are each independently hydrogen halogen, cyano, C$_1$-C$_6$ alkyl, C$_1$-C$_6$ haloalkyl, —OR, —SR, —NR$_2$, —C(O)OR, —C(O)NR$_2$, or —N(R)S(O)$_2$R.

(26) embodiment (25), wherein $R^1$ is hydrogen, C$_1$-C$_6$alkyl, or —(C$_1$-C$_6$)alkyl-R$^{B1}$ wherein $R^{B1}$ is $R^{B2}$, C$_3$-C$_8$cycloalkyl, heterocyclyl, aryl, or heteroaryl, wherein the cycloalkyl, heterocyclyl, aryl, and heteroaryl groups are optionally substituted by 1, 2, 3, or 4 $R^{B2}$ groups (e.g., 1 or 2 groups).

(27) embodiment (25), wherein $R^1$ is —(C$_1$-C$_6$)alkyl-R$^{B2}$.

(28) embodiment (27), wherein $R^{B2}$ is —OR, —SR, —NR$_2$, —C(O)R, —C(O)OR, —C(O)NR$_2$, —OC(O)R, —OC(O)OR, —OC(O)NR$_2$, —N(R)C(O)R, —N(R)C(O)OR, or —N(R)C(O)NR$_2$.

(29) embodiment (25), wherein $R^1$ is —(C$_1$-C$_6$)alkyl-R$^{B1}$ wherein $R^{B1}$ is C$_3$-C$_8$cycloalkyl, heterocyclyl, aryl, or heteroaryl, wherein the cycloalkyl, heterocyclyl, aryl, and heteroaryl groups are optionally substituted by 1, 2, 3, or 4 $R^{B2}$ groups (e.g., 1 or 2 groups).

(30) embodiment (29), wherein $R^{B1}$ is phenyl optionally substituted by 1, 2, 3, or 4 $R^{B2}$ groups (e.g., 1 or 2 groups).

(31) embodiment (30), wherein each $R^{B2}$ is independently halogen, cyano, nitro, —OR$^{B20}$, —SR$^{B20}$, —N(R$^{B20}$)$_2$, C$_1$-C$_6$ alkyl, or C$_1$-C$_6$ haloalkyl, wherein R$^{B20}$ is hydrogen or C$_1$-C$_6$ alkyl.

(32) embodiment (25), wherein $R^1$ is hydrogen.

(33) embodiment (1), wherein the compound is in Table 1:

TABLE 1
| # | Structure | Name |
|---|---|---|
| 6 | 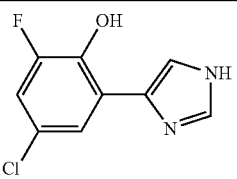 | 4-chloro-2-fluoro-6-(1H-imidazol-4-yl)phenol |
| 7 | 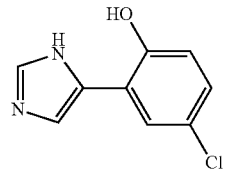 [SMILES: Oc1ccc(Cl)cc1-c1cnc[nH]1] | 4-chloro-2-(1H-imidazol-5-yl)phenol |
| 8 | 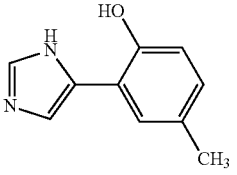 | 2-(1H-imidazol-5-yl)-4-methylphenol |
| 9 | 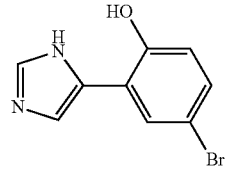 | 4-bromo-2-(1H-imidazol-5-yl)phenol |
| 10 | 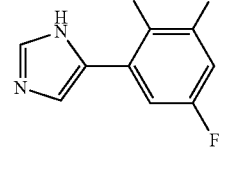 | 2,4-difluoro-6-(1H-imidazol-5-yl)phenol |
| 21 | 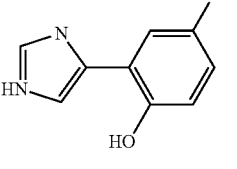 | 2-(1H-imidazol-4-yl)benzene-1,4-diol |
| 27 | 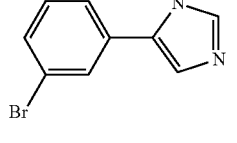 | 5-(3-bromophenyl)-1H-imidazole |
| 35 | 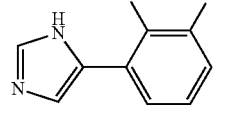 | 2-bromo-6-(1H-imidazol-5-yl)phenol |
| 41 | 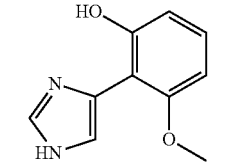 | 2-(1H-imidazol-5-yl)-3-methoxyphenol |

TABLE 1-continued

| # | Structure | Name |
|---|---|---|
| 59 | 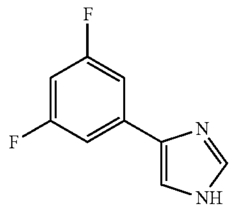 [SMILES: Fc1cc(F)cc(-c2c[nH]cn2)c1] | 4-(3,5-difluorophenyl)-1H-imidazole |
| 63 | 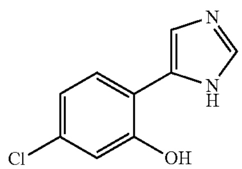 [SMILES: Oc1cc(Cl)ccc1-c1cnc[nH]1] | 5-chloro-2-(1H-imidazol-5-yl)phenol |
| 70 | 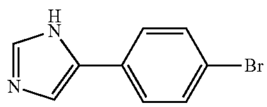 | 5-(4-bromophenyl)-1H-imidazole |
| 80 | 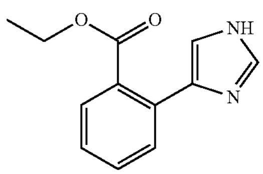 [SMILES: CCOC(=O)c1ccccc1-c1c[nH]cn1] | ethyl 2-(1H-imidazol-4-yl)benzoate |
| 101 | 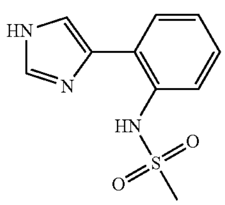 [SMILES: CS(=O)(=O)Nc1ccccc1-c1c[nH]cn1] | N-(2-(1H-imidazol-4-yl)phenyl)methanesulfonamide |
| 111 | 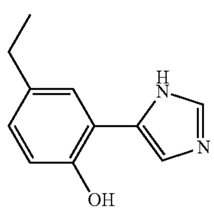 | 4-ethyl-2-(1H-imidazol-5-yl)phenol |
| 112 | 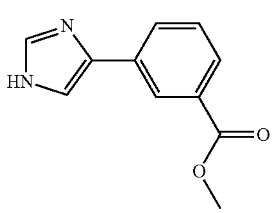 | methyl 3-(1H-imidazol-4-yl)benzoate |
| 113 | 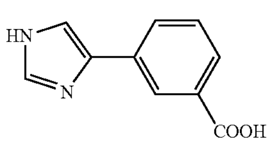 [SMILES: O=C(O)c1cccc(-c2c[nH]cn2)c1] | 3-(1H-imidazol-4-yl)benzoic acid |

TABLE 1-continued

| # | Structure | Name |
|---|---|---|
| 153 | 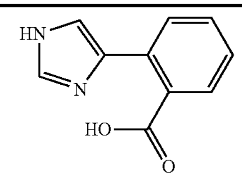 | 2-(1H-imidazol-4-yl)benzoic acid |
| 155 | 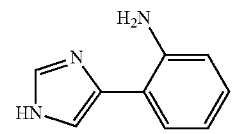 | 2-(1H-imidazol-4-yl)aniline |
| 156 | 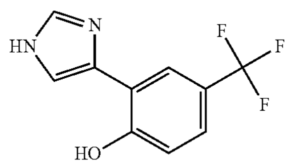 [SMILES: Oc1ccc(C(F)(F)F)cc1-c1c[nH]cn1] | 2-(1H-imidazol-4-yl)-4-(trifluoromethyl)phenol |

(34) embodiment (1), wherein the compound is in Table 2:

TABLE 2

| # | Structure | Name |
|---|---|---|
| 3 | 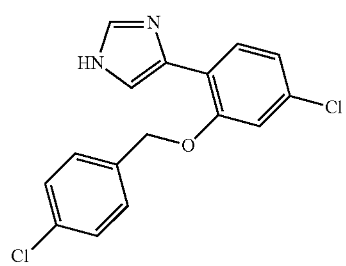 [SMILES: Clc1ccc(COc2cc(Cl)ccc2-c2c[nH]cn2)cc1] | 4-(4-chloro-2-(4-chlorobenzyloxy)phenyl)-1H-imidazole |
| 4 | 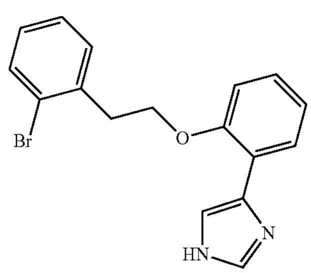 [SMILES: Brc1ccccc1CCOc1ccccc1-c1c[nH]cn1] | 4-(2-(2-bromophenethoxy)phenyl)-1H-imidazole |
| 5 | 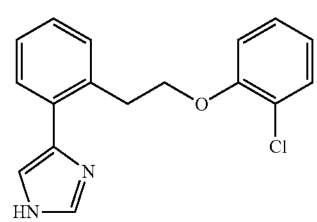 [SMILES: Clc1ccccc1OCCc1ccccc1-c1c[nH]cn1] | 4-(2-(2-(2-chlorophenoxy)ethyl)phenyl)-1H-imidazole |

TABLE 2-continued

| # | Structure | Name |
|---|---|---|
| 12 | 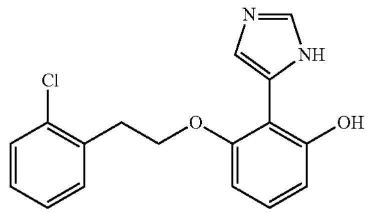 [SMILES: Oc1cccc(OCCc2ccccc2Cl)c1-c1cnc[nH]1] | 3-(2-chlorophenethoxy)-2-(1H-imidazol-5-yl)phenol |
| 13 | 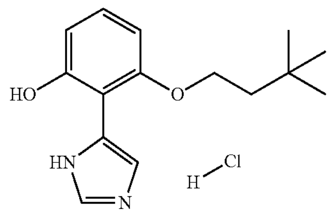 | 3-(3,3-dimethylbutoxy)-2-(1H-imidazol-5-yl)phenol hydrochloride |
| 14 | 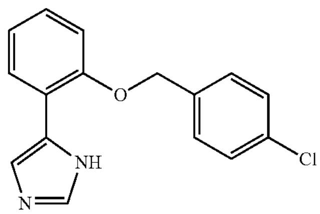 [SMILES: Clc1ccc(COc2ccccc2-c2cnc[nH]2)cc1] | 5-(2-(4-chlorobenzyloxy)phenyl)-1H-imidazole |
| 15 | 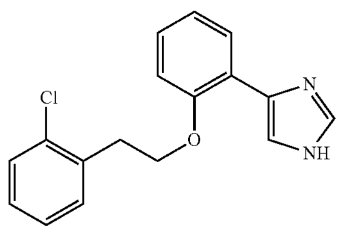 [SMILES: Clc1ccccc1CCOc1ccccc1-c1c[nH]cn1] | 4-(2-(2-chlorophenethoxy)phenyl)-1H-imidazole |
| 16 | 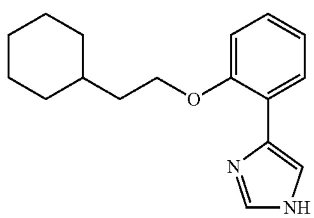 [SMILES: c1ccc(-c2c[nH]cn2)c(OCCC2CCCCC2)c1] | 4-(2-(2-cyclohexylethoxy)phenyl)-1H-imidazole |
| 18 | 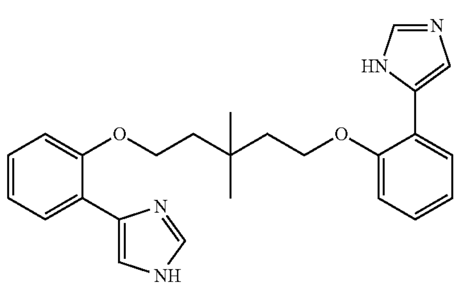 [SMILES: CC(C)(CCOc1ccccc1-c1c[nH]cn1)CCOc1ccccc1-c1cnc[nH]1] | 5,5'-(2,2'-(3,3-dimethylpentane-1,5-diyl)bis(oxy)bis(2,1-phenylene))bis(1H-imidazole) |
| 20 | 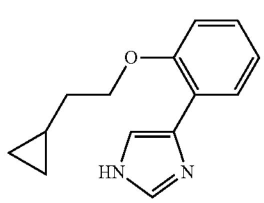 [SMILES: c1ccc(-c2c[nH]cn2)c(OCCC2CC2)c1] | 4-(2-(2-cyclopropylethoxy)phenyl)-1H-imidazole |

TABLE 2-continued

| # | Structure | Name |
|---|---|---|
| 22 | 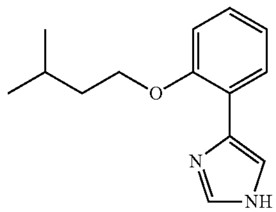 [SMILES: CC(C)CCOc1ccccc1-c1c[nH]cn1] | 4-(2-(isopentyloxy)phenyl)-1H-imidazole |
| 24 | 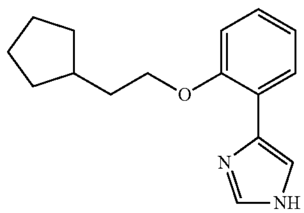 [SMILES: c1ccc(-c2c[nH]cn2)c(OCCC2CCCC2)c1] | 5-(2-(2-cyclopentylethoxy)phenyl)-1H-imidazole |
| 25 | 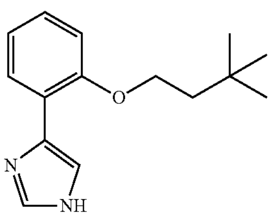 [SMILES: CC(C)(C)CCOc1ccccc1-c1c[nH]cn1] | 4-(2-(3,3-dimethylbutoxy)phenyl)-1H-imidazole |
| 26 | 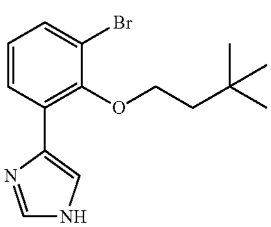 [SMILES: CC(C)(C)CCOc1c(Br)cccc1-c1c[nH]cn1] | 4-(3-bromo-2-(3,3-dimethylbutoxy)phenyl)-1H-imidazole |
| 28 | 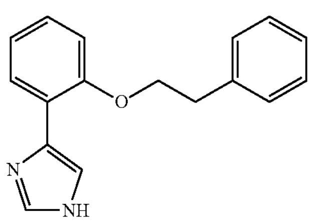 [SMILES: c1ccc(CCOc2ccccc2-c2c[nH]cn2)cc1] | 4-(2-phenethoxyphenyl)-1H-imidazole |
| 29 | 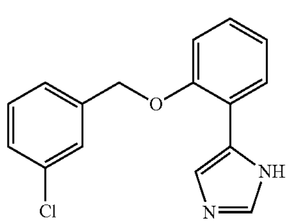 [SMILES: Clc1cccc(COc2ccccc2-c2cnc[nH]2)c1] | 5-(2-(3-chlorobenzyloxy)phenyl)-1H-imidazole |
| 30 | 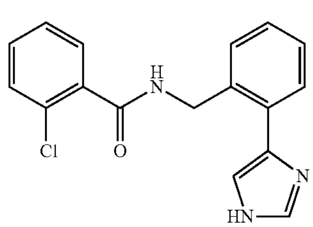 [SMILES: O=C(NCc1ccccc1-c1c[nH]cn1)c1ccccc1Cl] | N-(2-(1H-imidazol-4-yl)benzyl)-2-chlorobenzamide |

TABLE 2-continued

| # | Structure | Name |
|---|---|---|
| 31 | 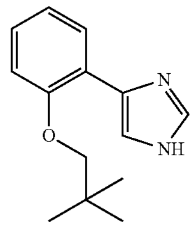 [SMILES: CC(C)(C)COc1ccccc1-c1c[nH]cn1] | 4-(2-(neopentyloxy)phenyl)-1H-imidazole |
| 33 | 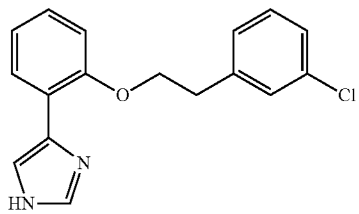 [SMILES: Clc1cccc(CCOc2ccccc2-c2c[nH]cn2)c1] | 4-(2-(3-chlorophenethoxy)phenyl)-1H-imidazole |
| 34 | 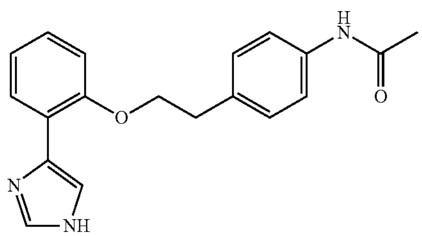 [SMILES: CC(=O)Nc1ccc(CCOc2ccccc2-c2c[nH]cn2)cc1] | N-(4-(2-(2-(1H-imidazol-4-yl)phenoxy)ethyl)phenyl)acetamide |
| 37 | 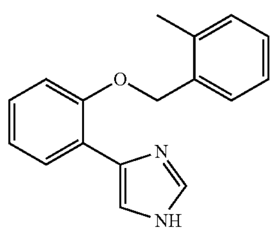 [SMILES: Cc1ccccc1COc1ccccc1-c1c[nH]cn1] | 4-(2-(2-methylbenzyloxy)phenyl)-1H-imidazole |
| 38 | 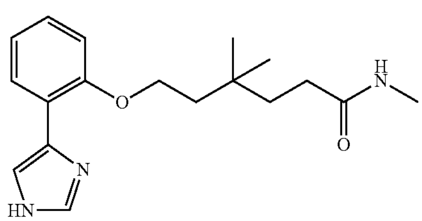 [SMILES: CNC(=O)CCC(C)(C)CCOc1ccccc1-c1c[nH]cn1] | 6-(2-(1H-imidazol-4-yl)phenoxy)-N,4,4-trimethylhexanamide |
| 39 | 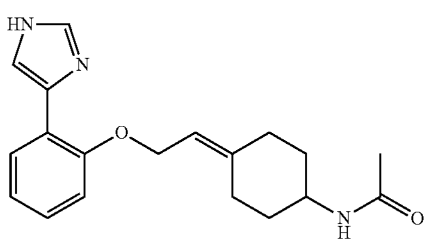 [SMILES: CC(=O)NC1CCC(=CCOc2ccccc2-c2c[nH]cn2)CC1] | N-(4-(2-(2-(1H-imidazol-4-yl)phenoxy)ethylidene)cyclohexyl)acetamide |
| 40 | 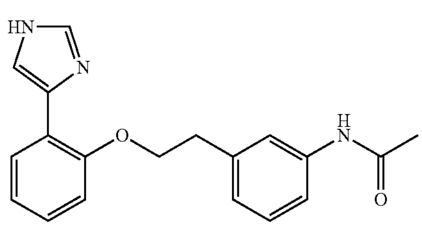 [SMILES: CC(=O)Nc1cccc(CCOc2ccccc2-c2c[nH]cn2)c1] | N-(3-(2-(2-(1H-imidazol-4-yl)phenoxy)ethyl)phenyl)acetamide |

TABLE 2-continued
| # | Structure | Name |
|---|---|---|
| 42 | 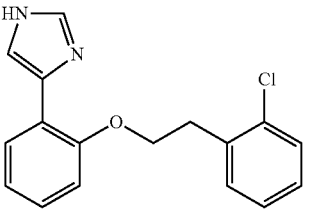 [SMILES: Clc1ccccc1CCOc1ccccc1-c1c[nH]cn1] | 4-(2-((2-chlorobenzyloxy)methyl)phenyl)-1H-imidazole |
| 44 | 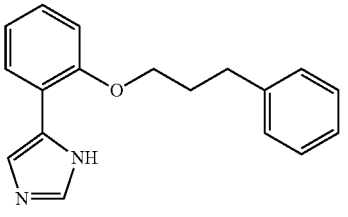 [SMILES: c1ccc(CCCOc2ccccc2-c2cnc[nH]2)cc1] | 5-(2-(3-phenylpropoxy)phenyl)-1H-imidazole |
| 45 | 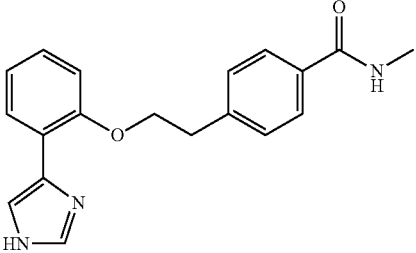 [SMILES: CNC(=O)c1ccc(CCOc2ccccc2-c2c[nH]cn2)cc1] | 4-(2-(2-(1H-imidazol-4-yl)phenoxy)ethyl)-N-methylbenzamide |
| 46 | 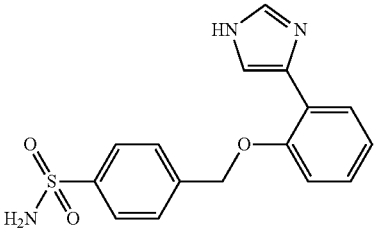 [SMILES: NS(=O)(=O)c1ccc(COc2ccccc2-c2c[nH]cn2)cc1] | 4-((2-(1H-imidazol-4-yl)phenoxy)methyl)benzenesulfonamide |
| 47 | 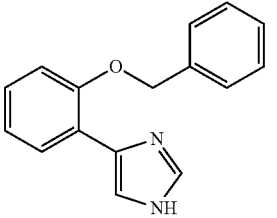 [SMILES: c1ccc(COc2ccccc2-c2c[nH]cn2)cc1] | 4-(2-(benzyloxy)phenyl)-1H-imidazole |
| 48 | 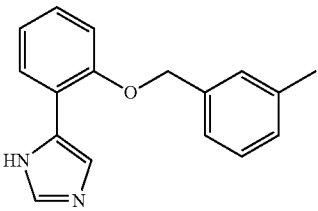 [SMILES: Cc1cccc(COc2ccccc2-c2cnc[nH]2)c1] | 5-(2-(3-methylbenzyloxy)phenyl)-1H-imidazole |

TABLE 2-continued

| # | Structure | Name |
|---|---|---|
| 49 | 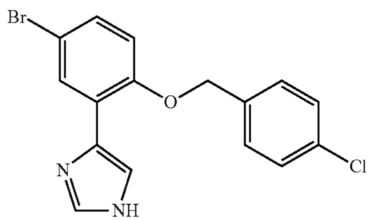 [SMILES: Clc1ccc(COc2ccc(Br)cc2-c2c[nH]cn2)cc1] | 4-(5-bromo-2-(4-chlorobenzyloxy)phenyl)-1H-imidazole |
| 50 | 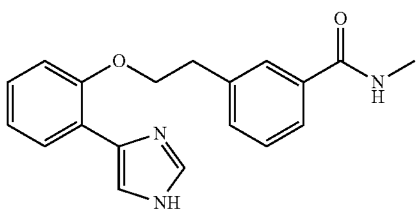 [SMILES: CNC(=O)c1cccc(CCOc2ccccc2-c2c[nH]cn2)c1] | 3-(2-(2-(1H-imidazol-4-yl)phenoxy)ethyl)-N-methylbenzamide |
| 53 | 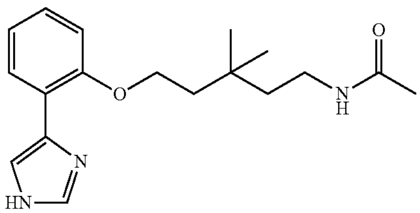 [SMILES: CC(=O)NCCC(C)(C)CCOc1ccccc1-c1c[nH]cn1] | N-(5-(2-(1H-imidazol-4-yl)phenoxy)-3,3-dimethylpentyl)acetamide |
| 55 | 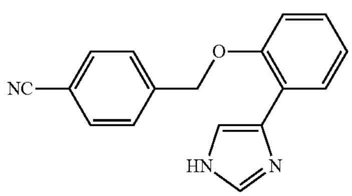 [SMILES: N#Cc1ccc(COc2ccccc2-c2c[nH]cn2)cc1] | 4-((2-(1H-imidazol-4-yl)phenoxy)methyl)benzonitrile |
| 57 | 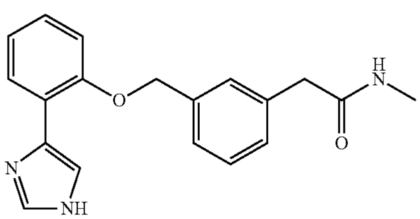 [SMILES: CNC(=O)Cc1cccc(COc2ccccc2-c2c[nH]cn2)c1] | 2-(3-((2-(1H-imidazol-4-yl)phenoxy)methyl)phenyl)-N-methylacetamide |
| 60 | 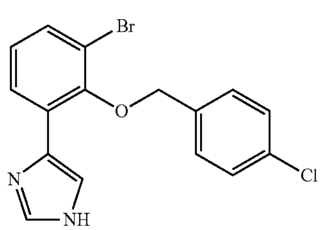 [SMILES: Clc1ccc(COc2c(Br)cccc2-c2c[nH]cn2)cc1] | 4-(3-bromo-2-(4-chlorobenzyloxy)phenyl)-1H-imidazole |
| 61 | 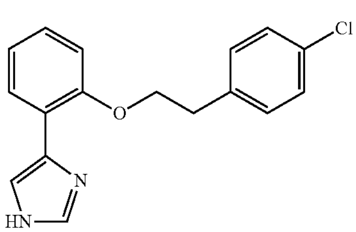 [SMILES: Clc1ccc(CCOc2ccccc2-c2c[nH]cn2)cc1] | 4-(2-(4-chlorophenethoxy)phenyl)-1H-imidazole |

TABLE 2-continued

| # | Structure | Name |
|---|---|---|
| 62 | 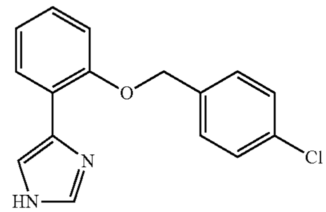 [SMILES: Clc1ccc(COc2ccccc2-c2c[nH]cn2)cc1] | N-(4-chlorobenzyl)-2-(1H-imidazol-4-yl)aniline |
| 66 | 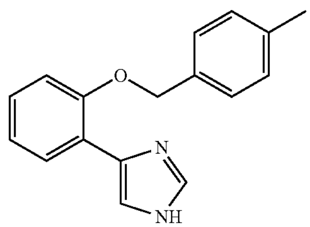 [SMILES: Cc1ccc(COc2ccccc2-c2c[nH]cn2)cc1] | 4-(2-(4-methylbenzyloxy)phenyl)-1H-imidazole |
| 73 | 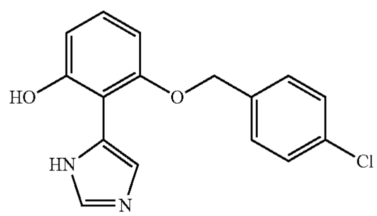 [SMILES: Oc1cccc(OCc2ccc(Cl)cc2)c1-c1cnc[nH]1] | 3-(4-chlorobenzyloxy)-2-(1H-imidazol-5-yl)phenol |
| 74 | 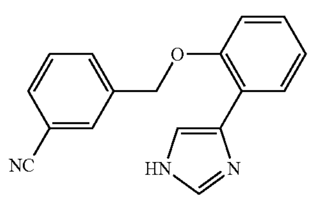 [SMILES: N#Cc1cccc(COc2ccccc2-c2c[nH]cn2)c1] | 3-((2-(1H-imidazol-4-yl)phenoxy)methyl)benzonitrile |
| 75 | 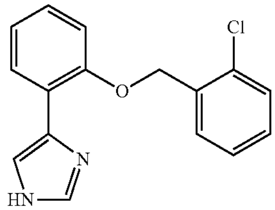 [SMILES: Clc1ccccc1COc1ccccc1-c1c[nH]cn1] | 4-(2-(2-chlorobenzyloxy)phenyl)-1H-imidazole |
| 76 | 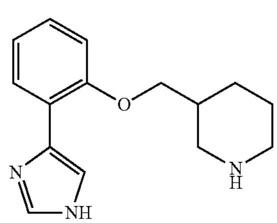 [SMILES: c1ccc(-c2c[nH]cn2)c(OCC2CCCNC2)c1] | 3-((2-(1H-imidazol-4-yl)phenoxy)methyl)piperidine |
| 78 | 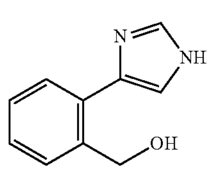 [SMILES: OCc1ccccc1-c1c[nH]cn1] | (2-(1H-imidazol-4-yl)phenyl)methanol |

TABLE 2-continued

| # | Structure | Name |
|---|---|---|
| 79 | 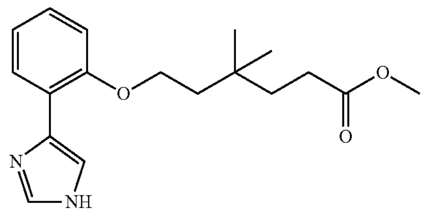 [SMILES: COC(=O)CCC(C)(C)CCOc1ccccc1-c1c[nH]cn1] | methyl 6-(2-(1H-imidazol-4-yl)phenoxy)-4,4-dimethylhexanoate |
| 83 | 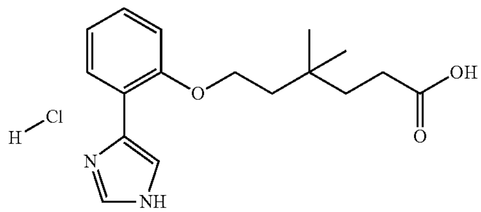 | 6-(2-(1H-imidazol-4-yl)phenoxy)-4,4-dimethylhexanoic acid hydrochloride |
| 84 | 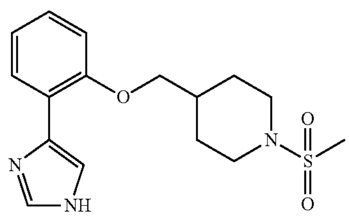 [SMILES: CS(=O)(=O)N1CCC(COc2ccccc2-c2c[nH]cn2)CC1] | 4-((2-(1H-imidazol-4-yl)phenoxy)methyl)-1-(methylsulfonyl)piperidine |
| 88 | 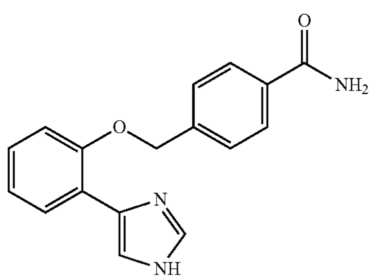 [SMILES: NC(=O)c1ccc(COc2ccccc2-c2c[nH]cn2)cc1] | 4-((2-(1H-imidazol-4-yl)phenoxy)methyl)benzamide |
| 91 | 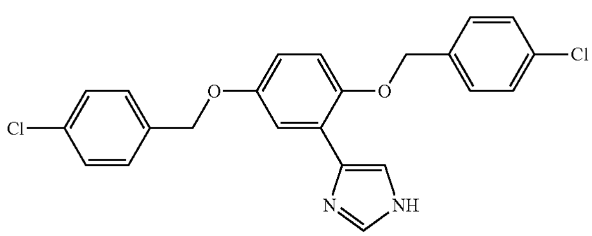 [SMILES: Clc1ccc(COc2ccc(OCc3ccc(Cl)cc3)c(-c3c[nH]cn3)c2)cc1] | 4-(2,5-bis(4-chlorobenzyloxy)phenyl)-1H-imidazole |
| 92 | 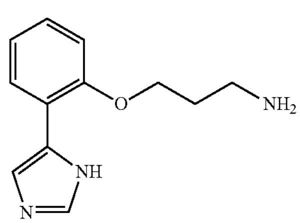 [SMILES: NCCCOc1ccccc1-c1cnc[nH]1] | 3-(2-(1H-imidazol-5-yl)phenoxy)propan-1-amine |
| 98 | 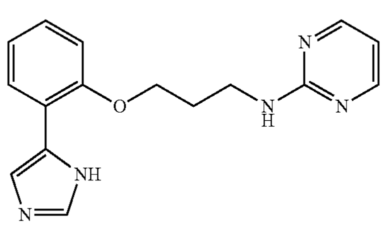 [SMILES: c1cnc(NCCCOc2ccccc2-c2cnc[nH]2)nc1] | N-(3-(2-(1H-imidazol-5-yl)phenoxy)propyl)pyrimidin-2-amine |

TABLE 2-continued

| # | Structure | Name |
|---|---|---|
| 99 | 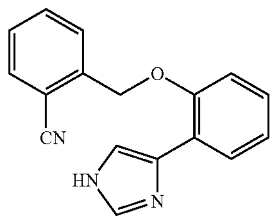 [SMILES: N#Cc1ccccc1COc1ccccc1-c1c[nH]cn1] | 2-((2-(1H-imidazol-4-yl)phenoxy)methyl)benzonitrile |
| 100 | 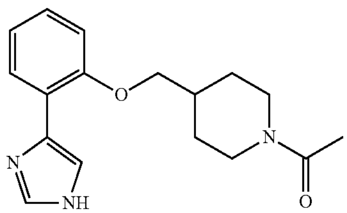 [SMILES: CC(=O)N1CCC(COc2ccccc2-c2c[nH]cn2)CC1] | 1-(4-((2-(1H-imidazol-4-yl)phenoxy)methyl)piperidin-1-yl)ethanone |
| 102 | 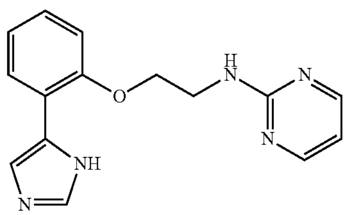 [SMILES: c1cnc(NCCOc2ccccc2-c2cnc[nH]2)nc1] | N-(2-(2-(1H-imidazol-5-yl)phenoxy)ethyl)pyrimidin-2-amine |
| 104 | 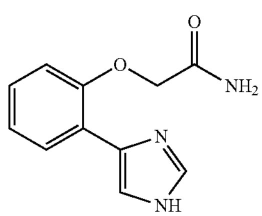 [SMILES: NC(=O)COc1ccccc1-c1c[nH]cn1] | 2-(2-(1H-imidazol-4-yl)phenoxy)acetamide |
| 107 | 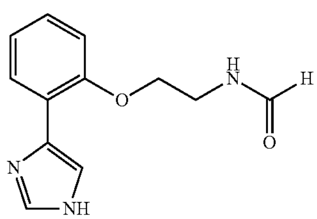 [SMILES: O=CNCCOc1ccccc1-c1c[nH]cn1] | N-(2-(2-(1H-imidazol-4-yl)phenoxy)ethyl)formamide |
| 117 | 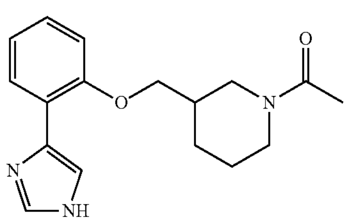 [SMILES: CC(=O)N1CCCC(COc2ccccc2-c2c[nH]cn2)C1] | 1-(3-((2-(1H-imidazol-4-yl)phenoxy)methyl)piperidin-1-yl)ethanone |
| 132 | 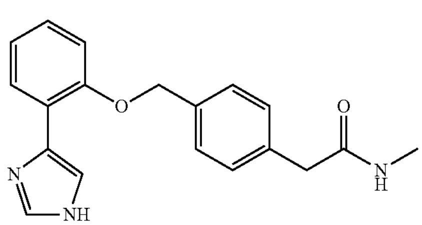 [SMILES: CNC(=O)Cc1ccc(COc2ccccc2-c2c[nH]cn2)cc1] | 2-(4-((2-(1H-imidazol-4-yl)phenoxy)methyl)phenyl)-N-methylacetamide |

TABLE 2-continued

| # | Structure | Name |
|---|---|---|
| 146 | 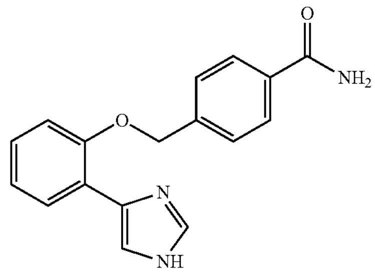 [SMILES: NC(=O)c1ccc(COc2ccccc2-c2c[nH]cn2)cc1] | 4-((2-(1H-imidazol-4-yl)phenoxy)methyl)benzamide |
| 147 | 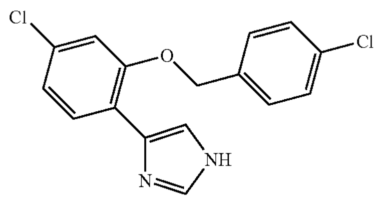 [SMILES: Clc1ccc(COc2cc(Cl)ccc2-c2c[nH]cn2)cc1] | 4-(4-chloro-2-(4-chlorobenzyloxy)phenyl)-1H-imidazole |
| 148 | 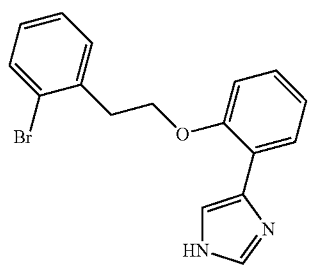 [SMILES: Brc1ccccc1CCOc1ccccc1-c1c[nH]cn1] | 4-(2-(2-bromophenethoxy)phenyl)-1H-imidazole |
| 149 | 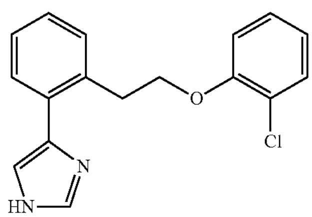 [SMILES: Clc1ccccc1OCCc1ccccc1-c1c[nH]cn1] | 4-(2-(2-(2-chlorophenoxy)ethyl)phenyl)-1H-imidazole |
| 150 | 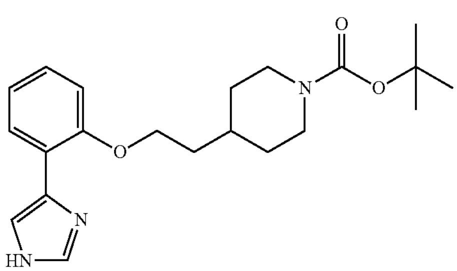 [SMILES: CC(C)(C)OC(=O)N1CCC(CCOc2ccccc2-c2c[nH]cn2)CC1] | tert-butyl 4-(2-(2-(1H-imidazol-4-yl)phenoxy)ethyl)piperidine-1-carboxylate |
| 151 | 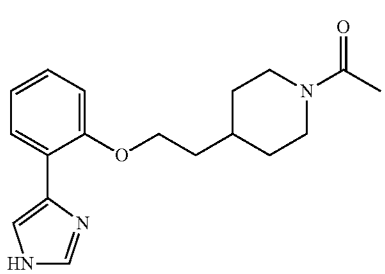 [SMILES: CC(=O)N1CCC(CCOc2ccccc2-c2c[nH]cn2)CC1] | 1-(4-(2-(2-(1H-imidazol-4-yl)phenoxy)ethyl)piperidin-1-yl)ethanone |

TABLE 2-continued

| # | Structure | Name |
|---|---|---|
| 152 | 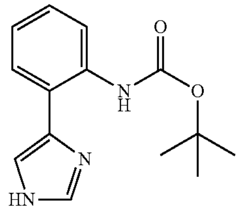 [SMILES: CC(C)(C)OC(=O)Nc1ccccc1-c1c[nH]cn1] | tert-butyl 2-(1H-imidazol-4-yl)phenylcarbamate |
| 154 | 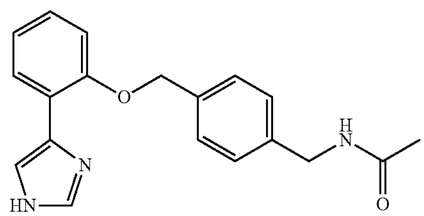 [SMILES: CC(=O)NCc1ccc(COc2ccccc2-c2c[nH]cn2)cc1] | N-(4-((2-(1H-imidazol-4-yl)phenoxy)methyl)benzyl)acetamide |
| 157 | 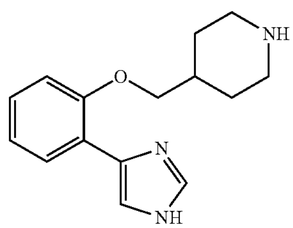 [SMILES: c1ccc(-c2c[nH]cn2)c(OCC2CCNCC2)c1] | 4-((2-(1H-imidazol-4-yl)phenoxy)methyl)piperidine |
| 158 | 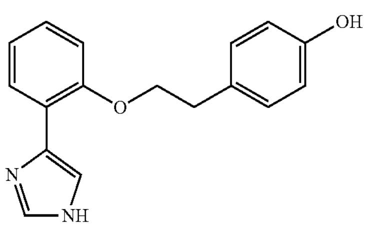 [SMILES: Oc1ccc(CCOc2ccccc2-c2c[nH]cn2)cc1] | 4-(2-(2-(1H-imidazol-4-yl)phenoxy)ethyl)phenol |
| 159 | 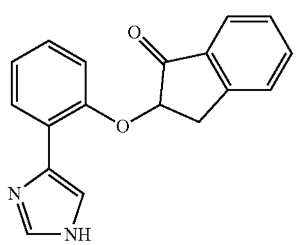 [SMILES: O=C1c2ccccc2CC1Oc1ccccc1-c1c[nH]cn1] | 2-(2-(1H-imidazol-4-yl)phenoxy)-2,3-dihydro-1H-inden-1-one |
| 160 | 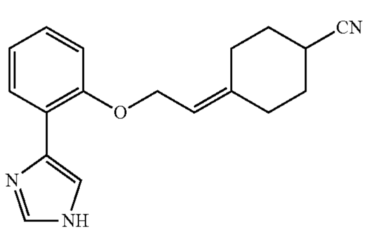 [SMILES: N#CC1CCC(=CCOc2ccccc2-c2c[nH]cn2)CC1] | 4-(2-(2-(1H-imidazol-4-yl)phenoxy)ethylidene)cyclohexanecarbonitrile |
| 161 | 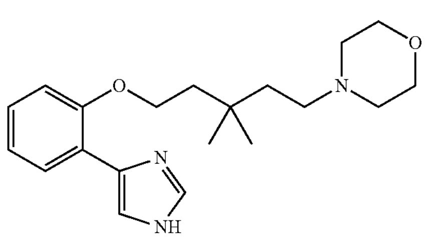 [SMILES: CC(C)(CCOc1ccccc1-c1c[nH]cn1)CCN1CCOCC1] | 4-(5-(2-(1H-imidazol-4-yl)phenoxy)-3,3-dimethylpentyl)morpholine |

TABLE 2-continued

| # | Structure | Name |
|---|---|---|
| 162 | 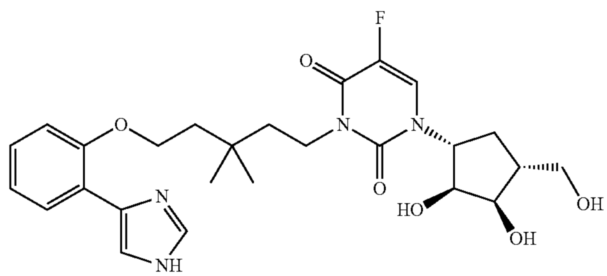 [SMILES: CC(C)(CCOc1ccccc1-c1c[nH]cn1)CCn1c(=O)c(F)cn([C@@H]2C[C@H](CO)[C@@H](O)[C@H]2O)c1=O] | 3-(5-(2-(1H-imidazol-4-yl)phenoxy)-3,3-dimethylpentyl)-1-((2R,3R,4S,5R)-3,4-dihydroxy-5-(hydroxymethyl)tetrahydrofuran-2-yl)-5-fluoropyrimidine-2,4(1H,3H)-dione |
| 163 | 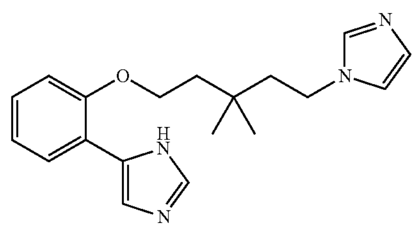 [SMILES: CC(C)(CCOc1ccccc1-c1cnc[nH]1)CCn1ccnc1] | 5-(2-(5-(1H-imidazol-1-yl)-3,3-dimethylpentyloxy)phenyl)-1H-imidazole |
| 164 | 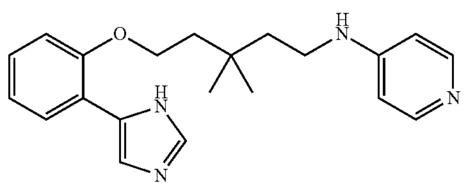 [SMILES: CC(C)(CCNc1ccncc1)CCOc1ccccc1-c1cnc[nH]1] | N-(5-(2-(1H-imidazol-5-yl)phenoxy)-3,3-dimethylpentyl)pyridin-4-amine |
| 165 | 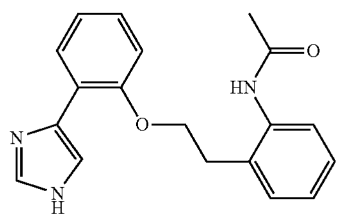 [SMILES: CC(=O)Nc1ccccc1CCOc1ccccc1-c1c[nH]cn1] | N-(2-(2-(2-(1H-imidazol-4-yl)phenoxy)ethyl)phenyl)acetamide |
| 166 | 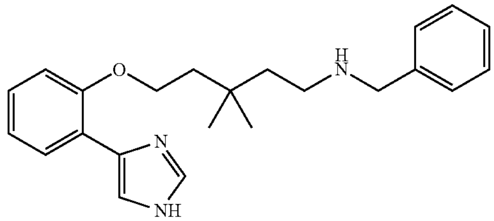 [SMILES: CC(C)(CCNCc1ccccc1)CCOc1ccccc1-c1c[nH]cn1] | 5-(2-(1H-imidazol-4-yl)phenoxy)-N-benzyl-3,3-dimethylpentan-1-amine |
| 167 | 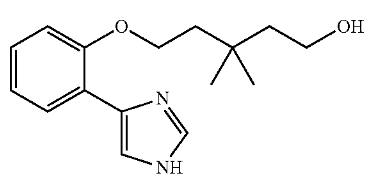 [SMILES: CC(C)(CCO)CCOc1ccccc1-c1c[nH]cn1] | 5-(2-(1H-imidazol-4-yl)phenoxy)-3,3-dimethylpentan-1-ol |
| 168 | 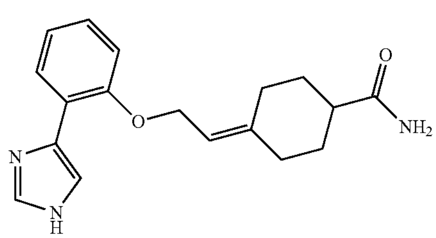 [SMILES: NC(=O)C1CCC(=CCOc2ccccc2-c2c[nH]cn2)CC1] | 4-(2-(2-(1H-imidazol-4-yl)phenoxy)ethylidene)cyclohexanecarboxamide |

(35) embodiment (1), wherein the compound is in Table 3:

TABLE 3

| # | Structure | Name |
|---|-----------|------|
| 32 | 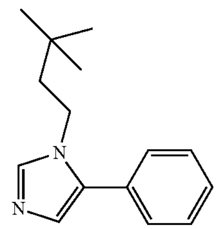 [SMILES: CC(C)(C)CCn1cncc1-c1ccccc1] | 1-(3,3-dimethylbutyl)-5-phenyl-1H-imidazole |
| 51 | 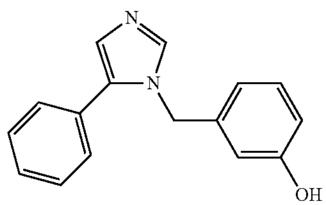 [SMILES: Oc1cccc(Cn2cncc2-c2ccccc2)c1] | 3-((5-phenyl-1H-imidazol-1-yl)methyl)phenol |
| 52 | 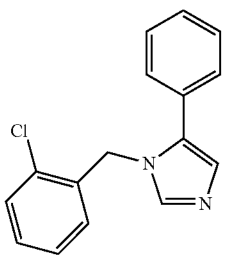 [SMILES: Clc1ccccc1Cn1cncc1-c1ccccc1] | 1-(2-chlorobenzyl)-5-phenyl-1H-imidazole |
| 54 | 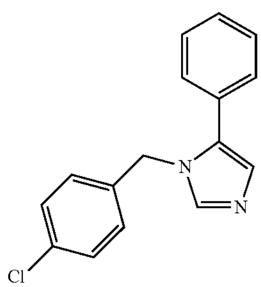 [SMILES: Clc1ccc(Cn2cncc2-c2ccccc2)cc1] | 1-(4-chlorobenzyl)-5-phenyl-1H-imidazole |
| 58 | 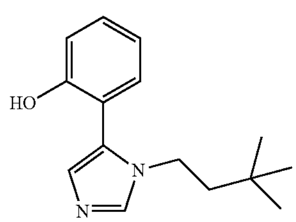 [SMILES: CC(C)(C)CCn1cncc1-c1ccccc1O] | 2-(1-(3,3-dimethylbutyl)-1H-imidazol-5-yl)phenol |
| 64 | 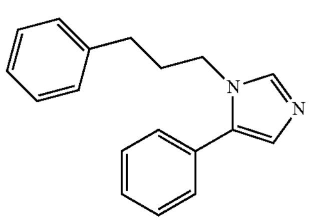 [SMILES: c1ccc(CCCn2cncc2-c2ccccc2)cc1] | 5-phenyl-1-(3-phenylpropyl)-1H-imidazole |

TABLE 3-continued

| # | Structure | Name |
|---|---|---|
| 65 | 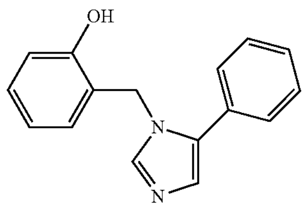 [SMILES: Oc1ccccc1Cn1cncc1-c1ccccc1] | 2-((5-phenyl-1H-imidazol-1-yl)methyl)phenol |
| 68 | 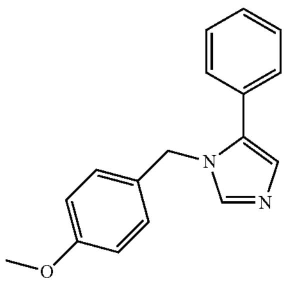 [SMILES: COc1ccc(Cn2cncc2-c2ccccc2)cc1] | 1-(4-methoxybenzyl)-5-phenyl-1H-imidazole |
| 69 | 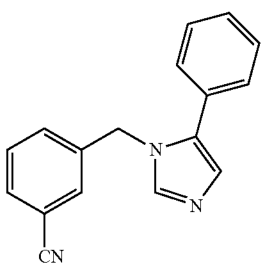 [SMILES: N#Cc1cccc(Cn2cncc2-c2ccccc2)c1] | 3-((5-phenyl-1H-imidazol-1-yl)methyl)benzonitrile |
| 71 | 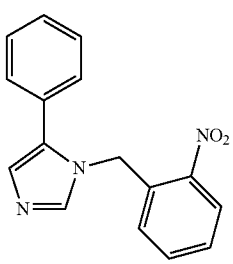 [SMILES: O=[N+]([O-])c1ccccc1Cn1cncc1-c1ccccc1] | 1-(2-nitrobenzyl)-5-phenyl-1H-imidazole |
| 72 | 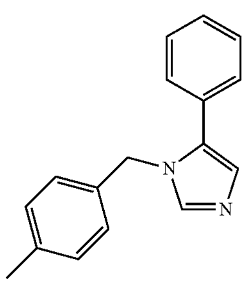 [SMILES: Cc1ccc(Cn2cncc2-c2ccccc2)cc1] | 1-(4-methylbenzyl)-5-phenyl-1H-imidazole |
| 77 | 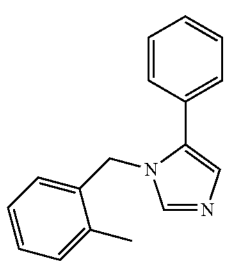 [SMILES: Cc1ccccc1Cn1cncc1-c1ccccc1] | 1-(2-methylbenzyl)-5-phenyl-1H-imidazole |

TABLE 3-continued

| # | Structure | Name |
| --- | --- | --- |
| 82 | 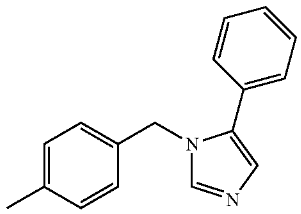 [SMILES: Cc1ccc(Cn2cncc2-c2ccccc2)cc1] | 1-(4-methylbenzyl)-5-phenyl-1H-imidazole |
| 85 | 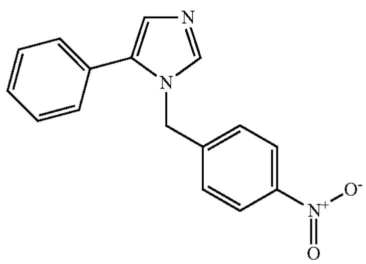 [SMILES: O=[N+]([O-])c1ccc(Cn2cncc2-c2ccccc2)cc1] | 1-(4-nitrobenzyl)-5-phenyl-1H-imidazole |
| 86 | 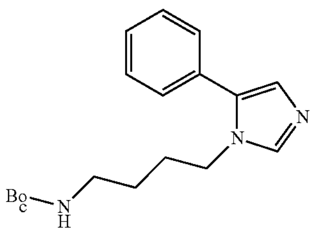 [SMILES: CC(C)(C)OC(=O)NCCCCn1cncc1-c1ccccc1] | tert-butyl 4-(5-phenyl-1H-imidazol-1-yl)butylcarbamate |
| 87 | 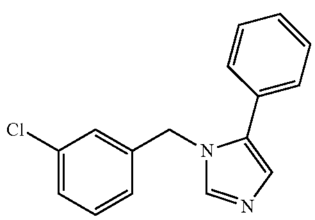 [SMILES: Clc1cccc(Cn2cncc2-c2ccccc2)c1] | 1-(3-chlorobenzyl)-5-phenyl-1H-imidazole |
| 89 | 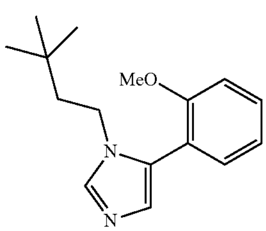 [SMILES: COc1ccccc1-c1cncn1CCC(C)(C)C] | 1-(3,3-dimethylbutyl)-5-(2-methoxyphenyl)-1H-imidazole |
| 90 | 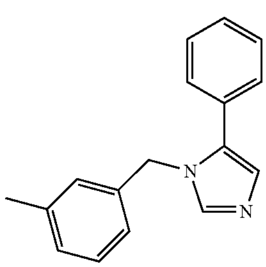 [SMILES: Cc1cccc(Cn2cncc2-c2ccccc2)c1] | 1-(3-methylbenzyl)-5-phenyl-1H-imidazole |

TABLE 3-continued

| # | Structure | Name |
|---|---|---|
| 93 | 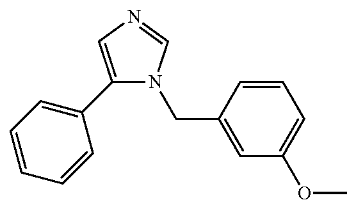 [SMILES: COc1cccc(Cn2cncc2-c2ccccc2)c1] | 1-(3-methoxybenzyl)-5-phenyl-1H-imidazole |
| 95 | 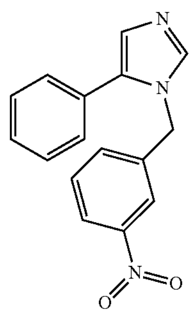 [SMILES: O=[N+]([O-])c1cccc(Cn2cncc2-c2ccccc2)c1] | 1-(3-nitrobenzyl)-5-phenyl-1H-imidazole |
| 96 | 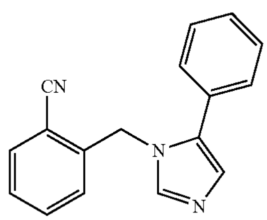 | 2-((5-phenyl-1H-imidazol-1-yl)methyl)benzonitrile |
| 97 | 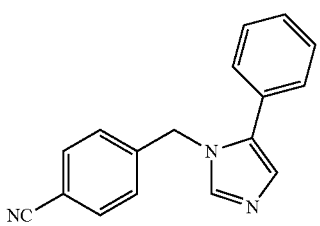 [SMILES: N#Cc1ccc(Cn2cncc2-c2ccccc2)cc1] | 4-((5-phenyl-1H-imidazol-1-yl)methyl)benzonitrile |
| 105 | 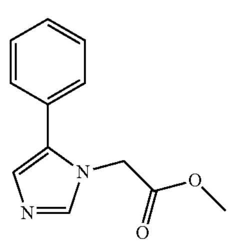 [SMILES: COC(=O)Cn1cncc1-c1ccccc1] | methyl 2-(5-phenyl-1H-imidazol-1-yl)acetate |
| 106 | 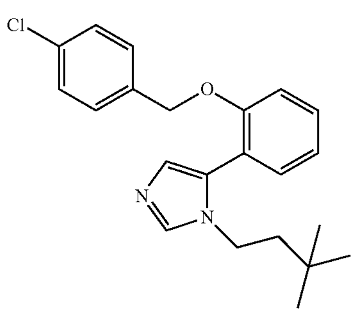 [SMILES: CC(C)(C)CCn1cncc1-c1ccccc1OCc1ccc(Cl)cc1] | 5-(2-(4-chlorobenzyloxy)phenyl)-1-(3,3-dimethylbutyl)-1H-imidazole |

TABLE 3-continued

| # | Structure | Name |
|---|---|---|
| 108 | 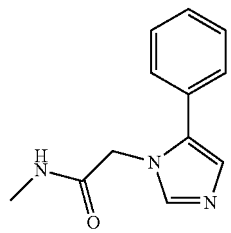 [SMILES: CNC(=O)Cn1cncc1-c1ccccc1] | N-methyl-2-(5-phenyl-1H-imidazol-1-yl)acetamide |
| 110 | 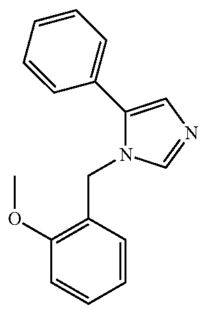 [SMILES: COc1ccccc1Cn1cncc1-c1ccccc1] | 1-(2-methoxybenzyl)-5-phenyl-1H-imidazole |
| 114 | 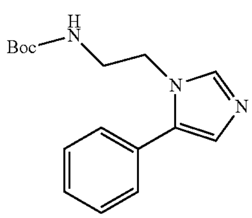 [SMILES: CC(C)(C)OC(=O)NCCn1cncc1-c1ccccc1] | tert-butyl 2-(5-phenyl-1H-imidazol-1-yl)ethylcarbamate |
| 116 | 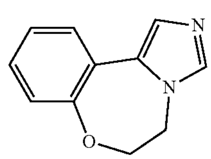 [SMILES: c1ccc2c(c1)OCCn1cncc1-2] | 5,6-dihydrobenzo[f]imidazo[1,5-d][1,4]oxazepine |
| 121 | 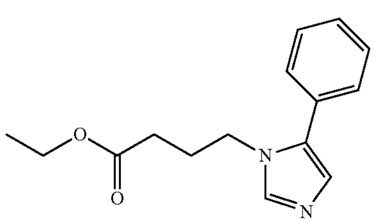 [SMILES: CCOC(=O)CCCn1cncc1-c1ccccc1] | ethyl 4-(5-phenyl-1H-imidazol-1-yl)butanoate |
| 124 | 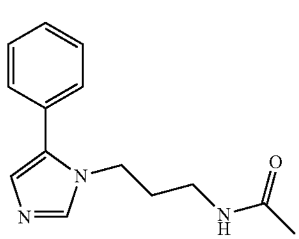 [SMILES: CC(=O)NCCCn1cncc1-c1ccccc1] | N-(3-(5-phenyl-1H-imidazol-1-yl)propyl)acetamide |

TABLE 3-continued

| # | Structure | Name |
|---|---|---|
| 125 | 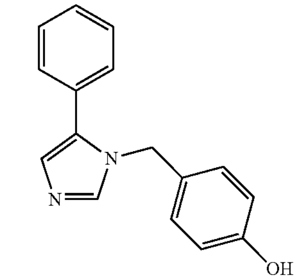 [SMILES: Oc1ccc(Cn2cncc2-c2ccccc2)cc1] | 4-((5-phenyl-1H-imidazol-1-yl)methyl)phenol |
| 127 | 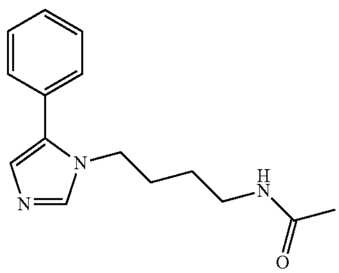 [SMILES: CC(=O)NCCCCn1cncc1-c1ccccc1] | N-(4-(5-phenyl-1H-imidazol-1-yl)butyl)acetamide |
| 128 | 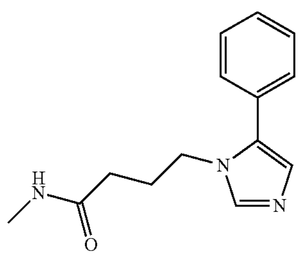 [SMILES: CNC(=O)CCCn1cncc1-c1ccccc1] | N-methyl-4-(5-phenyl-1H-imidazol-1-yl)butanamide |
| 129 | 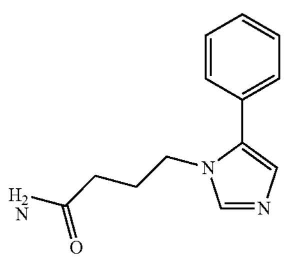 [SMILES: NC(=O)CCCn1cncc1-c1ccccc1] | 4-(5-phenyl-1H-imidazol-1-yl)butanamide |

(36) embodiment (1), wherein the compound is in Table 4:

TABLE 4

| # | Structure | Name |
|---|---|---|
| 1 | 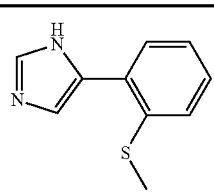 | 5-(2-(methylthio)phenyl)-1H-imidazole |
| 2 | 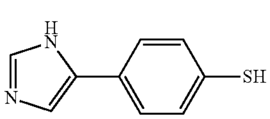 [SMILES: Sc1ccc(-c2cnc[nH]2)cc1] | 4-(1H-imidazol-5-yl)benzenethiol |
| 11 | | 2-(1H-imidazol-5-yl)phenol |
| 17 | | 3-(1H-imidazol-5-yl)benzenethiol |

TABLE 4-continued

| # | Structure | Name |
|---|---|---|
| 19 | 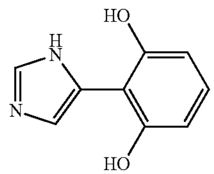 [SMILES: Oc1cccc(O)c1-c1cnc[nH]1] | 2-(1H-imidaozl-5-yl)benzene-1,3-diol |
| 23 | 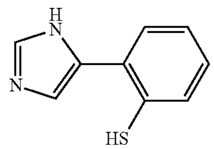 [SMILES: Sc1ccccc1-c1cnc[nH]1] | 2-(1H-imidazol-5-yl)benzenethiol |
| 36 | 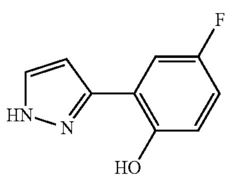 [SMILES: Oc1ccc(F)cc1-c1cc[nH]n1] | 4-fluoro-2-(1H-pyrazol-3-yl)phenol |
| 43 | 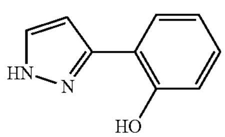 [SMILES: Oc1ccccc1-c1cc[nH]n1] | 2-(1H-pyrazol-3-yl)phenol |
| 103 | 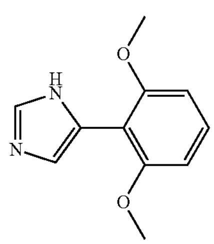 | 5-(2,6-dimethoxyphenyl)-1H-imidazole |
| 139 | 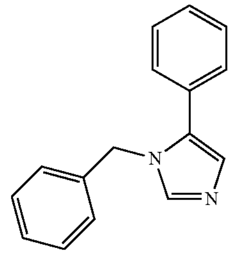 [SMILES: c1ccc(Cn2cncc2-c2ccccc2)cc1] | 1-benzyl-5-phenyl-1H-imidazole |
| 254 | 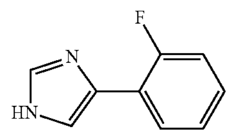 [SMILES: Fc1ccccc1-c1c[nH]cn1] | 4-(2-fluorophenyl)-1H-imidazole |
| 255 | 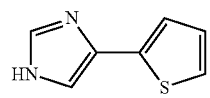 | 4-(thiophen-2-yl)-1H-imidazole |
| 256 | 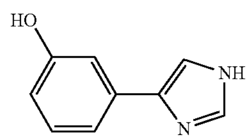 [SMILES: Oc1cccc(-c2c[nH]cn2)c1] | 3-(1H-imidazol-4-yl)phenol |
| 257 | 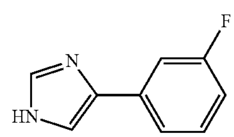 [SMILES: Fc1cccc(-c2c[nH]cn2)c1] | 4-(3-fluorophenyl)-1H-imidazole |
| 258 | 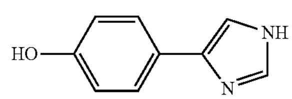 [SMILES: Oc1ccc(-c2c[nH]cn2)cc1] | 4-(1H-imidazol-4-yl)phenol |
| 259 | 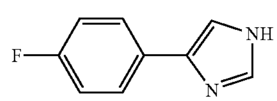 | 4-(4-fluorophenyl)-1H-imidazole |

(37) embodiment (1), wherein the compound is in Table 5:

TABLE 5

| # | Structure | Name |
|---|---|---|
| 201 | 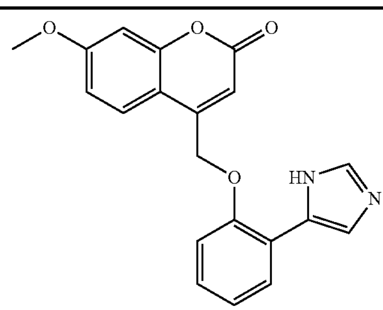 | 4-((2-(1H-imidazol-5-yl)phenoxy)methyl)-7-methoxy-2H-chromen-2-one |

TABLE 5-continued

| # | Structure | Name |
|---|---|---|
| 202 | 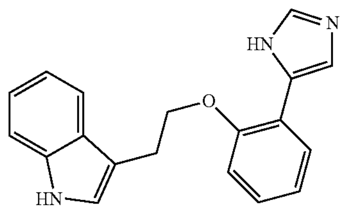 [SMILES: c1ccc(-c2cnc[nH]2)c(OCCc2c[nH]c3ccccc23)c1] | 3-(2-(2-(1H-imidazol-5-yl)phenoxy)ethyl)-1H-indole |
| 203 | 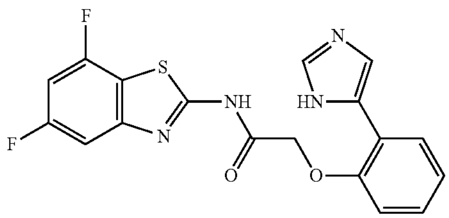 [SMILES: O=C(COc1ccccc1-c1cnc[nH]1)Nc1nc2cc(F)cc(F)c2s1] | 2-(2-(1H-imidazol-5-yl)phenoxy)-N-(5,7-difluorobenzo[d]thiazol-2-yl)acetamide |
| 204 | 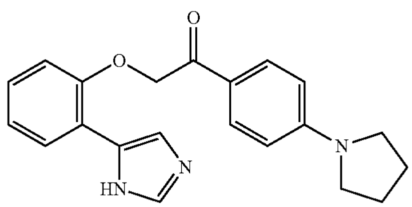 [SMILES: O=C(COc1ccccc1-c1cnc[nH]1)c1ccc(N2CCCC2)cc1] | 2-(2-(1H-imidazol-5-yl)phenoxy)-1-(4-(pyrrolidin-1-yl)phenyl)ethanone |
| 205 | 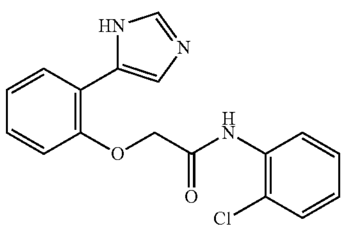 [SMILES: O=C(COc1ccccc1-c1cnc[nH]1)Nc1ccccc1Cl] | 2-(2-(1H-imidazol-5-yl)phenoxy)-N-(2-chlorophenyl)acetamide |
| 206 | 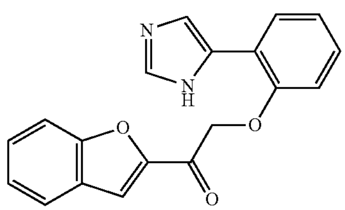 [SMILES: O=C(COc1ccccc1-c1cnc[nH]1)c1cc2ccccc2o1] | 2-(2-(1H-imidazol-5-yl)phenoxy)-1-(benzofuran-2-yl)ethanone |
| 207 | 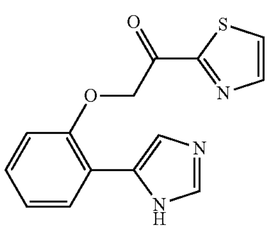 [SMILES: O=C(COc1ccccc1-c1cnc[nH]1)c1nccs1] | 2-(2-(1H-imidazol-5-yl)phenoxy)-1-(thiazol-2-yl)ethanone |
| 208 | 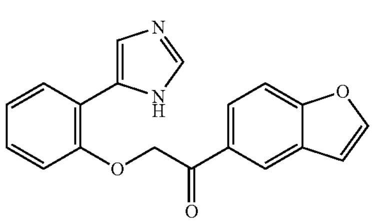 [SMILES: O=C(COc1ccccc1-c1cnc[nH]1)c1ccc2occc2c1] | 2-(2-(1H-imidazol-5-yl)phenoxy)-1-(benzofuran-5-yl)ethanone |

TABLE 5-continued

| # | Structure | Name |
|---|-----------|------|
| 209 | 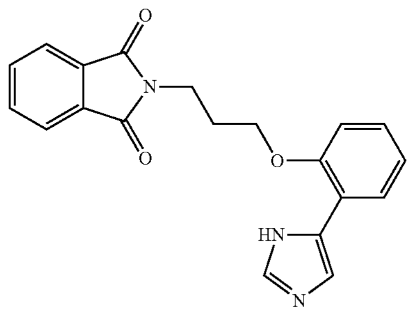 [SMILES: O=C1c2ccccc2C(=O)N1CCCOc1ccccc1-c1cnc[nH]1] | 2-(3-(2-(1H-imidazol-5-yl)phenoxy)propyl)isoindoline-1,3-dione |
| 210 | 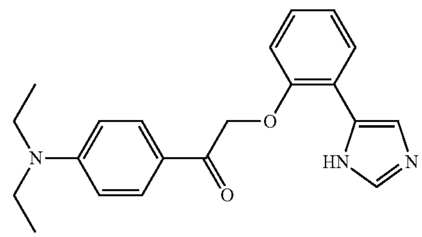 [SMILES: CCN(CC)c1ccc(C(=O)COc2ccccc2-c2cnc[nH]2)cc1] | 2-(2-(1H-imidazol-5-yl)phenoxy)-1-(4-(diethylamino)phenyl)ethanone |
| 211 | 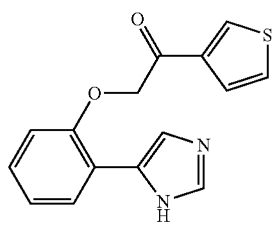 [SMILES: O=C(COc1ccccc1-c1cnc[nH]1)c1ccsc1] | 2-(2-(1H-imidazol-5-yl)phenoxy)-1-(thiophen-3-yl)ethanone |
| 212 | 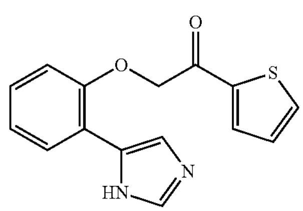 [SMILES: O=C(COc1ccccc1-c1cnc[nH]1)c1cccs1] | 2-(2-(1H-imidazol-5-yl)phenoxy)-1-(thiophen-2-yl)ethanone |
| 213 | 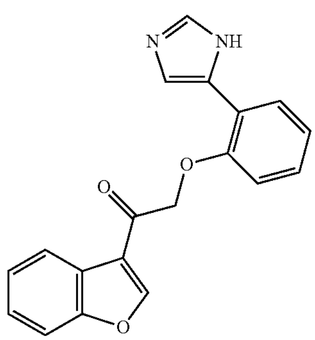 [SMILES: O=C(COc1ccccc1-c1cnc[nH]1)c1coc2ccccc12] | 2-(2-(1H-imidazol-5-yl)phenoxy)-1-(benzofuran-3-yl)ethanone |
| 214 | 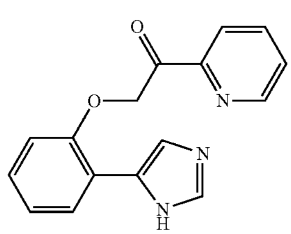 [SMILES: O=C(COc1ccccc1-c1cnc[nH]1)c1ccccn1] | 2-(2-(1H-imidazol-5-yl)phenoxy)-1-(pyridin-2-yl)ethanone |

TABLE 5-continued

| # | Structure | Name |
|---|---|---|
| 215 | 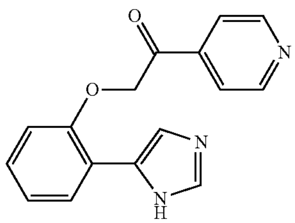 [SMILES: O=C(COc1ccccc1-c1cnc[nH]1)c1ccncc1] | 2-(2-(1H-imidazol-5-yl)phenoxy)-1-(pyridin-4-yl)ethanone |
| 216 | 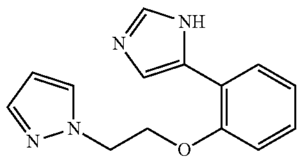 [SMILES: c1ccc(-c2cnc[nH]2)c(OCCn2cccn2)c1] | 1-(2-(2-(1H-imidazol-5-yl)phenoxy)ethyl)-1H-pyrazole |
| 217 | 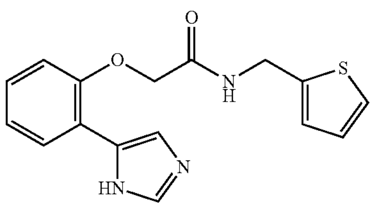 [SMILES: O=C(COc1ccccc1-c1cnc[nH]1)NCc1cccs1] | 2-(2-(1H-imidazol-5-yl)phenoxy)-N-(thiophen-2-ylmethyl)acetamide |
| 218 | 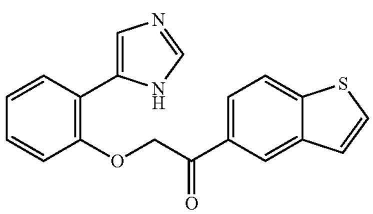 [SMILES: O=C(COc1ccccc1-c1cnc[nH]1)c1ccc2sccc2c1] | 2-(2-(1H-imidazol-5-yl)phenoxy)-1-(benzo[b]thiophen-5-yl)ethanone |
| 219 | 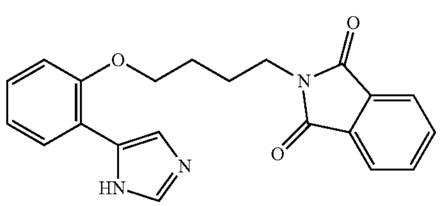 [SMILES: O=C1c2ccccc2C(=O)N1CCCCOc1ccccc1-c1cnc[nH]1] | 2-(4-(2-(1H-imidazol-5-yl)phenoxy)butyl)isoindoline-1,3-dione |
| 220 | 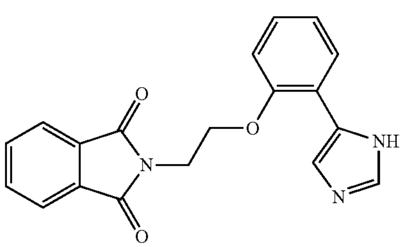 [SMILES: O=C1c2ccccc2C(=O)N1CCOc1ccccc1-c1cnc[nH]1] | 2-(2-(2-(1H-imidazol-5-yl)phenoxy)ethyl)isoindoline-1,3-dione |
| 221 | 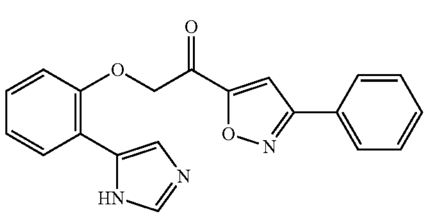 [SMILES: O=C(COc1ccccc1-c1cnc[nH]1)c1cc(-c2ccccc2)no1] | 2-(2-(1H-imidazol-5-yl)phenoxy)-1-(3-phenylisoxazol-5-yl)ethanone |

TABLE 5-continued

| # | Structure | Name |
|---|---|---|
| 222 | 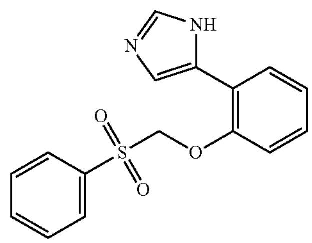 [SMILES: O=S(=O)(COc1ccccc1-c1cnc[nH]1)c1ccccc1] | 5-(2-(phenylsulfonylmethoxy)phenyl)-1H-imidazole |
| 223 | 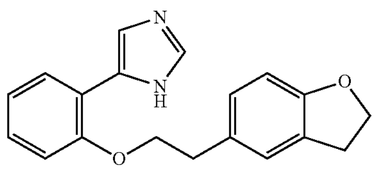 [SMILES: c1ccc(-c2cnc[nH]2)c(OCCc2ccc3c(c2)CCO3)c1] | 5-(2-(2-(2,3-dihydrobenzofuran-5-yl)ethoxy)phenyl)-1H-imidazole |
| 224 | 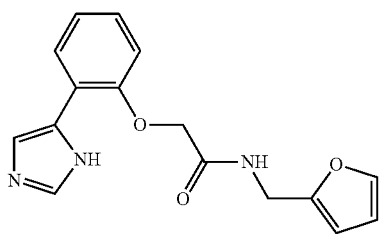 [SMILES: O=C(COc1ccccc1-c1cnc[nH]1)NCc1ccco1] | 2-(2-(1H-imidazol-5-yl)phenoxy)-N-(furan-2-ylmethyl)acetamide |
| 225 | 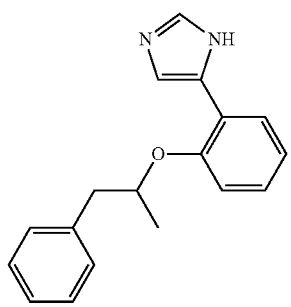 [SMILES: CC(Cc1ccccc1)Oc1ccccc1-c1cnc[nH]1] | 5-(2-(1-phenylpropan-2-yloxy)phenyl)-1H-imidazole |
| 226 | 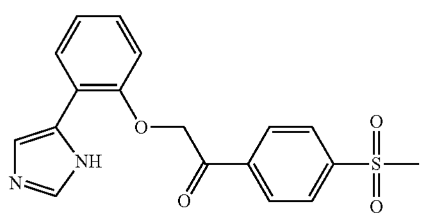 [SMILES: CS(=O)(=O)c1ccc(C(=O)COc2ccccc2-c2cnc[nH]2)cc1] | 2-(2-(1H-imidazol-5-yl)phenoxy)-1-(4-(methylsulfonyl)phenyl)ethanone |
| 227 | 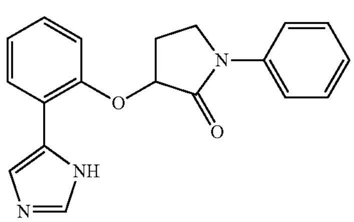 [SMILES: O=C1C(Oc2ccccc2-c2cnc[nH]2)CCN1c1ccccc1] | 3-(2-(1H-imidazol-5-yl)phenoxy)-1-phenylpyrrolidin-2-one |

TABLE 5-continued

| # | Structure | Name |
|---|---|---|
| 228 | 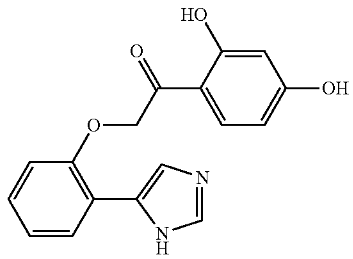 [SMILES: O=C(COc1ccccc1-c1cnc[nH]1)c1ccc(O)cc1O] | 2-(2-(1H-imidazol-5-yl)phenoxy)-1-(2,4-dihydroxyphenyl)ethanone |
| 229 | 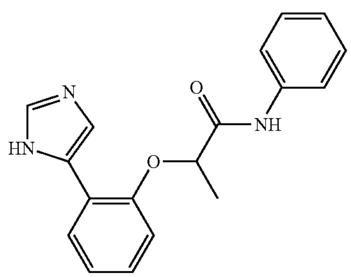 [SMILES: CC(Oc1ccccc1-c1cnc[nH]1)C(=O)Nc1ccccc1] | 2-(2-(1H-imidazol-5-yl)phenoxy)-N-phenylpropanamide |
| 230 | 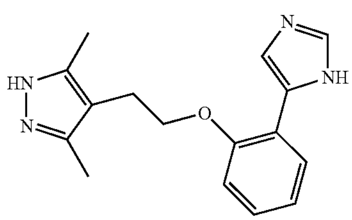 [SMILES: Cc1n[nH]c(C)c1CCOc1ccccc1-c1cnc[nH]1] | 4-(2-(2-(1H-imidazol-5-yl)phenoxy)ethyl)-3,5-dimethyl-1H-pyrazole |
| 231 | 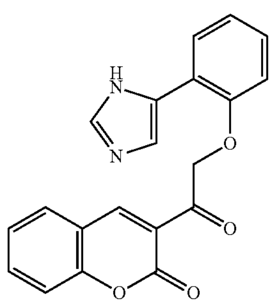 [SMILES: O=C(COc1ccccc1-c1cnc[nH]1)c1cc2ccccc2oc1=O] | 3-(2-(2-(1H-imidazol-5-yl)phenoxy)acetyl)-2H-chromen-2-one |
| 232 | 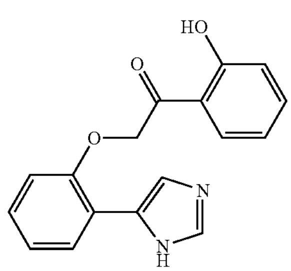 [SMILES: O=C(COc1ccccc1-c1cnc[nH]1)c1ccccc1O] | 2-(2-(1H-imidaozl-5-yl)phenoxy)-1-(2-hydroxyphenyl)ethanone |
| 233 | 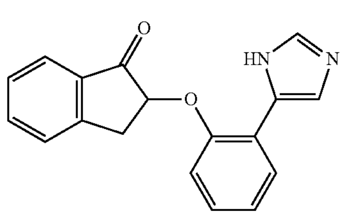 [SMILES: O=C1c2ccccc2CC1Oc1ccccc1-c1cnc[nH]1] | 2-(2-(1H-imidazol-5-yl)phenoxy)-2,3-dihydro-1H-inden-1-one |

TABLE 5-continued

| # | Structure | Name |
|---|---|---|
| 234 | 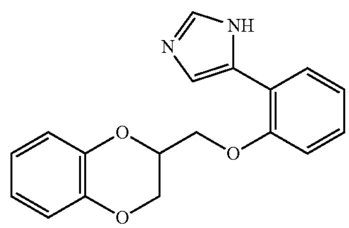 [SMILES: c1ccc2c(c1)OCC(COc1ccccc1-c1cnc[nH]1)O2] | 5-(2-((2,3-dihydrobenzo[b][1,4]dioxin-2-yl)methoxy)phenyl)-1H-imidazole |
| 235 | 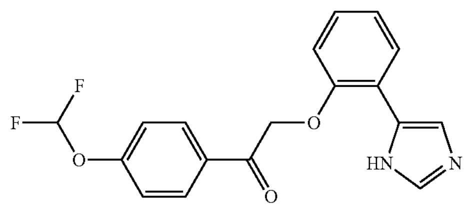 [SMILES: O=C(COc1ccccc1-c1cnc[nH]1)c1ccc(OC(F)F)cc1] | 2-(2-(1H-imidazol-5-yl)phenoxy)-1-(4-(difluoromethoxy)phenyl)ethanone |
| 236 | 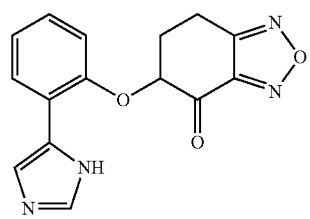 [SMILES: O=C1c2nonc2CCC1Oc1ccccc1-c1cnc[nH]1] | 5-(2-(1H-imidazol-5-yl)phenoxy)-6,7-dihydrobenzo[c][1,2,5]oxadiazol-4(5H)-one |
| 237 | 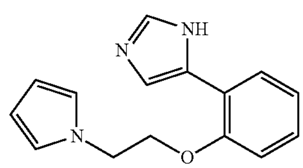 [SMILES: c1ccc(-c2cnc[nH]2)c(OCCn2cccc2)c1] | 5-(2-(2-(1H-pyrrol-1-yl)ethoxy)phenyl)-1H-imidazole |
| 238 | 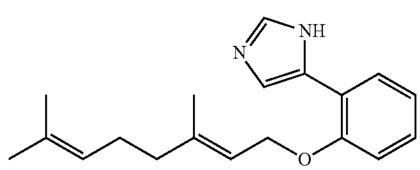 [SMILES: CC(C)=CCC/C(C)=C/COc1ccccc1-c1cnc[nH]1] | (E)-5-(2-(3,7-dimethylocta-2,6-dienyloxy)phenyl)-1H-imidazole |
| 239 | 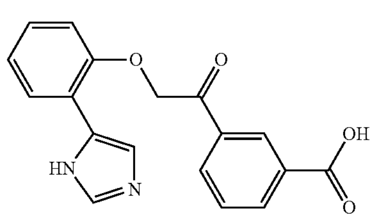 [SMILES: O=C(O)c1cccc(C(=O)COc2ccccc2-c2cnc[nH]2)c1] | 3-(2-(2-(1H-imidazol-5-yl)phenoxy)acetyl)benzoic acid |
| 240 | 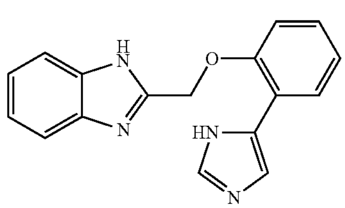 [SMILES: c1ccc(-c2cnc[nH]2)c(OCc2nc3ccccc3[nH]2)c1] | 2-((2-(1H-imidazol-5-yl)phenoxy)methyl)-1H-benzo[d]imidazole |

TABLE 5-continued

| # | Structure | Name |
|---|---|---|
| 241 | 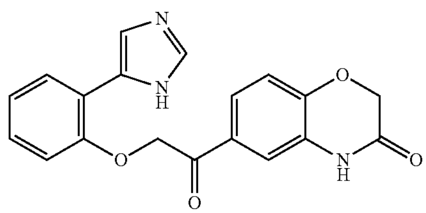 [SMILES: O=C1COc2ccc(C(=O)COc3ccccc3-c3cnc[nH]3)cc2N1] | 6-(2-(2-(1H-imidazol-5-yl)phenoxy)acetyl)-2H-benzo[b][1,4]oxazin-3(4H)-one |
| 242 | 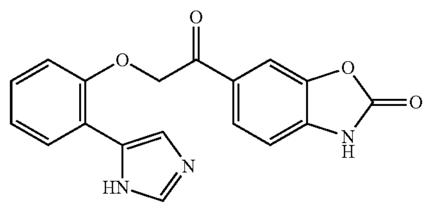 [SMILES: O=C(COc1ccccc1-c1cnc[nH]1)c1ccc2[nH]c(=O)oc2c1] | 6-(2-(2-(1H-imidazol-5-yl)phenoxy)acetyl)benzo[d]oxazol-2(3H)-one |
| 243 | 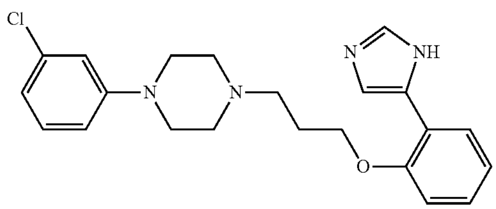 [SMILES: Clc1cccc(N2CCN(CCCOc3ccccc3-c3cnc[nH]3)CC2)c1] | 1-(3-(2-(1H-imidazol-5-yl)phenoxy)propyl)-4-(3-chlorophenyl)piperazine |
| 244 | 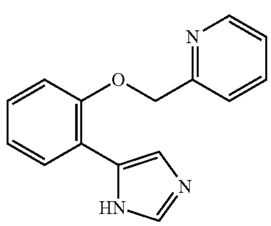 [SMILES: c1ccc(COc2ccccc2-c2cnc[nH]2)nc1] | 2-((2-(1H-imidazol-5-yl)phenoxy)methyl)pyridine |
| 245 | 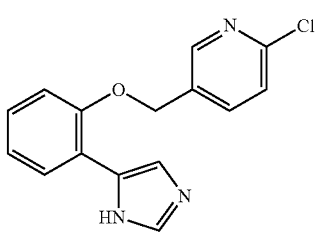 [SMILES: Clc1ccc(COc2ccccc2-c2cnc[nH]2)cn1] | 5-((2-(1H-imidazol-5-yl)phenoxy)methyl)-2-chloropyridine |
| 246 | 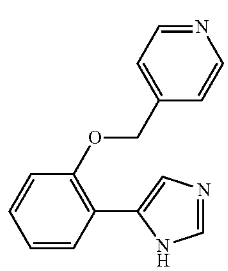 [SMILES: c1ccc(-c2cnc[nH]2)c(OCc2ccncc2)c1] | 4-((2-(1H-imidazol-5-yl)phenoxy)methyl)pyridine |
| 247 | 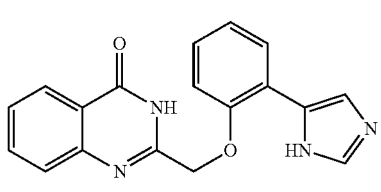 [SMILES: O=c1[nH]c(COc2ccccc2-c2cnc[nH]2)nc2ccccc12] | 2-((2-(1H-imidazol-5-yl)phenoxy)methyl)quinazolin-4(3H)-one |

TABLE 5-continued

| # | Structure | Name |
|---|---|---|
| 248 | 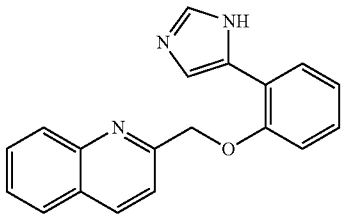 [SMILES: c1ccc(-c2cnc[nH]2)c(OCc2ccc3ccccc3n2)c1] | 2-((2-(1H-imidazol-5-yl)phenoxy)methyl)quinoline |
| 249 | 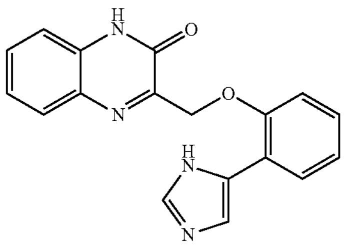 [SMILES: O=c1[nH]c2ccccc2nc1COc1ccccc1-c1cnc[nH]1] | 3-((2-(1H-imidazol-5-yl)phenoxy)methyl)quinoxalin-2(1H)-one |
| 250 | 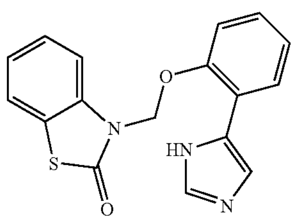 [SMILES: O=c1sc2ccccc2n1COc1ccccc1-c1cnc[nH]1] | 3-((2-(1H-imidazol-5-yl)phenoxy)methyl)benzo[d]thiazol-2(3H)-one |
| 251 | 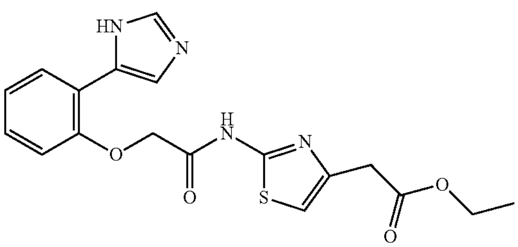 [SMILES: CCOC(=O)Cc1csc(NC(=O)COc2ccccc2-c2cnc[nH]2)n1] | ethyl 2-(2-(2-(2-(1H-imidazol-5-yl)phenoxy)acetamido)thiazol-4-yl)acetate |
| 252 | 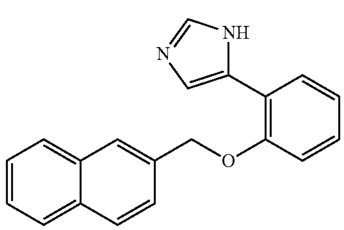 [SMILES: c1ccc(-c2cnc[nH]2)c(OCc2ccc3ccccc3c2)c1] | 5-(2-(naphthalen-2-ylmethoxy)phenyl)-1H-imidazole |
| 253 | 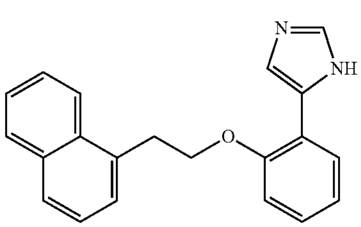 [SMILES: c1ccc(-c2cnc[nH]2)c(OCCc2cccc3ccccc23)c1] | 5-(2-(2-(naphthalen-1-yl)ethoxy)phenyl)-1H-imidazole |

In a second aspect, the present disclosure provides compounds and pharmaceutical compositions comprising the compounds together with a pharmaceutically acceptable excipient, diluent, or carrier, wherein the comnounds are according to formula (III),

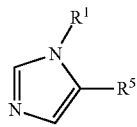

(III)

or a pharmaceutically acceptable salt thereof, wherein $R^1$ is —$C_1$-$C_6$ alkyl, —$C_1$-$C_6$ haloalkyl, or —($C_1$-$C_6$) alkyl-$R^{B1}$, wherein $R^{B1}$ is $R^{B2}$, $C_3$-$C_8$cycloalkyl, heterocyclyl, aryl, or heteroaryl, wherein the cycloalkyl, heterocyclyl, aryl, and heteroaryl groups are optionally substituted by 1, 2, 3, or 4 $R^{B2}$ groups, wherein each $R^{B2}$ is independently halogen, cyano, nitro, $C_1$-$C_6$ alkyl, $C_1$-$C_6$ haloalkyl, —OR, —SR, —$NR_2$, —C(O)R, —C(O)OR, —C(O)$NR_2$, —S(O)R, —S(O)$_2$R, —S(O)OR, —S(O)$_2$OR, —S(O)$NR_2$, —S(O)$_2NR_2$, —OC(O)R, —OC(O)OR, —OC(O)$NR_2$, —N(R)C(O)R, —N(R)C(O)OR, —N(R)C(O)$NR_2$, —N(R)S(O)R, or —N(R)S(O)$_2$R, and $R^5$ is (i)

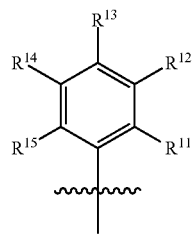

wherein $R^{13}$ is hydrogen or —SH; and $R^{11}$, $R^{12}$, $R^{14}$, and $R^{15}$ are each independently hydrogen or $R^{20}$, or one of $R^{11}$ and $R^{12}$ or $R^{14}$ and $R^{15}$ taken together with the carbon atoms to which they are attached form a fused phenyl, fused 5 or 6 membered monocyclic heteroaryl, fused 5 or 6 membered monocyclic cycloalkyl, fused 5 or 6 membered monocyclic cycloalkenyl, or fused monocyclic 5 or 6 membered heterocyclyl, each fused ring optionally substituted with 1, 2, 3, or 4 $R^{20}$ groups;

or (ii) $R^5$ is heteroaryl optionally substituted with 1, 2, 3, or 4 groups which are each independently $R^{20}$, wherein each $R^{20}$ is independently halogen, cyano, —OR, —SR, —$NR_2$, —C(O)OR, —C(O)$NR_2$, —N(R)S(O)$_2$R, —C(O)$R^2$, —S(O)R, —S(O)$_2$R, —S(O)OR, —S(O)$_2$OR, —S(O)$NR_2$, —S(O)$_2NR_2$, —OC(O)R, —OC(O)OR, —OC(O)$NR_2$, —N(R)C(O)R, —N(R)C(O)OR, —N(R)C(O)$NR_2$, —N(R)S(O)R, $C_1$-$C_6$alkyl, $C_2$-$C_6$alkenyl, $C_2$-$C_6$alkynyl, $C_1$-$C_6$haloalkyl, $C_3$-$C_8$cycloalkyl, heterocyclyl, aryl, heteroaryl, $C_3$-$C_8$cycloalkyl($C_1$-$C_6$)alkyl, heterocyclyl($C_1$-$C_6$)alkyl, aryl($C_1$-$C_6$)alkyl, heteroaryl($C_1$-$C_6$)alkyl, —$C_1$-$C_6$alkyl-$R^{41}$, -Q-($C_1$-$C_6$)alkyl-$R^{41}$, —$C_1$-$C_6$alkyl-Q-$R^{41}$, -Q-($C_1$-$C_6$)alkyl-Q-$R^{41}$, —$C_1$-$C_6$alkyl-Q-($C_1$-$C_6$)alkyl-$R^{41}$, -Q($C_1$-$C_6$)alkyl-Q-($C_1$-$C_6$)alkyl-$R^{41}$, or -Q($C_1$-$C_6$)alkyl-Q-($C_1$-$C_6$)alkyl-Q$R^{41}$, wherein each Q is independently —C($R^{42}$)$_2$—, —O—, —N($R^{42}$)—, —S—, —C(O)—, —S(O)—, —S(O)$_2$—, —C(O)N($R^{42}$)—, —N($R^{42}$)C(O)—, —C(O)O—, or —OC(O)—, wherein each $R^{42}$ is independently hydrogen, $C_1$-$C_6$alkyl, or $C_1$-$C_6$haloalkyl;

$R^{41}$ is $R^{43}$, $C_1$-$C_6$ alkyl, —$C_1$-$C_6$ alkyl-$R^{43}$, $C_1$-$C_6$ haloalkyl, $C_3$-$C_8$cycloalkyl, heterocyclyl, aryl, or heteroaryl, wherein the cycloalkyl, heterocyclyl, aryl, and heteroaryl groups are optionally substituted by 1, 2, 3, or 4 $R^{43}$ groups, wherein each $R^{43}$ is independently halogen, cyano, nitro, —OR, —SR, —$NR_2$, —C(O)R, —C(O)OR, —C(O)$NR_2$, —S(O)R, —S(O)$_2$R, —S(O)OR, —S(O)$_2$OR, —S(O)$NR_2$, —S(O)$_2NR_2$, —OC(O)R, —OC(O)OR, —OC(O)$NR_2$, —N(R)C(O)R, —N(R)C(O)OR, —N(R)C(O)$NR_2$, —N(R)S(O)R, —N(R)S(O)$_2$R, $C_1$-$C_6$ alkyl, $C_1$-$C_6$ haloalkyl, $C_2$-$C_6$ alkenyl, $C_2$-$C_6$ alkynyl, $C_3$-$C_8$cycloalkyl, heterocyclyl, aryl, or heteroaryl, wherein the cycloalkyl, heterocyclyl, aryl, heteroaryl, are each optionally substituted with 1, 2, 3, or 4 groups which are each independently halogen, cyano, nitro, —$OR^{411}$, —$SR^{411}$, —N($R^{411}$)$_2$, —C(O)$OR^{411}$, —C(O)N($R^{411}$)$_2$, —C(O)$R^{411}$, —S(O)$R^{411}$, —S(O)$_2R^{411}$, —S(O)$OR^{411}$, —S(O)$_2OR^{411}$, —S(O)N($R^{411}$)$_2$, —S(O)$_2$N($R^{411}$)$_2$, —OC(O)$R^{411}$, —OC(O)$OR^{411}$, —OC(O)N($R^{411}$)$_2$, —N($R^{411}$)C(O)$R^{411}$, —N($R^{411}$)C(O)$OR^{411}$, —N($R^{411}$)C(O)N($R^{411}$)$_2$, —N($R^{411}$)S(O)$R^{411}$, —N($R^{411}$)S(O)$_2R^{411}$, $C_1$-$C_6$ alkyl, or $C_1$-$C_6$ haloalkyl, wherein each $R^{411}$ is independently hydrogen, $C_1$-$C_6$ alkyl, $C_2$-$C_6$ alkenyl, $C_2$-$C_6$ alkynyl, $C_1$-$C_6$ haloalkyl, $C_3$-$C_8$cycloalkyl, heterocyclyl, aryl, heteroaryl, $C_3$-$C_8$cycloalkyl($C_1$-$C_6$)alkyl, heterocyclyl($C_1$-$C_6$)alkyl, aryl($C_1$-$C_6$)alkyl, or heteroaryl($C_1$-$C_6$)alkyl;

or $R^{41}$ and $R^{42}$ taken together, when attached to the same carbon atom, form =$C_3$-$C_8$cycloalkyl, or =heterocyclyl, wherein the cycloalkyl and heterocyclyl are optionally substituted with 1, 2, 3, or 4 groups which are each independently halogen, cyano, nitro, —OR, —SR, —$NR_2$, —C(O)OR, —C(O)$NR_2$, —C(O)R, —S(O)R, —S(O)$_2$R, —S(O)OR, —S(O)$_2$OR, —S(O)$NR_2$, —S(O)$_2NR_2$, —OC(O)R, —OC(O)OR, —OC(O)$NR_2$, —N(R)C(O)R, —N(R)C(O)OR, —N(R)C(O)$NR_2$, —N(R)S(O)R, —N(R)S(O)$_2$R, $C_1$-$C_6$ alkyl, or $C_1$-$C_6$ haloalkyl;

or $R^{20}$ and $R^1$ taken together form —$CH_2CH_2$W—, —$CH_2WCH_2$—, —$WCH_2CH_2$—, —C(H)=C(H)—, —C(H)=C(H)W—, or —WC(H)=C(H)—, wherein W is —O—, —S—, —S(O)—, —S(O)$_2$—, or —NH—; and each R is independently hydrogen or $R^2$, wherein $R^2$ is $C_1$-$C_6$ alkyl, $C_2$-$C_6$ alkenyl, $C_2$-$C_6$ alkynyl, $C_1$-$C_6$ haloalkyl, $C_3$-$C_8$cycloalkyl, heterocyclyl, aryl, heteroaryl, $C_3$-$C_8$cycloalkyl($C_1$-$C_6$)alkyl, heterocyclyl($C_1$-$C_6$)alkyl, aryl($C_1$-$C_6$)alkyl, or heteroaryl($C_1$-$C_6$)alkyl, wherein the alkyl, $C_3$-$C_8$cycloalkyl, heterocyclyl, aryl, heteroaryl, cycloalkylalkyl, heterocyclylalkyl, arylalkyl, and heteroarylalkyl are each optionally substituted with 1, 2, 3, or 4 groups which are each independently halogen, cyano, nitro, —$OR^{10}$, —$SR^{10}$, —N($R^{10}$)$_2$, —C(O)$OR^{10}$, —C(O)N($R^{10}$)$_2$, —C(O)$R^{10}$, —S(O)$R^{10}$, —S(O)$_2R^{10}$, —S(O)$OR^{10}$, —S(O)$_2OR^{10}$, —S(O)N($R^{10}$)$_2$, —S(O)$_2$N($R^{10}$)$_2$, —OC(O)$R^{10}$, —OC(O)$OR^{10}$, —OC(O)N($R^{10}$)$_2$, —N($R^{10}$)C(O)$R^{10}$, —N($R^{10}$)C(O)$OR^{10}$, —N($R^{10}$)C(O)N($R^{10}$)$_2$, —N($R^{10}$)S(O)$R^{10}$, —N($R^{10}$)S(O)$_2R^{10}$, $C_1$-$C_6$ alkyl, $C_2$-$C_6$ alkenyl, $C_2$-$C_6$ alkynyl, $C_1$-$C_6$ haloalkyl, $C_3$-$C_8$cycloalkyl, heterocyclyl, aryl, or heteroaryl, wherein each $R^{10}$ is independently hydrogen, $C_1$-$C_6$ alkyl, $C_2$-$C_6$ alkenyl, $C_2$-$C_6$ alkynyl, $C_1$-$C_6$ haloalkyl, $C_3$-$C_8$cycloalkyl, heterocyclyl, aryl, heteroaryl, $C_3$-$C_8$cycloalkyl($C_1$-$C_6$)alkyl, heterocyclyl($C_1$-$C_6$)alkyl, aryl($C_1$-$C_6$)alkyl, or heteroaryl($C_1$-$C_6$)alkyl, provided that (i) $R^1$ is not —$(CH_2)_{3-4}$—$NH_2$, —$(CH_2)_{1-2}$—C(O)$NH_2$, —$(CH_2)_{2-3}$—C(O)N(H)$CH_3$, —$(CH_2)_{1-2}$N(H)C(O)$CH_3$, —$(CH_2)_2$—OH, or —$(CH_2)_3$-thiomorpholinyl; and (ii) the compound is not
1-(2-phenylethyl)-5-phenyl-1H-imidazole;
1-(2-aminoethyl)-5-phenyl-1H-imidazole;
1-(2-ethoxycarbonylethyl)-5-phenyl-1H-imidazole;
ethyl-3-[7-(3-methyl-3H-imidazol-4-yl)-5-pyridin-3-yl-benzothiazol-2-yl]urea;
5-(3-Methyl-3H-imidazol-4-yl)-benzofuran-7ylmethyl]-(2S-phenyl-piperidin-3S -yl)-amine; and
(4-Benzyloxy-phenyl)-(6-(3-methyl-3H-imidazol-4-yl)-quinazolin-4-yl)-amine.

The invention further comprises embodiments of the second aspect in which the substituents are selected as any and all combinations $R^1$ and $R^5$ as defined herein, including without limitation, the following:

$R^5$ is one of the following groups (2a)-(2ll):

(2a) $R^5$ is

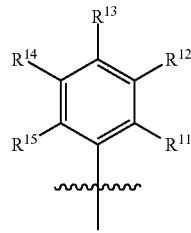

wherein $R^{11}$, $R^{12}$, $R^{14}$, and $R^{15}$ are each independently hydrogen or $R^{20}$, or one of $R^{11}$ and $R^{12}$ or $R^{14}$ and $R^{15}$ taken together with the carbon atoms to which they are attached form a fused phenyl, fused 5 or 6 membered monocyclic heteroaryl, fused 5 or 6 membered monocyclic cycloalkyl, fused 5 or 6 membered monocyclic cycloalkenyl, or fused monocyclic 5 or 6 membered heterocyclyl, each fused ring optionally substituted with 1, 2, 3, or 4 $R^{20}$ groups; and $R^{13}$ is hydrogen or —SH; provided at least one of $R^{11}$, $R^{12}$, $R^{13}$, $R^{14}$, and $R^{15}$ is not hydrogen.

(2b) $R^5$ is according to group (2a), wherein one of $R^{11}$, $R^{12}$, $R^{14}$, and $R^{15}$ is halogen, cyano, —OR, —SR, —$NR_2$, —C(O)OR, —C(O)$NR_2$, —N(R)S(O)$_2$R, —$C_1$-$C_6$alkyl-$R^{41}$, -Q-($C_1$-$C_6$)alkyl-$R^{41}$, —$C_1$-$C_6$alkyl-Q-$R^{41}$, -Q-($C_1$-$C_6$)alkyl-Q-$R^{41}$, —$C_1$-$C_6$alkyl-Q-($C_1$-$C_6$)alkyl-$R^{41}$, -Q($C_1$-$C_6$)alkyl-Q-($C_1$-$C_6$)alkyl-$R^{41}$, or -Q($C_1$-$C_6$)alkyl-Q-($C_1$-$C_6$)alkyl-Q$R^{41}$, and $R^{13}$ is hydrogen or —SH.

(2c) $R^5$ is according to group (2a), wherein $R^{11}$ is —OR, —SR, —$NR_2$, —$C_1$-$C_6$alkyl-$R^{41}$, -Q-($C_1$-$C_6$)alkyl-$R^{41}$, —$C_1$-$C_6$alkyl-Q-$R^{41}$, -Q-($C_1$-$C_6$)alkyl-Q-$R^{41}$, —$C_1$-$C_6$alkyl-Q-($C_1$-$C_6$)alkyl-$R^{41}$, -Q($C_1$-$C_6$)alkyl-Q-($C_1$-$C_6$)alkyl-$R^{41}$, or -Q($C_1$-$C_6$)alkyl-Q-($C_1$-$C_6$)alkyl-Q$R^{41}$.

(2d) $R^5$ is according to group (2a), wherein $R^{12}$, $R^{14}$, and $R^{15}$ are each independently hydrogen, halogen, cyano, $C_1$-$C_6$alkyl, $C_1$-$C_6$haloalkyl, —OR, —SR, —$NR_2$, —C(O)OR, —C(O)$NR_2$, —N(R)S(O)$_2$R; $R^{13}$ is hydrogen or —SH, and $R^{11}$ is —OR, —SR, —$NR_2$, —$C_1$-$C_6$alkyl-$R^{41}$, -Q-($C_1$-$C_6$)alkyl-$R^{41}$, —$C_1$-$C_6$alkyl-Q-$R^{41}$, -Q-($C_1$-$C_6$)alkyl-Q-$R^{41}$, —$C_1$-$C_6$alkyl-Q-($C_1$-$C_6$)alkyl-$R^{41}$, -Q($C_1$-$C_6$)alkyl-Q-($C_1$-$C_6$)alkyl-$R^{41}$, or -Q($C_1$-$C_6$)alkyl-Q-($C_1$-$C_6$)alkyl-Q$R^{41}$.

(2e) $R^5$ is according to group (2a), wherein $R^{12}$, $R^{14}$, and $R^{15}$ are each independently hydrogen, fluoro, chloro, bromo, methyl, or ethyl, $R^{13}$ is hydrogen or —SH, and $R^{11}$ is —OR, —SR, —$NR_2$, —$C_1$-$C_6$alkyl-$R^{41}$, -Q-($C_1$-$C_6$)alkyl-$R^{41}$, —$C_1$-$C_6$alkyl-Q-$R^{41}$, -Q-($C_1$-$C_6$)alkyl-Q-$R^{41}$, —$C_1$-$C_6$alkyl-Q-($C_1$-$C_6$)alkyl-$R^{41}$, -Q($C_1$-$C_6$)alkyl-Q-($C_1$-$C_6$)alkyl-$R^{41}$, or -Q($C_1$-$C_6$)alkyl-Q-($C_1$-$C_6$)alkyl-Q$R^{41}$.

(2f) $R^5$ is

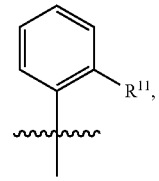

wherein $R^{11}$ is —OR, —SR, —$NR_2$, —$C_1$-$C_6$alkyl-$R^{41}$, -Q-($C_1$-$C_6$)alkyl-$R^{41}$, —$C_1$-$C_6$alkyl-Q-$R^{41}$, -Q-($C_1$-$C_6$)alkyl-Q-$R^{41}$, —$C_1$-$C_6$alkyl-Q-($C_1$-$C_6$)alkyl-$R^{41}$, -Q($C_1$-$C_6$)alkyl-Q-($C_1$-$C_6$)alkyl-$R^{41}$, or -Q($C_1$-$C_6$)alkyl-Q-($C_1$-$C_6$)alkyl-Q$R^{41}$.

(2g) $R^5$ is according to group (2a), wherein $R^{11}$ is —OR or —SR.

(2h) $R^5$ is according to group (2a), wherein $R^{11}$ is —$OR^{21}$ or —$SR^{21}$, wherein $R^{21}$ is hydrogen, $C_1$-$C_6$ alkyl, $C_2$-$C_6$ alkenyl, $C_3$-$C_8$cycloalkyl($C_1$-$C_6$)alkyl, heterocyclyl($C_1$-$C_6$)alkyl, aryl($C_1$-$C_6$)alkyl, or heteroaryl($C_1$-$C_6$)alkyl, wherein the cycloalkylalkyl, heterocyclylalkyl, arylalkyl, and heteroarylalkyl are each optionally substituted with 1, 2, 3, or 4 groups (e.g., 1 or 2 groups) which are each independently halogen, cyano, nitro, $C_1$-$C_6$ alkyl, $C_1$-$C_6$ haloalkyl, —$OR^{10}$, —$SR^{10}$, —N($R^{10}$)$_2$, —C(O)$OR^{10}$, —C(O)N($R^{10}$)$_2$, —C(O)$R^{10}$, —S(O)$_2R^{10}$, —S(O)$_2$N($R^{10}$)$_2$, —OC(O)$R^{10}$, —OC(O)$OR^{10}$, —OC(O)N($R^{10}$)$_2$, —N($R^{10}$)C(O)$R^{10}$, —N($R^{10}$)C(O)$OR^{10}$, —N($R^{10}$)C(O)N($R^{10}$)$_2$, —N($R^{10}$)S(O)$_2R^{10}$, wherein each $R^{10}$ is independently hydrogen, $C_1$-$C_6$ alkyl, or $C_1$-$C_6$ haloalkyl.

(2i) $R^5$ is according to group (2a), wherein $R^{11}$ is —$OR^{21}$ or —$SR^{21}$, wherein $R^{21}$ is hydrogen, $C_1$-$C_6$ alkyl, $C_2$-$C_6$ alkenyl, $C_3$-$C_8$cycloalkyl($C_1$-$C_6$)alkyl, heterocyclyl($C_1$-$C_6$)alkyl, aryl($C_1$-$C_6$)alkyl, or heteroaryl($C_1$-$C_6$)alkyl.

(2j) $R^5$ is according to group (2a), wherein $R^{12}$, $R^{14}$, and $R^{15}$ are each independently hydrogen, halogen, cyano, $C_1$-$C_6$alkyl, $C_1$-$C_6$haloalkyl, —OR, —SR, —$NR_2$, —C(O)OR, —C(O)$NR_2$, —N(R)S(O)$_2$R, $R^{13}$ is hydrogen or —SH, and $R^{11}$ is —OR or —SR.

(2k) $R^5$ is according to group (2a), wherein $R^{12}$, $R^{14}$, and $R^{15}$ are each independently hydrogen, halogen, cyano, $C_1$-$C_6$alkyl, $C_1$-$C_6$haloalkyl, —OR, —SR, —$NR_2$, —C(O)OR, —C(O)$NR_2$, —N(R)S(O)$_2$R, $R^{13}$ is hydrogen or —SH, and $R^{11}$ is —$OR^{21}$ or —$SR^{21}$, wherein $R^{21}$ is hydrogen, $C_1$-$C_6$ alkyl, $C_2$-$C_6$ alkenyl, $C_3$-$C_8$cycloalkyl($C_1$-$C_6$)alkyl, heterocyclyl($C_1$-$C_6$)alkyl, aryl($C_1$-$C_6$)alkyl, or heteroaryl($C_1$-$C_6$)alkyl, wherein the cycloalkylalkyl, heterocyclylalkyl, arylalkyl, and heteroarylalkyl are each optionally substituted with 1, 2, 3, or 4 groups (e.g., 1 or 2 groups) which are each independently halogen, cyano, nitro, $C_1$-$C_6$ alkyl, $C_1$-$C_6$ haloalkyl, —$OR^{10}$, —$SR^{10}$, —N($R^{10}$)$_2$, —C(O)$OR^{10}$, —C(O)N($R^{10}$)$_2$, —C(O)$R^{10}$, —S(O)$_2R^{10}$, —S(O)$_2OR^{10}$, —S(O)$_2$N($R^{10}$)$_2$, —OC(O)$R^{10}$, —OC(O)$OR^{10}$, —OC(O)N($R^{10}$)$_2$, —N($R^{10}$)C(O)$R^{10}$, —N($R^{10}$)C(O)$OR^{10}$, —N($R^{10}$)C(O)N($R^{10}$)$_2$, —N(R$^{10}$)S(O)$_2$R$^{10}$, wherein each R$^{10}$ is independently hydrogen, C$_1$-C$_6$ alkyl, or C$_1$-C$_6$ haloalkyl.

(2l) R$^5$ is according to group (2a), wherein R$^{12}$, R$^{14}$, and R$^{15}$ are each independently hydrogen, halogen, cyano, C$_1$-C$_6$alkyl, C$_1$-C$_6$haloalkyl, —OR, —SR, —NR$_2$, —C(O)OR, —C(O)NR$_2$, —N(R)S(O)$_2$R, R$^{13}$ is hydrogen or —SH, and R$^{11}$ is —OR$^{21}$ or —SR$^{21}$, wherein R$^{21}$ is hydrogen, C$_1$-C$_6$ alkyl, C$_2$-C$_6$ alkenyl, C$_3$-C$_8$cycloalkyl(C$_1$-C$_6$)alkyl, heterocyclyl(C$_1$-C$_6$)alkyl, aryl(C$_1$-C$_6$)alkyl, or heteroaryl(C$_1$-C$_6$)alkyl.

(2m) R$^5$ is according to group (2a), wherein R$^{12}$, R$^{14}$, and R$^{15}$ are each independently hydrogen, fluoro, chloro, bromo, methyl, or ethyl, R$^{13}$ is hydrogen or —SH, and R$^{11}$ is —OR or —SR.

(2n) R$^5$ is according to group (2a), wherein R$^{12}$, R$^{14}$, and R$^{15}$ are each independently hydrogen, fluoro, chloro, bromo, methyl, or ethyl, R$^{13}$ is hydrogen or —SH, and R$^{11}$ is —OR$^{21}$ or —SR$^{21}$, wherein R$^{21}$ is hydrogen, C$_1$-C$_6$ alkyl, C$_2$-C$_6$ alkenyl, C$_3$-C$_8$cycloalkyl(C$_1$-C$_6$)alkyl, heterocyclyl(C$_1$-C$_6$)alkyl, aryl(C$_1$-C$_6$)alkyl, or heteroaryl(C$_1$-C$_6$)alkyl.

(2o) R$^5$ is

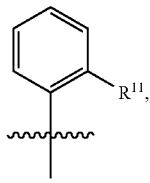

wherein R$^{11}$ is —OR or —SR.

(2p) R$^5$ is

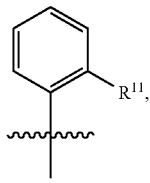

wherein R$^{11}$ is —OR$^{21}$ or —SR$^{21}$, wherein R$^{21}$ is hydrogen, C$_1$-C$_6$ alkyl, C$_2$-C$_6$ alkenyl, C$_3$-C$_8$cycloalkyl(C$_1$-C$_6$) alkyl, heterocyclyl(C$_1$-C$_6$)alkyl, aryl(C$_1$-C$_6$)alkyl, or heteroaryl(C$_1$-C$_6$)alkyl, wherein the cycloalkylalkyl, heterocyclylalkyl, arylalkyl, and heteroarylalkyl are each optionally substituted with 1, 2, 3, or 4 groups (e.g., 1 or 2 groups) which are each independently halogen, cyano, nitro, C$_1$-C$_6$ alkyl, C$_1$-C$_6$ haloalkyl, —OR$^{10}$, —SR$^{10}$, —N(R$^{10}$)$_2$, —C(O)OR$^{10}$, —C(O)N(R$^{10}$)$_2$, —C(O)R$^{10}$, —S(O)$_2$R$^{10}$, —S(O)$_2$OR$^{10}$, —S(O)$_2$N(R$^{10}$)$_2$, —OC(O)R$^{10}$, —OC(O)OR$^{10}$, —OC(O)N(R$^{10}$)$_2$, —N(R$^{10}$)C(O)R$^{10}$, —N(R$^{10}$)C(O)OR$^{10}$, —N(R$^{10}$)C(O)N(R$^{10}$)$_2$, —N(R$^{10}$)S(O)$_2$R$^{10}$, wherein each R$^{10}$ is independently hydrogen, C$_1$-C$_6$ alkyl, or C$_1$-C$_6$ haloalkyl.

(2q) R$^5$ is

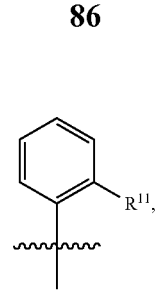

wherein R$^{11}$ is —OR$^{21}$ or —SR$^{21}$, wherein R$^{21}$ is hydrogen, C$_1$-C$_6$ alkyl, C$_2$-C$_6$ alkenyl, C$_3$-C$_8$cycloalkyl(C$_1$-C$_6$) alkyl, heterocyclyl(C$_1$-C$_6$)alkyl, aryl(C$_1$-C$_6$)alkyl, or heteroaryl(C$_1$-C$_6$)alkyl.

(2r) R$^5$ is according to group (2a), wherein R$^{11}$ is —C$_1$-C$_6$alkyl-R$^{41}$, -Q-(C$_1$-C$_6$)alkyl-R$^{41}$, —C$_1$-C$_6$alkyl-Q-R$^{41}$, -Q-(C$_1$-C$_6$)alkyl-C(R$^{42}$)$_2$—R$^{41}$, or —(C$_1$-C$_6$)alkyl-Q-C$_1$-C$_6$ alkyl-R$^{41}$, or -Q(C$_1$-C$_6$)alkyl-C(R$^{42}$)$_2$—(C$_1$-C$_6$)alkyl-QR$^{41}$, wherein each is Q is independently —O—, —N(R$^{42}$)—, or —S—.

(2s) R$^5$ is according to group (2a), wherein R$^{12}$, R$^{14}$, and R$^{15}$ are each independently hydrogen, halogen, cyano, C$_1$-C$_6$alkyl, C$_1$-C$_6$haloalkyl, —OR, —SR, —NR$_2$, —C(O)OR, —C(O)NR$_2$, —N(R)S(O)$_2$R, R$^{13}$ is hydrogen or —SH, and R$^{11}$ is —C$_1$-C$_6$alkyl-R$^{41}$, -Q-(C$_1$-C$_6$)alkyl-R$^{41}$, —C$_1$-C$_6$alkyl-Q-R$^{41}$, -Q-(C$_1$-C$_6$)alkyl-C(R$^{42}$)$_2$—R$^{41}$, or —(C$_1$-C$_6$)alkyl-Q-C$_1$-C$_6$ alkyl-R$^{41}$, or -Q(C$_1$-C$_6$) alkyl-C(R$^{42}$)$_2$—C$_1$-C$_6$)alkyl-QR$^{41}$, wherein each is Q is independently —O—, —N(R$^{42}$)—, or —S—.

(2t) R$^5$ is according to group (2a), wherein R$^{12}$, R$^{14}$, and R$^{15}$ are each independently hydrogen, fluoro, chloro, bromo, methyl, or ethyl, R$^{13}$ is hydrogen or —SH, and R$^{11}$ is —C$_1$-C$_6$alkyl-R$^{41}$, -Q-(C$_1$-C$_6$)alkyl-R$^{41}$, —C$_1$-C$_6$alkyl-Q-R$^{41}$, -Q-(C$_1$-C$_6$)alkyl-C(R$^{42}$)$_2$—R$^{41}$, or —(C$_1$-C$_6$) alkyl-Q-C$_1$-C$_6$ alkyl-R$^{41}$, or -Q(C1-C6)alkyl-C(R$^{42}$)$_2$—(C$_1$-C$_6$)alkyl-QR$^{41}$, wherein each is Q is independently —O—, —N(R$^{42}$)—, or —S—.

(2u) R$^5$ is

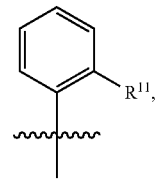

wherein R$^{11}$ is —C$_1$-C$_6$alkyl-R$^{41}$, -Q-(C$_1$-C$_6$)alkyl-R$^{41}$, —C$_1$-C$_6$alkyl-Q-R$^{41}$, -Q-(C$_1$-C$_6$)alkyl-C(R$^{42}$)$_2$—R$^{41}$, or —(C$_1$-C$_6$)alkyl-Q-C$_1$-C$_6$ alkyl-R$^{41}$, or -Q(C$_1$-C$_6$)alkyl-C(R$^{42}$)$_2$—(C$_1$-C$_6$)alkyl-QR$^{41}$, wherein each is Q is independently —O—, —N(R$^{42}$)—, or —S—.

(2v) R$^5$ is according to group (2a), wherein R$^{11}$ is —C$_1$-C$_6$alkyl-R$^{41}$, —O(C$_1$-C$_6$)alkyl-R$^{41}$, —C$_1$-C$_6$alkylOR$^{41}$, —C$_1$-C$_6$alkyl-C(R$^{42}$)$_2$—R$^{41}$, —O(C$_1$-C$_6$)alkyl-C(R$^{42}$)$_2$—R$^{41}$, —C$_1$-C$_6$alkyl-O(C$_1$-C$_6$)alkyl-R$^{41}$, or —O(C$_1$-C$_6$) alkyl-C(R$^{42}$)$_2$—(C$_1$-C$_6$)alkyl-OR$^{41}$.

(2w) R$^5$ is according to group (2a), wherein R$^{12}$, R$^{14}$, and R$^{15}$ are each independently hydrogen, halogen, cyano, C$_1$-C$_6$alkyl, C$_1$-C$_6$haloalkyl, —OR, —SR, —NR$_2$, —C(O)OR, —C(O)NR$_2$, —N(R)S(O)$_2$R, R$^{13}$ is hydrogen or —SH, and R$^{11}$ is —C$_1$-C$_6$alkyl-R$^{41}$, —O(C$_1$-C$_6$)alkyl-R$^{41}$, —C$_1$-C$_6$alkylOR$^{41}$, —C$_1$-C$_6$alkyl-C(R$^{42}$)$_2$—R$^{41}$, —O($C_1$-$C_6$)alkyl-C($R^{A2}$)$_2$—$R^{A1}$, —$C_1$-$C_6$alkyl-O($C_1$-$C_6$)alkyl-$R^{A1}$, or —O($C_1$-$C_6$)alkyl-C($R^{A2}$)$_2$—($C_1$-$C_6$)alkyl-O$R^{A1}$.

(2x) $R^5$ is according to group (2a), wherein $R^{12}$, $R^{14}$, and $R^{15}$ are each independently hydrogen, fluoro, chloro, bromo, methyl, or ethyl, $R^{13}$ is hydrogen or —SH, and $R^{11}$ is —$C_1$-$C_6$alkyl-$R^{A1}$, —O($C_1$-$C_6$)alkyl-$R^{A1}$, —$C_1$-$C_6$alkylO$R^{A1}$, —$C_1$-$C_6$alkyl-C($R^{A2}$)$_2$—$R^{A1}$, —O($C_1$-$C_6$)alkyl-C($R^{A2}$)$_2$—$R^{A1}$, —$C_1$-$C_6$alkyl-O($C_1$-$C_6$)alkyl-$R^{A1}$, or —O($C_1$-$C_6$)alkyl-C($R^{A2}$)$_2$—($C_1$-$C_6$)alkyl-O$R^{A1}$.

(2y) $R^5$ is

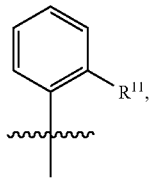

wherein $R^{11}$ is —$C_1$-$C_6$alkyl-$R^{A1}$, —O($C_1$-$C_6$)alkyl-$R^{A1}$, —$C_1$-$C_6$alkylO$R^{A1}$, —$C_1$-$C_6$alkyl-C($R^{A2}$)$_2$—$R^{A1}$, —O($C_1$-$C_6$)alkyl-C($R^{A2}$)$_2$—$R^{A1}$, —$C_1$-$C_6$alkyl-O($C_1$-$C_6$)alkyl-$R^{A1}$, or —O($C_1$-$C_6$)alkyl-C($R^{A2}$)$_2$—($C_1$-$C_6$)alkyl-O$R^{A1}$.

(2z) $R^5$ is according to group (2a), wherein $R^{11}$ is —O($C_1$-$C_6$)alkyl-$R^{A1}$, —$C_1$-$C_6$alkylO$R^{A1}$, —$C_1$-$C_6$alkyl-C(CH$_3$)$_2$—$R^{A1}$, —O($C_1$-$C_6$)alkyl-C(CH$_3$)$_2$—$R^{A1}$, —$C_1$-$C_6$alkyl-O($C_1$-$C_6$)alkyl-$R^{A1}$, or —O($C_1$-$C_6$)alkyl-C(CH$_3$)$_2$—($C_1$-$C_6$)alkyl-O$R^{A1}$.

(2aa) $R^5$ is according to group (2a), wherein $R^{12}$, $R^{14}$, and $R^{15}$ are each independently hydrogen, halogen, cyano, $C_1$-$C_6$alkyl, $C_1$-$C_6$haloalkyl, —OR, —SR, —NR$_2$, —C(O)OR, —C(O)NR$_2$, —N(R)S(O)$_2$R, $R^{13}$ is hydrogen or —SH, and $R^{11}$ is —O($C_1$-$C_6$)alkyl-$R^{A1}$, —$C_1$-$C_6$alkylO$R^{A1}$, —$C_1$-$C_6$alkyl-C(CH$_3$)$_2$—$R^{A1}$, —O($C_1$-$C_6$)alkyl-C(CH$_3$)$_2$—$R^{A1}$, —$C_1$-$C_6$alkyl-O($C_1$-$C_6$)alkyl-$R^{A1}$, or —O($C_1$-$C_6$)alkyl-C(CH$_3$)$_2$—($C_1$-$C_6$)alkyl-O$R^{A1}$.

(2bb) $R^5$ is according to group (2a), wherein $R^{12}$, $R^{14}$, and $R^{15}$ are each independently hydrogen, fluoro, chloro, bromo, methyl, or ethyl, $R^{13}$ is hydrogen or —SH, and $R^{11}$ is —O($C_1$-$C_6$)alkyl-$R^{A1}$, —$C_1$-$C_6$alkylO$R^{A1}$, —$C_1$-$C_6$alkyl-C(CH$_3$)$_2$—$R^{A1}$, —O($C_1$-$C_6$)alkyl-C(CH$_3$)$_2$—$R^{A1}$, —$C_1$-$C_6$alkyl-O($C_1$-$C_6$)alkyl-$R^{A1}$, or —O($C_1$-$C_6$)alkyl-C(CH$_3$)$_2$—($C_1$-$C_6$)alkyl-O$R^{A1}$.

(2cc) $R^5$ is

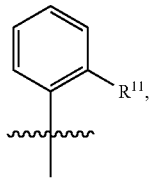

wherein $R^{11}$ is —O($C_1$-$C_6$)alkyl-$R^{A1}$, —$C_1$-$C_6$alkylO$R^{A1}$, —$C_1$-$C_6$alkyl-C(CH$_3$)$_2$—$R^{A1}$, —O($C_1$-$C_6$)alkyl-C(CH$_3$)$_2$—$R^{A1}$, —$C_1$-$C_6$alkyl-O($C_1$-$C_6$)alkyl-$R^{A1}$, or —O($C_1$-$C_6$)alkyl-C(CH$_3$)$_2$—($C_1$-$C_6$)alkyl-O$R^{A1}$.

(2dd) $R^5$ is according to group (2a), wherein $R^{11}$, $R^{12}$, $R^{14}$, and $R^{15}$ are independently hydrogen, halogen, cyano, $C_1$-$C_6$alkyl, $C_1$-$C_6$haloalkyl, —OR, —SR, —NR$_2$, —C(O)OR, —C(O)NR$_2$, —N(R)S(O)$_2$R, and $R^{13}$ is hydrogen or —SH.

(2ee) $R^5$ is according to group (2a), wherein at least one of $R^{12}$, $R^{14}$, and $R^{15}$ is fluoro, chloro, bromo, methyl, or ethyl, $R^{13}$ is hydrogen or —SH, and $R^{11}$ is —OH, —OCH$_3$, or —SH.

(2ff) $R^5$ is according to group (2a), wherein $R^{12}$, $R^{14}$, and $R^{15}$ are each independently hydrogen, fluoro, chloro, bromo, methyl, or ethyl, $R^{13}$ is hydrogen or —SH, and $R^{11}$ is —OH, —OCH$_3$, or —SH.

(2gg) $R^5$ is

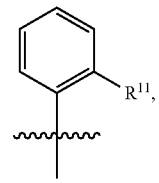

wherein $R^{11}$ is —OH, —OCH$_3$, or —SH.

(2hh) $R^5$ is heteroaryl optionally substituted with 1, 2, 3, or 4 groups (e.g., 1 or 2 groups) which are each independently $R^{20}$.

(2ii) $R^5$ is a 6-membered heteroaryl optionally substituted with 1, 2, 3, or 4 groups (e.g., 1 or 2 groups) which are each independently $R^{20}$.

(2jj) $R^5$ is a 6-membered heteroaryl optionally substituted with 1, 2, 3, or 4 groups (e.g., 1 or 2 groups) which are each independently $R^{20}$, wherein the para-position of $R^5$ with respect to the bond between $R^5$ and the parent imidazole or pyrazole ring is unsubstituted.

(2kk) $R^5$ is benzothiophenyl, pyrrolopyridinyl, imidazopyridinyl, quinolinyl, isoquinolinyl, naphthyridinyl, indolyl, indolinyl, benzothiadiazolyl, dihydrobenzodioxinyl, tetrahydropyrimidinyl, pyridinyl, pyrimidinyl, thienyl, or isoxazolyl, each optionally with 1, 2, 3, or 4 groups (e.g., 1 or 2 groups) which are each independently $R^{20}$.

(2ll) $R^5$ is benzo[b]thiophen-3-yl, 1H-pyrrolo[2,3-b]pyridin-3-yl, 1H-pyrrolo[2,3-b]pyridin-5-yl, 7-methylimidazo[1,2-a]pyridin-6-yl, quinolin-8-yl, 7-chloroquinolin-4-yl, 2,8-bis(trifluoromethyl)quinolin-4-yl, 5-chloro-8-hydroxyquinolin-7-yl, isoquinolin-4-yl, isoquinolin-5-yl, 2-carboxy-1,6-naphthyridin-8-yl, 1H-indol-7-yl, 1H-indol-6-yl, 1H-indol-5-yl, 9H-purin-6-yl,2-oxo-2,3-dihydro-1H-imidazo[4,5-b]pyridin-6-yl, 2,3-dioxoindolin-5-yl, 2,3-dioxoindolin-7-yl, benzo[c][1,2,5]thiadiazol-4-yl, 2,3-dihydrobenzo[b][1,4]dioxin-6-yl, 1,3-dimethyl-2,4-dioxo-1,2,3,4,-tetrahydropyrimidin-5-yl, 2-morpholinopyridin-3-yl, 4-hydroxybiphenyl-3-yl, 2-hydroxypyridin-3-yl, 2,5-dichlorothiophen-3-yl or 3,5-dimethylisoxazol-4-yl.

$R^1$ is one of the following groups (2mm)-(2ggg):

(2mm) $R^1$ is $C_1$-$C_6$alkyl or —($C_1$-$C_6$)alkyl-$R^{B1}$ wherein $R^{B1}$ is $R^{B2}$, $C_3$-$C_8$cycloalkyl, heterocyclyl, aryl, or heteroaryl, wherein the cycloalkyl, heterocyclyl, aryl, and heteroaryl groups are optionally substituted by 1, 2, 3, or 4 $R^{B2}$ groups (e.g., 1 or 2 groups).

(2nn) $R^1$ is $C_1$-$C_6$alkyl.

(2oo) $R^1$ is neohexyl.

(2pp) $R^1$ is —($C_1$-$C_6$)alkyl-$R^{B2}$.

(2qq) $R^1$ is —($C_1$-$C_6$)alkyl-$R^{B2}$, wherein $R^{B2}$ is —OR, —SR, —NR$_2$, —C(O)R, —C(O)OR, —C(O)NR$_2$, —OC(O)R, —OC(O)OR, —OC(O)NR$_2$, —N(R)C(O)R, —N(R)C(O)OR, or —N(R)C(O)NR$_2$.

(2rr) $R^1$ is —($C_1$-$C_6$)alkyl-$R^{B2}$, wherein $R^{B2}$ is —OR$^{22}$, —SR$^{22}$, —N(R$^{22}$)$_2$, —C(O)R$^{22}$, —C(O)OR$^{22}$, —C(O)N ($R^{22}$)$_2$, —OC(O)$R^{22}$, —OC(O)O$R^{22}$, —OC(O)N($R^{22}$)$_2$, —N($R^{22}$)C(O)$R^{22}$, —N($R^{22}$)C(O)O$R^{22}$, or —N($R^{22}$)C(O)N($R^{22}$)$_2$, wherein each $R^{22}$ is independently hydrogen or $C_1$-$C_6$ alkyl.

(2ss) $R^1$ is —($C_1$-$C_6$)alkyl-$R^{B1}$ wherein $R^{B1}$ is $C_3$-$C_8$cycloalkyl, heterocyclyl, aryl, or heteroaryl, wherein the cycloalkyl, heterocyclyl, aryl, and heteroaryl groups are optionally substituted by 1, 2, 3, or 4 $R^{B2}$ groups (e.g., 1 or 2 $R^{B2}$ groups).

(2tt) $R^1$ is —($C_1$-$C_4$)alkyl-$R^{B1}$ wherein $R^{B1}$ is $C_3$-$C_8$cycloalkyl, heterocyclyl, aryl, or heteroaryl, wherein the cycloalkyl, heterocyclyl, aryl, and heteroaryl groups are optionally substituted by 1, 2, 3, or 4 $R^{B2}$ groups (e.g., 1 or 2 $R^{B2}$ groups).

(2uu) $R^1$ is —($C_1$-$C_6$)alkyl-$R^{B1}$ wherein $R^{B1}$ is phenyl optionally substituted by 1, 2, 3, or 4 $R^{B2}$ groups (e.g., 1 or 2 $R^{B2}$ groups).

(2vv) $R^1$ is —($C_1$-$C_4$)alkyl-$R^{B1}$ wherein $R^{B1}$ is phenyl optionally substituted by 1, 2, 3, or 4 $R^{B2}$ groups (e.g., 1 or 2 $R^{B2}$ groups).

(2ww) $R^1$ is —($C_1$-$C_2$)alkyl-$R^{B1}$ wherein $R^{B1}$ is phenyl optionally substituted by 1, 2, 3, or 4 $R^{B2}$ groups (e.g., 1 or 2 $R^{B2}$ groups).

(2xx) $R^1$ is —CH$_2$—$R^{B1}$ wherein $R^{B1}$ is phenyl optionally substituted by 1, 2, 3, or 4 $R^{B2}$ groups (e.g., 1 or 2 $R^{B2}$ groups).

(2yy) $R^1$ is —CH$_2$—$R^{B1}$ wherein $R^{B1}$ is phenyl optionally substituted by one $R^{B2}$ group.

(2zz) $R^1$ is —($C_1$-$C_6$)alkyl-$R^{B1}$ wherein $R^{B1}$ is phenyl optionally substituted by 1, 2, 3, or 4 $R^{B2}$ groups (e.g., 1 or 2 $R^{B2}$ groups), wherein each $R^{B2}$ is independently halogen, cyano, nitro, —O$R^{B20}$, —S$R^{B20}$, —N($R^{B20}$)$_2$, $C_1$-$C_6$ alkyl, or $C_1$-$C_6$ haloalkyl, wherein $R^{B20}$ is hydrogen or $C_1$-$C_6$ alkyl.

(2aaa) $R^1$ is —($C_1$-$C_6$)alkyl-$R^{B1}$ wherein $R^{B1}$ is phenyl optionally substituted by one $R^{B2}$ group, wherein $R^{B2}$ is halogen, cyano, nitro, —O$R^{B20}$, —S$R^{B20}$, —N($R^{B20}$)$_2$, $C_1$-$C_6$ alkyl, or $C_1$-$C_6$ haloalkyl, wherein $R^{B20}$ is hydrogen or $C_1$-$C_6$ alkyl.

(2bbb) $R^1$ is —($C_1$-$C_4$)alkyl-$R^{B1}$ wherein $R^{B1}$ is phenyl optionally substituted by one $R^{B2}$ groups (e.g., 1 or 2 $R^{B2}$ groups), wherein each $R^{B2}$ is independently halogen, cyano, nitro, —O$R^{B20}$, —S$R^{B20}$, —N($R^{B20}$)$_2$, $C_1$-$C_6$ alkyl, or $C_1$-$C_6$ haloalkyl, wherein $R^{B20}$ is hydrogen or $C_1$-$C_6$ alkyl.

(2ccc) $R^1$ is —($C_1$-$C_4$)alkyl-$R^{B1}$ wherein $R^{B1}$ is phenyl optionally substituted by one $R^{B2}$ group, wherein $R^{B2}$ is halogen, cyano, nitro, —O$R^{B20}$, —S$R^{B20}$, —N($R^{B20}$)$_2$, $C_1$-$C_6$ alkyl, or $C_1$-$C_6$ haloalkyl, wherein $R^{B20}$ is hydrogen or $C_1$-$C_6$ alkyl.

(2ddd) $R^1$ is —($C_1$-$C_2$)alkyl-$R^{B1}$ wherein $R^{B1}$ is phenyl optionally substituted by 1, 2, 3, or 4 $R^{B2}$ groups (e.g., 1 or 2 $R^{B2}$ groups), wherein each $R^{B2}$ is independently halogen, cyano, nitro, —O$R^{B20}$, —S$R^{B20}$, —N($R^{B20}$)$_2$, $C_1$-$C_6$ alkyl, or $C_1$-$C_6$ haloalkyl, wherein $R^{B20}$ is hydrogen or $C_1$-$C_6$ alkyl.

(2eee) $R^1$ is —($C_1$-$C_2$)alkyl-$R^{B1}$ wherein $R^{B1}$ is phenyl optionally substituted by one $R^{B2}$ group, wherein $R^{B2}$ is halogen, cyano, nitro, —O$R^{B205}$, —S$R^{B20}$, —N($R^{B20}$)$_2$, $C_1$-$C_6$ alkyl, or $C_1$-$C_6$ haloalkyl, wherein $R^{B20}$ is hydrogen or $C_1$-$C_6$ alkyl.

(2fff) $R^1$ is —(CH$_2$)—$R^{B1}$ wherein $R^{B1}$ is phenyl optionally substituted by 1, 2, 3, or 4 $R^{B2}$ groups (e.g., 1 or 2 $R^{B2}$ groups), wherein each $R^{B2}$ is independently halogen, cyano, nitro, —O$R^{B20}$, —S$R^{B20}$, —N($R^{B20}$)$_2$, $C_1$-$C_6$ alkyl, or $C_1$-$C_6$ haloalkyl, wherein $R^{B20}$ is hydrogen or $C_1$-$C_6$ alkyl.

(2ggg) $R^1$ is —(CH$_2$)—$R^{B1}$ wherein $R^{B1}$ is phenyl optionally substituted by one $R^{B2}$ group, wherein $R^{B2}$ is halogen, cyano, nitro, —O$R^{B20}$, —S$R^{B20}$, —N($R^{B20}$)$_2$, $C_1$-$C_6$ alkyl, or $C_1$-$C_6$ haloalkyl, wherein $R^{B20}$ is hydrogen or $C_1$-$C_6$ alkyl.

In a third aspect, the present disclosure provides compounds and pharmaceutical compositions comprising the compounds together with a pharmaceutically acceptable excipient, diluent, or carrier, wherein the compounds are according to formula (IV) or its tautomer (V),

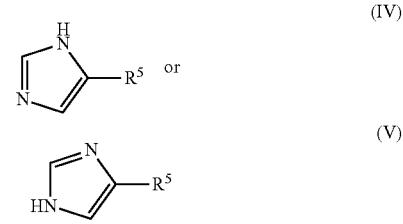

or a pharmaceutically acceptable salt thereof, wherein $R^5$ is (i)

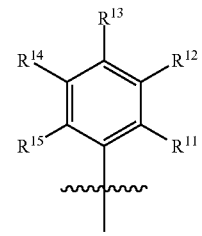

wherein
$R^{13}$ is hydrogen or —SH; and
$R^{11}$, $R^{12}$, $R^{14}$, and $R^{15}$ are each independently hydrogen or $R^{20}$, or
one of $R^{11}$ and $R^{12}$ or $R^{14}$ and $R^{15}$ taken together with the carbon atoms to which they are attached form a fused phenyl, fused 5 or 6 membered monocyclic heteroaryl, fused 5 or 6 membered monocyclic cycloalkyl, fused 5 or 6 membered monocyclic cycloalkenyl, or fused monocyclic 5 or 6 membered heterocyclyl, each fused ring optionally substituted with 1, 2, 3, or 4 $R^{20}$ groups
or (ii) $R^5$ is heteroaryl optionally substituted with 1, 2, 3, or 4 groups (e.g., 1 or 2 groups) which are each independently $R^{20}$, wherein
each $R^{20}$ is independently halogen, cyano, —OR, —SR, —NR$_2$, —C(O)OR, —C(O)NR$_2$, —N(R)S(O)$_2$R, —C(O)R$^2$, —S(O)R, —S(O)$_2$R, —S(O)OR, —S(O)$_2$OR, —S(O)NR$_2$, —S(O)$_2$NR$_2$, —OC(O)R, —OC(O)OR, —OC(O)NR$_2$, —N(R)C(O)R, —N(R)C(O)OR, —N(R)C(O)NR$_2$, —N(R)S(O)R, $C_1$-$C_6$alkyl, $C_2$-$C_6$alkenyl, $C_2$-$C_6$alkynyl, $C_1$-$C_6$haloalkyl, $C_3$-$C_8$cycloalkyl, heterocyclyl, aryl, heteroaryl, $C_3$-$C_8$cycloalkyl($C_1$-$C_6$)alkyl, heterocyclyl($C_1$-$C_6$)alkyl, aryl($C_1$-$C_6$)alkyl, heteroaryl($C_1$-$C_6$)alkyl, —$C_1$-$C_6$alkyl-$R^{A1}$, -Q-($C_1$-$C_6$)alkyl-$R^{A1}$, —($C_1$-$C_6$)alkyl-Q-$R^{A1}$, -Q-($C_1$-$C_6$)alkyl-Q-$R^{A1}$, —$C_1$-$C_6$alkyl-Q-($C_1$-$C_6$)alkyl-$R^{A1}$, -Q($C_1$-$C_6$)alkyl-Q-($C_1$-$C_6$)alkyl-$R^{A1}$, or -Q($C_1$-$C_6$)alkyl-Q-($C_1$-$C_6$)alkyl-Q$R^{A1}$, wherein
each Q is independently —C($R^{A2}$)$_2$—, —O—, —N($R^{A2}$)—, —S—, —C(O)—, —S(O)—, —S(O)$_2$—, —C(O)N($R^{A2}$)—, —N($R^{A2}$)C(O)—, —C(O)O—, or —OC(O)—, wherein each $R^{A2}$ is independently hydrogen, $C_1$-$C_6$ alkyl, or $C_1$-$C_6$haloalkyl;

$R^{A1}$ is $R^{A3}$, $C_1$-$C_6$ alkyl, —$C_1$-$C_6$ alkyl-$R^{A3}$, $C_1$-$C_6$ haloalkyl, $C_3$-$C_8$cycloalkyl, heterocyclyl, aryl, or heteroaryl, wherein the cycloalkyl, heterocyclyl, aryl, and heteroaryl groups are optionally substituted by 1, 2, 3, or 4 $R^{A3}$ groups, wherein each $R^{A3}$ is independently halogen, cyano, nitro, —OR, —SR, —$NR_2$, —C(O)R, —C(O)OR, —C(O)$NR_2$, —S(O)R, —S(O)$_2$R, —S(O)OR, —S(O)$_2$OR, —S(O)$NR_2$, —S(O)$_2$$NR_2$, —OC(O)R, —OC(O)OR, —OC(O)$NR_2$, —N(R)C(O)R, —N(R)C(O)OR, —N(R)C(O)$NR_2$, —N(R)S(O)R, —N(R)S(O)$_2$R, $C_1$-$C_6$ alkyl, $C_1$-$C_6$ haloalkyl, $C_2$-$C_6$ alkenyl, $C_2$-$C_6$ alkynyl, $C_3$-$C_8$cycloalkyl, heterocyclyl, aryl, or heteroaryl, wherein the cycloalkyl, heterocyclyl, aryl, heteroaryl, are each optionally substituted with 1, 2, 3, or 4 groups which are each independently halogen, cyano, nitro, —$OR^{411}$, —$SR^{411}$, —N($R^{411}$)$_2$, —C(O)$OR^{411}$, —C(O)N($R^{411}$)$_2$, —C(O)$R^{411}$, —S(O)$R^{411}$, —S(O)$_2$$R^{411}$, —S(O)$OR^{411}$, —S(O)$_2$$OR^{411}$, —S(O)N($R^{411}$)$_2$, —S(O)$_2$N($R^{411}$)$_2$, —OC(O)$R^{411}$, —OC(O)$OR^{411}$, —OC(O)N($R^{411}$)$_2$, —N($R^{411}$)C(O)$R^{411}$, —N($R^{411}$)C(O)$OR^{411}$, —N($R^{411}$)C(O)N($R^{411}$)$_2$, —N($R^{411}$)S(O) $R^{411}$, —N($R^{411}$)S(O)$_2$$R^{411}$, $C_1$-$C_6$ alkyl, or $C_1$-$C_6$ haloalkyl, wherein each $R^{411}$ is independently hydrogen, $C_1$-$C_6$ alkyl, $C_2$-$C_6$ alkenyl, $C_2$-$C_6$ alkynyl, $C_1$-$C_6$ haloalkyl, $C_3$-$C_8$cycloalkyl, heterocyclyl, aryl, heteroaryl, $C_3$-$C_8$cycloalkyl($C_1$-$C_6$)alkyl, heterocyclyl($C_1$-$C_6$)alkyl, aryl($C_1$-$C_6$)alkyl, or heteroaryl($C_1$-$C_6$)alkyl;

or $R^{A1}$ and $R^{A2}$ taken together, when attached to the same carbon atom, form =$C_3$-$C_8$cycloalkyl, or =heterocyclyl, wherein the cycloalkyl and heterocyclyl are optionally substituted with 1, 2, 3, or 4 groups which are each independently halogen, cyano, nitro, —OR, —SR, —$NR_2$, —C(O)OR, —C(O)$NR_2$, —C(O)R, —S(O)R, —S(O)$_2$R, —S(O)OR, —S(O)$_2$OR, —S(O)$NR_2$, —S(O)$_2$$NR_2$, —OC(O)R, —OC(O)OR, —OC(O)$NR_2$, —N(R)C(O)R, —N(R)C(O)OR, —N(R)C(O)$NR_2$, —N(R)S(O)R, —N(R)S(O)$_2$R, $C_1$-$C_6$ alkyl, or $C_1$-$C_6$ haloalkyl; and each R is independently hydrogen or $R^2$, wherein $R^2$ is $C_1$-$C_6$ alkyl, $C_2$-$C_6$ alkenyl, $C_2$-$C_6$ alkynyl, $C_1$-$C_6$ haloalkyl, $C_3$-$C_8$cycloalkyl, heterocyclyl, aryl, heteroaryl, $C_3$-$C_8$cycloalkyl($C_1$-$C_6$)alkyl, heterocyclyl($C_1$-$C_6$)alkyl, aryl($C_1$-$C_6$)alkyl, or heteroaryl($C_1$-$C_6$)alkyl, wherein the alkyl, $C_3$-$C_8$cycloalkyl, heterocyclyl, aryl, heteroaryl, cycloalkylalkyl, heterocyclylalkyl, arylalkyl, and heteroarylalkyl are each optionally substituted with 1, 2, 3, or 4 groups which are each independently halogen, cyano, nitro, —$OR^{10}$, —$SR^{10}$, —N($R^{10}$)$_2$, —C(O)$OR^{10}$, —C(O)N($R^{10}$)$_2$, —C(O)$R^{10}$, —S(O)$R^{10}$, —S(O)$_2$$R^{10}$, —S(O)$OR^{10}$, —S(O)$_2$$OR^{10}$, —S(O)N($R^{10}$)$_2$, —S(O)$_2$N($R^{10}$)$_2$, —OC(O)$R^{10}$, —OC(O)$OR^{10}$, —OC(O)N($R^{10}$)$_2$, —N($R^{10}$)C(O)$R^{10}$, —N($R^{10}$)C(O)$OR^{10}$, —N($R^{10}$)C(O)N($R^{10}$)$_2$, —N($R^{10}$)S(O)$R^{10}$, —N($R^{10}$)S(O)$_2$$R^{10}$, $C_1$-$C_6$ alkyl, $C_2$-$C_6$ alkenyl, $C_2$-$C_6$ alkynyl, $C_1$-$C_6$ haloalkyl, $C_3$-$C_8$cycloalkyl, heterocyclyl, aryl, or heteroaryl, wherein each $R^{10}$ is independently hydrogen, $C_1$-$C_6$ alkyl, $C_2$-$C_6$ alkenyl, $C_2$-$C_6$ alkynyl, $C_1$-$C_6$ haloalkyl, $C_3$-$C_8$cycloalkyl, heterocyclyl, aryl, heteroaryl, $C_3$-$C_8$cycloalkyl($C_1$-$C_6$)alkyl, heterocyclyl($C_1$-$C_6$)alkyl, aryl($C_1$-$C_6$)alkyl, or heteroaryl($C_1$-$C_6$)alkyl;

provided that the compound is not
4-phenyl-1H-imidazole;
4-(4-methoxycarbonylphenyl)-1H-imidazole;
4-(4-carboxyphenyl) 1H-imidazole;
4-(4-cyanophenyl)-1H-imidazole);
2-(2-(1H-imidazol-5-yl)phenoxy)ethanamine;

(3S-trans)-N-(6-cyano-3,4-dihydro-3-hydroxy-2,2-dimethyl-2H-1-benzopyran-4-yl)-N'-[3-(5-imidazolyl)phenyl]urea;
1H,1'H-[2,4]biimidazolyl-4-carbonitrile;
2-(1H-imidazol-4-yl)-phenylamine;
2-(3-chloroanilino)-4-(imidazol-5-yl)pyrimidine;
2,6-dichloro-3-(1H-imidazol-5-yl)-4-phenylquinoline;
2-chloro-3-(1H-imidazol-5-yl)-4-phenylquinoline-6-carbonitrile;
3-(1H-imidazol-4-yl)-4-(phenylsulfonyl)-1,2,5-oxadiazole;
3-(4-(1H-imidazol-4-yl)-1,2,5-oxadiazol-3-yloxy)-N,N-dimethylpropan-1-amine;
3-amino-4-[3-(4-imidazolyl)anilino]-3-cyclobutene-1,2-dione;
3-amino-4-ethoxy-7-(1H-imidazol-4-yl)-benzo[b]thiophene-2-carboxylic acid amide;
4-((3-(1-methyl-1H-imidazol-5-yl)-5-(trifluoromethyl)benzyloxy)methyl)-4-phenylpiperidine;
4-(1H-imidazol-4-yl)-pyridine;
4-(2-isopropoxyphenyl)-1H-imidazole;
4-(2-isopropoxy-phenyl)-1H-imidazole;
4-(3-aminophenyl)imidazole;
4-(3-cyanophenyl)imidazole;
4-(3-hydroxy-phenyl)-1H-imidazole;
4-(3-pyridinyl)-1H-imidazole;
4-(3-trifluoromethyl-phenyl)-1H-imidazole;
4-[(pyridin-2-yl)methylphenyl]-1H-imidazole;
4-benzo[b]thiophen-4-yl-1H-imidazole;
4-trifluoromethyl-1H,1'H-[2,4]biimidazolyl;
5-(2-chlorophenyl)-imidazole;
5-(4,5-dihydro-1H-imidazol-2-yl)-2-(1H-imidazol-5-yl)-1H-benzimidazole;
6-(1H-imidazol-4-yl)-5-methoxy-pyridine-2-carboxylic acid;
6-(1H-imidazol-4-yl)-5-methoxy-pyridine-2-carboxylic acid methyl ester;
6-chloro-3-(1H-imidazol-5-yl)-4-phenylquinolin-2(1H)-one;
ethyl-[4-(1H-imidazol-4-yl)-pyridin-2-yl]-amine;
methyl[3-(1H-imidazol-4-yl)-phenoxy]-acetate;
N-(2-(1H-imidazol-4-yl)phenyl)-2-(pyridin-4-ylmethylamino)nicotinamide;
5-(1H-imidazol-4-yl)-1H-indazol-3-amine; and
(4-bromo-2-chloro-phenyl)-[4-fluoro-6-(3H-imidazol-4-yl)-1H-benzoimidazol-5-yl]-amine.

The invention further comprises embodiments of the third aspect in which $R^5$ is one of the following groups (3a)-(3ll):
(3a) $R^5$ is

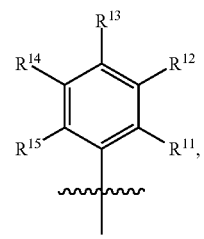

wherein $R^{11}$, $R^{12}$, $R^{14}$, $R^{15}$ are each independently hydrogen or $R^{20}$, or one of $R^{11}$ and $R^{12}$ or $R^{14}$ and $R^{15}$ taken together with the carbon atoms to which they are attached form a fused phenyl, fused 5 or 6 membered monocyclic heteroaryl, fused 5 or 6 membered monocyclic cycloalkyl, fused 5 or 6 membered monocyclic cycloalkenyl, or fused monocyclic 5 or 6 membered heterocyclyl, each fused ring optionally substituted with 1, 2, 3, or 4 $R^{20}$ groups; and $R^{13}$ is hydrogen or —SH; provided at least one of $R^{11}$, $R^{12}$, $R^{13}$, $R^{14}$, and $R^{15}$ is not hydrogen.

(3b) $R^5$ is according to group (3a), wherein one of $R^{11}$, $R^{12}$, $R^{14}$, and $R^{15}$ is halogen, cyano, —OR, —SR, —NR$_2$, —C(O)OR, —C(O)NR$_2$, —N(R)S(O)$_2$R, —C$_1$-C$_6$alkyl-$R^{41}$, -Q-(C$_1$-C$_6$)alkyl-$R^{41}$, —C$_1$-C$_6$alkyl-Q-$R^{41}$, -Q-(C$_1$-C$_6$)alkyl-Q-$R^{41}$, —C$_1$-C$_6$alkyl-Q-(C$_1$-C$_6$)alkyl-$R^{41}$, -Q(C$_1$-C$_6$)alkyl-Q-(C$_1$-C$_6$)alkyl-$R^{41}$, or -Q(C$_1$-C$_6$)alkyl-Q-(C$_1$-C$_6$)alkyl-QR$^{41}$, and $R^{13}$ is hydrogen or —SH.

(3c) $R^5$ is according to group (3a), wherein $R^{11}$ is —OR, —SR, —NR$_2$, —C$_1$-C$_6$alkyl-$R^{41}$, -Q-(C$_1$-C$_6$)alkyl-$R^{41}$, —C$_1$-C$_6$alkyl-Q-$R^{41}$, -Q-(C$_1$-C$_6$)alkyl-Q-$R^{41}$, —C$_1$-C$_6$alkyl-Q-(C$_1$-C$_6$)alkyl-$R^{41}$, -Q(C$_1$-C$_6$)alkyl-Q-(C$_1$-C$_6$)alkyl-$R^{41}$, or -Q(C$_1$-C$_6$)alkyl-Q-(C$_1$-C$_6$)alkyl-QR$^{41}$.

(3d) $R^5$ is according to group (3a), wherein $R^{12}$, $R^{14}$, and $R^{15}$ are each independently hydrogen, halogen, cyano, C$_1$-C$_6$alkyl, C$_1$-C$_6$haloalkyl, —OR, —SR, —NR$_2$, —C(O)OR, —C(O)NR$_2$, —N(R)S(O)$_2$R; $R^{13}$ is hydrogen or —SH, and $R^{11}$ is —OR, —SR, —NR$_2$, —C$_1$-C$_6$alkyl-$R^{41}$, -Q-(C$_1$-C$_6$)alkyl-$R^{41}$, —C$_1$-C$_6$alkyl-Q-$R^{41}$, -Q-(C$_1$-C$_6$)alkyl-Q-$R^{41}$, —C$_1$-C$_6$alkyl-Q-(C$_1$-C$_6$)alkyl-$R^{41}$, -Q(C$_1$-C$_6$)alkyl-Q-(C$_1$-C$_6$)alkyl-$R^{41}$, or -Q(C$_1$-C$_6$)alkyl-Q-(C$_1$-C$_6$)alkyl-QR$^{41}$.

(3e) $R^5$ is according to group (3a), wherein $R^{12}$, $R^{14}$, and $R^{15}$ are each independently hydrogen, fluoro, chloro, bromo, methyl, or ethyl, $R^{13}$ is hydrogen or —SH, and $R^{11}$ is —OR, —SR, —NR$_2$, —C$_1$-C$_6$alkyl-$R^{41}$, -Q-(C$_1$-C$_6$)alkyl-$R^{41}$, —C$_1$-C$_6$alkyl-Q-$R^{41}$, -Q-(C$_1$-C$_6$)alkyl-Q-$R^{41}$, —C$_1$-C$_6$alkyl-Q-(C$_1$-C$_6$)alkyl-$R^{41}$, -Q(C$_1$-C$_6$)alkyl-Q-(C$_1$-C$_6$)alkyl-$R^{41}$, or -Q(C$_1$-C$_6$)alkyl-Q-(C$_1$-C$_6$)alkyl-QR$^{41}$.

(3f) $R^5$ is

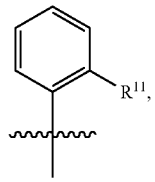

wherein $R^{11}$ is —OR, —SR, —NR$_2$, —C$_1$-C$_6$alkyl-$R^{41}$, -Q-(C$_1$-C$_6$)alkyl-$R^{41}$, —C$_1$-C$_6$alkyl-Q-$R^{41}$, -Q-(C$_1$-C$_6$)alkyl-Q-$R^{41}$, —C$_1$-C$_6$alkyl-Q-(C$_1$-C$_6$)alkyl-$R^{41}$, -Q(C$_1$-C$_6$)alkyl-Q-(C$_1$-C$_6$)alkyl-$R^{41}$, or -Q(C$_1$-C$_6$)alkyl-Q-(C$_1$-C$_6$)alkyl-QR$^{41}$.

(3g) $R^5$ is according to group (3a), wherein $R^{11}$ is —OR or —SR.

(3h) $R^5$ is according to group (3a), wherein $R^{11}$ is —OR$^{21}$ or —SR$^{21}$, wherein $R^{21}$ is hydrogen, C$_1$-C$_6$ alkyl, C$_2$-C$_6$ alkenyl, C$_3$-C$_8$cycloalkyl(C$_1$-C$_6$)alkyl, heterocyclyl(C$_1$-C$_6$)alkyl, aryl(C$_1$-C$_6$)alkyl, or heteroaryl(C$_1$-C$_6$)alkyl, wherein the cycloalkylalkyl, heterocyclylalkyl, arylalkyl, and heteroarylalkyl are each optionally substituted with 1, 2, 3, or 4 groups (e.g., 1 or 2 groups) which are each independently halogen, cyano, nitro, C$_1$-C$_6$ alkyl, C$_1$-C$_6$ haloalkyl, —OR$^{10}$, —SR$^{10}$, —N(R$^{10}$)$_2$, —C(O)OR$^{10}$, —C(O)N(R$^{10}$)$_2$, —C(O)R$^{10}$, —S(O)$_2$R$^{10}$, —S(O)$_2$OR$^{10}$, —S(O)$_2$N(R$^{10}$)$_2$, —OC(O)R$^{10}$, —OC(O)OR$^{10}$, —OC(O)N(R$^{10}$)$_2$, —N(R$^{10}$)C(O)R$^{10}$, —N(R$^{10}$)C(O)OR$^{10}$, —N(R$^{10}$)C(O)N(R$^{10}$)$_2$, —N(R$^{10}$)S(O)$_2$R$^{10}$, wherein each $R^{10}$ is independently hydrogen, C$_1$-C$_6$ alkyl, or C$_1$-C$_6$ haloalkyl.

(3i) $R^5$ is according to group (3a), wherein $R^{11}$ is —OR$^{21}$ or —SR$^{21}$, wherein $R^{21}$ is hydrogen, C$_1$-C$_6$ alkyl, C$_2$-C$_6$ alkenyl, C$_3$-C$_8$cycloalkyl(C$_1$-C$_6$)alkyl, heterocyclyl(C$_1$-C$_6$)alkyl, aryl(C$_1$-C$_6$)alkyl, or heteroaryl(C$_1$-C$_6$)alkyl.

(3j) $R^5$ is according to group (3a), wherein $R^{12}$, $R^{14}$, and $R^{15}$ are each independently hydrogen, halogen, cyano, C$_1$-C$_6$alkyl, C$_1$-C$_6$haloalkyl, —OR, —SR, —NR$_2$, —C(O)OR, —C(O)NR$_2$, —N(R)S(O)$_2$R, $R^{13}$ is hydrogen or —SH, and $R^{11}$ is —OR or —SR.

(3k) $R^5$ is according to group (3a), wherein $R^{12}$, $R^{14}$, and $R^{15}$ are each independently hydrogen, halogen, cyano, C$_1$-C$_6$alkyl, C$_1$-C$_6$haloalkyl, —OR, —SR, —NR$_2$, —C(O)OR, —C(O)NR$_2$, —N(R)S(O)$_2$R, $R^{13}$ is hydrogen or —SH, and $R^{11}$ is —OR$^{21}$ or —SR$^{21}$, wherein $R^{21}$ is hydrogen, C$_1$-C$_6$ alkyl, C$_2$-C$_6$ alkenyl, C$_3$-C$_8$cycloalkyl(C$_1$-C$_6$)alkyl, heterocyclyl(C$_1$-C$_6$)alkyl, aryl(C$_1$-C$_6$)alkyl, or heteroaryl(C$_1$-C$_6$)alkyl, wherein the cycloalkylalkyl, heterocyclylalkyl, arylalkyl, and heteroarylalkyl are each optionally substituted with 1, 2, 3, or 4 groups (e.g., 1 or 2 groups) which are each independently halogen, cyano, nitro, C$_1$-C$_6$ alkyl, C$_1$-C$_6$ haloalkyl, —OR$^{10}$, —SR$^{10}$, —N(R$^{10}$)$_2$, —C(O)OR$^{10}$, —C(O)N(R$^{10}$)$_2$, —C(O)R$^{10}$, —S(O)$_2$R$^{10}$, —S(O)$_2$OR$^{10}$, —S(O)$_2$N(R$^{10}$)$_2$, —OC(O)R$^{10}$, —OC(O)OR$^{10}$, —OC(O)N(R$^{10}$)$_2$, —N(R$^{10}$)C(O)R$^{10}$, —N(R$^{10}$)C(O)OR$^{10}$, —N(R$^{10}$)C(O)N(R$^{10}$)$_2$, —N(R$^{10}$)S(O)$_2$R$^{10}$, wherein each $R^{10}$ is independently hydrogen, C$_1$-C$_6$ alkyl, or C$_1$-C$_6$ haloalkyl.

(3l) $R^5$ is according to group (3a), wherein $R^{12}$, $R^{14}$, and $R^{15}$ are each independently hydrogen, halogen, cyano, C$_1$-C$_6$alkyl, C$_1$-C$_6$haloalkyl, —OR, —SR, —NR$_2$, —C(O)OR, —C(O)NR$_2$, —N(R)S(O)$_2$R, $R^{13}$ is hydrogen or —SH, and $R^{11}$ is —OR$^{21}$ or —SR$^{21}$, wherein $R^{21}$ is hydrogen, C$_1$-C$_6$ alkyl, C$_2$-C$_6$ alkenyl, C$_3$-C cycloalkyl(C$_1$-C$_6$)alkyl, heterocyclyl(C$_1$-C$_6$)alkyl, aryl(C$_1$-C$_6$)alkyl, or heteroaryl(C$_1$-C$_6$)alkyl.

(3m) $R^5$ is according to group (3a), wherein $R^{12}$, $R^{14}$, and $R^{15}$ are each independently hydrogen, fluoro, chloro, bromo, methyl, or ethyl, $R^{13}$ is hydrogen or —SH, and $R^{11}$ is —OR or —SR.

(3n) $R^5$ is according to group (3a), wherein $R^{12}$, $R^{14}$, and $R^{15}$ are each independently hydrogen, fluoro, chloro, bromo, methyl, or ethyl, $R^{13}$ is hydrogen or —SH, and $R^{11}$ is —OR$^{21}$ or —SR$^{21}$, wherein $R^{21}$ is hydrogen, C$_1$-C$_6$ alkyl, C$_2$-C$_6$ alkenyl, C$_3$-C$_8$cycloalkyl(C$_1$-C$_6$)alkyl, heterocyclyl(C$_1$-C$_6$)alkyl, aryl(C$_1$-C$_6$)alkyl, or heteroaryl(C$_1$-C$_6$)alkyl.

(3o) $R^5$ is

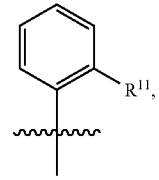

wherein $R^{11}$ is —OR or —SR.

(3p) $R^5$ is

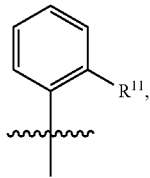

wherein $R^{11}$ is —$OR^{21}$ or —$SR^{21}$, wherein $R^{21}$ is hydrogen, $C_1$-$C_6$ alkyl, $C_2$-$C_6$ alkenyl, $C_3$-$C_8$cycloalkyl($C_1$-$C_6$) alkyl, heterocyclyl($C_1$-$C_6$)alkyl, aryl($C_1$-$C_6$)alkyl, or heteroaryl($C_1$-$C_6$)alkyl, wherein the cycloalkylalkyl, heterocyclylalkyl, arylalkyl, and heteroarylalkyl are each optionally substituted with 1, 2, 3, or 4 groups (e.g., 1 or 2 groups) which are each independently halogen, cyano, nitro, $C_1$-$C_6$ alkyl, $C_1$-$C_6$ haloalkyl, —$OR^{10}$, —$SR^{10}$, —$N(R^{10})_2$, —$C(O)OR^{10}$, —$C(O)N(R^{10})_2$, —$C(O)R^{10}$, —$S(O)_2R^{10}$, —$S(O)_2OR^{10}$, —$S(O)_2N(R^{10})_2$, —$OC(O)R^{10}$, —$OC(O)OR^{10}$, —$OC(O)N(R^{10})_2$, —$N(R^{10})C(O)R^{10}$, —$N(R^{10})C(O)OR^{10}$, —$N(R^{10})C(O)N(R^{10})_2$, —$N(R^{10})S(O)_2R^{10}$, wherein each $R^{10}$ is independently hydrogen, $C_1$-$C_6$ alkyl, or $C_1$-$C_6$ haloalkyl.

(3q) $R^5$ is

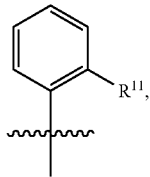

wherein $R^{11}$ is —$OR^{21}$ or —$SR^{21}$, wherein $R^{21}$ is hydrogen, $C_1$-$C_6$ alkyl, $C_2$-$C_6$ alkenyl, $C_3$-$C_8$cycloalkyl($C_1$-$C_6$) alkyl, heterocyclyl($C_1$-$C_6$)alkyl, aryl($C_1$-$C_6$)alkyl, or heteroaryl($C_1$-$C_6$)alkyl.

(3r) $R^5$ is according to group (3a), wherein $R^{11}$ is —$C_1$-$C_6$alkyl-$R^{A1}$, -Q-($C_1$-$C_6$)alkyl-$R^{A1}$, —$C_1$-$C_6$alkyl-Q-$R^{A1}$, -Q-($C_1$-$C_6$)alkyl-C($R^{A2}$)$_2$—$R^{A1}$, or —($C_1$-$C_6$)alkyl-Q-$C_1$-$C_6$ alkyl-$R^{A1}$, or -Q($C_1$-$C_6$)alkyl-C($R^{A2}$)$_2$—($C_1$-$C_6$)alkyl-Q$R^{A1}$, wherein each is Q is independently —O—, —N($R^{A2}$)—, or —S—.

(3s) $R^5$ is according to group (3a), wherein $R^{12}$, $R^{14}$, and $R^{15}$ are each independently hydrogen, halogen, cyano, $C_1$-$C_6$alkyl, $C_1$-$C_6$haloalkyl, —OR, —SR, —$NR_2$, —C(O)OR, —C(O)$NR_2$, —N(R)S(O)$_2$R, $R^{13}$ is hydrogen or —SH, and $R^{11}$ is —$C_1$-$C_6$alkyl-$R^{A1}$, -Q-($C_1$-$C_6$)alkyl-$R^{A1}$, —$C_1$-$C_6$alkyl-Q-$R^{A1}$, -Q-($C_1$-$C_6$)alkyl-C($R^{A2}$)$_2$—$R^{A1}$, or —($C_1$-$C_6$)alkyl-Q-$C_1$-$C_6$ alkyl-$R^{A1}$, or -Q($C_1$-$C_6$)alkyl-C($R^{A2}$)$_2$—($C_1$-$C_6$)alkyl-Q$R^{A1}$, wherein each is Q is independently —O—, —N($R^{A2}$)—, or —S—.

(3t) $R^5$ is according to group (3a), wherein $R^{12}$, $R^{14}$, and $R^{15}$ are each independently hydrogen, fluoro, chloro, bromo, methyl, or ethyl, $R^{13}$ is hydrogen or —SH, and $R^{11}$ is —$C_1$-$C_6$alkyl-$R^{A1}$, -Q-($C_1$-$C_6$)alkyl-$R^{A1}$, —$C_1$-$C_6$alkyl-Q-$R^{A1}$, -Q-($C_1$-$C_6$)alkyl-C($R^{A2}$)$_2$—$R^{A1}$, or —($C_1$-$C_6$)alkyl-Q-$C_1$-$C_6$ alkyl-$R^{A1}$, or -Q($C_1$-$C_6$)alkyl-C($R^{A2}$)$_2$—($C_1$-$C_6$)alkyl-Q$R^{A1}$, wherein each is Q is independently —O—, —N($R^{A2}$)—, or —S—.

(3u) $R^5$ is

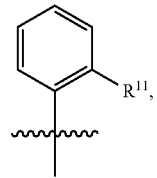

wherein $R^{11}$ is —$C_1$-$C_6$alkyl-$R^{A1}$, -Q-($C_1$-$C_6$)alkyl-$R^{A1}$, —$C_1$-$C_6$alkyl-Q-$R^{A1}$, -Q-($C_1$-$C_6$)alkyl-C($R^{A2}$)$_2$—$R^{A1}$, or —($C_1$-$C_6$)alkyl-Q-$C_1$-$C_6$ alkyl-$R^{A1}$, or -Q($C_1$-$C_6$)alkyl-C($R^{A2}$)$_2$—($C_1$-$C_6$)alkyl-Q$R^{A1}$, wherein each is Q is independently —O—, —N($R^{A2}$)—, or —S—.

(3v) $R^5$ is according to group (3a), wherein $R^{11}$ is —$C_1$-$C_6$alkyl-$R^{A1}$, —O($C_1$-$C_6$)alkyl-$R^{A1}$, —$C_1$-$C_6$alkylO$R^{A1}$, —$C_1$-$C_6$alkyl-C($R^{A2}$)$_2$—$R^{A1}$, —O($C_1$-$C_6$)alkyl-C($R^{A2}$)$_2$—$R^{A1}$, —$C_1$-$C_6$alkyl-O($C_1$-$C_6$)alkyl-$R^{A1}$, or —O($C_1$-$C_6$)alkyl-C($R^{A2}$)$_2$—($C_1$-$C_6$)alkyl-O$R^{A1}$.

(3w) $R^5$ is according to group (3a), wherein $R^{12}$, $R^{14}$, and $R^{15}$ are each independently hydrogen, halogen, cyano, $C_1$-$C_6$alkyl, $C_1$-$C_6$haloalkyl, —OR, —SR, —$NR_2$, —C(O)OR, —C(O)$NR_2$, —N(R)S(O)$_2$R, $R^{13}$ is hydrogen or —SH, and $R^{11}$ is —$C_1$-$C_6$alkyl-$R^{A1}$, —O($C_1$-$C_6$)alkyl-$R^{A1}$, —$C_1$-$C_6$alkylO$R^{A1}$, —$C_1$-$C_6$alkyl-C($R^{A2}$)$_2$—$R^{A1}$, —O($C_1$-$C_6$)alkyl-C($R^{A2}$)$_2$—$R^{A1}$, —$C_1$-$C_6$alkyl-O($C_1$-$C_6$)alkyl-$R^{A1}$, or —O($C_1$-$C_6$)alkyl-C($R^{A2}$)$_2$—($C_1$-$C_6$)alkyl-O$R^{A1}$.

(3x) $R^5$ is according to group (3a), wherein $R^{12}$, $R^{14}$, and $R^{15}$ are each independently hydrogen, fluoro, chloro, bromo, methyl, or ethyl, $R^{13}$ is hydrogen or —SH, and $R^{11}$ is —$C_1$-$C_6$alkyl-$R^{A1}$, —O($C_1$-$C_6$)alkyl-$R^{A1}$, —$C_1$-$C_6$alkylO$R^{A1}$, —$C_1$-$C_6$alkyl-C($R^{A2}$)$_2$—$R^{A1}$, —O($C_1$-$C_6$)alkyl-C($R^{A2}$)$_2$—$R^{A1}$, —$C_1$-$C_6$alkyl-O($C_1$-$C_6$)alkyl-$R^{A1}$, or —O($C_1$-$C_6$)alkyl-C($R^{A2}$)$_2$—($C_1$-$C_6$)alkyl-O$R^{A1}$.

(3y) $R^5$ is

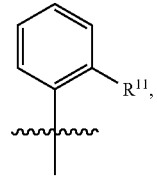

wherein $R^{11}$ is —$C_1$-$C_6$alkyl-$R^{A1}$, —O($C_1$-$C_6$)alkyl-$R^{A1}$, —$C_1$-$C_6$alkylO$R^{A1}$, —$C_1$-$C_6$alkyl-C($R^{A2}$)$_2$—$R^{A1}$, —O($C_1$-$C_6$)alkyl-C($R^{A2}$)$_2$—$R^{A1}$, —$C_1$-$C_6$alkyl-O($C_1$-$C_6$)alkyl-$R^{A1}$, or —O($C_1$-$C_6$)alkyl-C($R^{A2}$)$_2$—($C_1$-$C_6$)alkyl-O$R^{A1}$.

(3z) $R^5$ is according to group (3a), wherein $R^{11}$ is —O($C_1$-$C_6$)alkyl-$R^{A1}$, —$C_1$-$C_6$alkylO$R^{A1}$, —$C_1$-$C_6$alkyl-C(CH$_3$)$_2$—$R^{A1}$, —O($C_1$-$C_6$)alkyl-C(CH$_3$)$_2$—$R^{A1}$, —$C_1$-$C_6$alkyl-O($C_1$-$C_6$)alkyl-$R^{A1}$, or —O($C_1$-$C_6$)alkyl-C(CH$_3$)$_2$—($C_1$-$C_6$)alkyl-O$R^{A1}$.

(3aa) $R^5$ is according to group (3a), wherein $R^{12}$, $R^{14}$, and $R^{15}$ are each independently hydrogen, halogen, cyano, $C_1$-$C_6$alkyl, $C_1$-$C_6$haloalkyl, —OR, —SR, —$NR_2$, —C(O)OR, —C(O)$NR_2$, —N(R)S(O)$_2$R, $R^{13}$ is hydrogen or —SH, and $R^{11}$ is —O($C_1$-$C_6$)alkyl-$R^{A1}$, —$C_1$-$C_6$alkylO$R^{A1}$, —$C_1$-$C_6$alkyl-C(CH$_3$)$_2$—$R^{A1}$, —O($C_1$-$C_6$)alkyl-C(CH$_3$)$_2$—$R^{A1}$, —$C_1$-$C_6$alkyl-O($C_1$-$C_6$)alkyl-$R^{A1}$, or —O($C_1$-$C_6$)alkyl-C(CH$_3$)$_2$—($C_1$-$C_6$)alkyl-O$R^{A1}$.

(3bb) $R^5$ is according to group (3a), wherein $R^{12}$, $R^{14}$, and $R^{15}$ are each independently hydrogen, fluoro, chloro, bromo, methyl, or ethyl, $R^{13}$ is hydrogen or —SH, and $R^{11}$ is —O($C_1$-$C_6$)alkyl-$R^{41}$, —$C_1$-$C_6$alkylO$R^{41}$, —$C_1$-$C_6$alkyl-C(CH$_3$)$_2$—$R^{41}$, —O($C_1$-$C_6$)alkyl-C(CH$_3$)$_2$—$R^{41}$, —$C_1$-$C_6$alkyl-O($C_1$-$C_6$)alkyl-$R^{41}$, or —O($C_1$-$C_6$)alkyl-C(CH$_3$)$_2$—($C_1$-$C_6$)alkyl-O$R^{41}$.

(3cc) $R^5$ is

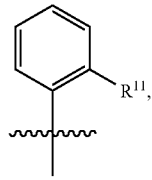

wherein $R^{11}$ is —O($C_1$-$C_6$)alkyl-$R^{41}$, —$C_1$-$C_6$alkylO$R^{41}$, —$C_1$-$C_6$alkyl-C(CH$_3$)$_2$—$R^{41}$, —O($C_1$-$C_6$)alkyl-C(CH$_3$)$_2$—$R^{41}$, —$C_1$-$C_6$alkyl-O($C_1$-$C_6$)alkyl-$R^{41}$, or —O($C_1$-$C_6$)alkyl-C(CH$_3$)$_2$—($C_1$-$C_6$)alkyl-O$R^{41}$.

(3dd) $R^5$ is according to group (3a), wherein $R^{11}$, $R^{12}$, $R^{14}$, and $R^{15}$ are independently hydrogen, halogen, cyano, $C_1$-$C_6$alkyl, $C_1$-$C_6$haloalkyl, —OR, —SR, —NR$_2$, —C(O)OR, —C(O)NR$_2$, —N(R)S(O)$_2$R, and $R^{13}$ is hydrogen or —SH (3ee) $R^5$ is according to group (3a), wherein at least one of $R^{12}$, $R^{14}$, and $R^{15}$ is fluoro, chloro, bromo, methyl, or ethyl, $R^{13}$ is hydrogen or —SH, and $R^{11}$ is —OH, —OCH$_3$, or —SH.

(3ff) $R^5$ is according to group (3a), wherein $R^{12}$, $R^{14}$, and $R^{15}$ are each independently hydrogen, fluoro, chloro, bromo, methyl, or ethyl, $R^{13}$ is hydrogen or —SH, and $R^{11}$ is —OH, —OCH$_3$, or —SH.

(3gg) $R^5$ is

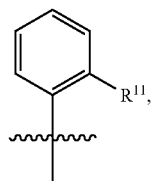

wherein $R^{11}$ is —OH, —OCH$_3$, or —SH.

(3hh) $R^5$ is heteroaryl optionally substituted with 1, 2, 3, or 4 groups (e.g., 1 or 2 groups) which are each independently $R^{20}$.

(3ii) $R^5$ is a 6-membered heteroaryl optionally substituted with 1, 2, 3, or 4 groups (e.g., 1 or 2 groups) which are each independently $R^{20}$.

(3jj) $R^5$ is a 6-membered heteroaryl optionally substituted with 1, 2, 3, or 4 groups (e.g., 1 or 2 groups) which are each independently $R^{20}$, wherein the para-position of $R^5$ with respect to the bond between $R^5$ and the parent imidazole or pyrazole ring is unsubstituted.

(3kk) $R^5$ is benzothiophenyl, pyrrolopyridinyl, imidazopyridinyl, quinolinyl, isoquinolinyl, naphthyridinyl, indolyl, indolinyl, benzothiadiazolyl, dihydrobenzodioxinyl, tetrahydropyrimidinyl, pyridinyl, pyrimidinyl, thienyl, or isoxazolyl, each optionally with 1, 2, 3, or 4 groups (e.g., 1 or 2 groups) which are each independently $R^{20}$.

(3ll) $R^5$ is benzo[b]thiophen-3-yl, 1H-pyrrolo[2,3-b]pyridin-3-yl, 1H-pyrrolo[2,3-b]pyridin-5-yl, 7-methylimidazo[1,2-a]pyridin-6-yl, quinolin-8-yl, 7-chloroquinolin-4-yl, 2,8-bis(trifluoromethyl)quinolin-4-yl, 5-chloro-8-hydroxyquinolin-7-yl, isoquinolin-4-yl, isoquinolin-5-yl, 2-carboxy-1,6-naphthyridin-8-yl, 1H-indol-7-yl, 1H-indol-6-yl, 1H-indol-5-yl, 9H-purin-6-yl, 2-oxo-2,3-dihydro-1H-imidazo[4,5-b]pyridin-6-yl, 2,3-dioxoindolin-5-yl, 2,3-dioxoindolin-7-yl, benzo[c][1,2,5]thiadiazol-4-yl, 2,3-dihydrobenzo[b][1,4]dioxin-6-yl, 1,3-dimethyl-2,4-dioxo-1,2,3,4,-tetrahydropyrimidin-5-yl, 2-morpholinopyridin-3-yl, 4-hydroxybiphenyl-3-yl, 2-hydroxypyridin-3-yl, 2,5-dichlorothiophen-3-yl or 3,5-dimethylisoxazol-4-yl.

In a fourth aspect, the present disclosure provides compounds and pharmaceutical compositions comprising the compounds together with a pharmaceutically acceptable excipient, diluent, or carrier, wherein the compounds are according to formula (VI) or its tautomer (VII),

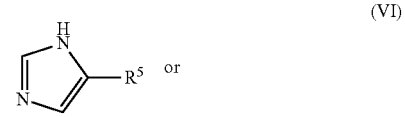

(VI)

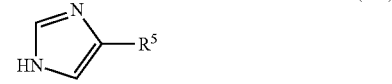

(VII)

or a pharmaceutically acceptable salt thereof, wherein $R^5$ is

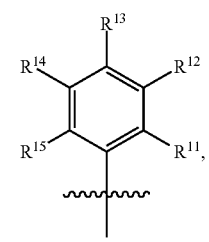

wherein $R^{11}$, $R^{12}$, $R^{14}$, and $R^{15}$ are each independently hydrogen, halogen, cyano, —OR, —SR, —NR$_2$, —C(O)OR, —C(O)NR$_2$, —N(R)S(O)$_2$R, —C(O)R$^2$, —S(O)R, —S(O)$_2$R, —S(O)OR, —S(O)$_2$OR, —S(O)NR$_2$, —S(O)$_2$NR$_2$, —OC(O)R, —OC(O)OR, —OC(O)NR$_2$, —N(R)C(O)R, —N(R)C(O)OR, —N(R)C(O)NR$_2$, —N(R)S(O)R, $C_1$-$C_6$alkyl, $C_2$-$C_6$alkenyl, $C_2$-$C_6$alkynyl, $C_1$-$C_6$haloalkyl, $C_3$-$C_8$cycloalkyl, heterocyclyl, aryl, heteroaryl, and $R^{13}$ is hydrogen or —SH, wherein each R is independently hydrogen or $R^2$, wherein $R^2$ is $C_1$-$C_6$ alkyl, $C_2$-$C_6$ alkenyl, $C_2$-$C_6$ alkynyl, $C_1$-$C_6$ haloalkyl, $C_3$-$C_8$cycloalkyl, heterocyclyl, aryl, heteroaryl, $C_3$-$C_8$cycloalkyl($C_1$-$C_6$)alkyl, heterocyclyl($C_1$-$C_6$)alkyl, aryl($C_1$-$C_6$)alkyl, or heteroaryl($C_1$-$C_6$)alkyl, wherein the alkyl, $C_3$-$C_8$cycloalkyl, heterocyclyl, aryl, heteroaryl, cycloalkylalkyl, heterocyclylalkyl, arylalkyl, and heteroarylalkyl are each optionally substituted with 1, 2, 3, or 4 groups which are each independently halogen, cyano, nitro, —OR$^{10}$, —SR$^{10}$, —N(R$^{10}$)$_2$, —C(O)OR$^{10}$, —C(O)N(R$^{10}$)$_2$, —C(O)R$^{10}$, —S(O)R$^{10}$, —S(O)$_2$R$^{10}$, —S(O)OR$^{10}$, —S(O)$_2$OR$^{10}$, —S(O)N(R$^{10}$)$_2$, —S(O)$_2$N(R$^{10}$)$_2$, —OC(O)R$^{10}$, —OC(O) OR$^{10}$, —OC(O)N(R$^{10}$)$_2$, —N(R$^{10}$)C(O)R$^{10}$, —N(R$^{10}$)C(O) OR$^{10}$, —N(R$^{10}$)C(O)N(R$^{10}$)$_2$, —N(R$^{10}$)S(O)R$^{10}$, —N(R$^{10}$)S(O)$_2$R$^{10}$, $C_1$-$C_6$ alkyl, $C_2$-$C_6$ alkenyl, $C_2$-$C_6$ alkynyl, $C_1$-$C_6$ haloalkyl, $C_3$-$C_8$cycloalkyl, heterocyclyl, aryl, or heteroaryl, wherein each $R^{10}$ is independently hydrogen, $C_1$-$C_6$ alkyl, $C_2$-$C_6$ alkenyl, $C_2$-$C_6$ alkynyl, $C_1$-$C_6$ haloalkyl, $C_3$-$C_8$cycloalkyl, heterocyclyl, aryl, heteroaryl, $C_3$-$C_8$cycloalkyl($C_1$-$C_6$)alkyl, heterocyclyl($C_1$-$C_6$)alkyl, aryl($C_1$-$C_6$)alkyl, or heteroaryl($C_1$-$C_6$)alkyl;

provided that the compound is not 4-phenyl-1H-imidazole;

4-(4-methoxycarbonylphenyl)-1H-imidazole;

4-(4-carboxyphenyl)1H-imidazole;

4-(4-cyanophenyl)-1H-imidazole;

2-(2-(1H-imidazol-5-yl)phenoxy)ethanamine;

(3S-trans)-N-(6-cyano-3,4-dihydro-3-hydroxy-2,2-dimethyl-2H-1-benzopyran-4-yl)-N'-[3-(5-imidazolyl)phenyl]urea;

2-(1H-imidazol-4-yl)-phenylamine;

3-amino-4-[3-(4-imidazolyl)anilino]-3-cyclobutene-1,2-dione;

4-(2-isopropoxyphenyl)-1H-imidazole;

4-(2-isopropoxy-phenyl)-1H-imidazole;

4-(3-aminophenyl)imidazole;

4-(3-cyanophenyl)imidazole;

4-(3-hydroxy-phenyl)-1H-imidazole;

4-(3-trifluoromethyl-phenyl)-1H-imidazole;

4-[(pyridin-2-yl)methylphenyl]-1H-imidazole;

5-(2-chlorophenyl)-imidazole;

methyl[3-(1H-imidazol-4-yl)-phenoxy]-acetate; and

N-(2-(1H-imidazol-4-yl)phenyl)-2-(pyridin-4-ylmethylamino)nicotinamide.

The invention further comprises embodiments of the fourth aspect in which $R^{11}$-$R^{15}$ of formula (VI) or (VII) are defined by one of the following groups (4a)-(4s):

(4a) $R^{11}$ is —OR or —SR.

(4b) $R^{11}$ is —OR$^{21}$ or —SR$^{21}$, wherein $R^{21}$ is hydrogen, $C_1$-$C_6$ alkyl, $C_2$-$C_6$ alkenyl, $C_3$-$C_8$cycloalkyl($C_1$-$C_6$)alkyl, heterocyclyl($C_1$-$C_6$)alkyl, aryl($C_1$-$C_6$)alkyl, or heteroaryl($C_1$-$C_6$)alkyl, wherein the cycloalkylalkyl, heterocyclylalkyl, arylalkyl, and heteroarylalkyl are each optionally substituted with 1, 2, 3, or 4 groups (e.g., 1 or 2 groups) which are each independently halogen, cyano, nitro, $C_1$-$C_6$ alkyl, $C_1$-$C_6$ haloalkyl, —OR$^{10}$, —SR$^{10}$, —N(R$^{10}$)$_2$, —C(O)OR$^{10}$, —C(O)N(R$^{10}$)$_2$, —C(O)R$^{10}$, —S(O)$_2$R$^{10}$, —S(O)$_2$OR$^{10}$, —S(O)$_2$N(R$^{10}$)$_2$, —OC(O)R$^{10}$, —OC(O)OR$^{10}$, —OC(O)N(R$^{10}$)$_2$, —N(R$^{10}$)C(O)R$^{10}$, —N(R$^{10}$)C(O)OR$^{10}$, —N(R$^{10}$)C(O)N(R$^{10}$)$_2$, —N(R$^{10}$)S(O)$_2$R$^{10}$, wherein each R$^{10}$ is independently hydrogen, $C_1$-$C_6$ alkyl, or $C_1$-$C_6$ haloalkyl.

(4c) $R^{11}$ is —OR$^{21}$ or —SR$^{21}$, wherein $R^{21}$ is hydrogen, $C_1$-$C_6$ alkyl, $C_2$-$C_6$ alkenyl, $C_3$-$C_8$cycloalkyl($C_1$-$C_6$)alkyl, heterocyclyl($C_1$-$C_6$)alkyl, aryl($C_1$-$C_6$)alkyl, or heteroaryl ($C_1$-$C_6$)alkyl.

(4d) $R^{11}$ is —OH, —OCH$_3$, or —SH.

(4e) $R^{12}$, $R^{14}$, and $R^{15}$ are each independently hydrogen, halogen, cyano, $C_1$-$C_6$alkyl, $C_1$-$C_6$haloalkyl, —OR, —SR, —NR$_2$, —C(O)OR, —C(O)NR$_2$, or —N(R)S(O)$_2$R, and $R^{13}$ is hydrogen or —SH.

(4f) $R^{12}$, $R^{14}$, and $R^{15}$ are each independently hydrogen, halogen, cyano, nitro, $C_1$-$C_6$alkyl, $C_1$-$C_6$haloalkyl, —OR, —SR, —NR$_2$, —C(O)OR, —C(O)NR$_2$, or —N(R)S(O)$_2$R, $R^{13}$ is hydrogen or —SH, and $R^{11}$ is —OR or —SR.

(4g) $R^{12}$, $R^{14}$, and $R^{15}$ are each independently hydrogen, halogen, cyano, $C_1$-$C_6$alkyl, $C_1$-$C_6$haloalkyl, —OR, —SR, —NR$_2$, —C(O)OR, —C(O)NR$_2$, or —N(R)S(O)$_2$R, $R^{13}$ is hydrogen or —SH, and $R^{11}$ is OR$^{21}$ or —SR$^{21}$, wherein $R^{21}$ is hydrogen, $C_1$-$C_6$ alkyl, $C_2$-$C_6$ alkenyl, $C_3$-$C_8$cycloalkyl($C_1$-$C_6$)alkyl, heterocyclyl($C_1$-$C_6$)alkyl, aryl($C_1$-$C_6$)alkyl, or heteroaryl($C_1$-$C_6$)alkyl, wherein the cycloalkylalkyl, heterocyclylalkyl, arylalkyl, and heteroarylalkyl are each optionally substituted with 1, 2, 3, or 4 groups (e.g., 1 or 2 groups) which are each independently halogen, cyano, nitro, $C_1$-$C_6$ alkyl, $C_1$-$C_6$ haloalkyl, —OR$^{10}$, —SR$^{10}$, —N(R$^{10}$)$_2$, —C(O)OR$^{10}$, —C(O)N (R$^{10}$)$_2$, —C(O)R$^{10}$, —S(O)$_2$R$^{10}$, —S(O)$_2$OR$^{10}$, —S(O)$_2$N (R$^{10}$)$_2$, —OC(O)R$^{10}$, —OC(O)OR$^{10}$, —OC(O)N(R$^{10}$)$_2$, —N(R$^{10}$)C(O)R$^{10}$, —N(R$^{10}$)C(O)OR$^{10}$, —N(R$^{10}$)C(O)N (R$^{10}$)$_2$, —N(R$^{10}$)S(O)$_2$R$^{10}$, wherein each R$^{10}$ is independently hydrogen, $C_1$-$C_6$ alkyl, or $C_1$-$C_6$ haloalkyl.

(4h) $R^{12}$, $R^{14}$, and $R^{15}$ are each independently hydrogen, halogen, cyano, $C_1$-$C_6$alkyl, $C_1$-$C_6$haloalkyl, —OR, —SR, —NR$_2$, —C(O)OR, —C(O)NR$_2$, or —N(R)S(O)$_2$R, $R^{13}$ is hydrogen or —SH, and $R^{11}$ is —OH, —OCH$_3$, or —SH.

(4i) $R^{12}$, $R^{14}$, and $R^{15}$ are each independently hydrogen, fluoro, chloro, bromo, methyl, or ethyl and $R^{13}$ is hydrogen or —SH, (4j) $R^{12}$, $R^{14}$, and $R^{15}$ are each independently hydrogen, fluoro, chloro, bromo, methyl, or ethyl, $R^{13}$ is hydrogen or —SH, and $R^{11}$ is —OR or —SR.

(4k) $R^{12}$, $R^{14}$, and $R^{15}$ are each independently hydrogen, fluoro, chloro, bromo, methyl, or ethyl, $R^{13}$ is hydrogen or —SH, and $R^{11}$ is OR$^{21}$ or —SR$^{21}$, wherein $R^{21}$ is hydrogen, $C_1$-$C_6$ alkyl, $C_2$-$C_6$ alkenyl, $C_3$-$C_8$cycloalkyl($C_1$-$C_6$) alkyl, heterocyclyl($C_1$-$C_6$)alkyl, aryl($C_1$-$C_6$)alkyl, or heteroaryl($C_1$-$C_6$)alkyl, wherein the cycloalkylalkyl, heterocyclylalkyl, arylalkyl, and heteroarylalkyl are each optionally substituted with 1, 2, 3, or 4 groups (e.g., 1 or 2 groups) which are each independently halogen, cyano, nitro, $C_1$-$C_6$ alkyl, $C_1$-$C_6$ haloalkyl, —OR$^{10}$, —SR$^{10}$, —N(R$^{10}$)$_2$, —C(O)OR$^{10}$, —C(O)N(R$^{10}$)$_2$, —C(O)R$^{10}$, —S(O)$_2$R$^{10}$, —S(O)$_2$OR$^{10}$, —S(O)$_2$N(R$^{10}$)$_2$, —OC(O) R$^{10}$, —OC(O)OR$^{10}$, —OC(O)N(R$^{10}$)$_2$, —N(R$^{10}$)C(O) R$^{10}$, —N(R$^{10}$)C(O)OR$^{10}$, —N(R$^{10}$)C(O)N(R$^{10}$)$_2$, —N(R$^{10}$)S(O)$_2$R$^{10}$, wherein each R$^{10}$ is independently hydrogen, $C_1$-$C_6$ alkyl, or $C_1$-$C_6$ haloalkyl.

(4l) $R^{12}$, $R^{14}$, and $R^{15}$ are each independently hydrogen, fluoro, chloro, bromo, methyl, or ethyl, $R^{13}$ is hydrogen or —SH, and $R^{11}$ is —OH, —OCH$_3$, or —SH.

(4m) $R^{12}$, $R^{14}$, and $R^{15}$ are each hydrogen, $R^{13}$ is hydrogen or —SH, and $R^{11}$ is —OR or —SR.

(4n) $R^{12}$, $R^{14}$, and $R^{15}$ are each hydrogen, $R^{13}$ is hydrogen or —SH, and $R^{11}$ is —OR$^{21}$ or —SR$^{21}$, wherein $R^{21}$ is hydrogen, $C_1$-$C_6$ alkyl, $C_2$-$C_6$ alkenyl, $C_3$-$C_8$cycloalkyl($C_1$-$C_6$) alkyl, heterocyclyl($C_1$-$C_6$)alkyl, aryl($C_1$-$C_6$)alkyl, or heteroaryl($C_1$-$C_6$)alkyl, wherein the cycloalkylalkyl, heterocyclylalkyl, arylalkyl, and heteroarylalkyl are each optionally substituted with 1, 2, 3, or 4 groups (e.g., 1 or 2 groups) which are each independently halogen, cyano, nitro, $C_1$-$C_6$ alkyl, $C_1$-$C_6$ haloalkyl, —OR$^{10}$, —SR$^{10}$, —N(R$^{10}$)$_2$, —C(O)OR$^{10}$, —C(O)N(R$^{10}$)$_2$, —C(O)R$^{10}$, —S(O)$_2$R$^{10}$, —S(O)$_2$OR$^{10}$, —S(O)$_2$N(R$^{10}$)$_2$, —OC(O) R$^{10}$, —OC(O)OR$^{10}$, —OC(O)N(R$^{10}$)$_2$, —N(R$^{10}$)C(O) R$^{10}$, —N(R$^{10}$)C(O)OR$^{10}$, —N(R$^{10}$)C(O)N(R$^{10}$)$_2$, —N(R$^{10}$)S(O)$_2$R$^{10}$, wherein each R$^{10}$ is independently hydrogen, $C_1$-$C_6$ alkyl, or $C_1$-$C_6$ haloalkyl.

(4o) $R^{11}$, $R^{12}$, $R^{14}$, and $R^{15}$ are independently hydrogen, halogen, cyano, $C_1$-$C_6$alkyl, $C_1$-$C_6$haloalkyl, —OR, —SR, —NR$_2$, —C(O)OR, —C(O)NR$_2$, or —N(R)S(O)$_2$R, and $R^{13}$ is hydrogen or —SH, (4p) At least one of $R^{12}$, $R^{14}$, and $R^{15}$ is fluoro, chloro, bromo, methyl, or ethyl.

(4q) At least one of $R^{12}$, $R^{14}$, and $R^{15}$ is fluoro, chloro, bromo, methyl, or ethyl, and $R^{13}$ is hydrogen or —SH, $R^{11}$ is —OH, —OCH$_3$, or —SH.

(4r) $R^{12}$, $R^{14}$, and $R^{15}$ are each independently hydrogen, fluoro, chloro, bromo, methyl, or ethyl, $R^{13}$ is hydrogen or —SH, and $R^{11}$ is —OH, —OCH$_3$, or —SH.

(4s) $R^{12}$, $R^{14}$, and $R^{15}$ are each hydrogen, $R^{13}$ is hydrogen or —SH, and $R^{11}$ is —OH, —OCH₃, or —SH.

In an embodiment of the first through fourth aspects, including embodiments thereof as described above, the compound is not
2-(1H-imidazol-4-yl)phenol;
4-(2-fluorophenyl)-1H-imidazole;
4-(thiophen-2-yl)-1H-imidazole;
3-(1H-imidazol-4-yl)phenol;
4-(3-fluorophenyl)-1H-imidazole;
3-(1H-imidazol-4-yl)benzonitrile;
3-(1H-imidazol-4-yl)pyridine;
4-(1H-imidazol-4-yl)phenol;
4-(4-fluorophenyl)-1H-imidazole;
4-(2,6-dimethoxyphenyl)-1H-imidazole;
2-(1H-imidazol-4-yl)benzene-1,3-diol;
3-(1H-imidazol-4-yl)benzaldehyde;
4-(2-(methylthio)phenyl)-1H-imidazole;
4-(3-(methylthio)phenyl)-1H-imidazole;
4-(4-(methylthio)phenyl)-1H-imidazole;
2-(1H-imidazol-4-yl)benzenethiol;
3-(1H-imidazol-4-yl)benzenethiol;
3-(1H-imidazol-4-yl)benzenethiol;
1-benzyl-5-phenyl-1H-imidazole;
5-(2-hydroxy-5-fluorophenyl)pyrazole;
5-(2-hydroxyphenyl)pyrazole;
and 3-phenyl-1H-pyrazole.

In an embodiment of the first through fourth aspects, including embodiments thereof as described above, the compound is not
1-(2,2-Dimethyl-propyl)-5-(2-ethoxy-phenyl)-1H-imidazole;
1-(2,2-Dimethyl-propyl)-5-phenyl-1H-imidazole;
1-Butyl-5-[2-((E)-3,7-dimethyl-octa-2,6-dienyloxy)-phenyl]-1H-imidazole;
1-Ethyl-5-phenyl-1H-imidazole;
1-Isobutyl-5-(3-phenoxy-phenyl)-1H-imidazole;
1-Isobutyl-5-phenyl-1H-imidazole;
1-Isopropyl-5-(3-methoxy-phenyl)-1H-imidazole;
1-Isopropyl-5-(3-phenoxy-phenyl)-1H-imidazole;
1-Isopropyl-5-[3-(3-methoxy-benzyloxy)-phenyl]-1H-imidazole;
1-Isopropyl-5-[3-(4-methoxy-benzyloxy)-phenyl]-1H-imidazole;
1-Methyl-5-phenyl-1H-imidazole;
1-Methyl-5-p-tolyl-1H-imidazole;
1-tert-Butyl-5-phenyl-1H-imidazole;
2-(3-Ethyl-3H-imidazol-4-yl)-phenol;
2-(3-Isopropyl-3H-imidazol-4-yl)-phenol;
3-(3-Butyl-3H-imidazol-4-yl)-phenol;
3-(3-Ethyl-3H-imidazol-4-yl)-phenol;
3-(3-Isobutyl-3H-imidazol-4-yl)-phenol;
3-(3-Isopropyl-3H-imidazol-4-yl)-phenol;
3-(3-Methyl-3H-imidazol-4-yl)-phenol;
3-(3-Propyl-3H-imidazol-4-yl)-phenol;
3-[3-(2,2-Dimethyl-propyl)-3H-imidazol-4-yl]-phenol;
3-tert-butyl-1-ethyl-N-(3-(1-methyl-1H-imidazol-5-yl)phenyl)-1H-pyrazole-5-carboxamide;
5-(2-Allyloxy-phenyl)-1-isobutyl-1H-imidazole;
5-(2-Benzyloxy-phenyl)-1-ethyl-1H-imidazole;
5-(2-Benzyloxy-phenyl)-1-isopropyl-1H-imidazole;
5-(3-Allyloxy-phenyl)-1-isobutyl-1H-imidazole;
5-(3-Benzyloxy-phenyl)-1-(2,2-dimethyl-propyl)-1H-imidazole;
5-(3-Benzyloxy-phenyl)-1-butyl-1H-imidazole;
5-(3-Benzyloxy-phenyl)-1-ethyl-1H-imidazole;
5-(3-Benzyloxy-phenyl)-1-isobutyl-1H-imidazole;
5-(3-Benzyloxy-phenyl)-1-methyl-1H-imidazole;
5-(3-Benzyloxy-phenyl)-1-propyl-1H-imidazole;
5-(3-Bromo-phenyl)-1H-imidazole;
5-(3-Isobutoxy-phenyl)-1-isopropyl-1H-imidazole;
5-(3-Methoxy-phenyl)-1H-imidazole;
5-[3-((E)-3,7-Dimethyl-octa-2,6-dienyloxy)-phenyl]-1-isobutyl-1H-imidazole;
5-[3-(3-Chloro-benzyloxy)-phenyl]-1-isopropyl-1H-imidazole;
5-[3-(4-Chloro-benzyloxy)-phenyl]-1-isopropyl-1H-imidazole;
5-[3-(4-Fluoro-benzyloxy)-phenyl]-1-isopropyl-1H-imidazole;
5-m-Tolyl-1H-imidazole;
5-Naphthalen-1-yl-1H-imidazole;
5-o-Tolyl-1H-imidazole;
5-Phenyl-1-propyl-1H-imidazole; and
1-Butyl-5-phenyl-1H-imidazole.

In a fifth aspect, the present disclosure provides pharmaceutical compositions comprising a pharmaceutically acceptable excipient, diluent, or carrier, and a compound according to the formula,

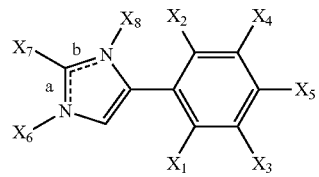

(VIII)

wherein $X_1$ and $X_2$ are independently selected from the group consisting of H, OH, SH, and SCH₃; wherein $X_3$, $X_4$, and $X_5$ are independently selected from the group consisting of H and SH; wherein $X_1$, $X_2$, $X_3$, $X_4$, and $X_5$ are not all H; wherein $X_6$ is H or absent when a is a double bond; wherein $X_7$ is selected from the group consisting of H, alkyl, alkenyl, and aryl; wherein $X_8$ is selected from the group consisting of H, alkyl, alkenyl, and aryl, or is absent when b is a double bond; and wherein either a or b is a double bond. In a particular embodiment, $X_7$ is not HOCH₂— or (H₃C)NHCH₂—. In yet another embodiment, $X_7$ is not a lower alkyl.

In an embodiment of the fifth aspect, $X_1$ and $X_2$ are independently selected from the group consisting of H, OH, SH, and SCH₃; $X_3$, $X_4$, and $X_5$ are independently selected from the group consisting of H and SH; wherein $X_1$, $X_2$, $X_3$, $X_4$, and $X_5$ are not all H; $X_6$ is H or absent when a is a double bond; $X_7$ is H; $X_8$ is selected from the group consisting of H, $C_1$-$C_{20}$alkyl, $C_3$-$C_{20}$cycloalkyl, $C_2$-$C_{20}$alkenyl, aryl, and heteroaryl, wherein the alkyl, alkenyl, cycloalkyl, aryl, and heteroaryl groups are optionally interrupted by one or more oxygen, nitrogen, or sulfur atoms; and the alkyl, alkenyl, cycloalkyl, aryl, and heteroaryl groups are optionally substituted at any substitutable position with $C_1$-$C_{20}$alkyl, $C_2$-$C_{20}$alkenyl, halogen, $C_1$-$C_{20}$haloalkyl (CCl₃, CF₃), $C_1$-$C_{20}$alkoxyl, $C_1$-$C_{20}$alkylthio, hydroxy, methoxy, carboxyl, oxo, epoxy, $C_1$-$C_{20}$alkyloxycarbonyl, $C_1$-$C_{20}$alkylcarbonyloxy, amino, —C(O)NH₂, —C(O)N(H)R, wherein R is $C_1$-$C_{20}$alkyl, —NHCONH₂, aryl, nitrile, nitro, and thiol; or $X_8$ is absent when a is a double bond; and either a or b is a double bond.

In a sixth aspect, the invention provides methods for treating indoleamine 2,3-dioxygenase (IDO) mediated immunosuppression in a subject in need thereof, comprising administering an effective indoleamine 2,3-dioxygenase inhibiting amount of a pharmaceutical composition of any one of the first through fifth aspects.

In an embodiment of the sixth aspect, the immunosuppression is associated with an infectious disease, or cancer.

In another embodiment of the sixth aspect, the immunosuppression is associated with an infectious disease and the infectious disease is a viral infection selected from the group consisting of: hepatitis C virus (HCV), human papilloma virus (HPV), cytomegalovirus (CMV), Epstein-Barr virus (EBV), poliovirus, varicella zoster virus, coxsackie virus, human immunodeficiency virus (HIV).

In an embodiment of the sixth aspect, the immunosuppression is immunosupression associated with HIV-1 infection.

In another embodiment of the sixth aspect, the immunosuppression is associated with an infectious disease and the infectious disease is tuberculosis or *Leishmaniasis*.

In another embodiment of the sixth aspect, the immunosuppression is associated with a cancer.

In an embodiment of the sixth aspect, the immunosuppression is tumor-specific immunosuppression associated with cancer.

In another embodiment of the sixth aspect, the immunosuppression is associated with a cancer, wherein the cancer is colon, pancreas, breast, prostate, lung, brain, ovary, cervix, testes, renal, head, or neck cancer, or lymphoma, leukemia, or melanoma.

In a seventh aspect, the invention provides methods for treating indoleamine 2,3-dioxygenase (IDO) mediated immunosuppression in a subject in need thereof, comprising administering an effective indoleamine 2,3-dioxygenase inhibiting amount of compound according to formula (I) or (II), and any embodiment thereof, as described above, or a compound according to formula (XI) or (XII),

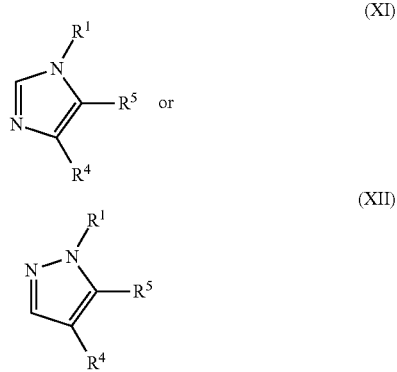

a tautomer thereof, or a pharmaceutically acceptable salt thereof, wherein $R^1$ and $R^4$ are each independently hydrogen, $C_1$-$C_6$ alkyl, $C_1$-$C_6$ haloalkyl, —($C_1$-$C_6$)alkyl-$R^{B1}$, —($C_1$-$C_6$)alkyl-Z—($C_1$-$C_6$)alkyl-$R^{B1}$, or —($C_1$-$C_6$)alkyl-Z—($C_1$-$C_6$)alkyl-Z—$R^{B1}$, provided that at least one of W and $R^4$ is hydrogen, wherein each Z is independently —O—, —N($R^z$)—, —S—, —S(O)—, or —S(O)$_2$—, wherein $R^z$ is hydrogen or $C_1$-$C_6$alkyl; and $R^{B1}$ is $R^{B2}$, $C_3$-$C_8$cycloalkyl, heterocyclyl, aryl, or heteroaryl, wherein the cycloalkyl, heterocyclyl, aryl, and heteroaryl groups are optionally substituted by 1, 2, 3, or 4 $R^{B2}$ groups, wherein each $R^{B2}$ is independently halogen, cyano, nitro, $C_1$-$C_6$ alkyl, $C_1$-$C_6$ haloalkyl, —OR, —SR, —NR$_2$, —C(O)R, —C(O)OR, —C(O)NR$_2$, —S(O)R, —S(O)$_2$R, —S(O)OR, —S(O)$_2$OR, —S(O)NR$_2$, —S(O)$_2$NR$_2$, —OC(O)R, —OC(O)OR, —OC(O)NR$_2$, —N(R)C(O)R, —N(R)C(O)OR, —N(R)C(O)NR$_2$, —N(R)S(O)R, or —N(R)S(O)$_2$R; and $R^5$ is aryl or heteroaryl, each optionally substituted with 1, 2, 3, or 4 groups which are each independently $R^{20}$, wherein each $R^{20}$ is independently halogen, cyano, —OR, —SR, —NR$_2$, —C(O)OR, —C(O)NR$_2$, —N(R)S(O)$_2$R, —C(O)R$^2$, —S(O)R, —S(O)$_2$R, —S(O)OR, —S(O)$_2$OR, —S(O)NR$_2$, —S(O)$_2$NR$_2$, —OC(O)R, —OC(O)OR, —OC(O)NR$_2$, —N(R)C(O)R, —N(R)C(O)OR, —N(R)C(O)NR$_2$, —N(R)S(O)R, $C_1$-$C_6$alkyl, $C_2$-$C_6$alkenyl, $C_2$-$C_6$alkynyl, $C_1$-$C_6$haloalkyl, $C_3$-$C_8$cycloalkyl, heterocyclyl, aryl, heteroaryl, $C_3$-$C_8$cycloalkyl($C_1$-$C_6$)alkyl, heterocyclyl($C_1$-$C_6$)alkyl, aryl($C_1$-$C_6$)alkyl, heteroaryl($C_1$-$C_6$)alkyl, —$C_1$-$C_6$alkyl-$R^{41}$, -Q-$C_1$-$C_6$alkyl-$R^{41}$, —$C_1$-$C_6$alkyl-Q-$R^{41}$, -Q-$C_1$-$C_6$alkyl-Q-$R^{41}$, —$C_1$-$C_6$alkyl-Q-($C_1$-$C_6$)alkyl-$R^{41}$, -Q($C_1$-$C_6$)alkyl-Q-($C_1$-$C_6$)alkyl-$R^{41}$, or -Q($C_1$-$C_6$)alkyl-Q-($C_1$-$C_6$)alkyl-Q$R^{41}$, wherein each Q is independently —C($R^{42}$)$_2$—, —O—, —N($R^{42}$)—, —S—, —C(O)—, —S(O)—, —S(O)$_2$—, —C(O)N($R^{42}$)—, —N($R^{42}$)C(O)—, —C(O)O—, or —OC(O)—, wherein each $R^{42}$ is independently hydrogen, $C_1$-$C_6$alkyl, or $C_1$-$C_6$haloalkyl;

$R^{41}$ is $R^{43}$, $C_1$-$C_6$ alkyl, —$C_1$-$C_6$ alkyl-$R^{43}$, $C_1$-$C_6$ haloalkyl, $C_3$-$C_8$cycloalkyl, heterocyclyl, aryl, or heteroaryl, wherein the cycloalkyl, heterocyclyl, aryl, and heteroaryl groups are optionally substituted by 1, 2, 3, or 4 $R^{43}$ groups, wherein each $R^{43}$ is independently halogen, cyano, nitro, —OR, —SR, —NR$_2$, —C(O)R, —C(O)OR, —C(O)NR$_2$, —S(O)R, —S(O)$_2$R, —S(O)OR, —S(O)$_2$OR, —S(O)NR$_2$, —S(O)$_2$NR$_2$, —OC(O)R, —OC(O)OR, —OC(O)NR$_2$, —N(R)C(O)R, —N(R)C(O)OR, —N(R)C(O)NR$_2$, —N(R)S(O)R, —N(R)S(O)$_2$R, $C_1$-$C_6$ alkyl, $C_1$-$C_6$ haloalkyl, $C_2$-$C_6$ alkenyl, $C_2$-$C_6$ alkynyl, $C_3$-$C_8$cycloalkyl, heterocyclyl, aryl, or heteroaryl, wherein the cycloalkyl, heterocyclyl, aryl, heteroaryl, are each optionally substituted with 1, 2, 3, or 4 groups which are each independently $R^{30}$ or —$C_1$-$C_6$ alkyl-$R^{30}$ wherein $R^{30}$ is halogen, cyano, nitro —OR$^{411}$, —SR$^{411}$, —N(R$^{411}$)$_2$, —C(O)OR$^{411}$, —C(O)N(R$^{411}$)$_2$, —C(O)R$^{411}$, —S(O)R$^{411}$, —S(O)$_2$R$^{411}$, —S(O)OR$^{411}$, —S(O)$_2$OR$^{411}$, —S(O)N(R$^{411}$)$_2$, —S(O)$_2$N(R$^{411}$)$_2$, —OC(O)R$^{411}$, —OC(O)OR$^{411}$, —OC(O)N(R$^{411}$)$_2$, —N(R$^{411}$)C(O)R$^{11}$, —N(R$^{411}$)C(O)OR$^{411}$, —N(R$^{411}$)C(O)N(R$^{411}$)$_2$, —N(R$^{411}$)S(O)R$^{411}$, —N(R$^{411}$)S(O)$_2$R$^{411}$, $C_1$-$C_6$ alkyl, or $C_1$-$C_6$ haloalkyl, wherein each R$^{411}$ is independently hydrogen, $C_1$-$C_6$ alkyl, $C_2$-$C_6$ alkenyl, $C_2$-$C_6$ alkynyl, $C_1$-$C_6$ haloalkyl, $C_3$-$C_8$cycloalkyl, heterocyclyl, aryl, heteroaryl, $C_3$-$C_8$cycloalkyl($C_1$-$C_6$)alkyl, heterocyclyl($C_1$-$C_6$)alkyl, aryl($C_1$-$C_6$)alkyl, or heteroaryl($C_1$-$C_6$)alkyl, or $R^{41}$ and $R^{42}$ taken together, when attached to the same carbon atom, form =$C_3$-$C_8$cycloalkyl, or =heterocyclyl, wherein the cycloalkyl and heterocyclyl are optionally substituted with 1, 2, 3, or 4 groups which are each independently halogen, cyano, nitro, —OR, —SR, —NR$_2$, —C(O)OR, —C(O)NR$_2$, —C(O)R, —S(O)R, —S(O)$_2$R, —S(O)OR, —S(O)$_2$OR, —S(O)NR$_2$, —S(O)$_2$NR$_2$, —OC(O)R, —OC(O)OR, —OC(O)NR$_2$, —N(R)C(O)R, —N(R)C(O)OR, —N(R)C(O)NR$_2$, —N(R)S(O)R, —N(R)S(O)$_2$R, $C_1$-$C_6$ alkyl, or $C_1$-$C_6$ haloalkyl;

or $R^{20}$ and $R^1$ taken together form —CH$_2$CH$_2$W—, —CH$_2$WCH$_2$—, —WCH$_2$CH$_2$—, —C(H)=C(H)—, —C(H)=C(H)W—, or —WC(H)=C(H)—, wherein W is —O—, —S—, —S(O)—, —S(O)$_2$—, or —NH—; and each R is independently hydrogen or $R^2$, wherein $R^2$ is $C_1$-$C_6$ alkyl, $C_2$-$C_6$ alkenyl, $C_2$-$C_6$ alkynyl, $C_1$-$C_6$ haloalkyl, $C_3$-$C_8$cycloalkyl, heterocyclyl, aryl, heteroaryl, $C_3$-$C_8$cycloalkyl($C_1$-$C_6$)alkyl, heterocyclyl($C_1$-$C_6$)alkyl, aryl($C_1$-$C_6$)alkyl, or heteroaryl($C_1$-$C_6$)alkyl, wherein the alkyl, cycloalkyl, heterocyclyl, aryl, heteroaryl, cycloalkylalkyl, heterocyclylalkyl, arylalkyl, and heteroarylalkyl are each optionally substituted with 1, 2, 3, or 4 groups which are each independently halogen, cyano, nitro, —$OR^{10}$, —$SR^{10}$, —$N(R^{10})_2$, —$C(O)OR^{10}$, —$C(O)N(R^{10})_2$, —$C(O)R^{10}$, —$S(O)_2R^{10}$, —$S(O)OR^{10}$, —$S(O)_2R^{10}$, —$S(O)N(R^{10})_2$, —$S(O)_2N(R^{10})_2$, —$OC(O)R^{10}$, —$OC(O)OR^{10}$, —$OC(O)N(R^{10})_2$, —$N(R^{10})C(O)R^{10}$, —$N(R^{10})C(O)OR^{10}$, —$N(R^{10})C(O)N(R^{10})_2$, —$N(R^{10})S(O)R^{10}$, —$N(R^{10})S(O)_2R^{10}$, $C_1$-$C_6$ alkyl, $C_2$-$C_6$ alkenyl, $C_2$-$C_6$ alkynyl, $C_1$-$C_6$ haloalkyl, $C_3$-$C_8$cycloalkyl, heterocyclyl, aryl, or heteroaryl, wherein each $R^{10}$ is independently hydrogen, $C_1$-$C_6$ alkyl, $C_2$-$C_6$ alkenyl, $C_2$-$C_6$ alkynyl, $C_1$-$C_6$ haloalkyl, $C_3$-$C_8$cycloalkyl, heterocyclyl, aryl, heteroaryl, $C_3$-$C_8$cycloalkyl($C_1$-$C_6$)alkyl, heterocyclyl($C_1$-$C_6$)alkyl, aryl($C_1$-$C_6$)alkyl, or hetero aryl ($C_1$-$C_6$)alkyl, provided that (i) $R^1$ is not —$(CH_2)_{3-4}$—$NH_2$, —$(CH_2)_{1-2}$—$C(O)NH_2$, —$(CH_2)_{2-3}$—$C(O)N(H)CH_3$, —$(CH_2)_{1-2}N(H)C(O)CH_3$, —$(CH_2)_2$—OH, or —$(CH_2)_3$-thiomorpholinyl; and (ii) the compound is not 4-phenyl-1H-imidazole;

4-(4-cyanophenyl)-1H-imidazole;

2-(2-(1H-imidazol-5-yl)phenoxy)ethanamine;

4-methyl-5-phenyl-1H-imidazole;

imidazo[5,1-a]isoquinoline; and 4-phenyl-1H-pyrazole.

The seventh aspect further comprises subgenera of the preceding in which the substituents are selected as any and all combinations of structural formula (XI) or (XII), $R^1$, $R^4$, and $R^5$ as defined herein, including without limitation, the following:

Structural formula XI is one of formulae (XI)-(XIf):

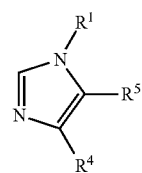
(XI)

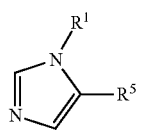
(XIa)

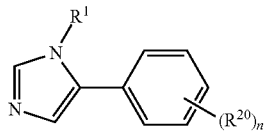
(XIb)

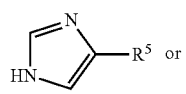
(XIc)

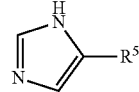
(XIc')

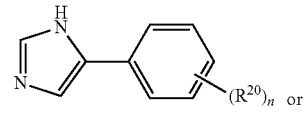
(XId)

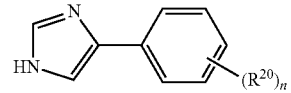
(XId')

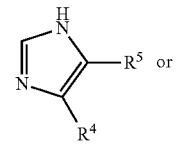
(XIe)

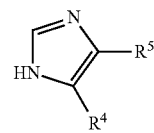
(XIe')

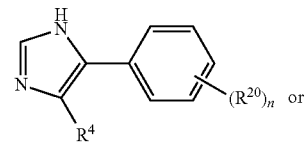
(XIf)

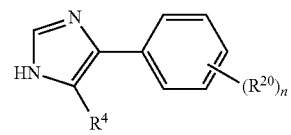
(XIf')

wherein n is 0, 1, 2, 3, 4, or 5; or n is 0, 1, or 2.

Structural Formula (XII) is One of Formulae (XII)-(XIIe):

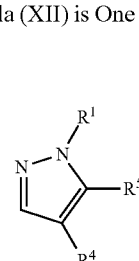
(XII)

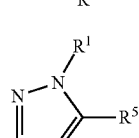
(XIIa)

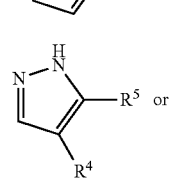
(XIIb)

-continued

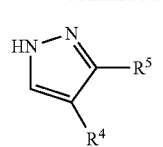 (XIIb')

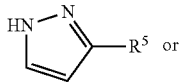 (XIIc)

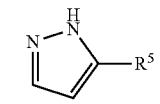 or (XIIc')

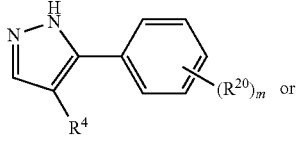 (XIId)

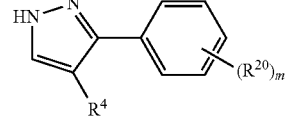 or (XIId')

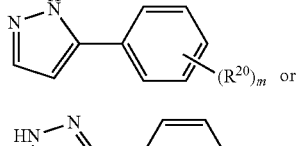 (XIIe)

or (XIIe')

wherein m is 0, 1, 2, 3, 4, or 5; or m is 0, 1, or 2.

$R^5$ is one of the following groups (7a)-(7mm):

(7a) $R^5$

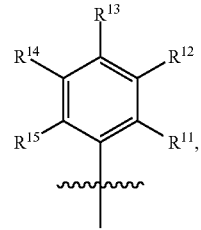

is wherein $R^{11}$, $R^{12}$ and $R^5$ are each independently hydrogen or $R^{20}$, provided at least one of $R^{11}$, $R^{12}$, $R^{13}$, $R^{14}$, and $R^{15}$ is not hydrogen.

(7b) $R^5$ is according to group (a), wherein one of $R^{11}$, $R^{12}$, $R^{13}$, $R^{14}$, and $R^{15}$ is halogen, cyano, —OR, —SR, —NR$_2$, —C(O)OR, —C(O)NR$_2$, —N(R)S(O)$_2$R, —C$_1$-C$_6$alkyl-R$^{A1}$, -Q-(C$_1$-C$_6$)alkyl-R$^{A1}$, —C$_1$-C$_6$alkyl-Q-R$^{A1}$, -Q-(C$_1$-C$_6$)alkyl-Q-R$^{A1}$, —C$_1$-C$_6$alkyl-Q-(C$_1$-C$_6$)alkyl-R$^{A1}$, -Q(C$_1$-C$_6$)alkyl-Q-(C$_1$-C$_6$)alkyl-R$^{A1}$, or -Q(C$_1$-C$_6$)alkyl-Q-(C$_1$-C$_6$)alkyl-QR$^{A1}$.

(7c) $R^5$ is according to group (7a), wherein $R^{11}$ is —OR, —SR, —NR$_2$, —C$_1$-C$_6$alkyl-R$^{A1}$, -Q-(C$_1$-C$_6$)alkyl-R$^{A1}$, —C$_1$-C$_6$alkyl-Q-R$^{A1}$, -Q-(C$_1$-C$_6$)alkyl-Q-R$^{A1}$, —C$_1$-C$_6$alkyl-Q-(C$_1$-C$_6$)alkyl-R$^{A1}$, -Q(C$_1$-C$_6$)alkyl-Q-(C$_1$-C$_6$)alkyl-R$^{A1}$, or -Q(C$_1$-C$_6$)alkyl-Q-(C$_1$-C$_6$)alkyl-QR$^{A1}$.

(7d) $R^5$ is according to group (7a), wherein $R^{12}$, $R^{13}$, $R^{14}$, and $R^{15}$ are each independently hydrogen, halogen, cyano, C$_1$-C$_6$alkyl, C$_1$-C$_6$haloalkyl, —OR, —SR, —NR$_2$, —C(O)OR, —C(O)NR$_2$, —N(R)S(O)$_2$R; and $R^{11}$ is —OR, —SR, —NR$_2$, —C$_1$-C$_6$alkyl-R$^{A1}$, -Q-(C$_1$-C$_6$)alkyl-R$^{A1}$, —C$_1$-C$_6$alkyl-Q-R$^{A1}$, -Q-(C 1-C$_6$)alkyl-Q-R$^{A1}$, —C$_1$-C$_6$alkyl-Q-(C$_1$-C$_6$)alkyl-R$^{A1}$, -Q(C$_1$-C$_6$)alkyl-Q-(C$_1$-C$_6$)alkyl-R$^{A1}$, or -Q(C$_1$-C$_6$)alkyl-Q-(C$_1$-C$_6$)alkyl-QR$^{A1}$.

(7e) $R^5$ is according to group (7a), wherein $R^{12}$, $R^{13}$, $R^{14}$, and $R^{15}$ are each independently hydrogen, fluoro, chloro, bromo, methyl, or ethyl, and $R^{11}$ is —OR, —SR, —NR$_2$, —C$_1$-C$_6$alkyl-R$^{A1}$, -Q-(C$_1$-C$_6$)alkyl-R$^{A1}$, —C$_1$-C$_6$alkyl-Q-R$^{A1}$, -Q-(C$_1$-C$_6$)alkyl-Q-R$^{A1}$, —C$_1$-C$_6$alkyl-Q-(C$_1$-C$_6$)alkyl-R$^{A1}$, -Q(C$_1$-C$_6$)alkyl-Q-(C$_1$-C$_6$)alkyl-R$^{A1}$, or -Q(C$_1$-C$_6$)alkyl-Q-(C$_1$-C$_6$)alkyl-QR$^{A1}$.

(7f) $R^5$ is

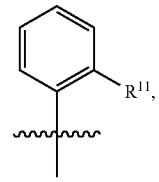

wherein $R^{11}$ is —OR, —SR, —NR$_2$, —C$_1$-C$_6$ alkyl-R$^{A1}$, -Q-(C$_1$-C$_6$)alkyl-R$^{A1}$, —C$_1$-C$_6$alkyl-Q-R$^{A1}$, -Q-(C$_1$-C$_6$)alkyl-Q-R$^{A1}$, —C$_1$-C$_6$alkyl-Q-(C$_1$-C$_6$)alkyl-R$^{A1}$, -Q(C$_1$-C$_6$)alkyl-Q-(C$_1$-C$_6$)alkyl-R$^{A1}$, or -Q(C$_1$-C$_6$)alkyl-Q-(C$_1$-C$_6$)alkyl-QR$^{A1}$.

(7g) $R^5$ is according to group (7a), wherein $R^{11}$ is —OR or —SR.

(7h) $R^5$ is according to group (7a), wherein $R^{11}$ is —OR$^{21}$ or —SR$^{21}$, wherein $R^{21}$ is hydrogen, C$_1$-C$_6$ alkyl, C$_2$-C$_6$ alkenyl, C$_3$-C$_8$cycloalkyl(C$_1$-C$_6$)alkyl, heterocyclyl(C$_1$-C$_6$)alkyl, aryl(C$_1$-C$_6$)alkyl, or heteroaryl(C$_1$-C$_6$)alkyl, wherein the cycloalkylalkyl, heterocyclylalkyl, arylalkyl, and heteroarylalkyl are each optionally substituted with 1, 2, 3, or 4 groups (e.g., 1 or 2 groups) which are each independently halogen, cyano, nitro, C$_1$-C$_6$ alkyl, C$_1$-C$_6$ haloalkyl, —OR$^{10}$, —SR$^{10}$, —N(R$^{10}$)$_2$, —C(O)OR$^{10}$, —C(O)N(R$^{10}$)$_2$, —C(O)R$^{10}$, —S(O)$_2$R$^{10}$, —S(O)$_2$OR$^{10}$, —S(O)$_2$N(R$^{10}$)$_2$, —OC(O)R$^{10}$, —OC(O)OR$^{10}$, —OC(O)N(R$^{10}$)$_2$, —N(R$^{10}$)C(O)R$^{10}$, —N(R$^{10}$)C(O)OR$^{10}$, —N(R$^{10}$)C(O)N(R$^{10}$)$_2$, —N(R$^{10}$)S(O)$_2$R$^{10}$, wherein each $R^{10}$ is independently hydrogen, C$_1$-C$_6$ alkyl, or C$_1$-C$_6$ haloalkyl.

(7i) $R^5$ is according to group (7a), wherein $R^{11}$ is —OR$^{21}$ or —SR$^{21}$, wherein $R^{21}$ is hydrogen, C$_1$-C$_6$ alkyl, C$_2$-C$_6$ alkenyl, C$_3$-C$_8$cycloalkyl(C$_1$-C$_6$)alkyl, heterocyclyl(C$_1$-C$_6$)alkyl, aryl(C$_1$-C$_6$)alkyl, or heteroaryl(C$_1$-C$_6$)alkyl.

(7j) $R^5$ is according to group (7a), wherein $R^{12}$, $R^{13}$R, $^{14}$, and $R^{15}$ are each independently hydrogen, halogen, cyano, C$_1$-C$_6$alkyl, C$_1$-C$_6$haloalkyl, —OR, —SR, —NR$_2$, —C(O)OR, —C(O)NR$_2$, —N(R)S(O)$_2$R, and $R^{11}$ is —OR or —SR.

(7k) $R^5$ is according to group (7a), wherein $R^{12}$, $R^{13}$, $R^{14}$, and $R^{15}$ are each independently hydrogen, halogen, cyano, C$_1$-C$_6$alkyl, C$_1$-C$_6$haloalkyl, —OR, —SR, —NR$_2$, —C(O)OR, —C(O)NR$_2$, —N(R)S(O)$_2$R, and $R^{11}$ is —OR$^{21}$ or —SR$^{21}$, wherein $R^{21}$ is hydrogen, C$_1$-C$_6$ alkyl, C$_2$-C$_6$ alkenyl, C$_3$-C$_8$cycloalkyl(C$_1$-C$_6$)alkyl, heterocyclyl (C$_1$-C$_6$)alkyl, aryl(C$_1$-C$_6$)alkyl, or heteroaryl(C$_1$-C$_6$)alkyl, wherein the cycloalkylalkyl, heterocyclylalkyl, arylalkyl, and heteroarylalkyl are each optionally substituted with 1, 2, 3, or 4 groups (e.g., 1 or 2 groups) which are each independently halogen, cyano, nitro, $C_1$-$C_6$ alkyl, $C_1$-$C_6$ haloalkyl, —$OR^{10}$, —$SR^{10}$, —$N(R^{10})_2$, —$C(O)OR^{10}$, —$C(O)N(R^{10})_2$, —$C(O)R^{10}$, —$S(O)_2R^{10}$, —$S(O)_2OR^{10}$, —$S(O)_2N(R^{10})_2$, —$OC(O)R^{10}$, —$OC(O)OR^{10}$, —$OC(O)N(R^{10})_2$, —$N(R^{10})C(O)R^{10}$, —$N(R^{10})C(O)OR^{10}$, —$N(R^{10})C(O)N(R^{10})_2$, —$N(R^{10})S(O)_2R^{10}$, wherein each $R^{10}$ is independently hydrogen, $C_1$-$C_6$ alkyl, or $C_1$-$C_6$ haloalkyl.

(7l) $R^5$ is according to group (7a), wherein $R^{12}$, $R^{13}$, $R^{14}$, and $R^{15}$ are each independently hydrogen, halogen, cyano, $C_1$-$C_6$alkyl, $C_1$-$C_6$haloalkyl, —OR, —SR, —$NR_2$, —C(O)OR, —C(O)$NR_2$, —N(R)S(O)$_2$R, and $R^{11}$ is —$OR^{21}$ or —$SR^{21}$, wherein $R^{21}$ is hydrogen, $C_1$-$C_6$ alkyl, $C_2$-$C_6$ alkenyl, $C_3$-$C_8$cycloalkyl($C_1$-$C_6$)alkyl, heterocyclyl($C_1$-$C_6$)alkyl, aryl($C_1$-$C_6$)alkyl, or heteroaryl($C_1$-$C_6$)alkyl.

(7m) $R^5$ is according to group (7a), wherein $R^{12}$, $R^{13}$, $R^{14}$, and $R^{15}$ are each independently hydrogen, fluoro, chloro, bromo, methyl, or ethyl, and $R^{11}$ is —OR or —SR.

(7n) $R^5$ is according to group (7a), wherein $R^{12}$, $R^{13}$, $R^{14}$, and $R^{15}$ are each independently hydrogen, fluoro, chloro, bromo, methyl, or ethyl, and $R^{11}$ is —$OR^{21}$ or —$SR^{21}$, wherein $R^{21}$ is hydrogen, $C_1$-$C_6$ alkyl, $C_2$-$C_6$ alkenyl, $C_3$-$C_8$cycloalkyl($C_1$-$C_6$)alkyl, heterocyclyl($C_1$-$C_6$)alkyl, aryl($C_1$-$C_6$)alkyl, or heteroaryl($C_1$-$C_6$)alkyl.

(7o) $R^5$ is

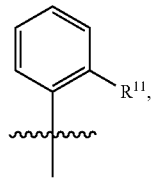

wherein $R^{11}$ is —OR or —SR.

(7p) $R^5$ is

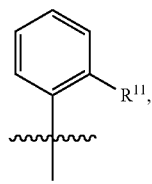

wherein $R^{11}$ is —$OR^{21}$ or —$SR^{21}$, wherein $R^{21}$ is hydrogen, $C_1$-$C_6$ alkyl, $C_2$-$C_6$ alkenyl, $C_3$-$C_8$cycloalkyl($C_1$-$C_6$) alkyl, heterocyclyl($C_1$-$C_6$)alkyl, aryl($C_1$-$C_6$)alkyl, or heteroaryl($C_1$-$C_6$)alkyl, wherein the cycloalkylalkyl, heterocyclylalkyl, arylalkyl, and heteroarylalkyl are each optionally substituted with 1, 2, 3, or 4 groups (e.g., 1 or 2 groups) which are each independently halogen, cyano, nitro, $C_1$-$C_6$ alkyl, $C_1$-$C_6$ haloalkyl, —$OR^{10}$, —$SR^{10}$, —$N(R^{10})_2$, —$C(O)OR^{10}$, —$C(O)N(R^{10})_2$, —$C(O)R^{10}$, —$S(O)_2R^{10}$, —$S(O)_2OR^{10}$, —$S(O)_2N(R^{10})_2$, —$OC(O)R^{10}$, —$OC(O)OR^{10}$, —$OC(O)N(R^{10})_2$, —$N(R^{10})C(O)R^{10}$, —$N(R^{10})C(O)OR^{10}$, —$N(R^{10})C(O)N(R^{10})_2$, —$N(R^{10})S(O)_2R^{10}$, wherein each $R^{10}$ is independently hydrogen, $C_1$-$C_6$ alkyl, or $C_1$-$C_6$ haloalkyl.

(7q) $R^5$ is

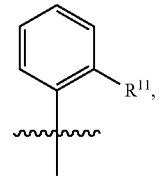

wherein $R^{11}$ is —$OR^{21}$ or —$SR^{21}$, wherein $R^{21}$ is hydrogen, $C_1$-$C_6$ alkyl, $C_2$-$C_6$ alkenyl, $C_3$-$C_8$cycloalkyl($C_1$-$C_6$) alkyl, heterocyclyl($C_1$-$C_6$)alkyl, aryl($C_1$-$C_6$)alkyl, or heteroaryl($C_1$-$C_6$)alkyl.

(7r) $R^5$ is according to group (7a), wherein $R^{11}$ is —$C_1$-$C_6$alkyl-$R^{A1}$, -Q-($C_1$-$C_6$)alkyl-$R^{A1}$, —$C_1$-$C_6$alkyl-Q-$R^{A1}$, -Q-($C_1$-$C_6$)alkyl-C($R^{A2}$)$_2$—$R^{A1}$, or —($C_1$-$C_6$)alkyl-Q-$C_1$-$C_6$ alkyl-$R^{A1}$, or -Q($C_1$-$C_6$)alkyl-C($R^{A2}$)$_2$—($C_1$-$C_6$)alkyl-Q$R^{A1}$, wherein each is Q is independently —O—, —N($R^{A2}$)—, or —S—.

(7s) $R^5$ is according to group (7a), wherein $R^{12}$, $R^{13}$, $R^{14}$, and $R^{15}$ are each independently hydrogen, halogen, cyano, $C_1$-$C_6$alkyl, $C_1$-$C_6$haloalkyl, —OR, —SR, —$NR_2$, —C(O)OR, —C(O)$NR_2$, —N(R)S(O)$_2$R, and $R^{11}$ is —$C_1$-$C_6$alkyl-$R^{A1}$, -Q-($C_1$-$C_6$)alkyl-$R^{A1}$, —$C_1$-$C_6$alkyl-Q-$R^{A1}$, -Q-($C_1$-$C_6$)alkyl-C($R^{A2}$)$_2$—$R^{A1}$ or —($C_1$-$C_6$)alkyl-Q-$C_1$-$C_6$ alkyl-$R^{A1}$, or -Q($C_1$-$C_6$)alkyl-C($R^{A2}$)$_2$—($C_1$-$C_6$)alkyl-Q$R^{A1}$, wherein each is Q is independently —O—, —N($R^{A2}$)—, or —S—.

(7t) $R^5$ is according to group (7a), wherein $R^{12}$, $R^{13}$, $R^{14}$, and $R^{15}$ are each independently hydrogen, fluoro, chloro, bromo, methyl, or ethyl, and $R^{11}$ is —$C_1$-$C_6$alkyl-$R^{A1}$, -Q-($C_1$-$C_6$)alkyl-$R^{A1}$, —$C_1$-$C_6$alkyl-Q-$R^{A1}$, -Q-($C_1$-$C_6$) alkyl-C($R^{A2}$)$_2$—$R^{A1}$, or —($C_1$-$C_6$)alkyl-Q-$C_1$-$C_6$alkyl-$R^{A1}$, or -Q($C_1$-$C_6$)alkyl-C($R^{A2}$)$_2$—($C_1$-$C_6$)alkyl-Q$R^{A1}$, wherein each is Q is independently —O—, —N($R^{A2}$)—, or —S—.

(7u) $R^5$ is

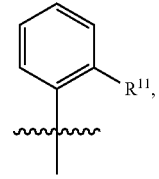

wherein $R^{11}$ is —$C_1$-$C_6$alkyl-$R^{A1}$, -Q-($C_1$-$C_6$)alkyl-$R^{A1}$, —$C_1$-$C_6$alkyl-Q-$R^{A1}$, -Q-($C_1$-$C_6$)alkyl-C($R^{A2}$)$_2$—$R^{A1}$, or —($C_1$-$C_6$)alkyl-Q-$C_1$-$C_6$ alkyl-$R^{A1}$, or -Q($C_1$-$C_6$)alkyl-C($R^{A2}$)$_2$—$C_1$-$C_6$)alkyl-Q$R^{A1}$, wherein each is Q is independently —O—, —N($R^{A2}$)—, or —S—.

(7v) $R^5$ is according to group (7a), wherein $R^{11}$ is —$C_1$-$C_6$alkyl-$R^{A1}$, —O($C_1$-$C_6$)alkyl-$R^{A1}$, —$C_1$-$C_6$alkylO$R^{A1}$, —$C_1$-$C_6$alkyl-C($R^{A2}$)$_2$—$R^{A1}$, —O($C_1$-$C_6$)alkyl-C($R^{A2}$)$_2$—$R^{A1}$, —$C_1$-$C_6$alkyl-O($C_1$-$C_6$)alkyl-$R^{A1}$, or —O($C_1$-$C_6$) alkyl-C($R^{A2}$)$_2$—($C_1$-$C_6$)alkyl-O$R^{A1}$.

(7w) $R^5$ is according to group (7a), wherein $R^{12}$, $R^{13}$, $R^{14}$, and $R^{15}$ are each independently hydrogen, halogen, cyano, $C_1$-$C_6$alkyl, $C_1$-$C_6$haloalkyl, —OR, —SR, —$NR_2$, —C(O)OR, —C(O)$NR_2$, —N(R)S(O)$_2$R, and $R^{11}$ is —$C_1$-$C_6$alkyl-$R^{A1}$, —O($C_1$-$C_6$)alkyl-$R^{A1}$, —$C_1$-$C_6$alkylO$R^{A1}$, —$C_1$-$C_6$alkyl-C($R^{A2}$)$_2$—$R^{A1}$, —O($C_1$-$C_6$)alkyl-C($R^{A2}$)$_2$—$R^{A1}$, —$C_1$-$C_6$alkyl-O($C_1$-$C_6$)alkyl-$R^{A1}$, or —O($C_1$-$C_6$) alkyl-C($R^{A2}$)$_2$—($C_1$-$C_6$)alkyl-O$R^{A1}$.

(7x) $R^5$ is according to group (7a), wherein $R^{12}$, $R^{13}$, $R^{14}$, and $R^{15}$ are each independently hydrogen, fluoro, chloro, bromo, methyl, or ethyl, and $R^{11}$ is —$C_1$-$C_6$alkyl-$R^{A1}$, —$O(C_1$-$C_6)$alkyl-$R^{A1}$, —$C_1$-$C_6$alkylO$R^{A1}$, —$C_1$-$C_6$alkyl-$C(R^{A2})_2$—$R^{A1}$, —$O(C_1$-$C_6)$alkyl-$C(R^{A2})_2$—$R^{A1}$, —$C_1$-$C_6$alkyl-$O(C_1$-$C_6)$alkyl-$R^{A1}$, or —$O(C_1$-$C_6)$alkyl-$C(R^{A2})_2$—$(C_1$-$C_6)$alkyl-O$R^{A1}$.

(7y) $R^5$ is

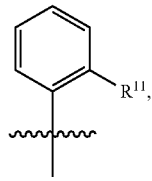

wherein $R^{11}$ is —$C_1$-$C_6$alkyl-$R^{A1}$, —$O(C_1$-$C_6)$alkyl-$R^{A1}$, —$C_1$-$C_6$alkylO$R^{A1}$, —$C_1$-$C_6$alkyl-$C(R^{A2})_2$—$R^{A1}$, —$O(C_1$-$C_6)$alkyl-$C(R^{A2})_2$—$R^{A1}$, —$C_1$-$C_6$alkyl-$O(C_1$-$C_6)$alkyl-$R^{A1}$, or —$O(C_1$-$C_6)$alkyl-$C(R^{A2})_2$—$(C_1$-$C_6)$alkyl-O$R^{A1}$.

(7z) $R^5$ is according to group (7a), wherein $R^{11}$ is —$O(C_1$-$C_6)$alkyl-$R^{A1}$, —$C_1$-$C_6$alkylO$R^{A1}$, —$C_1$-$C_6$alkyl-$C(CH_3)_2$—$R^{A1}$, —$O(C_1$-$C_6)$alkyl-$C(CH_3)_2$—$R^{A1}$, —$C_1$-$C_6$alkyl-$O(C_1$-$C_6)$alkyl-$R^{A1}$, or —$O(C_1$-$C_6)$alkyl-$C(CH_3)_2$—, —$(C_1$-$C_6)$alkyl-O$R^{A1}$.

(7aa) $R^5$ is according to group (7a), wherein $R^{12}$, $R^{13}$, $R^{14}$, and $R^{15}$ are each independently hydrogen, halogen, cyano, $C_1$-$C_6$alkyl, $C_1$-$C_6$haloalkyl, —OR, —SR, —$NR_2$, —C(O)OR, —C(O)$NR_2$, —N(R)S(O)$_2$R, and $R^{11}$ is —$O(C_1$-$C_6)$alkyl-$R^{A1}$, —$C_1$-$C_6$alkylO$R^{A1}$, —$C_1$-$C_6$alkyl-$C(CH_3)_2$—$R^{A1}$, —$O(C_1$-$C_6)$alkyl-$C(CH_3)_2$—$R^{A1}$, —$C_1$-$C_6$alkyl-$O(C_1$-$C_6)$alkyl-$R^{A1}$, or —$O(C_1$-$C_6)$alkyl-$C(CH_3)_2$—$(C_1$-$C_6)$alkyl-O$R^{A1}$.

(7bb) $R^5$ is according to group (7a), wherein $R^{12}$, $R^{13}$, $R^{14}$, and $R^{15}$ are each independently hydrogen, fluoro, chloro, bromo, methyl, or ethyl, and $R^{11}$ is —$O(C_1$-$C_6)$alkyl-$R^{A1}$, —$C_1$-$C_6$alkylO$R^{A1}$, —$C_1$-$C_6$alkyl-$C(CH_3)_2$—$R^{A1}$, —$O(C_1$-$C_6)$alkyl-$C(CH_3)_2$—$R^{A1}$, —$C_1$-$C_6$alkyl-$O(C_1$-$C_6)$alkyl-$R^{A1}$, or —$O(C_1$-$C_6)$alkyl-$C(CH_3)_2$—$(C_1$-$C_6)$alkyl-O$R^{A1}$.

(7cc) $R^5$ is

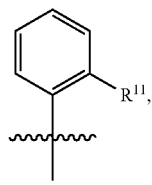

wherein $R^{11}$ is —$O(C_1$-$C_6)$alkyl-$R^{A1}$, —$C_1$-$C_6$alkylO$R^{A1}$, —$C_1$-$C_6$alkyl-$C(CH_3)_2$—$R^{A1}$, —$O(C_1$-$C_6)$alkyl-$C(CH_3)_2$—$R^{A1}$, —$C_1$-$C_6$alkyl-$O(C_1$-$C_6)$alkyl-$R^{A1}$, or —$O(C_1$-$C_6)$alkyl-$C(CH_3)_2$—$(C_1$-$C_6)$alkyl-O$R^{A1}$.

(7dd) $R^5$ is according to group (7a), wherein $R^{11}$, $R^{12}$, $R^{13}$, $R^{14}$, and $R^{15}$ are independently hydrogen, halogen, cyano, $C_1$-$C_6$alkyl, $C_1$-$C_6$haloalkyl, —OR, —SR, —$NR_2$, —C(O)OR, —C(O)$NR_2$, —N(R)S(O)$_2$R.

(7ee) $R^5$ is according to group (7a), wherein $R^{12}$, $R^{13}$, $R^{14}$, and $R^{15}$ are each independently hydrogen or $R^{20}$, wherein at least one of $R^{12}$, $R^{13}$, $R^{14}$, and $R^{15}$ is fluoro, chloro, bromo, methyl, or ethyl, and $R^{11}$ is —OH, —OCH$_3$, or —SH.

(7ff) $R^5$ is according to group (7a), wherein $R^{12}$, $R^{13}$, $R^{14}$, and $R^{15}$ are each independently hydrogen, fluoro, chloro, bromo, methyl, or ethyl, and $R^{11}$ is —OH, —OCH$_3$, or —SH.

(7gg) $R^5$ is

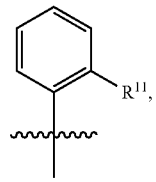

wherein $R^{11}$ is —OH, —OCH$_3$, or —SH.

(7hh) $R^5$ is heteroaryl optionally substituted with 1, 2, 3, or 4 groups (e.g., 1 or 2 groups) which are each independently $R^{20}$.

(7ii) $R^5$ is benzothiophenyl, pyrrolopyridinyl, imidazopyridinyl, quinolinyl, isoquinolinyl, naphthyridinyl, indolyl, indolinyl, benzothiadiazolyl, dihydrobenzodioxinyl, tetrahydropyrimidinyl, pyridinyl, pyrimidinyl, thienyl, or isoxazolyl, each optionally with 1, 2, 3, or 4 groups (e.g., 1 or 2 groups) which are each independently $R^{20}$.

(7jj) $R^5$ is benzo[b]thiophen-3-yl, 1H-pyrrolo[2,3-b]pyridin-3-yl, 1H-pyrrolo[2,3-b]pyridin-5-yl, 7-methylimidazo[1,2-a]pyridin-6-yl, quinolin-8-yl, 7-chloroquinolin-4-yl, 2,8-bis(trifluoromethyl)quinolin-4-yl, 5-chloro-8-hydroxyquinolin-7-yl, isoquinolin-4-yl, isoquinolin-5-yl, 2-carboxy-1,6-naphthyridin-8-yl, 1H-indol-7-yl, 1H-indol-6-yl, 1H-indol-5-yl, 9H-purin-6-yl, 2-oxo-2,3-dihydro-1H-imidazo[4,5-b]pyridin-6-yl, 2,3-dioxoindolin-5-yl, 2,3-dioxoindolin-7-yl, benzo[c][1,2,5]thiadiazol-4-yl, 2,3-dihydrobenzo[b][1,4]dioxin-6-yl, 1,3-dimethyl-2,4-dioxo-1,2,3,4,-tetrahydropyrimidin-5-yl, 2-morpholinopyridin-3-yl, 4-hydroxybiphenyl-3-yl, 2-hydroxypyridin-3-yl, 2,5-dichlorothiophen-3-yl or 3,5-dimethylisoxazol-4-yl.

(7kk) $R^5$ is according to group (7a), wherein $R^{11}$ and $R^1$ taken together form —$CH_2CH_2W$—, —$CH_2WCH_2$—, —$WCH_2CH_2$—, —C(H)=C(H)—, —C(H)=C(H)W—, or —WC(H)=C(H)—, wherein W is —O—, —S—, —S(O)—, —S(O)$_2$—, or —NH—.

(7ll) $R^5$ is according to group (7a), wherein $R^{12}$, $R^{13}$, $R^{14}$, and $R^{15}$ are each independently hydrogen, halogen, cyano, $C_1$-$C_6$alkyl, $C_1$-$C_6$haloalkyl, —OR, —SR, —$NR_2$, —C(O)OR, —C(O)$NR_2$, —N(R)S(O)$_2$R, and $R^{11}$ and $R^1$ taken together form —$CH_2CH_2W$—, —$CH_2WCH_2$—, —$WCH_2CH_2$—, —C(H)=C(H)—, —C(H)=C(H)W—, or —WC(H)=C(H)—, wherein W is —O—, —S—, —S(O)—, —S(O)$_2$—, or —NH—.

(7mm) $R^5$ is according to group (7a), wherein $R^{12}$, $R^{13}$, $R^{14}$, and $R^{15}$ are each independently hydrogen, fluoro, chloro, bromo, methyl, or ethyl, and $R^{11}$ and $R^1$ taken together form —$CH_2CH_2W$—, —$CH_2WCH_2$—, —$WCH_2CH_2$—, —C(H)=C(H)—, —C(H)=C(H)W—, or —WC(H)=C(H)—, wherein W is —O—, —S—, —S(O)—, —S(O)$_2$—, or —NH—.

$R^4$ is Hydrogen and $R^1$ is one of the following groups (7nn)-(7iii):

(7nn) $R^1$ is hydrogen, $C_1$-$C_6$alkyl, or —$(C_1$-$C_6)$alkyl-$R^{B1}$ wherein $R^{B1}$ is $R^{B2}$, $C_3$-$C_8$cycloalkyl, heterocyclyl, aryl, or heteroaryl, wherein the cycloalkyl, heterocyclyl, aryl, and heteroaryl groups are optionally substituted by 1, 2, 3, or 4 $R^{B2}$ groups (e.g., 1 or 2 groups).

(7oo) $R^1$ is hydrogen or $C_1$-$C_6$alkyl.

(7pp) $R^1$ is neohexyl.

(7qq) $R^1$ is —($C_1$-$C_6$)alkyl-$R^{B2}$.

(7rr) $R^1$ is —($C_1$-$C_6$)alkyl-$R^{B2}$, wherein $R^{B2}$ is —OR, —SR, —NR$_2$, —C(O)R, —C(O)OR, —C(O)NR$_2$, —OC(O)R, —OC(O)OR, —OC(O)NR$_2$, —N(R)C(O)R, —N(R)C(O)OR, or —N(R)C(O)NR$_2$.

(7ss) $R^1$ is —($C_1$-$C_6$)alkyl-$R^{B2}$, wherein $R^{B2}$ is —OR$^{22}$, —SR$^{22}$, —N(R$^{22}$)$_2$, —C(O)R$^{22}$, —C(O)OR$^{22}$, —C(O)N(R$^{22}$)$_2$, —OC(O)R$^{22}$, —OC(O)OR$^{22}$, —OC(O)N(R$^{22}$)$_2$, —N(R$^{22}$)C(O)R$^{22}$, —N(R$^{22}$)C(O)OR$^{22}$, or —N(R$^{22}$)C(O)N(R$^{22}$)$_2$, wherein each $R^{22}$ is independently hydrogen or $C_1$-$C_6$ alkyl.

(7tt) $R^1$ is —($C_1$-$C_6$)alkyl-$R^{B1}$ wherein $R^{B1}$ is $C_3$-$C_8$cycloalkyl, heterocyclyl, aryl, or heteroaryl, wherein the cycloalkyl, heterocyclyl, aryl, and heteroaryl groups are optionally substituted by 1, 2, 3, or 4 $R^{B2}$ groups (e.g., 1 or 2 $R^{B2}$ groups).

(7uu) $R^1$ is —($C_1$-$C_4$)alkyl-$R^{B1}$ wherein $R^{B1}$ is $C_3$-$C_8$cycloalkyl, heterocyclyl, aryl, or heteroaryl, wherein the cycloalkyl, heterocyclyl, aryl, and heteroaryl groups are optionally substituted by 1, 2, 3, or 4 $R^{B2}$ groups (e.g., 1 or 2 $R^{B2}$ groups).

(7vv) $R^1$ is —($C_1$-$C_6$)alkyl-$R^{B1}$ wherein $R^{B1}$ is phenyl optionally substituted by 1, 2, 3, or 4 $R^{B2}$ groups (e.g., 1 or 2 $R^{B2}$ groups).

(7ww) $R^1$ is —($C_1$-$C_4$)alkyl-$R^{B1}$ wherein $R^{B1}$ is phenyl optionally substituted by 1, 2, 3, or 4 $R^{B2}$ groups (e.g., 1 or 2 $R^{B2}$ groups).

(7xx) $R^1$ is —($C_1$-$C_2$)alkyl-$R^{B1}$ wherein $R^{B1}$ is phenyl optionally substituted by 1, 2, 3, or 4 $R^{B2}$ groups (e.g., 1 or 2 $R^{B2}$ groups).

(7yy) $R^1$ is —CH$_2$—$R^{B1}$ wherein $R^{B1}$ is phenyl optionally substituted by 1, 2, 3, or 4 $R^{B2}$ groups (e.g., 1 or 2 $R^{B2}$ groups).

(7zz) $R^1$ is —CH$_2$—$R^{B1}$ wherein $R^{B1}$ is phenyl optionally substituted by one $R^{B2}$ group.

(7aaa) $R^1$ is —($C_1$-$C_6$)alkyl-$R^{B1}$ wherein $R^{B1}$ is phenyl optionally substituted by 1, 2, 3, or 4 $R^{B2}$ groups (e.g., 1 or 2 $R^{B2}$ groups), wherein each $R^{B2}$ is independently halogen, cyano, nitro, —OR$^{B20}$, —SR$^{B20}$, —N(R$^{B20}$)$_2$, $C_1$-$C_6$ alkyl, or $C_1$-$C_6$ haloalkyl, wherein $R^{B20}$ is hydrogen or $C_1$-$C_6$ alkyl.

(7bbb) $R^1$ is —($C_1$-$C_6$)alkyl-$R^{B1}$ wherein $R^{B1}$ is phenyl optionally substituted by one $R^{B2}$ group, wherein $R^{B2}$ is halogen, cyano, nitro, —OR$^{B20}$, —SR$^{B20}$, —N(R$^{B20}$)$_2$, $C_1$-$C_6$ alkyl, or $C_1$-$C_6$ haloalkyl, wherein $R^{B20}$ is hydrogen or $C_1$-$C_6$ alkyl.

(7ccc) $R^1$ is —($C_1$-$C_4$)alkyl-$R^{B1}$ wherein $R^{B1}$ is phenyl optionally substituted by one $R^{B2}$ groups (e.g., 1 or 2 $R^{B2}$ groups), wherein each $R^{B2}$ is independently halogen, cyano, nitro, —OR$^{B20}$, —SR$^{B20}$, —N(R$^{B20}$)$_2$, $C_1$-$C_6$ alkyl, or $C_1$-$C_6$ haloalkyl, wherein $R^{B20}$ is hydrogen or $C_1$-$C_6$ alkyl.

(7ddd) $R^1$ is —($C_1$-$C_4$)alkyl-$R^{B1}$ wherein $R^{B1}$ is phenyl optionally substituted by one $R^{B2}$ group, wherein $R^{B2}$ is halogen, cyano, nitro, —OR$^{B20}$, —SR$^{B20}$, —N(R$^{B20}$)$_2$, $C_1$-$C_6$ alkyl, or $C_1$-$C_6$ haloalkyl, wherein $R^{B20}$ is hydrogen or $C_1$-$C_6$ alkyl.

(7eee) $R^1$ is —($C_1$-$C_2$)alkyl-$R^{B1}$ wherein $R^{B1}$ is phenyl optionally substituted by 1, 2, 3, or 4 $R^{B2}$ groups (e.g., 1 or 2 $R^{B2}$ groups), wherein each $R^{B2}$ is independently halogen, cyano, nitro, —OR$^{B20}$, —SR$^{B20}$, —N(R$^{B20}$)$_2$, $C_1$-$C_6$ alkyl, or $C_1$-$C_6$ haloalkyl, wherein $R^{B20}$ is hydrogen or $C_1$-$C_6$ alkyl.

(7fff) $R^1$ is —($C_1$-$C_2$)alkyl-$R^{B1}$ wherein $R^{B1}$ is phenyl optionally substituted by one $R^{B2}$ group, wherein $R^{B2}$ is halogen, cyano, nitro, —OR$^{B20}$, —SR$^{B20}$, —N(R$^{B20}$)$_2$, $C_1$-$C_6$ alkyl, or $C_1$-$C_6$ haloalkyl, wherein $R^{B20}$ is hydrogen or $C_1$-$C_6$ alkyl.

(7ggg) $R^1$ is —(CH$_2$)—$R^{B1}$ wherein $R^{B1}$ is phenyl optionally substituted by 1, 2, 3, or 4 $R^{B2}$ groups (e.g., 1 or 2 $R^{B2}$ groups), wherein each $R^{B2}$ is independently halogen, cyano, nitro, —OR$^{B20}$, —SR$^{B20}$, —N(R$^{B20}$)$_2$, $C_1$-$C_6$ alkyl, or $C_1$-$C_6$ haloalkyl, wherein $R^{B20}$ is hydrogen or $C_1$-$C_6$ alkyl.

(7hhh) $R^1$ is —(CH$_2$)—$R^{B1}$ wherein $R^{B1}$ is phenyl optionally substituted by one $R^{B2}$ group, wherein $R^{B2}$ is halogen, cyano, nitro, —OR$^{B20}$, —SR$^{B20}$, —N(R$^{B20}$)$_2$, $C_1$-$C_6$ alkyl, or $C_1$-$C_6$ haloalkyl, wherein $R^{B20}$ is hydrogen or $C_1$-$C_6$ alkyl.

(7iii) $R^{20}$ and $R^1$ taken together form —CH$_2$CH$_2$W—, —CH$_2$WCH$_2$—, —WCH$_2$CH$_2$—, —C(H)=C(H)—, —C(H)=C(H)W—, or —WC(H)=C(H)—, wherein W is —O—, —S—, —S(O)—, —S(O)$_2$—, or —NH—.

$R^1$ is Hydrogen and $R^4$ is one of the following groups (7111i)-(7dddd):

(7jjj) $R^4$ is hydrogen, $C_1$-$C_6$alkyl, or —($C_1$-$C_6$)alkyl-$R^{B1}$ wherein $R^{B1}$ is $R^{B2}$, $C_3$-$C_8$cycloalkyl, heterocyclyl, aryl, or heteroaryl, wherein the cycloalkyl, heterocyclyl, aryl, and heteroaryl groups are optionally substituted by 1, 2, 3, or 4 $R^{B2}$ groups.

(7kkk) $R^4$ is hydrogen or $C_1$-$C_6$alkyl.

(7lll) $R^4$ is neohexyl.

(7mmm) $R^4$ is —($C_1$-$C_6$)alkyl-$R^{B2}$.

(7nnn) $R^4$ is —($C_1$-$C_6$)alkyl-$R^{B2}$, wherein $R^{B2}$ is —OR, —SR, —NR$_2$, —C(O)R, —C(O)OR, —C(O)NR$_2$, —OC(O)R, —OC(O)OR, —OC(O)NR$_2$, —N(R)C(O)R, —N(R)C(O)OR, or —N(R)C(O)NR$_2$.

(7ooo) $R^4$ is —($C_1$-$C_6$)alkyl-$R^{B2}$, wherein RB2 is —OR$^{22}$, —SR$^{22}$, —N(R$^{22}$)$_2$, —C(O)R$^{22}$, C(O)OR$^{22}$, —C(O)N(R$^{22}$)$_2$, —OC(O)R$^{22}$, —OC(O)OR$^{22}$, —OC(O)N(R$^{22}$)$_2$, —N(R$^{22}$)C(O)R$^{22}$, —N(R$^{22}$)C(O)OR$^{22}$, or —N(R$^{22}$)C(O)N(R$^{22}$)$_2$, wherein each $R^{22}$ is independently hydrogen or $C_1$-$C_6$ alkyl.

(7ppp) $R^4$ is —($C_1$-$C_6$)alkyl-$R^{B1}$ wherein $R^{B1}$ is $C_3$-$C_8$cycloalkyl, heterocyclyl, aryl, or heteroaryl, wherein the cycloalkyl, heterocyclyl, aryl, and heteroaryl groups are optionally substituted by 1, 2, 3, or 4 $R^{B2}$ groups (e.g., 1 or 2 $R^{B2}$ groups).

(7qqq) $R^1$ is —($C_1$-$C_4$)alkyl-$R^{B1}$ wherein $R^{B1}$ is $C_3$-$C_8$cycloalkyl, heterocyclyl, aryl, or heteroaryl, wherein the cycloalkyl, heterocyclyl, aryl, and heteroaryl groups are optionally substituted by 1, 2, 3, or 4 $R^{B2}$ groups (e.g., 1 or 2 $R^{B2}$ groups).

(7rrr) $R^4$ is —($C_1$-$C_6$)alkyl-$R^{B1}$ wherein $R^{B1}$ is phenyl optionally substituted by 1, 2, 3, or 4 $R^{B2}$ groups (e.g., 1 or 2 $R^{B2}$ groups).

(7sss) $R^4$ is —($C_1$-$C_4$)alkyl-$R^{B1}$ wherein $R^{B1}$ is phenyl optionally substituted by 1, 2, 3, or 4 $R^{B2}$ groups (e.g., 1 or 2 $R^{B2}$ groups).

(7ttt) $R^4$ is —($C_1$-$C_2$)alkyl-$R^{B1}$ wherein $R^{B1}$ is phenyl optionally substituted by 1, 2, 3, or 4 $R^{B2}$ groups (e.g., 1 or 2 $R^{B2}$ groups).

(7uuu) $R^4$ is —CH$_2$—$R^{B1}$ wherein $R^{B1}$ is phenyl optionally substituted by 1, 2, 3, or 4 $R^{B2}$ groups (e.g., 1 or 2 $R^{B2}$ groups).

(7vvv) $R^4$ is —CH$_2$—$R^{B1}$ wherein $R^{B1}$ is phenyl optionally substituted by one $R^{B2}$ group.

(7www) $R^4$ is —($C_1$-$C_6$)alkyl-$R^{B1}$ wherein $R^{B1}$ is phenyl optionally substituted by 1, 2, 3, or 4 $R^{B2}$ groups (e.g., 1 or 2 $R^{B2}$ groups), wherein each $R^{B2}$ is independently halogen, cyano, nitro, —OR$^{B20}$, —SR$^{B20}$, —N(R$^{B20}$)$_2$, C$_1$-C$_6$ alkyl, or C$_1$-C$_6$ haloalkyl, wherein R$^{B20}$ is hydrogen or C$_1$-C$_6$ alkyl.

(7xxx) R$^4$ is —(C$_1$-C$_6$)alkyl-R$^{B1}$ wherein R$^{B1}$ is phenyl optionally substituted by one R$^{B2}$ group, wherein R$^{B2}$ is halogen, cyano, nitro, —OR$^{B20}$, —SR$^{B20}$, —N(R$^{B20}$)$_2$, C$_1$-C$_6$ alkyl, or C$_1$-C$_6$ haloalkyl, wherein R$^{B20}$ is hydrogen or C$_1$-C$_6$ alkyl.

(7yyy) R$^4$ is —(C$_1$-C$_4$)alkyl-R$^{B1}$ wherein R$^{B1}$ is phenyl optionally substituted by one R$^{B2}$ groups (e.g., 1 or 2 R$^{B2}$ groups), wherein each R$^{B2}$ is independently halogen, cyano, nitro, —OR$^{B20}$, —SR$^{B20}$, —N(R$^{B20}$)$_2$, C$_1$-C$_6$ alkyl, or C$_1$-C$_6$ haloalkyl, wherein R$^{B20}$ is hydrogen or C$_1$-C$_6$ alkyl.

(7zzz) R$^4$ is —(C$_1$-C$_4$)alkyl-R$^{B1}$ wherein R$^{B1}$ is phenyl optionally substituted by one R$^{B2}$ group, wherein R$^{B2}$ is halogen, cyano, nitro, —OR$^{B20}$, —SR$^{B20}$, —N(R$^{B20}$)$_2$, C$_1$-C$_6$ alkyl, or C$_1$-C$_6$ haloalkyl, wherein R$^{B20}$ is hydrogen or C$_1$-C$_6$ alkyl.

(7aaaa) R$^4$ is —(C$_1$-C$_2$)alkyl-R$^{B1}$ wherein R$^{B1}$ is phenyl optionally substituted by 1, 2, 3, or 4 R$^{B2}$ groups (e.g., 1 or 2 R$^{B2}$ groups), wherein each R$^{B2}$ is independently halogen, cyano, nitro, —OR$_{B20}$, —SR$^{B20}$, —N(R$^{B20}$)$_2$, C$_1$-C$_6$ alkyl, or C$_1$-C$_6$ haloalkyl, wherein R$^{B20}$ is hydrogen or C$_1$-C$_6$ alkyl.

(7bbbb) R$^4$ is —(C$_1$-C$_2$)alkyl-R$^{B1}$ wherein R$^{B1}$ is phenyl optionally substituted by one R$^{B2}$ group, wherein R$^{B2}$ is halogen, cyano, nitro, —OR$^{B20}$, —SR$^{B20}$, —N(R$^{B20}$)$_2$, C$_1$-C$_6$ alkyl, or C$_1$-C$_6$ haloalkyl, wherein R$^{B20}$ is hydrogen or C$_1$-C$_6$ alkyl.

(7cccc) R$^4$ is —(CH$_2$)—R$^{B1}$ wherein R$^{B1}$ is phenyl optionally substituted by 1, 2, 3, or 4 R$^{B2}$ groups (e.g., 1 or 2 R$^{B2}$ groups), wherein each R$^{B2}$ is independently halogen, cyano, nitro, —OR$^{B20}$, —SR$^{B20}$, —N(R$^{B20}$)$_2$, C$_1$-C$_6$ alkyl, or C$_1$-C$_6$ haloalkyl, wherein R$^{B20}$ is hydrogen or C$_1$-C$_6$ alkyl.

(7dddd) R$^4$ is —(CH$_2$)—R$^{B1}$ wherein R$^{B1}$ is phenyl optionally substituted by one R$^{B2}$ group, wherein R$^{B2}$ is halogen, cyano, nitro, —OR$^{B20}$, —SR$^{B20}$, —N(R$^{B20}$)$_2$, C$_1$-C$_6$ alkyl, or C$_1$-C$_6$ haloalkyl, wherein R$^{B20}$ is hydrogen or C$_1$-C$_6$ alkyl.

In another embodiment of the seventh aspect, the compound according to formula (XI) or (XII) is a compound in Table 1 or a pharmaceutically acceptable salt thereof.

In another embodiment of the seventh aspect, the compound according to formula (XI) or (XII) is a compound in Table 2 or a pharmaceutically acceptable salt thereof.

In another embodiment of the seventh aspect, the compound according to formula (XI) or (XII) is a compound in Table 3 or a pharmaceutically acceptable salt thereof.

In another embodiment of the seventh aspect, the compound according to formula (XI) or (XII) is a compound in Table 4 or a pharmaceutically acceptable salt thereof.

In another embodiment of the seventh aspect, the compound according to formula (XI) or (XII) is a compound in Table 5 or a pharmaceutically acceptable salt thereof.

In another embodiment of the seventh aspect, the compound according to formula (XI) or (XII) is a compound in Table 6 or a pharmaceutically acceptable salt thereof.

TABLE 6

| # | Structure | Name |
| --- | --- | --- |
| 81 | 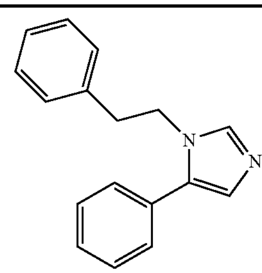 | 1-phenethyl-5-phenyl-1H-imidazole; |
| 94 | 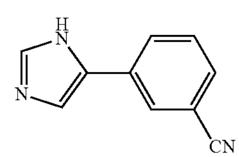 [SMILES: N#Cc1cccc(-c2cnc[nH]2)c1] | 3-(1H-imidazol-5-yl)benzonitrile; |
| 115 | 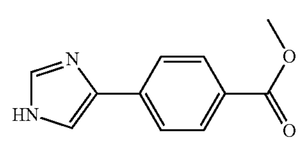 | methyl 4-(1H-imidazol-4-yl)benzoate; or |
| 118 | 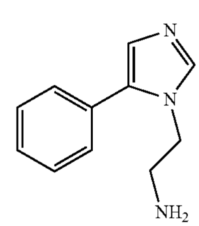 [SMILES: NCCn1cncc1-c1ccccc1] | 2-(5-phenyl-1H-imidazol-1-yl)ethanamine; |

TABLE 6-continued

| # | Structure | Name |
|---|---|---|
| 119 | 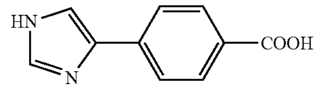 | 4-(1H-imidazol-4-yl)benzoic acid; |
| 122 | 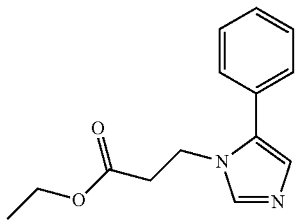 [SMILES: CCOC(=O)CCn1cncc1-c1ccccc1] | ethyl 3-(5-phenyl-1H-imidazol-1-yl)propanoate; |
| 123 | 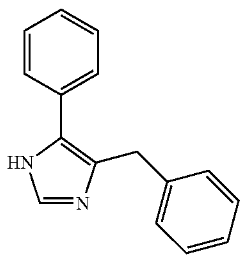 [SMILES: c1ccc(Cc2nc[nH]c2-c2ccccc2)cc1] | 4-benzyl-5-phenyl-1H-imidazole; |
| 126 | 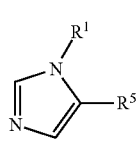 | 4-phenethyl-5-phenyl-1H-imidazole; or | or a pharmaceutically acceptable salt thereof.

In a eighth aspect, the invention provides methods for treating indoleamine 2,3-dioxygenase (IDO) mediated immunosuppression in a subject in need thereof, comprising administering an effective indoleamine 2,3-dioxygenase inhibiting amount of compound according to formula (III), and any embodiment thereof, as described above, or a compound according to formula (XIII), (XIII)

or a pharmaceutically acceptable salt thereof, wherein $R^1$ is —$C_1$-$C_6$ alkyl, —$C_1$-$C_6$ haloalkyl, or —($C_1$-$C_6$) alkyl-$R^{B1}$, wherein $R^{B1}$ is $R^{B2}$, $C_3$-$C_8$cycloalkyl, heterocyclyl, aryl, or heteroaryl, wherein the cycloalkyl, heterocyclyl, aryl, and heteroaryl groups are optionally substituted by 1, 2, 3, or 4 $R^{B2}$ groups, wherein each $R^{B2}$ is independently halogen, cyano, nitro, $C_1$-$C_6$ alkyl, $C_1$-$C_6$ haloalkyl, —OR, —SR, —$NR_2$, —C(O)R, —C(O)OR, —C(O)$NR_2$, —S(O)R, —S(O)$_2$R, —S(O)OR, —S(O)$_2$OR, —S(O)$NR_2$, —S(O)$_2NR_2$, —OC(O)R, —OC(O)OR, —OC(O)$NR_2$, —N(R)C(O)R, —N(R)C(O)OR, —N(R)C(O)$NR_2$, —N(R)S(O)R, or —N(R)S(O)$_2$R, and $R^5$ is aryl or heteroaryl, each optionally substituted with 1, 2, 3, or 4 groups which are each independently $R^{20}$, wherein each $R^{20}$ is independently halogen, cyano, —OR, —SR, —$NR_2$, —C(O)OR, —C(O)$NR_2$, —N(R)S(O)$_2$R, —C(O)$R^2$, —S(O)R, —S(O)$_2$R, —S(O)OR, —S(O)$_2$OR, —S(O)$NR_2$, —S(O)$_2NR_2$, —OC(O)R, —OC(O)OR, —OC(O)$NR_2$, —N(R)C(O)R, —N(R)C(O)OR, —N(R)C(O)$NR_2$, —N(R)S(O)R, $C_1$-$C_6$alkyl, $C_2$-$C_6$alkenyl, $C_2$-$C_6$alkynyl, $C_1$-$C_6$haloalkyl, $C_3$-$C_8$cycloalkyl, heterocyclyl, aryl, heteroaryl, $C_3$-$C_8$cycloalkyl($C_1$-$C_6$)alkyl, heterocyclyl($C_1$-$C_6$)alkyl, aryl($C_1$-$C_6$)alkyl, heteroaryl($C_1$-$C_6$)alkyl, —$C_1$-$C_6$alkyl-$R^{A1}$, -Q-($C_1$-$C_6$)alkyl-$R^{A1}$, —$C_1$-$C_6$alkyl-Q-$R^{A1}$, -Q-($C_1$-$C_6$)alkyl-Q-$R^{A1}$, —$C_1$-$C_6$alkyl-Q-($C_1$-$C_6$)alkyl-$R^{A1}$, -Q($C_1$-$C_6$)alkyl-Q-($C_1$-$C_6$)alkyl-$R^{A1}$, or -Q($C_1$-$C_6$)alkyl-Q-($C_1$-$C_6$)alkyl-Q$R^{A1}$, wherein each Q is independently —$C(R^{A2})_2$—, —O—, —$N(R^{A2})$—, —S—, —C(O)—, —S(O)—, —S(O)$_2$—, —C(O)$N(R^{A2})$—, —$N(R^{A2})C(O)$—, —C(O)O—, or —OC(O)—, wherein each $R^{A2}$ is independently hydrogen, $C_1$-$C_6$alkyl, or $C_1$-$C_6$haloalkyl;

$R^{A1}$ is $R^{A3}$, $C_1$-$C_6$ alkyl, —$C_1$-$C_6$ alkyl-$R^{A3}$, $C_1$-$C_6$ haloalkyl, $C_3$-$C_8$cycloalkyl, heterocyclyl, aryl, or heteroaryl, wherein the cycloalkyl, heterocyclyl, aryl, and heteroaryl groups are optionally substituted by 1, 2, 3, or 4 $R^{A3}$ groups, wherein each $R^{A3}$ is independently halogen, cyano, nitro, —OR, —SR, —$NR_2$, —C(O)R, —C(O)OR, —C(O)$NR_2$, —S(O)R, —S(O)$_2$R, —S(O)OR, —S(O)$_2$OR, —S(O)$NR_2$, —S(O)$_2NR_2$, —OC(O)R, —OC(O)OR, —OC(O)$NR_2$, —N(R)C(O)

R, —N(R)C(O)OR, —N(R)C(O)NR$_2$, —N(R)S(O)R, —N(R)S(O)$_2$R, C$_1$-C$_6$ alkyl, C$_1$-C$_6$ haloalkyl, C$_2$-C$_6$ alkenyl, C$_2$-C$_6$ alkynyl, C$_3$-C$_8$cycloalkyl, heterocyclyl, aryl, or heteroaryl, wherein the cycloalkyl, heterocyclyl, aryl, heteroaryl, areeach optionally substituted with 1, 2, 3, or 4 groups which are each independently halogen, cyano, nitro, —OR$^{A11}$, —SR$^{A11}$, —N(R$^{A11}$)$_2$, —C(O)OR$^{A11}$, —C(O)N(R$^{A11}$)$_2$, —C(O)R$^{11}$, —S(O)R$^{A11}$, —S(O)$_2$R$^{A11}$, —S(O)OR$^{A11}$, —S(O)$_2$OR$^{A11}$, —S(O)N(R$^{A11}$)$_2$, —S(O)$_2$N(R$^{A11}$)$_2$, —OC(O)R$^{A11}$, —OC(O)OR$^{A11}$, —OC(O)N(R$^{A11}$)$_2$, —N(R$^{A11}$)C(O)R$^{A11}$, —N(R$^{A11}$)C(O)OR$^{A11}$, —N(R$^{A11}$)C(O)N(R$^{A11}$)$_2$, —N(R$^{A11}$)S(O)R$^{A11}$, —N(R$^{A11}$)S(O)$_2$R$^{A11}$, C$_1$-C$_6$ alkyl, or C$_1$-C$_6$ haloalkyl, wherein each R$^{A11}$ is independently hydrogen, C$_1$-C$_6$ alkyl, C$_2$-C$_6$ alkenyl, C$_2$-C$_6$ alkynyl, C$_1$-C$_6$ haloalkyl, C$_3$-C$_8$cycloalkyl, heterocyclyl, aryl, heteroaryl, C$_3$-C$_8$cycloalkyl(C$_1$-C$_6$)alkyl, heterocyclyl(C$_1$-C$_6$)alkyl, aryl(C$_1$-C$_6$)alkyl, or heteroaryl(C$_1$-C$_6$)alkyl;

or R$^{A1}$ and R$^{A2}$ taken together, when attached to the same carbon atom, form =C$_3$-C$_8$cycloalkyl, or =heterocyclyl, wherein the cycloalkyl and heterocyclyl are optionally substituted with 1, 2, 3, or 4 groups which are each independently halogen, cyano, nitro, —OR, —SR, —NR$_2$, —C(O)OR, —C(O)NR$_2$, —C(O)R, —S(O)R, —S(O)$_2$R, —S(O)OR, —S(O)$_2$OR, —S(O)NR$_2$, —S(O)$_2$NR$_2$, —OC(O)R, —OC(O)OR, —OC(O)NR$_2$, —N(R)C(O)R, —N(R)C(O)OR, —N(R)C(O)NR$_2$, —N(R)S(O)R, —N(R)S(O)$_2$R, C$_1$-C$_6$ alkyl, or C$_1$-C$_6$ haloalkyl;

or R$^{20}$ and R$^1$ taken together form —CH$_2$CH$_2$W—, —CH$_2$WCH$_2$—, —WCH$_2$CH$_2$, —C(H)=C(H)—, —C(H)=C(H)W—, or —WC(H)=C(H)—, wherein W is —O—, —S—, —S(O)—, —S(O)$_2$-, or —NH—; and each R is independently hydrogen or R$^2$, wherein R$^2$ is C$_1$-C$_6$ alkyl, C$_2$-C$_6$ alkenyl, C$_2$-C$_6$ alkynyl, C$_1$-C$_6$ haloalkyl, C$_3$-C$_8$cycloalkyl, heterocyclyl, aryl, heteroaryl, C$_3$-C$_8$cycloalkyl(C$_1$-C$_6$)alkyl, heterocyclyl(C$_1$-C$_6$)alkyl, aryl(C$_1$-C$_6$)alkyl, or heteroaryl(C$_1$-C$_6$)alkyl, wherein the alkyl, C$_3$-C$_8$cycloalkyl, heterocyclyl, aryl, heteroaryl, cycloalkylalkyl, heterocyclylalkyl, arylalkyl, and heteroarylalkyl are each optionally substituted with 1, 2, 3, or 4 groups which are each independently halogen, cyano, nitro, —OR$^{10}$, —SR$^{10}$, —N(R$^1$)$_2$, —C(O)OR$^{10}$, —C(O)N(R$^{10}$)$_2$, —C(O)R$^{10}$, —S(O)R$^{10}$, —S(O)$_2$R$^{10}$, —S(O)OR$^{10}$, —S(O)$_2$OR$^{10}$, —S(O)N(R$^{10}$)$_2$, —S(O)$_2$N(R$^{10}$)$_2$, —OC(O)R$^{10}$, —OC(O)OR$^{10}$, —OC(O)N(R$^{10}$)$_2$, —N(R$^{10}$)C(O)R$^{10}$, —N(R$^{10}$)C(O)OR$^{10}$)$_2$, —N(R$^{10}$)C(O)N(R$^{10}$)$_2$, —N(R$^{10}$)S(O)R$^{10}$, —N(R$^{10}$)S(O)$_2$R$^{10}$, C$_1$-C$_6$ alkyl, C$_2$-C$_6$ alkenyl, C$_2$-C$_6$ alkynyl, C$_1$-C$_6$ haloalkyl, C$_3$-C$_8$cycloalkyl, heterocyclyl, aryl, or heteroaryl, wherein each R$^{10}$ is independently hydrogen, C$_1$-C$_6$ alkyl, C$_2$-C$_6$ alkenyl, C$_2$-C$_6$ alkynyl, C$_1$-C$_6$ haloalkyl, C$_3$-C$_8$cycloalkyl, heterocyclyl, aryl, heteroaryl, C$_3$-C$_8$cycloalkyl(C$_1$-C$_6$)alkyl, heterocyclyl(C$_1$-C$_6$)alkyl, aryl(C$_1$-C$_6$)alkyl, or hetero aryl(C$_1$-C$_6$)alkyl, provided that R$^1$ is not —(CH$_2$)$_{3-4}$—NH$_2$, —(CH$_2$)$_{1-2}$—C(O)NH$_2$, —(CH$_2$)$_{2-3}$—C(O)N(H)CH$_3$, —(CH$_2$)$_{1-2}$N(H)C(O)CH$_3$, —(CH$_2$)$_2$—OH, or —(CH$_2$)$_3$-thiomorpholinyl.

The invention further comprises embodiments of the eighth aspect in which R$^5$ is one of the following groups (8a)-(8ii):

(8a) R$^5$ is

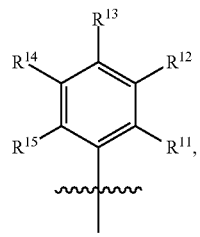

wherein R$^{11}$, R$^{12}$, R$^{13}$, R$^{14}$, and R$^{15}$ are each independently hydrogen or R$^{20}$, provided at least one of R$^{11}$, R$^{12}$, R$^{13}$, R$^{14}$, and R$^{15}$ is not hydrogen.

(8b) R$^5$ is according to group (8a), wherein one of R$^{11}$, R$^{12}$, R$^{13}$, R$^{14}$, and R$^{15}$ is halogen, cyano, —OR, SR, —NR$_2$, —C(O)OR, —C(O)NR$_2$, —N(R)S(O)$_2$R, —C$_1$-C$_6$alkyl-R$^{A1}$, -Q-(C$_1$-C$_6$)alkyl-R$^{A1}$, —C$_1$-C$_6$alkyl-Q-R$^{A1}$, -Q-(C$_1$-C$_6$)alkyl-Q-R$^{A1}$, —C$_1$-C$_6$alkyl-Q-(C$_1$-C$_6$)alkyl-R$^{A1}$, -Q(C$_1$-C$_6$)alkyl-Q-(C$_1$-C$_6$)alkyl-R$^{A1}$, or -Q(C$_1$-C$_6$)alkyl-Q-(C$_1$-C$_6$)alkyl-QR$^{A1}$.

(8c) R$^5$ is according to group (8a), wherein R$^{11}$ is —OR, —SR, —NR$_2$, —C$_1$-C$_6$alkyl-R$^{A1}$, -Q-(C$_1$-C$_6$)alkyl-R$^{A1}$, —C$_1$-C$_6$alkyl-Q-R$^{A1}$, -Q-(C$_1$-C$_6$)alkyl-Q-R$^{A1}$, —C$_1$-C$_6$alkyl-Q-(C$_1$-C$_6$)alkyl-R$^{A1}$, -Q(C$_1$-C$_6$)alkyl-Q-(C$_1$-C$_6$)alkyl-R$^{A1}$, or -Q(C$_1$-C$_6$)alkyl-Q-(C$_1$-C$_6$)alkyl-QR$^{A1}$.

(8d) R$^5$ is according to group (8a), wherein R$^{12}$, R$^{13}$, R$^{14}$, and R$^{15}$ are each independently hydrogen, halogen, cyano, C$_1$-C$_6$alkyl, C$_1$-C$_6$haloalkyl, —OR, —SR, —NR$_2$, —C(O)OR, —C(O)NR$_2$, —N(R)S(O)$_2$R; and R$^{11}$ is —OR, —SR, —NR$_2$, —C$_1$-C$_6$alkyl-R$^{A1}$, -Q-(C$_1$-C$_6$)alkyl-R$^{A1}$, —C$_1$-C$_6$alkyl-Q-R$^{A1}$, -Q-(C$_1$-C$_6$)alkyl-Q-R$^{A1}$, —C$_1$-C$_6$alkyl-Q-(C$_1$-C$_6$)alkyl-R$^{A1}$, -Q(C$_1$-C$_6$)alkyl-Q-(C$_1$-C$_6$)alkyl-R$^{A1}$, or -Q(C$_1$-C$_6$)alkyl-Q-(C$_1$-C$_6$)alkyl-QR$^{A1}$.

(8e) R$^5$ is according to group (8a), wherein R$^{12}$, R$^{13}$, R$^{14}$, and R$^{15}$ are each independently hydrogen, fluoro, chloro, Promo, methyl, or ethyl, and R$^{11}$ is —OR, —SR, —NR$_2$, —C$_1$-C$_6$alkyl-R$^{A1}$, -Q-(C$_1$-C$_6$)alkyl-R$^{A1}$, —C$_1$-C$_6$alkyl-Q-R$^{A1}$, -Q-(C$_1$-C$_6$)alkyl-Q-R$^{A1}$, —C$_1$-C$_6$alkyl-Q-(C$_1$-C$_6$)alkyl-R$^{A1}$, -Q(C$_1$-C$_6$)alkyl-Q-(C$_1$-C$_6$)alkyl-R$^{A1}$, or -Q(C$_1$-C$_6$)alkyl-Q-(C$_1$-C$_6$)alkyl-QR$^{A1}$.

(8f) R$^5$ is

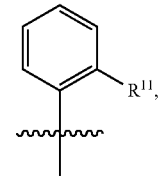

wherein R$^{11}$ is —OR, —SR, —NR$_2$, —C$_1$-C$_6$alkyl-R$^{A1}$, -Q-(C$_1$-C$_6$)alkyl-R$^{A1}$, —C$_1$-C$_6$alkyl-Q-R$^{A1}$, -Q-(C$_1$-C$_6$)alkyl-Q-R$^{A1}$, —C$_1$-C$_6$alkyl-Q-(C$_1$-C$_6$)alkyl-R$^{A1}$, -Q(C$_1$-C$_6$)alkyl-Q-(C$_1$-C$_6$)alkyl-R$^{A1}$, or -Q(C$_1$-C$_6$)alkyl-Q-(C$_1$-C$_6$)alkyl-QR$^{A1}$.

(8g) R$^5$ is according to group (8a), wherein R$^{11}$ is —OR or —SR.

(8h) R$^5$ is according to group (8a), wherein R$^{11}$ is —OR$^{21}$ or —SR$^{21}$, wherein R$^{21}$ is hydrogen, C$_1$-C$_6$ alkyl, C$_2$-C$_6$ alkenyl, C$_3$-C$_8$cycloalkyl(C$_1$-C$_6$)alkyl, heterocyclyl(C$_1$-C$_6$)alkyl, aryl(C$_1$-C$_6$)alkyl, or heteroaryl(C$_1$-C$_6$)alkyl, wherein the cycloalkylalkyl, heterocyclylalkyl, arylalkyl, and heteroarylalkyl are each optionally substituted with 1, 2, 3, or 4 groups (e.g., 1 or 2 groups) which are each independently halogen, cyano, nitro, C$_1$-C$_6$ alkyl, C$_1$-C$_6$ haloalkyl, —OR$^{10}$, —SR$^{10}$), —N(R$^{10}$)$_2$, —C(O)N(R$^{10}$)$_2$, —C(O)OR$^{10}$)$_2$, —C(O)R$^{10}$, —S(O)$_2$R$^{10}$), —S(O)$_2$OR$^{10}$, —S(O)$_2$N(R$^{10}$)$_2$, —OC(O)R$^{10}$, —OC(O)OR$^{10}$, —OC(O)N(R$^{10}$)$_2$, —N(R$^{10}$)C(O)R$^{10}$, —N(R$^{10}$)C(O)OR$^{10}$, —N(R$^{10}$)C(O)N(R$^{10}$)$_2$, —N(R$^{10}$)S(O)$_2$R$^{10}$, wherein each R$^{10}$ is independently hydrogen, C$_1$-C$_6$ alkyl, or C$_1$-C$_6$ haloalkyl.

(8i) $R^5$ is according to group (8a), wherein $R^{11}$ is —$OR^{21}$ or —$SR^{21}$, wherein $R^{21}$ is hydrogen, $C_1$-$C_6$ alkyl, $C_2$-$C_6$ alkenyl, $C_3$-$C_8$cycloalkyl($C_1$-$C_6$)alkyl, heterocyclyl($C_1$-$C_6$)alkyl, aryl($C_1$-$C_6$)alkyl, or heteroaryl($C_1$-$C_6$)alkyl.

(8j) $R^5$ is according to group (8a), wherein $R^{12}$, $R^{13}$, $R^{14}$, and $R^{15}$ are each independently hydrogen, halogen, cyano, $C_1$-$C_6$alkyl, $C_1$-$C_6$haloalkyl, —OR, —SR, —$NR_2$, —C(O)OR, —C(O)$NR_2$, —N(R)S(O)$_2$R, and $R^{11}$ is —OR or —SR.

(8k) $R^5$ is according to group (8a), wherein $R^{12}$, $R^{13}$, $R^{14}$, and $R^{15}$ are each independently hydrogen, halogen, cyano, $C_1$-$C_6$alkyl, $C_1$-$C_6$haloalkyl, —OR, —SR, —$NR_2$, —C(O)OR, —C(O)$NR_2$, —N(R)S(O)$_2$R, and $R^{11}$ is —$OR^{21}$ or —$SR^{21}$, wherein $R^{21}$ is hydrogen, $C_1$-$C_6$ alkyl, $C_2$-$C_6$ alkenyl, $C_3$-$C_8$cycloalkyl($C_1$-$C_6$)alkyl, heterocyclyl($C_1$-$C_6$)alkyl, aryl($C_1$-$C_6$)alkyl, or heteroaryl($C_1$-$C_6$)alkyl, wherein the cycloalkylalkyl, heterocyclylalkyl, arylalkyl, and heteroarylalkyl are each optionally substituted with 1, 2, 3, or 4 groups (e.g., 1 or 2 groups) which are each independently halogen, cyano, nitro, $C_1$-$C_6$ alkyl, $C_1$-$C_6$ haloalkyl, —$OR^{10}$, —$SR^{10}$, —$N(R^{10})_2$, —C(O)$OR^{10}$, —C(O)$N(R^{10})_2$, —C(O)$R^{10}$, —$S(OR)_2R^{10}$, —S(O)$_2R^{10}$, —S(O)$_2N(R^{10})_2$, —OC(O)$OR^{10}$, —OC(O)$N(R^{10})_2$, —$N(R^{10})$C(O)$R^{10}$, —$N(R^{10})$C(O)$OR^{10}$, —$N(R^{10})$C(O)$N(R^{10})_2$, —$N(R^{10})$S(O)$_2R^{10}$, wherein each $R^{10}$ is independently hydrogen, $C_1$-$C_6$ alkyl, or $C_1$-$C_6$ haloalkyl.

(8l) $R^5$ is according to group (8a), wherein $R^{12}$, $R^{13}$, $R^{14}$, and $R^{15}$ are each independently hydrogen, halogen, cyano, $C_1$-$C_6$alkyl, $C_1$-$C_6$haloalkyl, —OR, —SR, —$NR_2$, —C(O)OR, —C(O)$NR_2$, —N(R)S(O)$_2$R, and $R^{11}$ is —$OR^{21}$ or —$SR^{21}$, wherein $R^{21}$ is hydrogen, $C_1$-$C_6$ alkyl, $C_2$-$C_6$ alkenyl, $C_3$-$C_8$cycloalkyl($C_1$-$C_6$)alkyl, heterocyclyl($C_1$-$C_6$)alkyl, aryl($C_1$-$C_6$)alkyl, or heteroaryl($C_1$-$C_6$)alkyl.

(8m) $R^5$ is according to group (8a), wherein $R^{12}$, $R^{13}$, $R^{14}$, and $R^{15}$ are each independently hydrogen, fluoro, chloro, bromo, methyl, or ethyl, and $R^{11}$ is —OR or —SR.

(8n) $R^5$ is according to group (8a), wherein $R^{12}$, $R^{13}$, $R^{14}$, and $R^{15}$ are each independently hydrogen, fluoro, chloro, bromo, methyl, or ethyl, and $R^{11}$ is —$OR^{21}$ or —$SR^{21}$, wherein $R^{21}$ is hydrogen, $C_1$-$C_6$ alkyl, $C_2$-$C_6$ alkenyl, $C_3$-$C_8$cycloalkyl($C_1$-$C_6$)alkyl, heterocyclyl($C_1$-$C_6$)alkyl, aryl($C_1$-$C_6$)alkyl, or heteroaryl($C_1$-$C_6$)alkyl.

(8o) $R^5$ is

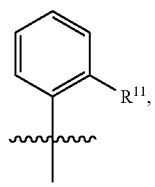

wherein $R^{11}$ is —OR or —SR.

(8p) $R^5$ is

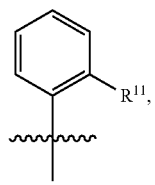

wherein $R^{11}$ is —$OR^{21}$ or —$SR^{21}$, wherein $R^{21}$ is hydrogen, $C_1$-$C_6$ alkyl, $C_2$-$C_6$ alkenyl, $C_3$-$C_8$cycloalkyl($C_1$-$C_6$)alkyl, heterocyclyl($C_1$-$C_6$)alkyl, aryl($C_1$-$C_6$)alkyl, or heteroaryl($C_1$-$C_6$)alkyl, wherein the cycloalkylalkyl, heterocyclylalkyl, arylalkyl, and heteroarylalkyl are each optionally substituted with 1, 2, 3, or 4 groups (e.g., 1 or 2 groups) which are each independently halogen, cyano, nitro, $C_1$-$C_6$ alkyl, $C_1$-$C_6$ haloalkyl, —$OR^{10}$, —$SR^{10}$, —$N(R^{10})_2$, —C(O)$OR^{10}$, —C(O)$N(R^{10})_2$, —C(O)$R^{10}$, —S(O)$_2R^{10}$, —S(O)$_2OR^{10}$, —S(O)$_2N(R^{10})_2$, —OC(O)$R^{10}$, —OC(O)$OR^{10}$, —OC(O)$N(R^{10})_2$, —$N(R^{10})$C(O)$R^{10}$, —$N(R^{10})$C(O)$OR^{10}$, —$N(R^{10})$C(O)$N(R^{10})_2$, —$N(R^{10})$S(O)$_2R^{10}$, wherein each $R^{10}$ is independently hydrogen, $C_1$-$C_6$ alkyl, or $C_1$-$C_6$ haloalkyl.

(8q) $R^5$ is

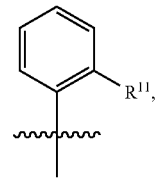

wherein $R^{11}$ is —$OR^{21}$ or —$SR^{21}$, wherein $R^{21}$ is hydrogen, $C_1$-$C_6$ alkyl, $C_2$-$C_6$ alkenyl, $C_3$-$C_8$cycloalkyl($C_1$-$C_6$)alkyl, heterocyclyl($C_1$-$C_6$)alkyl, aryl($C_1$-$C_6$)alkyl, or heteroaryl($C_1$-$C_6$)alkyl.

(8r) $R^5$ is according to group (8a), wherein $R^{11}$ is —$C_1$-$C_6$alkyl-$R^{41}$, -Q-($C_1$-$C_6$)alkyl-$R^{41}$, —$C_1$-$C_6$alkyl-Q-$R^{41}$, -Q-($C_1$-$C_6$)alkyl-C($R^{42}$)$_2$—$R^{41}$, or —($C_1$-$C_6$)alkyl-Q-$C_1$-$C_6$ alkyl-$R^{41}$, or -Q($C_1$-$C_6$)alkyl-C($R^{42}$)$_2$—($C_1$-$C_6$)alkyl-Q$R^{41}$, wherein each is Q is independently —O—, —N($R^{42}$)—, or —S—.

(8s) $R^5$ is according to group (8a), wherein $R^{12}$, $R^{13}$, $R^{14}$, and $R^{15}$ are each independently hydrogen, halogen, cyano, $C_1$-$C_6$alkyl, $C_1$-$C_6$haloalkyl, —OR, —SR, —$NR_2$, —C(O)OR, —C(O)$NR_2$, —N(R)S(O)$_2$R, and $R^{11}$ is —$C_1$-$C_6$alkyl-$R^{41}$, -Q-($C_1$-$C_6$)alkyl-$R^{41}$, —$C_1$-$C_6$alkyl-Q-$R^{41}$, -Q-($C_1$-$C_6$)alkyl-C($R^{42}$)$_2$—$R^{41}$, or —($C_1$-$C_6$)alkyl-Q-$C_1$-$C_6$ alkyl-$R^{41}$, or -Q($C_1$-$C_6$)alkyl-C($R^{42}$)$_2$—($C_1$-$C_6$)alkyl-Q$R^{41}$, wherein each is Q is independently —O—, —N($R^{42}$)—, or —S—.

(8t) $R^5$ is according to group (8a), wherein $R^{12}$, $R^{13}$, $R^{14}$, and $R^{15}$ are each independently hydrogen, fluoro, chloro, bromo, methyl, or ethyl, and $R^{11}$ is —$C_1$-$C_6$alkyl-$R^{41}$, -Q-($C_1$-$C_6$)alkyl-$R^{41}$, —$C_1$-$C_6$alkyl-Q-$R^{41}$, -Q-($C_1$-$C_6$)alkyl-C($R^{42}$)$_2$—$R^{41}$, or —($C_1$-$C_6$)alkyl-Q-$C_1$-$C_6$ alkyl-$R^{41}$, or -Q($C_1$-$C_6$)alkyl-C($R^{42}$)$_2$—($C_1$-$C_6$)alkyl-Q$R^{41}$, wherein each is Q is independently —O—, —N($R^{42}$)—, or —S—.

(8u) $R^5$ is

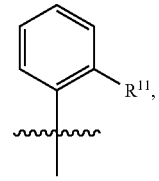

wherein $R^{11}$ is —$C_1$-$C_6$alkyl-$R^{41}$, -Q-($C_1$-$C_6$)alkyl-$R^{41}$, —$C_1$-$C_6$alkyl-Q-$R^{41}$, -Q-($C_1$-$C_6$)alkyl-C($R^{42}$)$_2$—$R^{41}$, or —($C_1$-$C_6$)alkyl-Q-$C_1$-$C_6$ alkyl-$R^{41}$, or -Q($C_1$-$C_6$)alkyl-C ($R^{A2}$)$_2$—(C$_1$-C$_6$)alkyl-QR$^{A1}$, wherein each is Q is independently —O—, —N(R$^{A2}$)—, or —S—.

(8v) R$^5$ is according to group (8a), wherein R$^{11}$ is —C$_1$-C$_6$alkyl-R$^{A1}$, —O(C$_1$-C$_6$)alkyl-R$^{A1}$, —C$_1$-C$_6$alkylOR$^{A1}$, —C$_1$-C$_6$alkyl-C(R$^{A2}$)$_2$—R$^{A1}$, —O(C$_1$-C$_6$)alkyl-C(R$^{A2}$)$_2$—R$^{A1}$, —C$_1$-C$_6$alkyl-O(C$_1$-C$_6$)alkyl-R$^{A1}$, or —O(C$_1$-C$_6$)alkyl-C(R$^{A2}$)$_2$—(C$_1$-C$_6$)alkyl-OR$^{A1}$.

(8w) R$^5$ is according to group (8a), wherein R$^{12}$, R$^{13}$, R$^{14}$, and R$^{15}$ are each independently hydrogen, halogen, cyano, C$_1$-C$_6$alkyl, C$_1$-C$_6$haloalkyl, —OR, —SR, —NR$_2$, —C(O)OR, —C(O)NR$_2$, —N(R)S(O)$_2$R, and R$^{11}$ is —C$_1$-C$_6$alkyl-R$^{A1}$, —O(C$_1$-C$_6$)alkyl-R$^{A1}$, —C$_1$-C$_6$alkylOR$^{A1}$, —C$_1$-C$_6$alkyl-C(R$^{A2}$)$_2$—R$^{A1}$, —O(C$_1$-C$_6$)alkyl-C(R$^{A2}$)$_2$—R$^{A1}$, —C$_1$-C$_6$alkyl-O(C$_1$-C$_6$)alkyl-R$^{A1}$, or —O(C$_1$-C$_6$)alkyl-C(R$^{A2}$)$_2$—(C$_1$-C$_6$)alkyl-OR$^{A1}$.

(8x) R$^5$ is according to group (8a), wherein R$^{12}$, R$^{13}$, R$^{14}$, and R$^{15}$ are each independently hydrogen, fluoro, chloro, bromo, methyl, or ethyl, and R$^{11}$ is —C$_1$-C$_6$alkyl-R$^{A1}$, —O(C$_1$-C$_6$)alkyl-R$^{A1}$, —C$_1$-C$_6$alkyl-C(R$^{A2}$)$_2$—R$^{A1}$, —O(C$_1$-C$_6$)alkyl-C(R$^{A2}$)$_2$—R$^{A1}$, —C$_1$-C$_6$alkyl-O(C$_1$-C$_6$)alkyl-R$^{A1}$, or —O(C$_1$-C$_6$)alkyl-C(R$^{A2}$)$_2$—(C$_1$-C$_6$)alkyl-OR$^{A1}$.

(8y) R$^5$ is

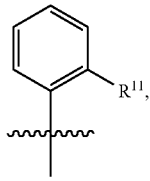

wherein R$^{11}$ is -C$_1$-C$_6$alkyl-R$^{A1}$, —O(C$_1$-C$_6$)alkyl-R$^{A1}$, —C$_1$-C$_6$alkylOR$^{A1}$, —C$_1$-C$_6$alkyl-C(R$^{A2}$)$_2$—R$^{A1}$, —O(C$_1$-C$_6$)alkyl-C(R$^{A2}$)$_2$—R$^{A1}$, —C$_1$-C$_6$alkyl-O(C$_1$-C$_6$)alkyl-R$^{A1}$, or —O(C$_1$-C$_6$)alkyl-C(R$^{A2}$)$_2$—(C$_1$-C$_6$)alkyl-OR$^{A1}$.

(8z) R$^5$ is according to group (8a), wherein R$^{11}$ is —O(C$_1$-C$_6$)alkyl-R$^{A1}$, —C$_1$-C$_6$alkylOR$^{A1}$, —C$_1$-C$_6$alkyl-C(CH$_3$)$_2$—R$^{A1}$, —O(C$_1$-C$_6$)alkyl-C(CH$_3$)$_2$—R$^{A1}$, —C$_1$-C$_6$alkyl-O(C$_1$-C$_6$)alkyl-R$^{A1}$, or —O(C$_1$-C$_6$)alkyl-C(CH$_3$)$_2$—(C$_1$-C$_6$)alkyl-OR$^{A1}$.

(8aa) R$^5$ is according to group (8a), wherein R$^{12}$, R$^{13}$, R$^{14}$, and R$^{15}$ are each independently hydrogen, halogen, cyano, C$_1$-C$_6$alkyl, C$_1$-C$_6$haloalkyl, —OR, —SR, —NR$_2$, —C(O)OR, —C(O)NR$_2$, —N(R)S(O)$_2$R, and R$^{11}$ is —O(C$_1$-C$_6$)alkyl-R$^{A1}$, —C$_1$-C$_6$alkylOR$^{A1}$, —C$_1$-C$_6$alkyl-C(CH$_3$)$_2$—R$^{A1}$, —O(C$_1$-C$_6$)alkyl-C(CH$_3$)$_2$—R$^{A1}$, —C$_1$-C$_6$alkyl-O(C$_1$-C$_6$)alkyl-R$^{A1}$, or —O(C$_1$-C$_6$)alkyl-C(CH$_3$)$_2$—(C$_1$-C$_6$)alkyl-OR$^{A1}$.

(8bb) R$^5$ is according to group (8a), wherein R$^{12}$, R$^{13}$, R$^{14}$, and R$^{15}$ are each independently hydrogen, fluoro, chloro, bromo, methyl, or ethyl, and R$^{11}$ is —O(C$_1$-C$_6$)alkyl-R$^{A1}$, —C$_1$-C$_6$alkylOR$^{A1}$, —C$_1$-C$_6$alkyl-C(CH$_3$)$_2$—R$^{A1}$, —O(C$_1$-C$_6$)alkyl-C(CH$_3$)$_2$—R$^{A1}$, —C$_1$-C$_6$alkyl-O(C$_1$-C$_6$)alkyl-R$^{A1}$, or —O(C$_1$-C$_6$)alkyl-C(CH$_3$)$_2$—(C$_1$-C$_6$)alkyl-OR$^{A1}$.

(8cc) R$^5$ is

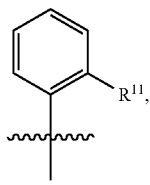

wherein R$^{11}$ is —O(C$_1$-C$_6$)alkyl-R$^{A1}$, —C$_1$-C$_6$alkylOR$^{A1}$, —C$_1$-C$_6$alkyl-C(CH$_3$)$_2$—R$^{A1}$, —O(C$_1$-C$_6$)alkyl-C(CH$_3$)$_2$—R$^{A1}$, —C$_1$-C$_6$alkyl-O(C$_1$-C$_6$)alkyl-R$^{A1}$, or —O(C$_1$-C$_6$)alkyl-C(CH$_3$)$_2$—(C$_1$-C$_6$)alkyl-OR$^{A1}$.

(8dd) R$^5$ is according to group (8a), wherein R$^{11}$, R$^{12}$, R$^{13}$, R$^{14}$, and R$^{15}$ are independently hydrogen, halogen, cyano, C$_1$-C$_6$alkyl, C$_1$-C$_6$haloalkyl, —OR, —SR, —NR$_2$, —C(O)OR, —C(O)NR$_2$, —N(R)S(O)$_2$R.

(8ee) R$^5$ is according to group (8a), wherein at least one of R$^{11}$, R$^{12}$, R$^{13}$, R$^{14}$, and R$^{15}$ is fluoro, chloro, bromo, methyl, or ethyl, and R$^{11}$ is —OH, —OCH$_3$, or —SH.

(8ff) R$^5$ is according to group (8a), wherein R$^{12}$, R$^{13}$, R$^{14}$, and R$^{15}$ are each independently hydrogen, fluoro, chloro, bromo, methyl, or ethyl, and R$^{11}$ is —OH, —OCH$_3$, or —SH.

(8gg) R$^5$ is

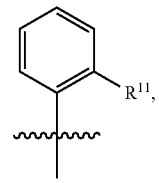

wherein R$^{11}$ is —OH, —OCH$_3$, or —SH.

(8hh) R$^5$ is heteroaryl optionally substituted with 1, 2, 3, or 4 groups (e.g., 1 or 2 groups) which are each independently R$^{20}$.

(8ii) R$^5$ is benzothiophenyl, pyrrolopyridinyl, imidazopyridinyl, quinolinyl, isoquinolinyl, naphthyridinyl, indolyl, indolinyl, benzothiadiazolyl, dihydrobenzodioxinyl, tetrahydropyrimidinyl, pyridinyl, pyrimidinyl, thienyl, or isoxazolyl, each optionally with 1, 2, 3, or 4 groups (e.g., 1 or 2 groups) which are each independently R$^{20}$.

(8jj) R$^5$ is benzo[b]thiophen-3-yl, 1H-pyrrolo[2,3-b]pyridin-3-yl, 1H-pyrrolo[2,3-b]pyridin-5-yl, 7-methylimidazo[1,2-c]pyridin-6-yl, quinolin-8-yl, 7-chloroquinolin-4-yl, 2,8-bis(trifluoromethyl)quinolin-4-yl, 5-chloro-8-hydroxyquinolin-7-yl, isoquinolin-4-yl, isoquinolin-5-yl, 2-carboxy-1,6-naphthyridin-8-yl, 1H-indol-7-yl, 1H-indol-6-yl, 1H-indol-5-yl, 9H-purin-6-yl, 2-oxo-2,3-dihydro-1H-imidazo[4,5-b]pyridin-6-yl, 2,3-dioxoindolin-5-yl, 2,3-dioxoindolin-7-yl, benzo[c][1,2,5]thiadiazol-4-yl, 2,3-dihydrobenzo[b][1,4]dioxin-6-yl, 1,3-dimethyl-2,4-dioxo-1,2,3,4,-tetrahydropyrimidin-5-yl, 2-morpholinopyridin-3-yl, 4-hydroxybiphenyl-3-yl, 2-hydroxypyridin-3-yl, 2,5-dichlorothiophen-3-yl or 3,5-dimethylisoxazol-4-yl.

The invention further comprises embodiments of the eighth aspect in which R$^1$ is one of the following groups (8kk)-(8eee):

(8kk) R$^1$ is C$_1$-C$_6$alkyl or —(C$_1$-C$_6$)alkyl-R$^{B1}$ wherein R$^{B1}$ is R$^{B2}$, C$_3$-C$_8$cycloalkyl, heterocyclyl, aryl, or heteroaryl, wherein the cycloalkyl, heterocyclyl, aryl, and heteroaryl groups are optionally substituted by 1, 2, 3, or 4 R$^{B2}$ groups (e.g., 1 or 2 groups).

(8ll) R$^1$ is C$_1$-C$_6$alkyl.

(8mm) R$^1$ is neohexyl.

(8nn) R$^1$ is —(C$_1$-C$_6$)alkyl-R$^{B2}$.

(8oo) R$^1$ is —(C$_1$-C$_6$)alkyl-R$^{B2}$, wherein R$^{B2}$ is—OR, —SR, —NR$_2$, —C(O)R, —C(O)OR, —C(O)NR$_2$, —OC(O)R, —OC(O)OR, —OC(O)NR$_2$, —N(R)C(O)R, —N(R)C(O)OR, or —N(R)C(O)NR$_2$.

(8pp) $R^1$ is —$(C_1-C_6)$alkyl-RB2. wherein $R^{B2}$ is —$OR^{22}$, —$SR^{22}$, —$N(R^{22})_2$, —$C(O)R^{22}$, —$C(O)OR^{22}$, —$C(O)N(R^{22})_2$, —$OC(O)R^{22}$, —$OC(O)OR^{22}$, —$OC(O)N(R^{22})_2$, —$N(R^{22})C(O)R^{22}$, —$N(R^{22})C(O)OR^{22}$, or —$N(R^{22})C(O)N(R^{22})_2$, wherein each $R^{22}$ is independently hydrogen or $C_1-C_6$ alkyl.

(8qq) $R^1$ is —$(C_1-C_6)$alkyl-$R^{B1}$ wherein $R^{B1}$ is $C_3-C_8$cycloalkyl, heterocyclyl, aryl, or heteroaryl, wherein the cycloalkyl, heterocyclyl, aryl, and heteroaryl groups are optionally substituted by 1, 2, 3, or 4 $R^{B2}$ groups (e.g., 1 or 2 $R^{B2}$ groups).

(8rr) $R^1$ is —$(C_1-C_4)$alkyl-$R^{B1}$ wherein $R^{B1}$ is $C_3-C_8$cycloalkyl, heterocyclyl, aryl, or heteroaryl, wherein the cycloalkyl, heterocyclyl, aryl, and heteroaryl groups are optionally substituted by 1, 2, 3, or 4 $R^{B2}$ groups (e.g., 1 or 2 $R^{B2}$ groups).

(8ss) $R^1$ is —$(C_1-C_6)$alkyl-$R^{B1}$ wherein $R^{B1}$ is phenyl optionally substituted by 1, 2, 3, or 4 $R^{B2}$ groups (e.g., 1 or 2 $R^{B2}$ groups).

(8tt) $R^1$ is —$(C_1-C_4)$alkyl-$R^{B1}$ wherein $R^{B1}$ is phenyl optionally substituted by 1, 2, 3, or 4 $R^{B2}$ groups (e.g., 1 or 2 $R^{B2}$ groups).

(8uu) $R^1$ is —$(C_1-C_2)$alkyl-$R^{B1}$ wherein $R^{B1}$ is phenyl optionally substituted by 1, 2, 3, or 4 $R^{B2}$ groups (e.g., 1 or 2 $R^{B2}$ groups).

(8vv) $R^1$ is —$CH_2$—$R^{B1}$ wherein $R^{B1}$ is phenyl optionally substituted by 1, 2, 3, or 4 $R^{B2}$ groups (e.g., 1 or 2 $R^{B2}$ groups).

(8ww) $R^1$ is —$CH_2$—$R^{B1}$ wherein $R^{B1}$ is phenyl optionally substituted by one $R^{B2}$ group.

(8xx) $R^1$ is —$(C_1-C_6)$alkyl-$R^{B1}$ wherein $R^{B1}$ is phenyl optionally substituted by 1, 2, 3, or 4 $R^{B2}$ groups (e.g., 1 or 2 $R^{B2}$ groups), wherein each $R^{B2}$ is independently halogen, cyano, nitro, —$OR^{B20}$, —$SR^{B20}$, —$N(R^{B20})_2$, $C_1-C_6$ alkyl, or $C_1-C_6$ haloalkyl, wherein $R^{B20}$ is hydrogen or $C_1-C_6$ alkyl.

(8yy) $R^1$ is —$(C_1-C_6)$alkyl-$R^{B1}$ wherein $R^{B1}$ is phenyl optionally substituted by one $R^{B2}$ group, wherein $R^{B2}$ is halogen, cyano, nitro, —$OR^{B20}$, —$SR^{B20}$, —$N(R^{B20})_2$, $C_1-C_6$ alkyl, or $C_1-C_6$ haloalkyl, wherein $R^{B20}$ is hydrogen or $C_1-C_6$ alkyl.

(8zz) $R^1$ is —$(C_1-C_4)$alkyl-$R^{B1}$ wherein $R^{B1}$ is phenyl optionally substituted by one $R^{B2}$ groups (e.g., 1 or 2 $R^{B2}$ groups), wherein each $R^{B2}$ is independently halogen, cyano, nitro, —$OR^{B20}$, —$SR^{B20}$, —$N(R^{B20})_2$, $C_1-C_6$ alkyl, or $C_1-C_6$ haloalkyl, wherein $R^{B20}$ is hydrogen or $C_1-C_6$ alkyl.

(8aaa) $R^1$ is —$(C_1-C_4)$alkyl-$R^{B1}$ wherein $R^{B1}$ is phenyl optionally substituted by one $R^{B2}$ group, wherein $R^{B2}$ is halogen, cyano, nitro, —$OR^{B20}$, —$SR^{B20}$, —$N(R^{B20})_2$, $C_1-C_6$ alkyl, or $C_1-C_6$ haloalkyl, wherein $R^{B20}$ is hydrogen or $C_1-C_6$ alkyl.

(8bbb) $R^{B1}$ is —$(C_1-C_2)$alkyl-$R^{B1}$ wherein $R^{B1}$ is phenyl optionally substituted by 1, 2, 3, or 4 $R^{B2}$ groups (e.g., 1 or 2 $R^{B2}$ groups), wherein each $R^{B2}$ is independently halogen, cyano, nitro, —$OR^{B20}$, —$SR^{B20}$, —$N(R^{B20})_2$, $C_1-C_6$ alkyl, or $C_1-C_6$ haloalkyl, wherein $R^{B20}$ is hydrogen or $C_1-C_6$ alkyl.

(8ccc) $R^1$ is —$(C_1-C_2)$alkyl-$R^{B1}$ wherein $R^{B1}$ is phenyl optionally substituted by one $R^{B2}$ group, wherein $R^{B2}$ is halogen, cyano, nitro, —$OR^{B20}$, —$SR^{B20}$, —$N(R^{B20})_2$, $C_1-C_6$ alkyl, or $C_1-C_6$ haloalkyl, wherein $R^{B20}$ is hydrogen or $C_1-C_6$ alkyl.

(8ddd) $R^1$ is —$(CH_2)$—$R^{B1}$ wherein $R^{B1}$ is phenyl optionally substituted by 1, 2, 3, or 4 $R^{B2}$ groups (e.g., 1 or 2 $R^{B2}$ groups), wherein each $R^{B2}$ is independently halogen, cyano, nitro, —$OR^{B20}$, $C_1-C_6$ alkyl, or $C_1-C_6$ haloalkyl, wherein $R^{B20}$ is hydrogen or $C_1-C_6$ alkyl.

(8eee) $R^1$ is —$(CH_2)$—$R^{B1}$ wherein $R^{B1}$ is phenyl optionally substituted by one $R^{B2}$ group, wherein $R^{B2}$ is halogen, cyano, nitro, —$OR^{B20}$, —$SR^{B20}$, —$N(R^{B20})_2$, $C_1-C_6$ alkyl, or $C_1-C_6$ haloalkyl, wherein $R^{B20}$ is hydrogen or $C_1-C_6$ alkyl.

In a ninth aspect, the invention provides methods for treating indoleamine 2,3-dioxygenase (IDO) mediated immunosuppression in a subject in need thereof, comprising administering an effective indoleamine 2,3-dioxygenase inhibiting amount of compound according to formula (IV) or (V) and any embodiment thereof, as described above, or a compound according to formula (XIV) or (XV),

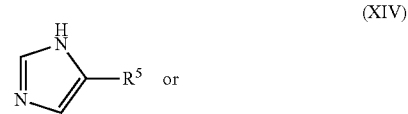

(XIV)

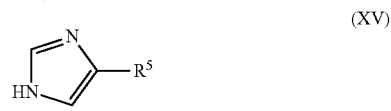

(XV)

or a pharmaceutically acceptable salt thereof, wherein $R^5$ is aryl or heteroaryl, each optionally substituted with 1, 2, 3, or 4 groups (e.g., 1 or 2 groups) which are each independently $R^{20}$, wherein each $R^{20}$ is independently halogen, cyano, —OR, —SR, —$NR_2$, —C(O)OR, —$C(O)NR_2$, —$N(R)S(O)_2R$, —$C(O)R^2$, —S(O)R, —$S(O)_2R$, —S(O)OR, —$S(O)_2OR$, —$S(O)NR_2$, —$S(O)_2NR_2$, —OC(O)R, —OC(O)OR, —$OC(O)NR_2$, —N(R)C(O)R, —N(R)C(O)OR, —$N(R)C(O)NR_2$, —N(R)S(O)R, $C_1-C_6$alkyl, $C_2-C_6$alkenyl, $C_2-C_6$alkynyl, $C_1-C_6$haloalkyl, $C_3-C_8$cycloalkyl, heterocyclyl, aryl, heteroaryl, $C_3-C_8$cycloalkyl($C_1-C_6$)alkyl, heterocyclyl($C_1-C_6$)alkyl, aryl($C_1-C_6$)alkyl, heteroaryl($C_1-C_6$)alkyl, —$C_1$-$C_6$alkyl-$R^{41}$, -Q-($C_1-C_6$)alkyl-$R^{41}$, —($C_1-C_6$)alkyl-Q-$R^{41}$, -Q-($C_1-C_6$)alkyl-Q-$R^{41}$, —$C_1$-$C_6$alkyl-Q-($C_1-C_6$)alkyl-$R^{41}$, -Q($C_1-C_6$)alkyl-Q-($C_1-C_6$)alkyl-$R^{41}$, or -Q($C_1-C_6$)alkyl-Q-($C_1-C_6$)alkyl-Q$R^{41}$, wherein each Q is independently —$C(R^{42})_2$—, —O—, —$N(R^{42})$—, —S—, —C(O)—. —S(O)—, —$S(O)_2$—, —$C(O)N(R^{42})$—, —$N(R^{42})C(O)$—, —C(O)O—, or —OC(O)—, wherein each $R^{42}$ is independently hydrogen, $C_1-C_6$alkyl, or $C_1-C_6$haloalkyl;

$R^{41}$ is $R^{43}$, $C_1-C_6$ alkyl, —$C_1-C_6$alkyl-$R^{43}$, $C_1-C_6$ haloalkyl, $C_3-C_8$cycloalkyl, heterocyclyl, aryl, or heteroaryl, wherein the cycloalkyl, heterocyclyl, aryl, and heteroaryl groups are optionally substituted by 1, 2, 3, or 4 $R^{43}$ groups, wherein each $R^{43}$ is independently halogen, cyano, nitro, —OR, —SR, —$NR_2$, —C(O)R, —C(O)OR, —$C(O)NR_2$, —S(O)R, —$S(O)_2R$, —S(O)OR, —$S(O)_2OR$, —$S(O)NR_2$, —$S(O)_2NR_2$, —OC(O)R, —OC(O)OR, —$OC(O)NR_2$, —N(R)C(O)R, —N(R)C(O)OR, —$N(R)C(O)NR_2$, —N(R)S(O)R, —$N(R)S(O)_2R$, $C_1-C_6$ alkyl, $C_1-C_6$ haloalkyl, $C_2-C_6$ alkenyl, $C_2-C_6$ alkynyl, $C_3-C_8$cycloalkyl, heterocyclyl, aryl, or heteroaryl, wherein the cycloalkyl, heterocyclyl, aryl, heteroaryl, are each optionally substituted with 1, 2, 3, or 4 groups which are each independently halogen, cyano, nitro, —$OR^{411}$, —$SR^{411}$, —$N(R^{411})_2$, —$C(O)OR^{411}$, —$C(O)N(R^{411})_2$, —$C(O)R^{11}$, —$S(O)R^{411}$, —$S(O)_2R^{411}$, —$S(O)OR^{411}$, —$S(O)_2OR^{411}$, —$S(O)N(R^{411})_2$, —$S(O)_2N(R^{411})_2$, —$OC(O)R^{411}$, —$OC(O)OR^{411}$, —$OC(O)N(R^{411})_2$, —$N(R^{411})C(O)R^{411}$, —$N(R^{411})C(O)OR^{411}$, —$N(R^{411})C(O)N(R^{411})_2$, —$N(R^{411})S(O)R^{411}$, —$N(R^{411})S(O)_2R^{411}$, $C_1$-$C_6$ alkyl, or $C_1$-$C_6$ haloalkyl, wherein each $R^{411}$ is independently hydrogen, $C_1$-$C_6$ alkyl, $C_2$-$C_6$ alkenyl, $C_2$-$C_6$ alkynyl, $C_1$-$C_6$ haloalkyl, $C_3$-$C_8$cycloalkyl, heterocyclyl, aryl, heteroaryl, $C_3$-$C_8$cycloalkyl($C_1$-$C_6$)alkyl, heterocyclyl($C_1$-$C_6$)alkyl, aryl($C_1$-$C_6$)alkyl, or hetero aryl($C_1$-$C_6$)alkyl;

or $R^{41}$ and $R^{42}$ taken together, when attached to the same carbon atom, form =$C_3$-$C_8$cycloalkyl, or =heterocyclyl, wherein the cycloalkyl and heterocyclyl are optionally substituted with 1, 2, 3, or 4 groups which are each independently halogen, cyano, nitro, —OR, —SR, —NR$_2$, —C(O)OR, —C(O)NR$_2$, —C(O)R, —S(O)R, —S(O)$_2$R, —S(O)OR, —S(O)$_2$OR, —S(O)NR$_2$, —S(O)$_2$NR$_2$, —OC(O)R, —OC(O)OR, —OC(O)NR$_2$, —N(R)C(O)R, —N(R)C(O)OR, —N(R)C(O)NR$_2$, —N(R)S(O)R, —N(R)S(O)$_2$R, $C_1$-$C_6$ alkyl, or $C_1$-$C_6$ haloalkyl; and each R is independently hydrogen or $R^2$, wherein $R^2$ is $C_1$-$C_6$ alkyl, $C_2$-$C_6$ alkenyl, $C_2$-$C_6$ alkynyl, $C_1$-$C_6$ haloalkyl, $C_3$-$C_8$cycloalkyl, heterocyclyl, aryl, heteroaryl, $C_3$-$C_8$cycloalkyl($C_1$-$C_6$)alkyl, heterocyclyl($C_1$-$C_6$)alkyl, aryl($C_1$-$C_6$)alkyl, or heteroaryl($C_1$-$C_6$)alkyl, wherein the alkyl, $C_3$-$C_8$cycloalkyl, heterocyclyl, aryl, heteroaryl, cycloalkylalkyl, heterocyclylalkyl, arylalkyl, and heteroarylalkyl are each optionally substituted with 1, 2, 3, or 4 groups which are each independently halogen, cyano, nitro, —OR$^{10}$, —SR$^{10}$, —N(R$^{10}$)$_2$, —C(O)OR$^{10}$, —C(O)N(R$^{10}$)$_2$, —C(O)R$^{10}$, S(O)R$^{10}$, —S(O)$_2$R$^{10}$, —S(O)OR$^{10}$, —S(O)$_2$OR$^{10}$, —S(O)N(R$^{10}$)$_2$, —S(O)$_2$N(R$^{10}$)$_2$, —OC(O)R$^{10}$, —OC(O)OR$^{10}$, —OC(O)N(R$^{10}$)$_2$, —N(R$^{10}$)C(O)R$^{10}$, —N(R$^{10}$)C(O)OR$^{10}$, —N(R$^{10}$)C(O)N(R$^{10}$)$_2$, —N(R$^{10}$)S(O)R$^{10}$, —N(R$^{10}$)S(O)$_2$R$^{10}$, $C_1$-$C_6$ alkyl, $C_2$-$C_6$ alkenyl, $C_2$-$C_6$ alkynyl, $C_1$-$C_6$ haloalkyl, $C_3$-$C_8$cycloalkyl, heterocyclyl, aryl, or heteroaryl, wherein each $R^{10}$ is independently hydrogen, $C_1$-$C_6$ alkyl, $C_2$-$C_6$ alkenyl, $C_2$-$C_6$ alkynyl, $C_1$-$C_6$ haloalkyl, $C_3$-$C_8$cycloalkyl, heterocyclyl, aryl, heteroaryl, $C_3$-$C_8$cycloalkyl($C_1$-$C_6$)alkyl, heterocyclyl($C_1$-$C_6$)alkyl, aryl($C_1$-$C_6$)alkyl, or hetero aryl($C_1$-$C_6$)alkyl;

provided that the compound is not 4-phenyl-1H-imidazole; 4-(4-cyanophenyl)-1H-imidazole; and 2-(2-(1H-imidazol-5-yl)phenoxy)ethanamine.

The invention further comprises embodiments of the ninth aspect in which $R^5$ is one of the following groups (9a)-(9jj):

(9a) $R^5$ is

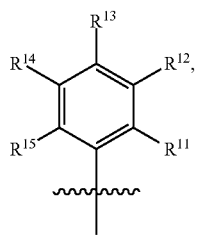

wherein $R^{11}$, $R^{12}$, $R^{13}$, $R^{14}$, $R^{15}$ are each independently hydrogen or $R^{20}$, provided at least one of $R^{11}$, $R^{12}$, $R^{13}$, $R^{14}$, and $R^{15}$ is not hydrogen.

(9b) $R^5$ is according to group (9a), wherein one of $R^{11}$, $R^{12}$, $R^{13}$, $R^{14}$, and $R^{15}$ is halogen, cyano, —OR, —SR, —NR$_2$, —C(O)OR, —C(O)NR$_2$, —N(R)S(O)$_2$R, —$C_1$-$C_6$alkyl-R$^{41}$, -Q-($C_1$-$C_6$)alkyl-R$^{41}$, —$C_1$-$C_6$alkyl-Q-R$^{41}$, -Q-($C_1$-$C_6$)alkyl-Q-R$^{41}$, —$C_1$-$C_6$alkyl-Q-($C_1$-$C_6$)alkyl-R$^{41}$, -Q($C_1$-$C_6$)alkyl-Q-($C_1$-$C_6$)alkyl-R$^{41}$, or -Q($C_1$-$C_6$)alkyl-Q-($C_1$-$C_6$)alkyl-QR$^{41}$.

(9c) $R^5$ is according to group (9a), wherein $R^{11}$ is —OR, —SR, —NR$_2$, —$C_1$-$C_6$alkyl-R$^{41}$, -Q-($C_1$-$C_6$)alkyl-R$^{41}$, —$C_1$-$C_6$alkyl-Q-R$^{41}$, -Q-($C_1$-$C_6$)alkyl-Q-R$^{41}$, —$C_1$-$C_6$alkyl-Q-($C_1$-$C_6$)alkyl-R$^{41}$, -Q($C_1$-$C_6$)alkyl-Q-($C_1$-$C_6$)alkyl-R$^{41}$, or -Q($C_1$-$C_6$)alkyl-Q-($C_1$-$C_6$)alkyl-QR$^{41}$.

(9d) $R^5$ is according to group (9a), wherein $R^{12}$, $R^{13}$, $R^{14}$, and $R^{15}$ are each independently hydrogen, halogen, cyano, $C_1$-$C_6$alkyl, $C_1$-$C_6$haloalkyl, —OR, —SR, —NR$_2$, —C(O)OR, —C(O)NR$_2$, —N(R)S(O)$_2$R; and $R^{11}$ is —OR, —SR, —NR$_2$, —$C_1$-$C_6$alkyl-R$^{41}$, -Q-($C_1$-$C_6$)alkyl-R$^{41}$, —$C_1$-$C_6$alkyl-Q-R$^{41}$, -Q-($C_1$-$C_6$)alkyl-Q-R$^{41}$, —$C_1$-$C_6$alkyl-Q-($C_1$-$C_6$)alkyl-R$^{41}$, -Q($C_1$-$C_6$)alkyl-Q-($C_1$-$C_6$)alkyl-R$^{41}$, or -Q($C_1$-$C_6$)alkyl-Q-($C_1$-$C_6$)alkyl-QR$^{41}$.

(9e) $R^5$ is according to group (9a), wherein $R^{12}$, $R^{13}$, $R^{14}$, and $R^{15}$ are each independently hydrogen, fluoro, chloro, bromo, methyl, or ethyl, and $R^{11}$ is —OR, —SR, —NR$_2$, —$C_1$-$C_6$alkyl-R$^{41}$, -Q-($C_1$-$C_6$)alkyl-R$^{41}$, —$C_1$-$C_6$alkyl-Q-R$^{41}$, -Q-($C_1$-$C_6$)alkyl-Q-R$^{41}$, —$C_1$-$C_6$alkyl-Q-($C_1$-$C_6$)alkyl-R$^{41}$, -Q($C_1$-$C_6$)alkyl-Q-($C_1$-$C_6$)alkyl-R$^{41}$, or -Q($C_1$-$C_6$)alkyl-Q-($C_1$-$C_6$)alkyl-QR$^{41}$.

(9l) $R^5$ is

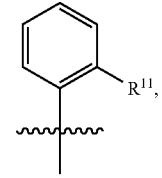

wherein $R^{11}$ is —OR, —SR, —NR$_2$, —$C_1$-$C_6$ alkyl-R$^{41}$, -Q-($C_1$-$C_6$)alkyl-R$^{41}$, —$C_1$-$C_6$alkyl-Q-R$^{41}$, -Q-($C_1$-$C_6$)alkyl-Q-R$^{41}$, —$C_1$-$C_6$alkyl-Q-($C_1$-$C_6$)alkyl-R$^{41}$, -Q($C_1$-$C_6$)alkyl-Q-($C_1$-$C_6$)alkyl-R$^{41}$, or -Q($C_1$-$C_6$)alkyl-Q-($C_1$-$C_6$)alkyl-QR$^{41}$.

(9g) $R^5$ is according to group (9a), wherein $R^{11}$ is —OR or —SR.

(9h) $R^5$ is according to group (9a), wherein $R^{11}$ is —OR$^{21}$ or —SR$^{21}$, wherein $R^{21}$ is hydrogen, $C_1$-$C_6$ alkyl, $C_2$-$C_6$ alkenyl, $C_3$-$C_8$cycloalkyl($C_1$-$C_6$)alkyl, heterocyclyl($C_1$-$C_6$)alkyl, aryl($C_1$-$C_6$)alkyl, or heteroaryl($C_1$-$C_6$)alkyl, wherein the cycloalkylalkyl, heterocyclylalkyl, arylalkyl, and heteroarylalkyl are each optionally substituted with 1, 2, 3, or 4 groups (e.g., 1 or 2 groups) which are each independently halogen, cyano, nitro, $C_1$-$C_6$ alkyl, $C_1$-$C_6$ haloalkyl, —OR$^{10}$, —SR$^{10}$, —N(R$^{10}$)$_2$, —C(O)OR$^{10}$, —C(O)N(R$^{10}$)$_2$, —C(O)R$^{10}$, —S(O)$_2$R$^{10}$, —S(O)$_2$OR$^{10}$, —S(O)$_2$N(R$^{10}$)$_2$, —OC(O)R$^{10}$, —OC(O)OR$^{10}$, —OC(O)N(R$^{10}$)$_2$, —N(R$^{10}$)C(O)R$^{10}$, —N(R$^{10}$)C(O)OR$^{10}$, —N(R$^{10}$)C(O)N(R$^{10}$)$_2$, —N(R$^{10}$)S(O)$_2$R$^{10}$, wherein each R$^{10}$ is independently hydrogen, $C_1$-$C_6$ alkyl, or $C_1$-$C_6$ haloalkyl.

(9i) $R^5$ is according to group (9a), wherein $R^{11}$ is —OR$^{21}$ or —SR$^{21}$, wherein $R^{21}$ is hydrogen, $C_1$-$C_6$ alkyl, $C_2$-$C_6$ alkenyl, $C_3$-$C_8$cycloalkyl($C_1$-$C_6$)alkyl, heterocyclyl($C_1$-$C_6$)alkyl, aryl($C_1$-$C_6$)alkyl, or heteroaryl($C_1$-$C_6$)alkyl.

(9j) $R^5$ is according to group (9a), wherein $R^{12}$, $R^{13}$, $R^{14}$, and $R^{15}$ are each independently hydrogen, halogen, cyano, $C_1$-$C_6$alkyl, $C_1$-$C_6$haloalkyl, —OR, —SR, —NR$_2$, —C(O)OR, —C(O)NR$_2$, —N(R)S(O)$_2$R, and $R^{11}$ is —OR or —SR.

(9k) $R^5$ is according to group (9a), wherein $R^{12}$, $R^{13}$, $R^{14}$, and $R^{15}$ are each independently hydrogen, halogen, cyano, $C_1$-$C_6$alkyl, $C_1$-$C_6$haloalkyl, —OR, —SR, —NR$_2$, —C(O)OR, —C(O)NR$_2$, —N(R)S(O)$_2$R, and $R^{11}$ is —OR$^{21}$ or —SR$^{21}$, wherein $R^{21}$ is hydrogen, $C_1$-$C_6$ alkyl, $C_2$-$C_6$ alkenyl, $C_3$-$C_8$cycloalkyl($C_1$-$C_6$)alkyl, heterocyclyl($C_1$-$C_6$)alkyl, aryl($C_1$-$C_6$)alkyl, or heteroaryl($C_1$-$C_6$)alkyl, wherein the cycloalkylalkyl, heterocyclylalkyl, arylalkyl, and heteroarylalkyl are each optionally substituted with 1, 2, 3, or 4 groups (e.g., 1 or 2 groups) which are each independently halogen, cyano, nitro, $C_1$-$C_6$ alkyl, $C_1$-$C_6$ haloalkyl, —$OR^{10}$, —$SR^{10}$, —$N(R^{10})_2$, —$C(O)OR^{10}$, —$C(O)N(R^{10})_2$, —$C(O)R^{10}$, —$S(O)_2R^{10}$, —$S(O)_2OR^{10}$, —$S(O)_2N(R^{10})_2$, —$OC(O)R^{10}$, —$OC(O)OR^{10}$, —$OC(O)N(R^{10})_2$, —$N(R^{10})C(O)R^{10}$, —$N(R^{10})C(O)OR^{10}$, —$N(R^{10})C(O)N(R^{10})_2$, —$N(R^{10})S(O)_2R^{10}$, wherein each $R^{10}$ is independently hydrogen, $C_1$-$C_6$ alkyl, or $C_1$-$C_6$ haloalkyl.

(9l) $R^5$ is according to group (9a), wherein $R^{12}$, $R^{13}$, $R^{14}$, and $R^{15}$ are each independently hydrogen, halogen, cyano, $C_1$-$C_6$alkyl, $C_1$-$C_6$haloalkyl, —OR, —SR, —$NR_2$, —C(O)OR, —C(O)$NR_2$, —N(R)S(O)$_2$R, and $R^{11}$ is —$OR^{21}$ or —$SR^{21}$, wherein $R^{21}$ is hydrogen, $C_1$-$C_6$ alkyl, $C_2$-$C_6$ alkenyl, $C_3$-$C_8$cycloalkyl($C_1$-$C_6$)alkyl, heterocyclyl($C_1$-$C_6$)alkyl, aryl($C_1$-$C_6$)alkyl, or heteroaryl($C_1$-$C_6$)alkyl.

(9m) $R^5$ is according to group (9a), wherein $R^{12}$, $R^{13}$, $R^{14}$, and $R^{15}$ are each independently hydrogen, fluoro, chloro, bromo, methyl, or ethyl, and $R^{11}$ is —OR or —SR.

(9n) $R^5$ is according to group (9a), wherein $R^{12}$, $R^{13}$, $R^{14}$, and $R^{15}$ are each independently hydrogen, fluoro, chloro, bromo, methyl, or ethyl, and $R^{11}$ is —$OR^{21}$ or —$SR^{21}$, wherein $R^{21}$ is hydrogen, $C_1$-$C_6$ alkyl, $C_2$-$C_6$ alkenyl, $C_3$-$C_8$cycloalkyl($C_1$-$C_6$)alkyl, heterocyclyl($C_1$-$C_6$)alkyl, aryl($C_1$-$C_6$)alkyl, or heteroaryl($C_1$-$C_6$)alkyl.

(9o) $R^5$ is

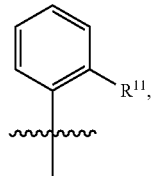

wherein $R^{11}$ is —OR or —SR.

(9p) $R^5$ is

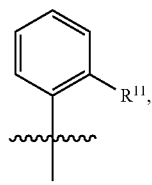

wherein $R^{11}$ is —$OR^{21}$ or —$SR^{21}$, wherein $R^{21}$ is hydrogen, $C_1$-$C_6$ alkyl, $C_2$-$C_6$ alkenyl, $C_3$-$C_8$cycloalkyl($C_1$-$C_6$) alkyl, heterocyclyl($C_1$-$C_6$)alkyl, aryl($C_1$-$C_6$)alkyl, or heteroaryl($C_1$-$C_6$)alkyl, wherein the cycloalkylalkyl, heterocyclylalkyl, arylalkyl, and heteroarylalkyl are each optionally substituted with 1, 2, 3, or 4 groups (e.g., 1 or 2 groups) which are each independently halogen, cyano, nitro, $C_1$-$C_6$ alkyl, $C_1$-$C_6$ haloalkyl, —$OR^{10}$, —$SR^{10}$, —$N(R^{10})_2$, —$C(O)OR^{10}$, —$C(O)N(R^{10})_2$, —$C(O)R^{10}$, —$S(O)_2R^{10}$, —$S(O)_2OR^{10}$, —$S(O)_2N(R^{10})_2$, —$OC(O)R^{10}$, 13 $OC(O)OR^{10}$, —$OC(O)N(R^{10})_2$, —$N(R^{10})C(O)R^{10}$, —$N(R^{10})C(O)OR^{10}$, —$N(R^{10})C(O)N(R^{10})_2$, —$N(R^{10})S(O)_2R^{10}$, wherein each $R^{10}$ is independently hydrogen, $C_1$-$C_6$ alkyl, or $C_1$-$C_6$ haloalkyl.

(9q) $R^5$ is

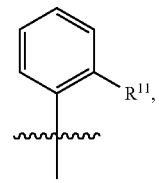

wherein $R^{11}$ is —$OR^{21}$ or —$SR^{21}$, wherein $R^{21}$ is hydrogen, $C_1$-$C_6$ alkyl, $C_2$-$C_6$ alkenyl, $C_3$-$C_8$cycloalkyl($C_1$-$C_6$) alkyl, heterocyclyl($C_1$-$C_6$)alkyl, aryl($C_1$-$C_6$)alkyl, or heteroaryl($C_1$-$C_6$)alkyl.

(9r) $R^5$ is according to group (9a), wherein $R^{11}$ is —$C_1$-$C_6$alkyl-$R^{A1}$, -Q-($C_1$-$C_6$)alkyl-$R^{A1}$, —$C_1$-$C_6$alkyl-Q-$R^{A1}$, -Q-($C_1$-$C_6$)alkyl-C($R^{A2}$)$_2$—$R^{A1}$, or —($C_1$-$C_6$)alkyl-Q-$C_1$-$C_6$ alkyl-$R^{A1}$, or -Q($C_1$-$C_6$)alkyl-C($R^{A2}$)$_2$—($C_1$-$C_6$)alkyl-Q$R^{A1}$, wherein each is Q is independently —O—, —N($R^{A2}$)—, or —S—.

(9s) $R^5$ is according to group (9a), wherein $R^{12}$, $R^{13}$, $R^{14}$, and $R^{15}$ are each independently hydrogen, halogen, cyano, $C_1$-$C_6$alkyl, $C_1$-$C_6$haloalkyl, —OR, —SR, —$NR_2$, —C(O)OR, —C(O)$NR_2$, —N(R)S(O)$_2$R, and $R^{11}$ is —$C_1$-$C_6$alkyl-$R^{A1}$, -Q-($C_1$-$C_6$)alkyl-$R^{A1}$, —$C_1$-$C_6$alkyl-Q-$R^{A1}$, -Q-($C_1$-$C_6$)alkyl-C($R^{A2}$)$_2$—$R^{A1}$, or —($C_1$-$C_6$)alkyl-Q-$C_1$-$C_6$alkyl-$R^{A1}$, or -Q($C_1$-$C_6$)alkyl-C($R^{A2}$)$_2$—($C_1$-$C_6$)alkyl-Q$R^{A1}$, wherein each is Q is independently —O—, —N($R^{A2}$)—, or —S—.

(9t) $R^5$ is according to group (9a), wherein $R^{12}$, $R^{13}$, $R^{14}$, and $R^{15}$ are each independently hydrogen, fluoro, chloro, bromo, methyl, or ethyl, and $R^{11}$ is —$C_1$-$C_6$alkyl-$R^{A1}$, -Q-($C_1$-$C_6$)alkyl-$R^{A1}$, —$C_1$-$C_6$alkyl-Q-$R^{A1}$, -Q-($C_1$-$C_6$)alkyl-C($R^{A2}$)$_2$—$R^{A1}$, or —($C_1$-$C_6$)alkyl-Q-$C_1$-$C_6$ alkyl-$R^{A1}$, or -Q ($C_1$-$C_6$)alkyl-C($R^2$)$_2$—$C_1$-$C_6$)alkyl-Q$R^{A1}$, wherein each is Q is independently —O—, —N($R^{A2}$)—, or —S—.

(9u) $R^5$ is

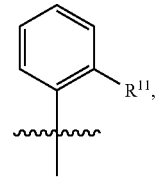

wherein $R^{11}$ is —$C_1$-$C_6$alkyl-$R^{A1}$, -Q-($C_1$-$C_6$)alkyl-$R^{A1}$, —$C_1$-$C_6$alkyl-Q-$R^{A1}$, -Q-($C_1$-$C_6$)alkyl-C($R^{A2}$)$_2$—$R^{A1}$, or —($C_1$-$C_6$)alkyl-Q-$C_1$-$C_6$ alkyl-$R^{A1}$, or -Q($C_1$-$C_6$)alkyl-C($R^{A2}$)$_2$—($C_1$-$C_6$)alkyl-Q$R^{A1}$, wherein each is Q is independently —O—, —N($R^{A2}$)—, or —S—.

(9v) $R^5$ is according to group (9a), wherein $R^{11}$ is —$C_1$-$C_6$alkyl-$R^{A1}$, —O($C_1$-$C_6$)alkyl-$R^{A1}$, —$C_1$-$C_6$alkylO$R^{A1}$, —$C_1$-$C_6$alkyl-C($R^{A2}$)$_2$—$R^{A1}$, —O($C_1$-$C_6$)alkyl-C($R^{A2}$)$_2$—$R^{A1}$, —$C_1$-$C_6$alkyl-O($C_1$-$C_6$)alkyl-$R^{A1}$, or —O($C_1$-$C_6$)alkyl-C($R^{A2}$)$_2$—($C_1$-$C_6$)alkyl-O$R^{A1}$.

(9w) $R^5$ is according to group (9a), wherein $R^{12}$, $R^{13}$, $R^{14}$, and $R^{15}$ are each independently hydrogen, halogen, cyano, $C_1$-$C_6$alkyl, $C_1$-$C_6$haloalkyl, —OR, —SR, —NR$_2$, —C(O)OR, —C(O)NR$_2$, —N(R)S(O)$_2$R, and R$^{11}$ is —C$_1$-C$_6$alkyl-R$^{A1}$, —O(C$_1$-C$_6$)alkyl-R$^{A1}$, —C$_1$-C$_6$alkylOR$^{A1}$, —C$_1$-C$_6$alkyl-C (R$^{A2}$)$_2$—R$^{A1}$, —O(C$_1$-C$_6$)alkyl-C(R$^{A2}$)$_2$—R$^{A1}$, —C$_1$-C$_6$alkyl-O(C$_1$-C$_6$)alkyl-R$^{A1}$, or —O(C$_1$-C$_6$)alkyl-C(R$^{A2}$)$_2$—(C$_1$-C$_6$)alkyl-OR$^{A1}$.

(9x) R$^5$ is according to group (9a), wherein R$^{12}$, R$^{13}$, R$^{14}$, and R$^{15}$ are each independently hydrogen, fluoro, chloro, bromo, methyl, or ethyl, and R$^{11}$ is —C$_1$-C$_6$alkyl-R$^{A1}$, —O(C$_1$-C$_6$)alkyl-R$^{A1}$, —C$_1$-C$_6$alkylOR$^{A1}$, —C$_1$-C$_6$alkyl-C(R$^{A2}$)$_2$—R$^{A1}$, —O(C$_1$-C$_6$)alkyl-C(R$^{A2}$)$_2$—R$^{A1}$, —C$_1$-C$_6$alkyl-O(C$_1$-C$_6$)alkyl-R$^{A1}$, or —O(C$_1$-C$_6$)alkyl-C(R$^{A2}$)$_2$—(C$_1$-C$_6$)alkyl-OR$^{A1}$.

(9y) R$^5$ is

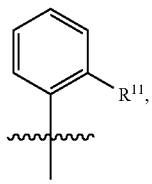

wherein R$^{11}$ is —C$_1$-C$_6$alkyl-R$^{A1}$, —O(C$_1$-C$_6$)alkyl-R$^{A1}$, —C$_1$-C$_6$alkylOR$^{A1}$, —C$_1$-C$_6$alkyl-C(R$^{A2}$)$_2$—R$^{A1}$, —O(C$_1$-C$_6$)alkyl-C(R$^{A2}$)$_2$—R$^{A1}$, —C$_1$-C$_6$alkyl-O(C$_1$-C$_6$)alkyl-R$^{A1}$, or —O(C$_1$-C$_6$)alkyl-C(R$^{A2}$)$_2$—(C$_1$-C$_6$)alkyl-OR$^{A1}$.

(9z) R$^5$ is according to group (9a), wherein R$^{11}$ is —O(C$_1$-C$_6$)alkyl-R$^{A1}$, —C$_1$-C$_6$alkylOR$^{A1}$, —C$_1$-C$_6$alkyl-C(CH$_3$)$_2$—R$^{A1}$, —O(C$_1$-C$_6$)alkyl-C(CH$_3$)$_2$—R$^{A1}$, —C$_1$-C$_6$alkyl-O(C$_1$-C$_6$)alkyl-R$^{A1}$, or —O(C$_1$-C$_6$)alkyl-C(CH$_3$)$_2$—(C$_1$-C$_6$)alkyl-OR$^{A1}$.

(9aa) R$^5$ is according to group (9a), wherein R$^{12}$, R$^{13}$, R$^{14}$, and R$^{15}$ are each independently hydrogen, halogen, cyano, $C_1$-$C_6$alkyl, $C_1$-$C_6$haloalkyl, —OR, —SR, —NR$_2$, —C(O)OR, —C(O)NR$_2$, —N(R)S(O)$_2$R, and R$^{11}$ is —O(C$_1$-C$_6$)alkyl-R$^{A1}$, —C$_1$-C$_6$alkylOR$^{A1}$, —C$_1$-C$_6$alkyl-C(CH$_3$)$_2$—R$^{A1}$, —O(C$_1$-C$_6$)alkyl-C (CH$_3$)$_2$—R$^{A1}$, —C$_1$-C$_6$alkyl-O(C$_1$-C$_6$)alkyl-R$^{A1}$, or —O(C$_1$-C$_6$)alkyl-C (CH$_3$)$_2$—(C$_1$-C$_6$)alkyl-OR$^{A1}$.

(9bb) R$^5$ is according to group (9a), wherein R$^{12}$, R$^{13}$, R$^{14}$, and R$^{15}$ are each independently hydrogen, fluoro, chloro, bromo, methyl, or ethyl, and R$^{11}$ is —O(C$_1$-C$_6$)alkyl-R$^{A1}$, —C$_1$-C$_6$alkylOR$^{A1}$, —C$_1$-C$_6$alkyl-C(CH$_3$)$_2$—R$^{A1}$, —O(C$_1$-C$_6$)alkyl-C(CH$_3$)$_2$—R$^{A1}$, —C$_1$-C$_6$alkyl-O(C$_1$-C$_6$)alkyl-R$^{A1}$, or —O(C$_1$-C$_6$)alkyl-C(CH$_3$)$_2$—(C$_1$-C$_6$)alkyl-OR$^{A1}$.

(9cc) R$^5$ is

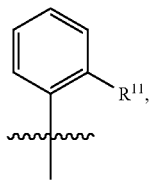

wherein R$^{11}$ is —O(C$_1$-C$_6$)alkyl-R$^{A1}$, —C$_1$-C$_6$alkylOR$^{A1}$, —C$_1$-C$_6$alkyl-C(CH$_3$)$_2$—R$^{A1}$, —O(C$_1$-C$_6$)alkyl-C(CH$_3$)$_2$—R$^{A1}$, —C$_1$-C$_6$alkyl-O(C$_1$-C$_6$)alkyl-R$^{A1}$, or —O(C$_1$-C$_6$)alkyl-C(CH$_3$)$_2$—(C$_1$-C$_6$)alkyl-OR$^{A1}$.

(9dd) R$^5$ is according to group (9a), wherein R$^{11}$, R$^{12}$, R$^{14}$, and R$^{15}$ are independently hydrogen, halogen, cyano, $C_1$-$C_6$alkyl, $C_1$-$C_6$haloalkyl, —OR, —SR, —NR$_2$, —C(O)OR, —C(O)NR$_2$, —N(R)S(O)$_2$R.

(9ee) R$^5$ is according to group (9a), wherein at least one of R$^{12}$, R$^{13}$, R$^{14}$, and R$^{15}$ is fluoro, chloro, bromo, methyl, or ethyl, and R$^{11}$ is —OH, —OCH$_3$, or —SH.

(9ff) R$^5$ is according to group (9a), wherein R$^{12}$, R$^{13}$, R$^{14}$, and R$^{15}$ are each independently hydrogen, fluoro, chloro, bromo, methyl, or ethyl, and R$^{11}$ is —OH, —OCH$_3$, or —SH.

(9gg) R$^5$ is

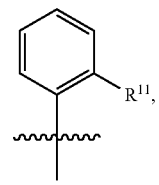

wherein R$^{11}$ is —OH, —OCH$_3$, or —SH.

(9hh) R$^5$ is heteroaryl optionally substituted with 1, 2, 3, or 4 groups (e.g., 1 or 2 groups) which are each independently R$^{20}$.

(9ii) R$^5$ is benzothiophenyl, pyrrolopyridinyl, imidazopyridinyl, quinolinyl, isoquinolinyl, naphthyridinyl, indolyl, indolinyl, benzothiadiazolyl, dihydrobenzodioxinyl, tetrahydropyrimidinyl, pyridinyl, pyrimidinyl, thienyl, or isoxazolyl, each optionally with (e.g., 1 or 2 groups) groups which are each independently R$^{20}$.

(9jj) R$^5$ is benzo[b]thiophen-3-yl, 1H-pyrrolo[2,3-b]pyridin-3-yl, 1H-pyrrolo[2,3-b]pyridin-5-yl, 7-methylimidazo[1,2-a]pyridin-6-yl, quinolin-8-yl, 7-chloroquinolin-4-yl, 2,8-bis(trifluoromethyl)quinolin-4-yl, 5-chloro-8-hydroxyquinolin-7-yl, isoquinolin-4-yl, isoquinolin-5-yl, 2-carboxy-1,6-naphthyridin-8-yl, 1H-indol-7-yl, 1H-indol-6-yl, 1H-indol-5-yl, 9H-purin-6-yl, 2-oxo-2,3-dihydro-1H-imidazo[4,5-b]pyridin-6-yl, 2,3-dioxoindolin-5-yl, 2,3-dioxoindolin-7-yl, benzo[c][1,2,5 ]thiadiazol-4-yl, 2,3-dihydrobenzo[b][1,4]dioxin-6-yl, 1,3-dimethyl-2,4-dioxo-1,2,3,4,-tetrahydropyrimidin-5-yl, 2-morpholinopyridin-3-yl, 4-hydroxybiphenyl-3-yl, 2-hydroxypyridin-3-yl, 2,5-dichlorothiophen-3-yl or 3,5-dimethylisoxazol-4-yl.

In a tenth aspect, the invention provides methods for treating indoleamine 2,3-dioxygenase (IDO) mediated immunosuppression in a subject in need thereof, comprising administering an effective indoleamine 2,3-dioxygenase inhibiting amount of compound according to formula (VI) or (VII), and any embodiment thereof, as described above, or a compound according to formula (XVI) or (XVII),

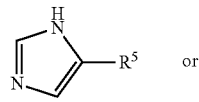
(XVI)

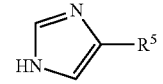
(XVII)

or a pharmaceutically acceptable salt thereof, wherein $R^5$ is

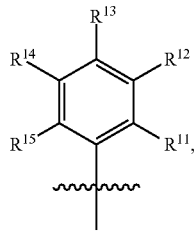

wherein $R^{11}$, $R^{12}$, $R^{13}$, $R^{14}$, and $R^{15}$ are each independently hydrogen, halogen, cyano, —OR, —SR, —NR$_2$, —C(O)OR, —C(O)NR$_2$, —N(R)S(O)$_2$R, —C(O)R$^2$, —S(O)R, —S(O)$_2$R, —S(O)OR, —S(O)$_2$OR, —S(O)NR$_2$, —S(O)$_2$NR$_2$, —OC(O)R, —OC(O)OR, —OC(O)NR$_2$, —N(R)C(O)R, —N(R)C(O)OR, —N(R)C(O)NR$_2$, —N(R)S(O)R, $C_1$-$C_6$alkyl, $C_2$-$C_6$alkenyl, $C_2$-$C_6$alkynyl, $C_1$-$C_6$haloalkyl, $C_3$-$C_8$cycloalkyl, heterocyclyl, aryl, heteroaryl, wherein
each R is independently hydrogen or $R^2$, wherein $R^2$ is $C_1$-$C_6$ alkyl, $C_2$-$C_6$ alkenyl, $C_2$-$C_6$ alkynyl, $C_1$-$C_6$ haloalkyl, $C_3$-$C_8$cycloalkyl, heterocyclyl, aryl, heteroaryl, $C_3$-$C_8$cycloalkyl($C_1$-$C_6$)alkyl, heterocyclyl($C_1$-$C_6$)alkyl, aryl($C_1$-$C_6$)alkyl, or heteroaryl($C_1$-$C_6$)alkyl, wherein the alkyl, $C_3$-$C_8$cycloalkyl, heterocyclyl, aryl, heteroaryl, cycloalkylalkyl, heterocyclylalkyl, arylalkyl, and heteroarylalkyl are each optionally substituted with one or more groups which are each independently halogen, cyano, nitro, —OR$^{10}$, —SR$^{10}$, —N(R$^{10}$)$_2$, —C(O)OR$^{10}$, —C(O)N(R$^{10}$)$_2$, —C(O)R$^{10}$, —S(O)R$^{10}$, —S(O)$_2$R$^{10}$, —S(O)OR$^{10}$, —S(O)$_2$OR$^{10}$, —S(O)N(R$^{10}$)$_2$, —S(O)$_2$N(R$^{10}$)$_2$, —OC(O)R$^{10}$, —OC(O)OR$^{10}$, —OC(O)N(R$^{10}$)$_2$, —N(R$^{10}$)C(O)R$^{10}$, —N(R$^{10}$)C(O)OR$^{10}$, —N(R$^{10}$)C(O)N(R$^{10}$)$_2$, —N(R$^{10}$)S(O)R$^{10}$, —N(R$^{10}$)S(O)$_2$R$^{10}$, $C_1$-$C_6$ alkyl, $C_2$-$C_6$ alkenyl, $C_2$-$C_6$ alkynyl, $C_1$-$C_6$ haloalkyl, $C_3$-$C_8$cycloalkyl, heterocyclyl, aryl, or heteroaryl, wherein each $R^{10}$ is independently hydrogen, $C_1$-$C_6$ alkyl, $C_2$-$C_6$ alkenyl, $C_2$-$C_6$ alkynyl, $C_1$-$C_6$ haloalkyl, $C_3$-$C_8$cycloalkyl, heterocyclyl, aryl, heteroaryl, $C_3$-$C_8$cycloalkyl($C_1$-$C_6$)alkyl, heterocyclyl($C_1$-$C_6$)alkyl, aryl($C_1$-$C_6$)alkyl, or heteroaryl($C_1$-$C_6$)alkyl;
provided that the compound is not 4-phenyl-1H-imidazole; 4-(4-cyanophenyl)-1H-imidazole; and 2-(2-(1H-imidazol-5-yl)phenoxy)ethanamine.

The invention further comprises embodiments of the tenth aspect in which $R^{11}$-$R^{15}$ are defined by one of the following groups (10a)-(10t):

(10a) $R^{11}$ is —OR or —SR.

(10b) $R^{11}$ is —OR$^{21}$ or —SR$^{21}$, wherein $R^{21}$ is hydrogen, $C_1$-$C_6$ alkyl, $C_2$-$C_6$ alkenyl, $C_3$-$C_8$cycloalkyl($C_1$-$C_6$)alkyl, heterocyclyl($C_1$-$C_6$)alkyl, aryl($C_1$-$C_6$)alkyl, or heteroaryl($C_1$-$C_6$)alkyl, wherein the cycloalkylalkyl, heterocyclylalkyl, arylalkyl, and heteroarylalkyl are each optionally substituted with 1, 2, 3, or 4 groups (e.g., 1 or 2 groups) which are each independently halogen, cyano, nitro, $C_1$-$C_6$ alkyl, $C_1$-$C_6$ haloalkyl, —OR$^{10}$, —SR$^{10}$, —N(R$^{10}$)$_2$, —C(O)OR$^{10}$, —C(O)N(R$^{10}$)$_2$, —C(O)R$^{10}$, —S(O)$_2$R$^{10}$, —S(O)$_2$OR$^{10}$, —S(O)$_2$N(R$^{10}$)$_2$, —OC(O)R$^{10}$, —OC(O)OR$^{10}$, —OC(O)N(R$^{10}$)$_2$, —N(R$^{10}$)C(O)R$^{10}$, —N(R$^{10}$)C(O)OR$^{10}$, —N(R$^{10}$)C(O)N(R$^{10}$)$_2$, —N(R$^{10}$)S(O)$_2$R$^{10}$, wherein each $R^{10}$ is independently hydrogen, $C_1$-$C_6$ alkyl, or $C_1$-$C_6$ haloalkyl.

(10c) $R^{11}$ is —OR$^{21}$ or —SR$^{21}$, wherein $R^{21}$ is hydrogen, $C_1$-$C_6$ alkyl, $C_2$-$C_6$ alkenyl, $C_3$-$C_8$cycloalkyl($C_1$-$C_6$)alkyl, heterocyclyl($C_1$-$C_6$)alkyl, aryl($C_1$-$C_6$)alkyl, or heteroaryl ($C_1$-$C_6$)alkyl.

(10d) $R^{11}$ is —OH, —OCH$_3$, or —SH.

(10e) $R^{12}$, $R^{13}$, $R^{14}$, and $R^{15}$ are each independently hydrogen, halogen, cyano, $C_1$-$C_6$alkyl, $C_1$-$C_6$haloalkyl, —OR, —SR, —NR$_2$, —C(O)OR, —C(O)NR$_2$, or —N(R)S(O)$_2$R.

(10f) $R^{12}$, $R^{13}$, $R^{14}$, and $R^{15}$ are each independently hydrogen, halogen, cyano, nitro, $C_1$-$C_6$alkyl, $C_1$-$C_6$haloalkyl, —OR, —SR, —NR$_2$, —C(O)OR, —C(O)NR$_2$, or —N(R)S(O)$_2$R, and $R^{11}$ is —OR or —SR.

(10g) $R^{12}$, $R^{13}$, $R^{14}$, and $R^{15}$ are each independently hydrogen, halogen, cyano, $C_1$-$C_6$alkyl, $C_1$-$C_6$haloalkyl, —OR, —SR, —NR$_2$, —C(O)OR, —C(O)NR$_2$, or —N(R)S(O)$_2$R, and $R^{11}$ is OR$^{21}$ or —SR$^{21}$, wherein $R^{21}$ is hydrogen, $C_1$-$C_6$ alkyl, $C_2$-$C_6$ alkenyl, $C_3$-$C_8$cycloalkyl($C_1$-$C_6$)alkyl, heterocyclyl($C_1$-$C_6$)alkyl, aryl($C_1$-$C_6$)alkyl, or heteroaryl ($C_1$-$C_6$)alkyl, wherein the cycloalkylalkyl, heterocyclylalkyl, arylalkyl, and heteroarylalkyl are each optionally substituted with 1, 2, 3, or 4 groups (e.g., 1 or 2 groups) which are each independently halogen, cyano, nitro, $C_1$-$C_6$ alkyl, $C_1$-$C_6$ haloalkyl, —OR$^{10}$, —SR$^{10}$, —N(R$^{10}$)$_2$, —C(O)OR$^{10}$, —C(O)N(R$^{10}$)$_2$, —C(O)R$^{10}$, —S(O)$_2$R$^{10}$, —S(O)$_2$OR$^{10}$, —S(O)$_2$N(R$^{10}$)$_2$, —OC(O)R$^{10}$, —OC(O)OR$^{10}$, —OC(O)N(R$^{10}$)$_2$, —N(R$^{10}$)C(O)R$^{10}$, —(R$^{10}$)C(O)OR$^{10}$, —N(R$^{10}$)C(O)N(R$^{10}$)$_2$, —N(R$^1$)S(O)$_2$R$^{10}$, wherein each $R^{10}$ is independently hydrogen, $C_1$-$C_6$ alkyl, or $C_1$-$C_6$ haloalkyl.

(10h) $R^{12}$, $R^{13}$, $R^{14}$, and $R^{15}$ are each independently hydrogen, halogen, cyano, $C_1$-$C_6$alkyl, $C_1$-$C_6$haloalkyl, —OR, —SR, —NR$_2$, —C(O)OR, —C(O)NR$_2$, or —N(R)S(O)$_2$R, and $R^{11}$ is —OH, —OCH$_3$, or —SH.

(10i) $R^{12}$, $R^{13}$, $R^{14}$, and $R^{15}$ are each independently hydrogen, fluoro, chloro, bromo, methyl, or ethyl.

(10j) $R^{12}$, $R^{13}$, $R^{14}$, and $R^{15}$ are each independently hydrogen, fluoro, chloro, bromo, methyl, or ethyl, and $R^{11}$ is —OR or —SR.

(10k) $R^{12}$, $R^{13}$, $R^{14}$, and $R^{15}$ are each independently hydrogen, fluoro, chloro, bromo, methyl, or ethyl, and $R^{11}$ is OR$^{21}$ or —SR$^{21}$, wherein $R^{21}$ is hydrogen, $C_1$-$C_6$ alkyl, $C_2$-$C_6$ alkenyl, $C_3$-$C_8$cycloalkyl($C_1$-$C_6$)alkyl, heterocyclyl ($C_1$-$C_6$)alkyl, aryl($C_1$-$C_6$)alkyl, or heteroaryl($C_1$-$C_6$)alkyl, wherein the cycloalkylalkyl, heterocyclylalkyl, arylalkyl, and heteroarylalkyl are each optionally substituted with 1, 2, 3, or 4 groups (e.g., 1 or 2 groups) which are each independently halogen, cyano, nitro, $C_1$-$C_6$ alkyl, $C_1$-$C_6$ haloalkyl, —OR$^{10}$, —SR$^{10}$, —N(R$^1$)$_2$, —C(O)OR$^{10}$, —C(O)N(R$^{10}$)$_2$, —C(O)R$^{10}$, —S(O)$_2$R$^{10}$, —S(O)$_2$OR$^{10}$, —S(O)$_2$N(R$^{10}$)$_2$, —OC(O)R$^{10}$, —OC(O)OR$^{10}$, —OC(O)N(R$^{10}$)$_2$, —N(R$^{10}$)C(O)R$^{10}$, —N(R$^{10}$)C(O)OR$^{10}$, —N(R$^{10}$)C(O)N(R$^{10}$)$_2$, —N(R$^{10}$)S(O)$_2$R$^{10}$, wherein each $R^{10}$ is independently hydrogen, $C_1$-$C_6$ alkyl, or $C_1$-$C_6$ haloalkyl.

(10l) $R^{12}$, $R^{13}$, $R^{14}$, and $R^{15}$ are each independently hydrogen, fluoro, chloro, bromo, methyl, or ethyl, and $R^{11}$ is —OH, —OCH$_3$, or —SH.

(10m) $R^{12}$, $R^{13}$, $R^{14}$, and $R^{15}$ are each hydrogen, and $R^{11}$ is —OR or —SR.

(10n) $R^{12}$, $R^{13}$, $R^{14}$, and $R^{15}$ are each hydrogen, and $R^{11}$ is —OR$^{21}$ or —SR$^{21}$, wherein $R^{21}$ is hydrogen, $C_1$-$C_6$ alkyl, $C_2$-$C_6$ alkenyl, $C_3$-$C_8$cycloalkyl($C_1$-$C_6$)alkyl, heterocyclyl ($C_1$-$C_6$)alkyl, aryl($C_1$-$C_6$)alkyl, or heteroaryl($C_1$-$C_6$)alkyl, wherein the cycloalkylalkyl, heterocyclylalkyl, arylalkyl, and heteroarylalkyl are each optionally substituted with 1, 2, 3, or 4 groups (e.g., 1 or 2 groups) which are each independently halogen, cyano, nitro, $C_1$-$C_6$ alkyl, $C_1$-$C_6$ haloalkyl, —OR$^{10}$, —SR$^{10}$, —N(R$^{10}$)$_2$, —C(O)OR$^{10}$, —C(O)N(R$^{10}$)$_2$, —C(O)R$^{10}$, —S(O)$_2$R$^{10}$, —S(O)$_2$OR$^{10}$, —S(O)$_2$N(R$^{10}$)$_2$, —OC(O)R$^{10}$, —OC(O)OR$^{10}$, —OC(O)

N(R¹⁰)₂, —N(R¹⁰)C(O)R¹⁰, —N(R¹⁰)C(O)OR¹⁰, —N(R¹⁰)C(O)N(R¹⁰)₂, —N(R¹⁰)S(O)₂R¹⁰, wherein each R¹⁰ is independently hydrogen, C₁-C₆ alkyl, or C₁-C₆ haloalkyl.

(10o) R¹¹, R¹², R¹³, R¹⁴, and R¹⁵ are independently hydrogen, halogen, cyano, C₁-C₆alkyl, C₁-C₆haloalkyl, —OR, —SR, —NR₂, —C(O)OR, —C(O)NR₂, or —N(R)S(O)₂R.

(10p) At least one of R¹², R¹³, R¹⁴, and R¹⁵ is fluoro, chloro, bromo, methyl, or ethyl.

(10q) At least one of R¹², R¹³, R¹⁴, and R¹⁵ is fluoro, chloro, bromo, methyl, or ethyl, and R¹¹ is —OH, —OCH₃, or —SH.

(10r) R¹², R¹³, R¹⁴, and R¹⁵ are each independently hydrogen, fluoro, chloro, bromo, methyl, or ethyl, and R¹¹ is —OH, —OCH₃, or —SH.

(10s) R¹², R¹³, R¹⁴, and R¹⁵ are each hydrogen, and R¹¹ is —OH, —OCH₃, or —SH.

(10t) R⁵ is heteroaryl optionally substituted with 1, 2, 3, or 4 groups (e.g., 1 or 2 groups) which are each independently R²⁰.

In a eleventh aspect, the invention provides methods for treating indoleamine 2,3-dioxygenase (IDO) mediated immunosuppression in a subject in need thereof, comprising administering an effective indoleamine 2,3-dioxygenase inhibiting amount of compound according to formula (VIII), as described above. Preferred embodiments of compounds of formula (VIII) are as described in the fifth aspect of the invention.

In an embodiment of the sixth through eleventh aspects, the immunosuppression is associated with an infectious disease, or cancer.

In another embodiment of the sixth through eleventh aspects, the immunosuppression is associated with an infectious disease and the infectious disease is a viral infection selected from the group consisting of: hepatitis C virus (HCV), human papilloma virus (HPV), cytomegalovirus (CMV), Epstein-Barr virus (EBV), poliovirus, varicella zoster virus, coxsackie virus, human immunodeficiency virus (HIV).

In an embodiment of the sixth through eleventh aspects, the immunosuppression is immunosupression associated with HIV-1 infection.

In another embodiment of the sixth through eleventh aspects, the immunosuppression is associated with an infectious disease and the infectious disease is tuberculosis or *Leishmaniasis*.

In another embodiment of the sixth through eleventh aspects, the immunosuppression is associated with a cancer.

In an embodiment of the sixth through eleventh aspects, the immunosuppression is tumor-specific immunosuppression associated with cancer.

In another embodiment of the sixth through eleventh aspects, the immunosuppression is associated with a cancer, wherein the cancer is colon, pancreas, breast, prostate, lung, brain, ovary, cervix, testes, renal, head, or neck cancer, or lymphoma, leukemia, or melanoma.

In a twelfth aspect, the invention provides the use of compounds described by formulae (I)-(XVII) in any of the preceding aspects (and any embodiment thereof), as defined above, for the preparation of a medicament for the treatment of medical conditions that benefit from the inhibition of enzymatic activity of indoleamine-2,3-dioxygenase. Medical conditions contemplated in this twelfth aspect include all the conditions described herein.

In a thirteenth aspect, the invention provides a use of compounds described by formulae (I)-(XVII) in any of the preceding aspects (and any embodiment thereof), as defined above, for the preparation of a medicament to stimulate T cell proliferation or to reverse an immunologic state of anergy or immunosuppression.

In an embodiment of the thirteenth aspect, the anergy or immunosuppression is caused by expression of the enzyme indoleamine-2,3-dioxygenase.

In a fourteenth aspect, the invention provides the use of compounds described by formulae (I)-(XVII) in any of the preceding aspects (and any embodiment thereof), as defined above, for the preparation of a medicament for the treatment of immunosuppression associated with cancer, infectious diseases, or viral infections.

In one embodiment of the fourteenth aspect, the invention provides the use of compounds described in any of the preceding aspects (and any embodiment thereof), as defined above, for the preparation of a medicament for the treatment of tumor-specific immunosuppression associated with cancer. Preferably, the cancer is cancer of the colon, pancreas, breast, prostate, lung, brain, ovary, cervix, testes, renal, or head and neck, lymphoma, leukemia, melanoma, and the like.

In another embodiment of the fourteenth aspect, the invention the use of compounds described in any of the preceding aspects (and any embodiment thereof), as defined above, and embodiments thereof as defined above, for the preparation of a medicament for the treatment of infectious diseases. Preferably, the infections disease is tuberculosis or *Leishmaniasis*.

In another embodiment of the fourteenth aspect, the invention provides the use of compounds described in any of the preceding aspects (and any embodiment thereof), as defined above, and embodiments thereof as defined above, for the preparation of a medicament for the treatment of infectious diseases where the infectious disease is a viral infection. Preferably, the viral infection is selected from the group consisting of: hepatitis C virus (HCV), human papilloma virus (HPV), cytomegalovirus (CMV), Epstein-Barr virus (EBV), varicella zoster virus, poliovirus, coxsackie virus, and human immunodeficiency virus (HIV). More preferably, the viral infection is human immunodeficiency virus (HIV).

In fifteenth aspect, the invention provides compounds of formula (XX),

(XX)

a tautomer thereof, or a pharmaceutically acceptable salt thereof, wherein

R¹ is hydrogen, C₁-C₆ alkyl, C₁-C₆ haloalkyl, or —(C₁-C₆)alkyl-R^{B1}, wherein

R^{B1} is R^{B2}, C₃-C₈cycloalkyl, heterocyclyl, aryl, or heteroaryl, wherein the cycloalkyl, heterocyclyl, aryl, and heteroaryl groups are optionally substituted by 1, 2, 3, or 4 R^{B2} groups, wherein each R^{B2} is independently halogen, cyano, nitro, C₁-C₆ alkyl, C₁-C₆ haloalkyl, —OR, —SR, —NR₂, —C(O)R, —C(O)OR, —C(O)NR₂, —S(O)R, —S(O)₂R, —S(O)OR, —S(O)₂OR, —S(O)NR₂, —S(O)₂NR₂, —OC(O)R, —OC(O)OR, —OC(O)NR₂, —N(R)C(O)R, —N(R)C(O)OR, —N(R)C(O)NR₂, —N(R)S(O)R, or —N(R)S(O)₂R; and R⁵ is (i)

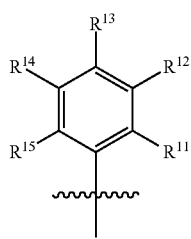

(i) wherein

R$^{11}$ is hydrogen, R$^{20}$, or R$^{40}$, wherein

R$^{40}$ is —OR, —SR, —NR$_2$, —C$_1$-C$_6$alkyl-R$^{41}$, -Q-C$_1$-C$_6$alkyl-R$^{41}$, —C$_1$-C$_6$alkyl-Q-R$^{41}$, -Q-C$_1$-C$_6$alkyl-Q-R$^{41}$, —C$_1$-C$_6$alkyl-Q-(C$_1$-C$_6$)alkyl-R$^{41}$, -Q(C$_1$-C$_6$)alkyl-Q-(C$_1$-C$_6$)alkyl-R$^{41}$, or -Q(C$_1$-C$_6$)alkyl-Q-(C$_1$-C$_6$)alkyl-QR$^{41}$, wherein each Q is independently —C(R$^{42}$)$_2$—, —O—, —N(R$^{42}$)—, —S—, —C(O)—, —S(O)—, —S(O)$_2$—, —C(O)N(R$^{42}$)—, —N(R$^{42}$)C(O)—, —C(O)O—, or —OC(O)—, wherein each R$^{42}$ is independently hydrogen, C$_1$-C$_6$alkyl, or C$_1$-C$_6$haloalkyl;

R$^{41}$ is R$^{43}$, C$_1$-C$_6$ alkyl, —C$_1$-C$_6$ alkyl-R$^{43}$, C$_1$-C$_6$ haloalkyl, C$_3$-C$_8$cycloalkyl, heterocyclyl, aryl, or heteroaryl, wherein the cycloalkyl, heterocyclyl, aryl, and heteroaryl groups are optionally substituted by 1, 2, 3, or 4 R$^{43}$ groups, wherein each R$^{43}$ is independently halogen, cyano, nitro, —OR, —SR, —NR$_2$, —C(O)R, —C(O)OR, —C(O)NR$_2$, —S(O)R, —S(O)$_2$R, —S(O)OR, —S(O)$_2$OR, —S(O)NR$_2$, —S(O)$_2$NR$_2$, —OC(O)R, —OC(O)OR, —OC(O)NR$_2$, —N(R)C(O)R, —N(R)C(O)OR, —N(R)C(O)NR$_2$, —N(R)S(O)R, —N(R)S(O)$_2$R, C$_1$-C$_6$ alkyl, C$_1$-C$_6$ haloalkyl, C$_2$-C$_6$ alkenyl, C$_2$-C$_6$ alkynyl, C$_3$-C$_8$cycloalkyl, heterocyclyl, aryl, or heteroaryl, wherein the cycloalkyl, heterocyclyl, aryl, heteroaryl, are each optionally substituted with 1, 2, 3, or 4 groups which are each independently R$^{30}$ or —C$_1$-C$_6$ alkyl-R$^{30}$, wherein R$^{30}$ is halogen, cyano, nitro, —OR$^{411}$, —SR$^{411}$, —N(R$^{411}$)$_2$, —C(O)OR$^{411}$, —C(O)N(R$^{411}$)$_2$, —C(O)R$^{411}$, —S(O)R$^{411}$, —S(O)$_2$R$^{411}$, —S(O)OR$^{411}$, —S(O)$_2$OR$^{411}$, —S(O)N(R$^{411}$)$_2$, —S(O)$_2$N(R$^{411}$)$_2$, —OC(O)R$^{411}$, —OC(O)OR$^{411}$, —OC(O)N(R$^{411}$)$_2$, —N(R$^{411}$)C(O)R$^{411}$, —N(R$^{411}$)C(O)OR$^{411}$, —N(R$^{411}$)C(O)N(R$^{411}$)$_2$, —N(R$^{411}$)S(O)R$^{411}$, —N(R$^{411}$)S(O)$_2$R$^{411}$, C$_1$-C$_6$ alkyl, or C$_1$-C$_6$ haloalkyl, wherein each R$^{411}$ is independently hydrogen, C$_1$-C$_6$ alkyl, C$_2$-C$_6$ alkenyl, C$_2$-C$_6$ alkynyl, C$_1$-C$_6$ haloalkyl, C$_3$-C$_8$cycloalkyl, heterocyclyl, aryl, heteroaryl, C$_3$-C$_8$cycloalkyl(C$_1$-C$_6$)alkyl, heterocyclyl(C$_1$-C$_6$)alkyl, aryl(C$_1$-C$_6$)alkyl, or heteroaryl(C$_1$-C$_6$)alkyl, or R$^{41}$ and R$^{42}$ taken together, when attached to the same carbon atom, form =C$_3$-C$_8$cycloalkyl, or =heterocyclyl, wherein the cycloalkyl and heterocyclyl are optionally substituted with 1, 2, 3, or 4 groups which are each independently halogen, cyano, nitro, —OR, —SR, —NR$_2$, —C(O)OR, —C(O)NR$_2$, —C(O)R, —S(O)R, —S(O)$_2$R, —S(O)OR, —S(O)$_2$OR, —S(O)NR$_2$, —S(O)$_2$NR$_2$, —OC(O)R, —OC(O)OR, —OC(O)NR$_2$, —N(R)C(O)R, —N(R)C(O)OR, —N(R)C(O)NR$_2$, —N(R)S(O)R, —N(R)S(O)$_2$R, C$_1$-C$_6$ alkyl, or C$_1$-C$_6$ haloalkyl;

R$^{13}$ is hydrogen or —SH; and

R$^{12}$, R$^{14}$, and R$^{15}$ are each independently hydrogen or R$^{20}$, or R$^{14}$ and R$^{15}$ taken together with the carbon atoms to which they are attached form a fused phenyl, fused 5 or 6 membered monocyclic heteroaryl, fused 5 or 6 membered monocyclic cycloalkyl, fused 5 or 6 membered monocyclic cycloalkenyl, or fused monocyclic 5 or 6 membered heterocyclyl, each fused ring optionally substituted with 1, 2, 3, or 4 R$^{20}$ groups;

or (ii) R$^5$ is heteroaryl optionally substituted with one R$^{40}$ group, and optionally substituted with 1, 2, or 3 groups which are each independently R$^{20}$;

each R$^{20}$ is independently halogen, cyano, —OR, —SR, —NR$_2$, —C(O)OR, —C(O)NR$_2$, —N(R)S(O)$_2$R, —C(O)R$^2$, —S(O)R, —S(O)$_2$R, —S(O)OR, —S(O)$_2$OR, —S(O)NR$_2$, —S(O)$_2$NR$_2$, —OC(O)R, —OC(O)OR, —OC(O)NR$_2$, —N(R)C(O)R, —N(R)C(O)OR, —N(R)C(O)NR$_2$, —N(R)S(O)R, C$_1$-C$_6$alkyl, C$_2$-C$_6$alkenyl, C$_2$-C$_6$alkynyl, C$_1$-C$_6$haloalkyl, C$_3$-C$_8$cycloalkyl, heterocyclyl, aryl, heteroaryl, C$_3$-C$_8$cycloalkyl(C$_1$-C$_6$)alkyl, heterocyclyl(C$_1$-C$_6$)alkyl, aryl(C$_1$-C$_6$)alkyl, or heteroaryl(C$_1$-C$_6$)alkyl;

each R is independently hydrogen or R$^2$, wherein R$^2$ is C$_1$-C$_6$ alkyl, C$_2$-C$_6$ alkenyl, C$_2$-C$_6$ alkynyl, C$_1$-C$_6$ haloalkyl, C$_3$-C$_8$cycloalkyl, heterocyclyl, aryl, heteroaryl, C$_3$-C$_8$cycloalkyl(C$_1$-C$_6$)alkyl, heterocyclyl(C$_1$-C$_6$)alkyl, aryl(C$_1$-C$_6$)alkyl, or heteroaryl(C$_1$-C$_6$)alkyl, wherein the alkyl, cycloalkyl, heterocyclyl, aryl, heteroaryl, cycloalkylalkyl, heterocyclylalkyl, arylalkyl, and heteroarylalkyl are each optionally substituted with 1, 2, 3, or 4 groups which are each independently halogen, cyano, nitro, —OR$^{10}$, —SR$^{10}$, —N(R$^{10}$)$_2$, —C(O)OR$^{10}$, —C(O)N(R$^{10}$)$_2$, —C(O)R$^{10}$, —S(O)R$^{10}$, —S(O)$_2$R$^{10}$, —S(O)OR$^{10}$, —S(O)$_2$OR$^{10}$, —S(O)N(R$^{10}$)$_2$, —S(O)$_2$N(R$^{10}$)$_2$, —OC(O)R$^{10}$, —OC(O)OR$^{10}$, —OC(O)N(R$^{10}$)$_2$, —N(R$^{10}$)C(O)R$^{10}$, —N(R$^{10}$)C(O)OR$^{10}$, —N(R$^{10}$)C(O)N(R$^{10}$)$_2$, —N(R$^{10}$)S(O)R$^{10}$, —N(R$^{10}$)S(O)$_2$R$^{10}$, C$_1$-C$_6$ alkyl, C$_2$-C$_6$ alkenyl, C$_2$-C$_6$ alkynyl, C$_1$-C$_6$ haloalkyl, C$_3$-C$_8$cycloalkyl, heterocyclyl, aryl, or heteroaryl, wherein each R$^{10}$ is independently hydrogen, C$_1$-C$_6$ alkyl, C$_2$-C$_6$ alkenyl, C$_2$-C$_6$ alkynyl, C$_1$-C$_6$ haloalkyl, C$_3$-C$_8$cycloalkyl, heterocyclyl, aryl, heteroaryl, C$_3$-C$_8$cycloalkyl(C$_1$-C$_6$)alkyl, heterocyclyl(C$_1$-C$_6$)alkyl, aryl(C$_1$-C$_6$)alkyl, or heteroaryl(C$_1$-C$_6$)alkyl, provided that (i) R$^1$ is not —(CH$_2$)$_{3-4}$—NH$_2$, —(CH$_2$)$_{1-2}$—C(O)NH$_2$, —(CH$_2$)$_{2-3}$—C(O)N(H)CH$_3$, —(CH$_2$)$_{1-2}$N(H)C(O)CH$_3$, —(CH$_2$)$_2$—OH, or —(CH$_2$)$_3$-thiomorpholinyl; and (ii) when R$^1$ is hydrogen or C$_1$-C$_5$ alkyl, then R$^{11}$ is R$^{40}$ and R$^{40}$ is not hydroxy, amino, thiol, C$_1$-C$_3$alkoxy or benzyloxy;

(iii) the compound is not 1-benzyl-5-phenyl-1H-imidazole;

1-(2-phenylethyl)-5-phenyl-1H-imidazole;

1-(2-aminoethyl)-5-phenyl-1H-imidazole;

1-(2-ethoxycarbonylethyl)-5-phenyl-1H-imidazole;

2-(2-(1H-imidazol-5-yl)phenoxy)ethanamine;

4-(2-(trifluoromethoxy)phenyl)-1H-imidazole;

1H,1'H-[2,4']biimidazolyl-4-carbonitrile;

2,6-dichloro-3-(1H-imidazol-5-yl)-4-phenylquinoline;

2-chloro-3-(1H-imidazol-5-yl)-4-phenylquinoline-6-carbonitrile;

3-(1H-imidazol-4-yl)-4-(phenylsulfonyl)-1,2,5-oxadiazole;

3-(4-(1H-imidazol-4-yl)-1,2,5-oxadiazol-3-yloxy)-N,N-dimethylpropan-1-amine;

3-amino-4-ethoxy-7-(1H-imidazol-4-yl)-benzo[b]thiophene-2-carboxylic acid amide;

4-(1H-imidazol-4-yl)-pyridine;

4-(3-pyridinyl)-1H-imidazole;

4-benzo[b]thiophen-4-yl-1H-imidazole;

4-trifluoromethyl-1H,1'H-[2,4']biimidazolyl;

5-(4,5-dihydro-1H-imidazol-2-yl)-2-(1H-imidazol-5-yl)-1H-benzimidazole;

6-(1H-imidazol-4-yl)-5-methoxy-pyridine-2-carboxylic acid;

6-(1H-imidazol-4-yl)-5-methoxy-pyridine-2-carboxylic acid methyl ester;

6-chloro-3-(1H-imidazol-5-yl)-4-phenylquinolin-2(1H)-one;

ethyl-[4-(1H-imidazol-4-yl)-pyridin-2-yl]-amine;

methyl[3-(1H-imidazol-4-yl)-phenoxy]-acetate;

(4-Benzyloxy-phenyl)-(6-(3-methyl-3H-imidazol-4-yl)-quinazolin-4-yl)-amine;

5-(1H-imidazol-4-yl)-1H-indazol-3-amine; and (4-bromo-2-chloro-phenyl)-[4-fluoro-6-(3H-imidazol-4-yl)-1H-benzoimidazol-5-yl]-amine;

ethyl-3-[7-(3-methyl-3H-imidazol-4-yl)-5-pyridin-3-yl-benzothiazol-2-yl]urea

[5-(3-Methyl-3H-imidazol-4-yl)-benzofuran-7ylmethyl]-(2S-phenyl-piperidin-3 S-yl)-amine;

1-Butyl-5-[24(E)-3,7-dimethyl-octa-2,6-dienyloxy)-phenyl]-1H-imidazole; and 5-(2-Allyloxy-phenyl)-1-isobutyl-1H-imidazole.

The invention further comprises subgenera of formula (XX) in which the substituents are selected as any and all combinations of $R^1$ and $R^5$ as defined herein, including without limitation, the following:

$R^5$ is one of the following groups (20a)-(20ii):

(20a) $R^5$ is

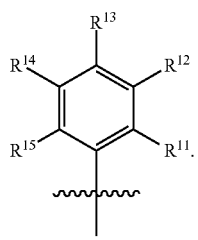

(20b) $R^5$ is according to group (a), wherein $R^{12}$, $R^{14}$ and $R^{15}$ are each independently hydrogen, halogen, cyano, $C_1$-$C_6$alkyl, $C_1$-$C_6$haloalkyl, —OR, —SR, —NR$_2$, —C(O)OR, —C(O)NR$_2$, —N(R)S(O)$_2$R.

(20c) $R^5$ is according to group (a), wherein $R^{12}$, $R^{14}$, and $R^{15}$ are each independently hydrogen, fluoro, chloro, bromo, methyl, or ethyl.

(20d) $R^5$ is according to group (a), wherein $R^{11}$ is —OR or —SR.

(20e) $R^5$ is according to group (a), wherein $R^{11}$ is —OR$^{25}$ or —SR$^{25}$, wherein $R^{25}$ is $C_1$-$C_6$ alkyl, $C_2$-$C_6$ alkenyl, $C_3$-$C_8$cycloalkyl($C_1$-$C_6$)alkyl, heterocyclyl($C_1$-$C_6$)alkyl, aryl($C_1$-$C_6$)alkyl, or heteroaryl($C_1$-$C_6$)alkyl, wherein the cycloalkylalkyl, heterocyclylalkyl, arylalkyl, and heteroarylalkyl are each optionally substituted with 1, 2, 3, or 4 groups (e.g., 1 or 2 groups) which are each independently halogen, cyano, nitro, $C_1$-$C_6$ alkyl, $C_1$-$C_6$ haloalkyl, —OR$^{10}$, —SR$^{10}$, —N(R$^{10}$)$_2$, —C(O)OR$^{10}$, —C(O)N(R$^{10}$)$_2$, —C(O)R$^{10}$, —S(O)$_2$R$^{10}$, —S(O)$_2$OR$^{10}$, —S(O)$_2$N(R$^{10}$)$_2$, —OC(O)R$^{10}$, —OC(O)OR$^{10}$, —OC(O)N(R$^{10}$)$_2$, —N(R$^{10}$)C(O)(R$^{10}$, —N(R$^{10}$)C(O)OR$^{10}$, —N(R$^{10}$)C(O)N(R$^{10}$)$_2$, —N(R$^{10}$)S(O)$_2$R$^{10}$, wherein each R$^{10}$ is independently hydrogen, $C_1$-$C_6$ alkyl, or $C_1$-$C_6$ haloalkyl.

(20f) $R^5$ is according to group (a), wherein $R^{11}$ is —OR$^{25}$ or —SR$^{25}$, wherein $R^{25}$ is $C_1$-$C_6$ alkyl, $C_2$-$C_6$ alkenyl, $C_3$-$C_8$cycloalkyl($C_1$-$C_6$)alkyl, heterocyclyl($C_1$-$C_6$)alkyl, aryl($C_1$-$C_6$)alkyl, or heteroaryl($C_1$-$C_6$)alkyl.

(20g) $R^5$ is according to group (a), wherein $R^{12}$, $R^{14}$, and $R^{15}$ are each independently hydrogen, halogen, cyano, $C_1$-$C_6$alkyl, $C_1$-$C_6$haloalkyl, —OR, —SR, —NR$_2$, —C(O)OR, —C(O)NR$_2$, —N(R)S(O)$_2$R, and $R^{11}$ is —OR or —SR.

(20h) $R^5$ is according to group (a), wherein $R^{12}$, $R^{14}$, and $R^{15}$ are each independently hydrogen, halogen, cyano, $C_1$-$C_6$alkyl, $C_1$-$C_6$haloalkyl, —OR, —SR, —NR$_2$, —C(O)OR, —C(O)NR$_2$, —N(R)S(O)$_2$R, and $R^{11}$ is —OR$^{25}$ or —SR$^{25}$, wherein $R^{25}$ is $C_1$-$C_6$ alkyl, $C_2$-$C_6$ alkenyl, $C_3$-$C_8$cycloalkyl($C_1$-$C_6$)alkyl, heterocyclyl($C_1$-$C_6$)alkyl, aryl($C_1$-$C_6$)alkyl, or heteroaryl($C_1$-$C_6$)alkyl, wherein the cycloalkylalkyl, heterocyclylalkyl, arylalkyl, and heteroarylalkyl are each optionally substituted with 1, 2, 3, or 4 groups (e.g., 1 or 2 groups) which are each independently halogen, cyano, nitro, $C_1$-$C_6$ alkyl, $C_1$-$C_6$ haloalkyl, —OR$^{10}$, —SR$^{10}$, —N(R$^{10}$)$_2$, —C(O)OR$^{10}$, —C(O)N(R$^{10}$)$_2$, —C(O)R$^{10}$, —S(O)$_2$R$^{10}$, —S(O)$_2$OR$^{10}$, —S(O)$_2$N(R$^{10}$)$_2$, —OC(O)R$^{10}$, —OC(O)OR$^{10}$, —OC(O)N(R$^{10}$)$_2$, —N(R$^{10}$)C(O)N(R$^{10}$, —N(R$^{10}$)C(O)OR$^{10}$, —N(R$^{10}$)C(O)N(R$^{10}$)$_2$, —N(R$^{10}$)S(O)$_2$R$^{10}$, wherein each R$^{10}$ is independently hydrogen, $C_1$-$C_6$ alkyl, or $C_1$-$C_6$ haloalkyl.

(20i) $R^5$ is according to group (a), wherein $R^{12}$, $R^{14}$, and $R^{15}$ are each independently hydrogen, halogen, cyano, $C_1$-$C_6$alkyl, $C_1$-$C_6$haloalkyl, —OR, —SR, —NR$_2$, —C(O)OR, —C(O)NR$_2$, —N(R)S(O)$_2$R, and $R^{11}$ is —OR$^{25}$ or —SR$^{25}$, wherein $R^{21}$ is $C_1$-$C_6$ alkyl, $C_2$-$C_6$ alkenyl, $C_3$-$C_8$cycloalkyl($C_1$-$C_6$)alkyl, heterocyclyl($C_1$-$C_6$)alkyl, aryl($C_1$-$C_6$)alkyl, or heteroaryl($C_1$-$C_6$)alkyl.

(20j) $R^5$ is according to group (a), wherein $R^{12}$, $R^{14}$, and $R^{15}$ are each independently hydrogen, fluoro, chloro, bromo, methyl, or ethyl, and $R^{11}$ is —OR or —SR.

(20k) $R^5$ is according to group (a), wherein $R^{12}$, $R^{14}$, and $R^{15}$ are each independently hydrogen, fluoro, chloro, bromo, methyl, or ethyl, and $R^{11}$ is —OR$^{25}$ or —SR$^{25}$, wherein $R^{25}$ is $C_1$-$C_6$ alkyl, $C_2$-$C_6$ alkenyl, $C_3$-$C_8$cycloalkyl($C_1$-$C_6$)alkyl, heterocyclyl($C_1$-$C_6$)alkyl, aryl($C_1$-$C_6$)alkyl, or heteroaryl($C_1$-$C_6$)alkyl.

(20l) $R^5$ is

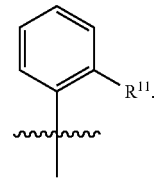

(20m) $R^5$ is

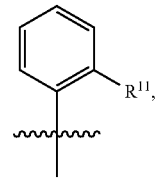

wherein $R^{11}$ is —OR or —SR.

(20n) R⁵ is

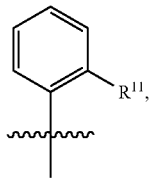

wherein $R^{11}$ is —$OR^{25}$ or —$SR^{25}$, wherein $R^{25}$ is $C_1$-$C_6$ alkyl, $C_2$-$C_6$ alkenyl, $C_3$-$C_8$cycloalkyl($C_1$-$C_6$)alkyl, heterocyclyl($C_1$-$C_6$)alkyl, aryl($C_1$-$C_6$)alkyl, or heteroaryl ($C_1$-$C_6$)alkyl, wherein the cycloalkylalkyl, heterocyclylalkyl, arylalkyl, and heteroarylalkyl are each optionally substituted with 1, 2, 3, or 4 groups (e.g., 1 or 2 groups) which are each independently halogen, cyano, nitro, $C_1$-$C_6$ alkyl, $C_1$-$C_6$ haloalkyl, —$OR^{10}$, —$SR^{10}$, —$N(R^{10})_2$, —$C(O)OR^{10}$, —$C(O)N(R^{10})_2$, —$C(O)R^{10}$, —$S(O)_2R^{10}$, —$S(O)_2OR^{10}$, —$S(O)_2N(R^{10})_2$, —$OC(O)R^{10}$, —$OC(O)OR^{10}$, —$OC(O)N(R^{10})_2$, —$N(R^{10})C(O)R^{10}$, —$N(R^{10})C(O)OR^{10}$, —$N(R^{10})C(O)N(R^{10})_2$, —$N(R^{10})S(O)_2R^{10}$, wherein each $R^{10}$ is independently hydrogen, $C_1$-$C_6$ alkyl, or $C_1$-$C_6$ haloalkyl.

(20o) R⁵ is

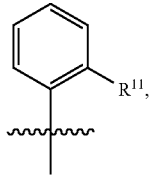

wherein $R^{11}$ is —$OR^{25}$ or —$SR^{25}$, wherein $R^{25}$ is $C_1$-$C_6$ alkyl, $C_2$-$C_6$ alkenyl, $C_3$-$C_8$cycloalkyl($C_1$-$C_6$)alkyl, heterocyclyl($C_1$-$C_6$)alkyl, aryl($C_1$-$C_6$)alkyl, or heteroaryl ($C_1$-$C_6$)alkyl.

(20p) R⁵ is according to group (a), wherein $R^{11}$ is —$C_1$-$C_6$alkyl-$R^{41}$, -Q-($C_1$-$C_6$)alkyl-$R^{41}$, —$C_1$-$C_6$alkyl-Q-$R^{41}$, -Q-($C_1$-$C_6$)alkyl-C($R^{42}$)$_2$—$R^{41}$, or —($C_1$-$C_6$)alkyl-Q-$C_1$-$C_6$ alkyl-$R^{41}$, or -Q($C_1$-$C_6$)alkyl-C($R^{42}$)$_2$—($C_1$-$C_6$)alkyl-Q$R^{41}$, wherein each is Q is independently —O—, —N($R^{42}$)—, or —S—.

(20q) R⁵ is according to group (a), wherein $R^{12}$, $R^{14}$, and $R^{15}$ are each independently hydrogen, halogen, cyano, $C_1$-$C_6$alkyl, $C_1$-$C_6$haloalkyl, —OR, —SR, —NR$_2$, —C(O)OR, —C(O)NR$_2$, —N(R)S(O)$_2$R, and $R^{11}$ is —$C_1$-$C_6$alkyl-$R^{41}$, -Q-($C_1$-$C_6$)alkyl-$R^{41}$, —$C_1$-$C_6$alkyl-Q-$R^{41}$, -Q-($C_1$-$C_6$)alkyl-C($R^{42}$)$_2$—$R^{41}$, or —($C_1$-$C_6$)alkyl-Q-$C_1$-$C_6$ alkyl-$R^{41}$, or -Q($C_1$-$C_6$)alkyl-C($R^{42}$)$_2$—($C_1$-$C_6$)alkyl-Q$R^{41}$, wherein each is Q is independently —O—, —N($R^{42}$)—, or —S—.

(20r) R⁵ is according to group (a), wherein $R^{12}$, $R^{14}$, and $R^{15}$ are each independently hydrogen, fluoro, chloro, bromo, methyl, or ethyl, and $R^{11}$ is —$C_1$-$C_6$alkyl-$R^{41}$, -Q-($C_1$-$C_6$) alkyl-$R^{41}$, —$C_1$-$C_6$alkyl-Q-$R^{41}$, -Q-($C_1$-$C_6$)alkyl-C($R^{42}$)$_2$—$R^{41}$, or —($C_1$-$C_6$)alkyl-Q-$C_1$-$C_6$ alkyl-$R^{41}$, or -Q($C_1$-$C_6$)alkyl-C($R^{42}$)$_2$—($C_1$-$C_6$)alkyl-Q$R^{41}$, wherein each is Q is independently —O—, —N($R^{42}$)—, or —S—.

(20s) R⁵ is

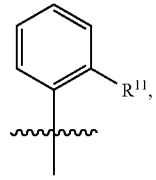

wherein $R^{11}$ is —$C_1$-$C_6$alkyl-$R^{41}$, -Q-($C_1$-$C_6$)alkyl-$R^{41}$, —$C_1$-$C_6$alkyl-Q-$R^{41}$, -Q-($C_1$-$C_6$)alkyl-C($R^{42}$)$_2$—$R^{41}$, or —($C_1$-$C_6$)alkyl-Q-$C_1$-$C_6$ alkyl-$R^{41}$, or -Q($C_1$-$C_6$)alkyl-C($R^{42}$)$_2$—($C_1$-$C_6$)alkyl-Q$R^{41}$, wherein each is Q is independently —O—, —N($R^{42}$)—, or —S—.

(20t) R⁵ is according to group (a), wherein $R^{11}$ is —$C_1$-$C_6$alkyl-$R^{41}$, —O($C_1$-$C_6$)alkyl-$R^{41}$, —$C_1$-$C_6$alkylOR$^{41}$, —$C_1$-$C_6$alkyl-C($R^{42}$)$_2$—$R^{41}$, —O($C_1$-$C_6$)alkyl-C($R^{42}$)$_2$—$R^{41}$, —$C_1$-$C_6$alkyl-O($C_1$-$C_6$)alkyl-$R^{41}$, or —O($C_1$-$C_6$)alkyl-C($R^{42}$)$_2$—($C_1$-$C_6$)alkyl-OR$^{41}$.

(20u) R⁵ is according to group (a), wherein $R^{12}$, $R^{14}$, and $R^{15}$ are each independently hydrogen, halogen, cyano, $C_1$-$C_6$alkyl, $C_1$-$C_6$haloalkyl, —OR, —SR, —NR$_2$, —C(O)OR, —C(O)NR$_2$, —N(R)S(O)$_2$R, and $R^{11}$ is —$C_1$-$C_6$alkyl-$R^{41}$, —O($C_1$-$C_6$)alkyl-$R^{41}$, —$C_1$-$C_6$alkylOR$^{41}$, —$C_1$-$C_6$alkyl-C(R)$^{42}$)$_2$—$R^{41}$, —O($C_1$-$C_6$)alkyl-C($R^{42}$)$_2$—$R^{41}$, —$C_1$-$C_6$alkyl-O($C_1$-$C_6$)alkyl-$R^{41}$, or —O($C_1$-$C_6$)alkyl-C($R^{42}$)$_2$—($C_1$-$C_6$)alkyl-OR$^{41}$.

(20v) R⁵ is according to group (a), wherein $R^{12}$, $R^{14}$, and $R^{15}$ are each independently hydrogen, fluoro, chloro, bromo, methyl, or ethyl, and $R^{11}$ is —$C_1$-$C_6$alkyl-$R^{41}$, —O($C_1$-$C_6$)alkyl-$R^{41}$, —$C_1$-$C_6$alkylOR$^{41}$, —$C_1$-$C_6$alkyl-C(R)$^{42}$)$_2$—$R^{41}$, —O($C_1$-$C_6$)alkyl-C($R^{42}$)$_2$—$R^{41}$, —$C_1$-$C_6$alkyl-O($C_1$-$C_6$)alkyl-$R^{41}$, or —O($C_1$-$C_6$)alkyl-C($R^{42}$)$_2$—($C_1$-$C_6$)alkyl-OR$^{41}$.

(20w) R⁵ is

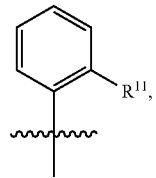

wherein $R^{11}$ is —$C_1$-$C_6$alkyl-$R^{41}$, —O($C_1$-$C_6$)alkyl-$R^{41}$, —$C_1$-$C_6$alkylOR$^{41}$, —$C_1$-$C_6$alkyl-C($R^{42}$)$_2$—$R^{41}$, —O($C_1$-$C_6$)alkyl-C($R^{42}$)$_2$—$R^{41}$, —$C_1$-$C_6$alkyl-O($C_1$-$C_6$)alkyl-$R^{41}$, or —O($C_1$-$C_6$)alkyl-C($R^{42}$)$_2$—($C_1$-$C_6$)alkyl-OR$^{41}$.

(20x) R⁵ is according to group (a), wherein $R^{11}$ is —O($C_1$-$C_6$)alkyl-$R^{41}$, —$C_1$-$C_6$alkylOR$^{41}$, —$C_1$-$C_6$alkyl-C(CH$_3$)$_2$—$R^{41}$, —O($C_1$-$C_6$)alkyl-C(CH$_3$)$_2$—$R^{41}$, —$C_1$-$C_6$alkyl-O($C_1$-$C_6$)alkyl-$R^{41}$, or —O($C_1$-$C_6$)alkyl-C(CH$_3$)$_2$—($C_1$-$C_6$)alkyl-OR$^{41}$.

(20y) R⁵ is according to group (a), wherein $R^{12}$, $R^{14}$, and $R^{15}$ are each independently hydrogen, halogen, cyano, $C_1$-$C_6$alkyl, $C_1$-$C_6$haloalkyl, —OR, —SR, —NR$_2$, —C(O)OR, —C(O)NR$_2$, —N(R)S(O)$_2$R, and $R^{11}$ is —O($C_1$-$C_6$)alkyl-$R^{41}$, —$C_1$-$C_6$alkylOR$^{41}$, —$C_1$-$C_6$alkyl-C(CH$_3$)$_2$—$R^{41}$, —O($C_1$-$C_6$)alkyl-C(CH$_3$)$_2$—$R^{41}$, —$C_1$-$C_6$alkyl-O($C_1$-$C_6$)alkyl-$R^{41}$, or —O($C_1$-$C_6$)alkyl-C(CH$_3$)$_2$—($C_1$-$C_6$)alkyl-OR$^{41}$.

(20z) R⁵ is according to group (a), wherein $R^{12}$, $R^{14}$, and $R^{15}$ are each independently hydrogen, fluoro, chloro, bromo, methyl, or ethyl, and $R^{11}$ is —O($C_1$-$C_6$)alkyl-$R^{41}$, —$C_1$-

$C_6$alkylOR$^{A1}$, —$C_1$-$C_6$alkyl-C(CH$_3$)$_2$—R$^{A1}$, —O($C_1$-$C_6$)alkyl-C(CH$_3$)$_2$—R$^{A1}$, —$C_1$-$C_6$alkyl-O($C_1$-$C_6$)alkyl-R$^{A1}$, or —O($C_1$-$C_6$)alkyl-C(CH$_3$)$_2$—($C_1$-$C_6$)alkyl-OR$^{A1}$.

(20aa) R$^5$ is

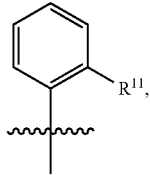

wherein R$^{11}$ is —O($C_1$-$C_6$)alkyl-R$^{A1}$, —$C_1$-$C_6$alkylOR$^{A1}$, —$C_1$-$C_6$alkyl-C(CH$_3$)$_2$—R$^{A1}$, —O($C_1$-$C_6$)alkyl-C(CH$_3$)$_2$—R$^{A1}$, —$C_1$-$C_6$alkyl-O($C_1$-$C_6$)alkyl-R$^{A1}$, or —O($C_1$-$C_6$)alkyl-C(CH$_3$)$_2$—($C_1$-$C_6$)alkyl-OR$^{A1}$.

(20bb) R$^5$ is heteroaryl optionally substituted with one R$^{40}$ group, and optionally substituted with 1, 2, or 3 groups which are each independently R$^{20}$.

(20cc) R$^5$ is heteroaryl substituted with one R$^{40}$ group.

(20dd) R$^5$ is a 6-membered heteroaryl optionally substituted with one R$^{40}$ group, and optionally substituted with 1, 2, or 3 groups which are each independently R$^{20}$.

(20ee) R$^5$ is a 6-membered heteroaryl substituted with one R$^{40}$ group.

(20ff) R$^5$ is a 6-membered heteroaryl substituted with one R$^{40}$ group, and optionally substituted with 1, 2, or 3 groups which are each independently R$^{20}$; wherein the para-position of R$^5$ with respect to the bond between R$^5$ and the imidazole ring is unsubstituted.

(20gg) R$^5$ is a 6-membered heteroaryl substituted with one R$^{40}$ group, wherein the para-position of R$^5$ with respect to the bond between R$^5$ and the imidazole ring is unsubstituted.

(20hh) R$^5$ is benzothiophenyl, pyrrolopyridinyl, imidazopyridinyl, quinolinyl, isoquinolinyl, naphthyridinyl, indolyl, indolinyl, benzothiadiazolyl, dihydrobenzodioxinyl, tetrahydropyrimidinyl, pyridinyl, pyrimidinyl, thienyl, or isoxazolyl, each optionally substituted with one R$^{40}$ group, and optionally substituted with 1, 2, or 3 groups (e.g., 1 or 2 groups) which are each independently R$^{20}$.

(20ii) R$^5$ is benzothiophenyl, pyrrolopyridinyl, imidazopyridinyl, quinolinyl, isoquinolinyl, naphthyridinyl, indolyl, indolinyl, benzothiadiazolyl, dihydrobenzodioxinyl, tetrahydropyrimidinyl, pyridinyl, pyrimidinyl, thienyl, or isoxazolyl, each substituted with one R$^{40}$ group.

R$^1$ is one of the following groups (20jj)-(20ddd):

(20jj) R$^1$ is $C_1$-$C_6$alkyl.

(20kk) R$^1$ is neohexyl.

(20ll) R$^1$ is hydrogen.

(20mm) R$^1$ is —($C_1$-$C_6$)alkyl-R$^{B2}$.

(20nn) R$^1$ is —($C_1$-$C_6$)alkyl-R$^{B2}$, wherein R$^{B2}$ is —OR, —SR, —NR$_2$, —C(O)R, —C(O)OR, —C(O)NR$_2$, —OC(O)R, —OC(O)OR, —OC(O)NR$_2$, —N(R)C(O)R, —N(R)C(O)OR, or —N(R)C(O)NR$_2$.

(20oo) R$^1$ is —($C_1$-$C_6$)alkyl-R$^{B2}$, wherein R$^{B2}$ is —OR$^{22}$, —SR$^{22}$, —N(R$^{22}$)$_2$, —C(O)R$^{22}$, —C(O)OR$^{22}$, —C(O)N(R$^{22}$)$_2$, —OC(O)R$^{22}$, —OC(O)OR$^{22}$, —OC(O)N(R$^{22}$)$_2$, —N(R$^{22}$)C(O)R$^{22}$, —N(R$^{22}$)C(O)OR$^{22}$, or —N(R$^{22}$)C(O)N(R$^{22}$)$_2$, wherein each R$^{22}$ is independently hydrogen or $C_1$-$C_6$ alkyl.

(20pp) R$^1$ is —($C_1$-$C_6$)alkyl-R$^{B1}$ wherein R$^{B1}$ is $C_3$-$C_8$cycloalkyl, heterocyclyl, aryl, or heteroaryl, wherein the cycloalkyl, heterocyclyl, aryl, and heteroaryl groups are optionally substituted by 1, 2, 3, or 4 R$^{B2}$ groups (e.g., 1 or 2 R$^{B2}$ groups).

(20qq) R$^1$ is —($C_1$-$C_4$)alkyl-R$^{B1}$ wherein R$^{B1}$ is $C_3$-$C_8$cycloalkyl, heterocyclyl, aryl, or heteroaryl, wherein the cycloalkyl, heterocyclyl, aryl, and heteroaryl groups are optionally substituted by 1, 2, 3, or 4 R$^{B2}$ groups (e.g., 1 or 2 R$^{B2}$ groups).

(20rr) R$^1$ is —($C_1$-$C_6$)alkyl-R$^{B1}$ wherein R$^{B1}$ is phenyl optionally substituted by 1, 2, 3, or 4R$^{B2}$ groups (e.g., 1 or 2 R$^{B2}$ groups).

(20ss) R$^1$ is —($C_1$-$C_4$)alkyl-R$^{B1}$ wherein R$^{B1}$ is phenyl optionally substituted by 1, 2, 3, or 4 R$^{B2}$ groups (e.g., 1 or 2 R$^{B2}$ groups).

(20tt) R$^1$ is —($C_1$-$C_2$)alkyl-R$^{B1}$ wherein R$^{B1}$ is phenyl optionally substituted by 1, 2, 3, or 4 R$^{B2}$ groups (e.g., 1 or 2 R$^{B2}$ groups).

(20uu) R$^1$ is —CH$_2$—R$^{B1}$ wherein R$^{B1}$ is phenyl optionally substituted by 1, 2, 3, or 4 R$^{B2}$ groups (e.g., 1 or 2 R$^{B2}$ groups).

(20vv) R$^1$ is —CH$_2$—R$^{B1}$ wherein R$^{B1}$ is phenyl optionally substituted by one R$^{B2}$ group.

(20ww) R$^1$ is —($C_1$-$C_6$)alkyl-R$^{B1}$ wherein R$^{B1}$ is phenyl optionally substituted by 1, 2, 3, or 4 R$^{B2}$ groups (e.g., 1 or 2 R$^{B2}$ groups), wherein each R$^{B2}$ is independently halogen, cyano, nitro, —OR$^{B20}$, —SR$^{B20}$, —N(R$^{B20}$)$_2$, $C_1$-$C_6$ alkyl, or $C_1$-$C_6$ haloalkyl, wherein R$^{B20}$ is hydrogen or $C_1$-$C_6$ alkyl.

(20xx) R$^1$ is —($C_1$-$C_6$)alkyl-R$^{B1}$ wherein R$^{B1}$ is phenyl optionally substituted by one R$^{B2}$ group, wherein R$^{B2}$ is halogen, cyano, nitro, —OR$^{B20}$, —SR$^{B20}$, —N(R$^{B20}$)$_2$, $C_1$-$C_6$ alkyl, or $C_1$-$C_6$ haloalkyl, wherein R$^{B20}$ is hydrogen or $C_1$-$C_6$ alkyl.

(20yy) R$^1$ is —($C_1$-$C_4$)alkyl-R$^{B1}$ wherein R$^{B1}$ is phenyl optionally substituted by one R$^{B2}$ groups (e.g., 1 or 2 R$^{B2}$ groups), wherein each R$^{B2}$ is independently halogen, cyano, nitro, —OR$^{B20}$, —SR$^{B20}$, —N(R$^{B20}$)$_2$, $C_1$-$C_6$ alkyl, or $C_1$-$C_6$ haloalkyl, wherein R$^{B20}$ is hydrogen or $C_1$-$C_6$ alkyl.

(20zz) R$^1$ is —($C_1$-$C_4$)alkyl-R$^{B1}$ wherein R$^{B1}$ is phenyl optionally substituted by one R$^{B2}$ group, wherein R$^{B2}$ is halogen, cyano, nitro, —OR$^{B20}$, —SR$^{B20}$, —N(R$^{B20}$)$_2$, $C_1$-$C_6$ alkyl, or $C_1$-$C_6$ haloalkyl, wherein R$^{B20}$ is hydrogen or $C_1$-$C_6$ alkyl.

(20aaa) R$^1$ is —($C_1$-$C_2$)alkyl-R$^{B1}$ wherein R$^{B1}$ is phenyl optionally substituted by 1, 2, 3, or 4 R$^{B2}$ groups (e.g., 1 or 2 R$^{B2}$ groups), wherein each R$^{B2}$ is independently halogen, cyano, nitro, —OR$^{B20}$, —SR$^{B20}$, —N(R$^{B20}$)$_2$, $C_1$-$C_6$ alkyl, or $C_1$-$C_6$ haloalkyl, wherein R$^{B20}$ is hydrogen or $C_1$-$C_6$ alkyl.

(20bbb) R$^1$ is —($C_1$-$C_2$)alkyl-R$^{B1}$ wherein R$^{B1}$ is phenyl optionally substituted by one R$^{B2}$group, wherein R$^{B2}$ is halogen, cyano, nitro, —OR$^{B20}$, —SR$^{B20}$, —N(R$^{B20}$)$_2$, $C_1$-$C_6$ alkyl, or $C_1$-$C_6$ haloalkyl, wherein R$^{B20}$ is hydrogen or $C_1$-$C_6$ alkyl.

(20ccc) R$^1$ is —(CH$_2$)—R$^{B1}$ wherein R$^{B1}$ is phenyl optionally substituted by 1, 2, 3, or 4 R$^{B2}$ groups (e.g., 1 or 2 R$^{B2}$ groups), wherein each R$^{B2}$ is independently halogen, cyano, nitro, —OR$^{B20}$, —SR$^{B20}$, —N(R$^{B20}$)$_2$, $C_1$-$C_6$ alkyl, or $C_1$-$C_6$ haloalkyl, wherein R$^{B20}$ is hydrogen or $C_1$-$C_6$ alkyl.

(20ddd) R$^1$ is —(CH$_2$)—R$^{B1}$ wherein R$^{B1}$ is phenyl optionally substituted by one R$^{B2}$ group, wherein R$^{B2}$ is halogen, cyano, nitro, —OR$^{B20}$, —SR$^{B20}$, —N(R$^{B20}$)$_2$, $C_1$-$C_6$ alkyl, or $C_1$-$C_6$ haloalkyl, wherein R$^{B20}$ is hydrogen or $C_1$-$C_6$ alkyl.

In another embodiment, the compound according to formula (XX) is a compound listed in Table 2 or a pharmaceutically acceptable salt thereof.

In another embodiment, the compound according to formula (XX) is one of the following compounds listed in Table 3, or a pharmaceutically acceptable salt thereof.

In another embodiment, the compound according to formula (XX) is one a compound listed in Table 5, or a pharmaceutically acceptable salt thereof.

In a sixteenth aspect, the invention provides pharmaceutical compositions comprising a pharmaceutically acceptable excipient, diluent, or carrier, and a compound according to the fifteenth aspect or any embodiment thereof.

In a seventeenth aspect, the invention provides methods for treating indoleamine 2,3-dioxygenase (IDO) mediated immunosuppression in a subject in need thereof, comprising administering an effective indoleamine 2,3-dioxygenase inhibiting amount of a compound according to the fifteenth aspect or any embodiment thereof or a pharmaceutical composition of according to the sixteenth aspect.

In an embodiment of the seventeenth aspect, the immunosuppression is associated with an infectious disease, or cancer.

In another embodiment of the seventeenth aspect, the immunosuppression is associated with an infectious disease and the infectious disease is a viral infection selected from the group consisting of: hepatitis C virus (HCV), human papilloma virus (HPV), cytomegalovirus (CMV), Epstein-Barr virus (EBV), poliovirus, varicella zoster virus, coxsackie virus, human immunodeficiency virus (HIV).

In an embodiment of the seventeenth aspect, the immunosuppression is immunosupression associated with HIV-1 infection.

In another embodiment of the seventeenth aspect, the immunosuppression is associated with an infectious disease and the infectious disease is tuberculosis or *Leishmaniasis.*

In another embodiment of the seventeenth aspect, the immunosuppression is associated with a cancer.

In an embodiment of the seventeenth aspect, the immunosuppression is tumor-specific immunosuppression associated with cancer.

In another embodiment of the seventeenth aspect, the immunosuppression is associated with a cancer, wherein the cancer is colon, pancreas, breast, prostate, lung, brain, ovary, cervix, testes, renal, head, or neck cancer, or lymphoma, leukemia, or melanoma.

Definitions

Terms used herein may be preceded and/or followed by a single dash, "—", or a double dash, "=", to indicate the bond order of the bond between the named substituent and its parent moiety; a single dash indicates a single bond and a double dash indicates a double bond. In the absence of a single or double dash it is understood that a single bond is formed between the substituent and its parent moiety; further, substituents are intended to be read "left to right" unless a dash indicates otherwise. For example, $C_1$-$C_6$alkoxycarbonyloxy and —OC(O)$C_1$-$C_6$alkyl indicate the same functionality; similarly arylalkyl and -alkylaryl indicate the same functionality.

The compounds described herein contain imidazole or pyrazole rings which, when one or the pyrazolyl or imidazolyl nitrogens is substituted by hydrogen, can exist in tautomeric forms as are familiar to one skilled in the art. The compounds described herein are understood to include all tautomeric forms thereof. For example, the following pairs of structures are merely tautomers of one another and represent the same chemical compound,

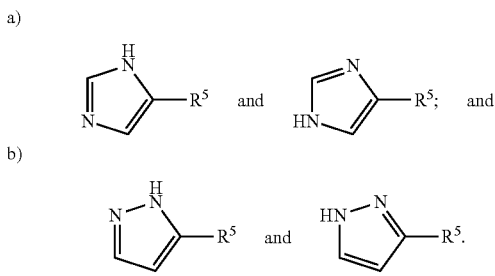

The term "alkenyl" as used herein, means a straight or branched chain hydrocarbon containing from 2 to 10 carbons, unless otherwise specified, and containing at least one carbon-carbon double bond. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, 3-decenyl, and 3,7-dimethylocta-2,6-dienyl.

The term "alkoxy" as used herein, means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkyl" as used herein, means a straight or branched chain hydrocarbon containing from 1 to 10 carbon atoms, unless otherwise specified. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl. When an "alkyl" group is a linking group between two other moieties, then it may also be a straight or branched chain; examples include, but are not limited to —CH$_2$—, —CH$_2$CH$_2$—, —CH$_2$CH$_2$CHC(CH$_3$)—, —CH$_2$CH(CH$_2$CH$_3$)CH$_2$—.

The term "alkyloxycarbonyl" as used herein means an —C(O)OR$^0$ group, where R$^0$ is an alkyl group as defined herein.

The term "alkylcarbonyloxy" as used herein means an —OC(O)R$^0$ group, where R$^0$ is an alkyl group as defined herein.

The term "alkylthio" as used herein, means an —SR$^0$ group, where R$^0$ is an alkyl group as defined herein.

The term "alkynyl" as used herein, means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "amino" as used herein, means a —NH$_2$ group.

The term "aryl," as used herein, means a phenyl (i.e., monocyclic aryl), or a bicyclic ring system containing at least one phenyl ring or an aromatic bicyclic ring containing only carbon atoms in the aromatic bicyclic ring system. The bicyclic aryl can be azulenyl, naphthyl, or a phenyl fused to a monocyclic cycloalkyl, a monocyclic cycloalkenyl, or a monocyclic heterocyclyl. The bicyclic aryl is attached to the parent molecular moiety through any carbon atom contained within the phenyl portion of the bicyclic system, or any carbon atom with the napthyl or azulenyl ring. The fused monocyclic cycloalkyl or monocyclic heterocyclyl portions of the bicyclic aryl are optionally substituted with one or two oxo and/or thia groups. Representative examples of the bicyclic aryls include, but are not limited to, azulenyl, naphthyl, dihydroinden-1-yl, dihydroinden-2-yl, dihydroinden-3-yl, dihydroinden-4-yl, 2,3-dihydroindol-4-yl, 2,3-dihydroindol-5-yl, 2,3-dihydroindol-6-yl, 2,3-dihyddroindol-7-yl, inden-1-yl, inden-2-yl, inden-3-yl, inden-4-yl, dihydronaphthalen-2-yl, dihydronaphthalen-3-yl, dihydronaphthalen-4-yl, dihydronaphthalen-1-yl, 5,6,7,8-tetrahydronaphthalen-1-yl, 5,6,7,8-tetrahydronaphthalen-2-yl, 2,3-dihydrobenzofuran-4-yl, 2,3-dihydrobenzofuran-5-yl, 2,3-dihydrobenzofuran-6-yl, 2,3-dihydrobenzofuran-7-yl, benzo[d][1,3]dioxol-4-yl, benzo[d][1,3]dioxol-5-yl, 2H-chromen-2-on-5-yl, 2H-chromen-2-on-6-yl, 2H-chromen-2-on-7-yl, 2H-chromen-2-on-8-yl, isoindoline-1,3-dion-4-yl, isoindoline-1,3-dion-5-yl, inden-1-on-4-yl, inden-1-on-5-yl, inden-1-on-6-yl, inden-1-on-7-yl, 2,3-dihydrobenzo[b][1,4]dioxan-5-yl, 2,3-dihydrobenzo[b][1,4]dioxan-6-yl, 2H-benzo[b][1,4]oxazin3 (4H)-on-5-yl, 2H-benzo[b][1,4]oxazin3 (4H)-on-6-yl, 2H-benzo[b][1,4]oxazin3 (4H)-on-7-yl, 2H-benzo[b][1,4]oxazin3 (4H)-on-8-yl, benzo[d]oxazin-2 (3H)-on-5-yl, benzo[d]oxazin-2 (3H)-on-6-yl, benzo[d]oxazin-2(3H)-on-7-yl, benzo[d]oxazin-2(3H)-on-8-yl, quinazolin-4(3H)-on-5-yl, quinazolin-4(3H)-on-6-yl, quinazolin-4(3H)-on-7-yl, quinazolin-4(3H)-on-8-yl, quinoxalin-2(1H)-on-5-yl, quinoxalin-2(1H)-on-6-yl, quinoxalin-2(1H)-on-7-yl, quinoxalin-2(1H)-on-8-yl, benzo[d]thiazol-2(3H)-on-4-yl, benzo[d]thiazol-2(3H)-on-5-yl, benzo[d]thiazol-2(3H)-on-6-yl, and, benzo[d]thiazol-2(3H)-on-7-yl. In certain embodiments, the bicyclic aryl is (i) naphthyl or (ii) a phenyl ring fused to either a 5 or 6 membered monocyclic cycloalkyl, a 5 or 6 membered monocyclic cycloalkenyl, or a 5 or 6 membered monocyclic heterocyclyl, wherein the fused cycloalkyl, cycloalkenyl, and heterocyclyl groups are optionally substituted with one or two groups which are independently oxo or thia.

The term "arylalkyl" and "-alkylaryl" as used herein, means an aryl group, as defined herein, appended to the parent molecular moiety through an alkyl group, as defined herein. Representative examples of arylalkyl include, but are not limited to, benzyl, 2-phenylethyl, 3-phenylpropyl, and 2-naphth-2-ylethyl.

The term "carboxy" as used herein, means a —CO$_2$H group.

The terms "cyano" and "nitrile" as used herein, mean a —CN group.

The term "cycloalkyl" as used herein, means a monocyclic or a bicyclic cycloalkyl ring system. Monocyclic ring systems are cyclic hydrocarbon groups containing from 3 to 8 carbon atoms, where such groups can be saturated or unsaturated, but not aromatic. In certain embodiments, cycloalkyl groups are fully saturated. Examples of monocyclic cycloalkyls include cyclopropyl, cyclobutyl, cyclopentyl, cyclopentenyl, cyclohexyl, cyclohexenyl, cycloheptyl, and cyclooctyl. Bicyclic cycloalkyl ring systems are bridged monocyclic rings or fused bicyclic rings. Bridged monocyclic rings contain a monocyclic cycloalkyl ring where two non-adjacent carbon atoms of the monocyclic ring are linked by an alkylene bridge of between one and three additional carbon atoms (i.e., a bridging group of the form —(CH$_2$)$_w$—, where w is 1, 2, or 3). Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane. Fused bicyclic cycloalkyl ring systems contain a monocyclic cycloalkyl ring fused to either a phenyl, a monocyclic cycloalkyl, a monocyclic cycloalkenyl, a monocyclic heterocyclyl, or a monocyclic heteroaryl. The bridged or fused bicyclic cycloalkyl is attached to the parent molecular moiety through any carbon atom contained within the monocyclic cycloalkyl ring. Cycloalkyl groups are optionally substituted with one or two groups which are independently oxo or thia. In certain embodiments, the fused bicyclic cycloalkyl is a 5 or 6 membered monocyclic cycloalkyl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused bicyclic cycloalkyl is optionally substituted by one or two groups which are independently oxo or thia.

"Cycloalkenyl" as used herein refers to a monocyclic or a bicyclic cycloalkenyl ring system. Monocyclic ring systems are cyclic hydrocarbon groups containing from 3 to 8 carbon atoms, where such groups are unsaturated (i.e., containing at least one annular carbon-carbon double bond), but not aromatic. Examples of monocyclic ring systems include cyclopentenyl and cyclohexenyl. Bicyclic cycloalkenyl rings are bridged monocyclic rings or a fused bicyclic rings. Bridged monocyclic rings contain a monocyclic cycloalkenyl ring where two non-adjacent carbon atoms of the monocyclic ring are linked by an alkylene bridge of between one and three additional carbon atoms (i.e., a bridging group of the form —(CH$_2$)$_w$—, where w is 1, 2, or 3). Representative examples of bicyclic cycloalkenyls include, but are not limited to, norbornenyl and bicyclo[2.2.2]oct-2-enyl. Fused bicyclic cycloalkenyl ring systems contain a monocyclic cycloalkenyl ring fused to either a phenyl, a monocyclic cycloalkyl, a monocyclic cycloalkenyl, a monocyclic heterocyclyl, or a monocyclic heteroaryl. The bridged or fused bicyclic cycloalkenyl is attached to the parent molecular moiety through any carbon atom contained within the monocyclic cycloalkenyl ring. Cycloalkenyl groups are optionally substituted with one or two groups which are independently oxo or thia.

The term "epoxy" as used herein, means a

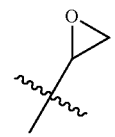 [SMILES: *C1CO1]

group.

The term "formyl" as used herein, means a —C(O)H group.

The term "halo" or "halogen" as used herein, means —Cl, —Br, —I or —F.

The term "haloalkyl" as used herein, means at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, and 2-chloro-3-fluoropentyl.

The term "heteroaryl," as used herein, means a monocyclic heteroaryl or a bicyclic ring system containing at least one heteroaromatic ring. The monocyclic heteroaryl can be a 5 or 6 membered ring. The 5 membered ring consists of two double bonds and one, two, three or four nitrogen atoms and optionally one oxygen or sulfur atom. The 6 membered ring consists of three double bonds and one, two, three or four nitrogen atoms. The 5 or 6 membered heteroaryl is connected to the parent molecular moiety through any carbon atom or any nitrogen atom contained within the heteroaryl. Representative examples of monocyclic heteroaryl include, but are not limited to, furyl, imidazolyl, isoxazolyl, isothiazolyl, oxadiazolyl, oxazolyl, pyridinyl, pyridazinyl, pyrimidinyl, pyrazinyl, pyrazolyl, pyrrolyl, tetrazolyl, thiadiazolyl, thiazolyl, thienyl, triazolyl, and triazinyl. The bicyclic heteroaryl consists of a monocyclic heteroaryl fused to a phenyl, a monocyclic cycloalkyl, a monocyclic cycloalkenyl, a monocyclic heterocyclyl, or a monocyclic heteroaryl. The fused cycloalkyl or heterocyclyl portion of the bicyclic heteroaryl group is optionally substituted with one or two groups which are independently oxo or thia. When the bicyclic heteroaryl contains a fused cycloalkyl, cycloalkenyl, or heterocyclyl ring, then the bicyclic heteroaryl group is connected to the parent molecular moiety through any carbon atom contained within the monocyclic heteroaryl portion of the bicyclic ring system. When the bicyclic heteroaryl is a monocyclic heteroaryl fused to a phenyl ring, then the bicyclic heteroaryl group is connected to the parent molecular moiety through any carbon atom or nitrogen atom within the bicyclic ring system. Representative examples of bicyclic heteroaryl include, but are not limited to, benzimidazolyl, benzofuranyl, benzothienyl, benzoxadiazolyl, benzoxathiadiazolyl, benzothiazolyl, cinnolinyl, 5,6-dihydroquinolin-2-yl, 5,6-dihydroisoquinolin-1-yl, furopyridinyl, indazolyl, indolyl, isoquinolinyl, naphthyridinyl, quinolinyl, purinyl, 5,6,7,8-tetrahydroquinolin-2-yl, 5,6,7,8-tetrahydroquinolin-3-yl, 5,6,7,8-tetrahydroquinolin-4-yl, 5,6,7,8-tetrahydroisoquinolin-1-yl, thienopyridinyl, 4,5,6,7-tetrahydrobenzo[c][1,2,5]oxadiazolyl, and 6,7-dihydrobenzo[c][1,2,5]oxadiazol-4(5H)-onyl. In certain embodiments, the fused bicyclic heteroaryl is a 5 or 6 membered monocyclic heteroaryl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused cycloalkyl, cycloalkenyl, and heterocyclyl groups are optionally substituted with one or two groups which are independently oxo or thia.

The term "heteroarylalkyl" and "-alkylheteroaryl" as used herein, means a heteroaryl, as defined herein, appended to the parent molecular moiety through an alkyl group, as defined herein. Representative examples of heteroarylalkyl include, but are not limited to, fur-3-ylmethyl, 1H-imidazol-2-ylmethyl, 1H-imidazol-4-ylmethyl, 1-(pyridin-4-yl)ethyl, pyridin-3-ylmethyl, pyridin-4-ylmethyl, pyrimidin-5-ylmethyl, 2-(pyrimidin-2-yl)propyl, thien-2-ylmethyl, and thien-3-ylmethyl.

The term "heterocyclyl" as used herein, means a monoclic heterocycle or a bicyclic heterocycle. The monocyclic heterocycle is a 3, 4, 5, 6 or 7 membered ring containing at least one heteroatom independently selected from the group consisting of O, N, and S where the ring is saturated or unsaturated, but not aromatic. The 3 or 4 membered ring contains 1 heteroatom selected from the group consisting of O, N and S. The 5 membered ring can contain zero or one double bond and one, two or three heteroatoms selected from the group consisting of O, N and S. The 6 or 7 membered ring contains zero, one or two double bonds and one, two or three heteroatoms selected from the group consisting of O, N and S. The monocyclic heterocycle is connected to the parent molecular moiety through any carbon atom or any nitrogen atom contained within the monocyclic heterocycle. Representative examples of monocyclic heterocycle include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to either a phenyl, a monocyclic cycloalkyl, a monocyclic cycloalkenyl, a monocyclic heterocycle, or a monocyclic heteroaryl. The bicyclic heterocycle is connected to the parent molecular moiety through any carbon atom or any nitrogen atom contained within the monocyclic heterocycle portion of the bicyclic ring system. Representative examples of bicyclic heterocyclyls include, but are not limited to, 2,3-dihydrobenzofuran-2-yl, 2,3-dihydrobenzofuran-3-yl, indolin-1-yl, indolin-2-yl, indolin-3-yl, 2,3-dihydrobenzothien-2-yl, decahydroquinolinyl, decahydroisoquinolinyl, octahydro-1H-indolyl, and octahydrobenzofuranyl. Heterocyclyl groups are optionally substituted with one or two groups which are independently oxo or thia. In certain embodiments, the bicyclic heterocyclyl is a 5 or 6 membered monocyclic heterocyclyl ring fused to phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the bicyclic heterocyclyl is optionally substituted by one or two groups which are independently oxo or thia.

The term "hydroxy" as used herein, means an —OH group.

The terms "mercapto" and "thiol" as used herein, mean a —SH group.

The term "nitro" as used herein, means a —NO$_2$ group.

The term "oxo" as used herein means a =O group.

The term "saturated" as used herein means the referenced chemical structure does not contain any multiple carbon-carbon bonds. For example, a saturated cycloalkyl group as defined herein includes cyclohexyl, cyclopropyl, and the like.

The term "thia" as used herein means a =S group.

The term "unsaturated" as used herein means the referenced chemical structure contains at least one multiple carbon-carbon bond, but is not aromatic. For example, a unsaturated cycloalkyl group as defined herein includes cyclohexenyl, cyclopentenyl, cyclohexadienyl, and the like.

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "contacting" refers to the bringing together of indicated moieties in an in vitro system or an in vivo system. For example, "contacting" the IDO enzyme with a compound includes the administration of a compound described herein to an individual or patient, such as a human, having IDO, as well as, for example, introducing a compound into a sample containing a cellular or purified preparation containing the IDO enzyme.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician, which includes one or more of the following:

(1) preventing the disease; for example, preventing a disease, condition or disorder in an individual who may be predisposed to the disease, condition or disorder but does not yet experience or display the pathology or symptomatology of the disease;

(2) inhibiting the disease; for example, inhibiting a disease, condition or disorder in an individual who is experiencing or displaying the pathology or symptomatology of the disease, condition or disorder; and (3) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease.

As used here, the terms "treatment" and "treating" means (i) ameliorating the referenced disease state, for example, ameliorating a disease, condition or disorder in an individual who is experiencing or displaying the pathology or symptomatology of the disease, condition or disorder (i.e., reversing or improving the pathology and/or symptomatology) such as decreasing the severity of disease; or (ii) eliciting the referenced biological effect (e.g., IDO modulation or tryptophan degradation inhibition).

As used herein, the terms "catalytic pocket", "catalytic site", "active site" collectively and indistinctly refer to a region of the enzyme that contains amino acid residues responsible for the substrate binding (charge, hydrophobicity, steric hindrance) and catalytic amino acid residues which act as proton donors or acceptors or are responsible for binding a cofactor and participate in the catalysis of a chemical reaction.

As used herein, the phrase "pharmaceutically acceptable salt" refers to both pharmaceutically acceptable acid and base addition salts and solvates. Such pharmaceutically acceptable salts include salts of acids such as hydrochloric, phosphoric, hydrobromic, sulfuric, sulfinic, formic, toluenesulfonic, methanesulfonic, nitric, benzoic, citric, tartaric, maleic, hydroiodic, alkanoic such as acetic, $HOOC-(CH_2)_n-COOH$ where n is 0-4, and the like. Non-toxic pharmaceutical base addition salts include salts of bases such as sodium, potassium, calcium, ammonium, and the like. Those skilled in the art will recognize a wide variety of non-toxic pharmaceutically acceptable addition salts.

Methods of Use

The compounds and pharmaceutical compositions described herein can modulate activity of the enzyme indoleamine-2,3-dioxygenase (IDO). The term "modulate" is meant to refer to an ability to decrease activity of an enzyme or receptor. Accordingly, compounds described herein can be used in methods of modulating IDO by contacting the enzyme with any one or more of the compounds or compositions described herein. In some embodiments, the compounds described herein can act as inhibitors of IDO. In further embodiments, the compounds described herein can be used to modulate activity of IDO in cell or in an individual in need of modulation of the enzyme by administering a modulating (e.g., inhibiting) amount of a compound described herein.

Further provided are methods of inhibiting the degradation of tryptophan and preventing the production of N-formylkynurenine in a system containing cells expressing IDO such as a tissue, living organism, or cell culture. In some embodiments methods of altering (e.g., increasing) extracellular tryptophan levels in a mammal comprise administering an effective amount of a compound or pharmaceutical composition provided herein. Methods of measuring tryptophan levels and tryptophan degradation are routine in the art.

Further provided are methods of inhibiting immunosuppression such as IDO-mediated immunosuppression in a patient by administering to the patient an effective amount of a compound or composition recited herein. IDO-mediated immunosuppression has been associated with, for example, cancers, tumor growth, metastasis, infectious diseases (e.g., viral infection), viral replication, etc.

Further provided are methods for treating tumor-specific immunosuppression associated with cancer in a patient by administering to the patient an effective amount of a compound or composition recited herein. Example tumor-specific immunosuppression associated with cancers treatable by the methods herein include immunosuppression associated with cancer of the colon, pancreas, breast, prostate, lung, brain, ovary, cervix, testes, renal, head and neck, lymphoma, leukemia, melanoma, and the like.

For example, IDO-mediated immunosuppression associated with viral infection, is associated with a viral infection selected from the group consisting of: hepatitis C virus (HCV), human papilloma virus (HPV), cytomegalovirus (CMV), Epstein-Barr virus (EBV), poliovirus, varicella zoster virus, coxsackie virus, human immunodeficiency virus (HIV).

Further provided are methods for treating immunosupression associated with an infectious disease, e.g., HIV-1 infection, in a patient by administering to the patient an effective amount of a compound or composition recited herein.

In other examples, IDO-mediated immunosuppression associated with and infectious diseases is associated with tuberculosis or *Leishmaniasis*.

For example, a patient undergoing or having completed a course of chemotherapy and/or radiation therapy for the treatment of a disease state, such as a cancer, can benefit from administering to the patient a therapeutically effective amount of a compound or composition recited herein for inhibiting immunosuppression resulting from the disease state and/or treatment thereof.

Further provided are methods of treating diseases associated with activity or expression, including abnormal activity and/or overexpression, of IDO in an individual (e.g., patient) by administering to the individual in need of such treatment a therapeutically effective amount or dose of a compound described herein or a pharmaceutical composition thereof. Example diseases can include any disease, disorder or condition that is directly or indirectly linked to expression or activity of the IDO enzyme, such as over expression or abnormal activity. An IDO-associated disease can also include any disease, disorder or condition that can be prevented, ameliorated, or cured by modulating enzyme activity.

Examples of IDO-associated diseases include cancer, viral infection such as HIV infection, depression, neurodegenerative disorders such as Alzheimer's disease and Huntington's disease, trauma, age-related cataracts, organ transplantation (e.g., organ transplant rejection), and autoimmune diseases including asthma, rheumatoid arthritis, multiple sclerosis, inflammatory bowel disease, psoriasis and systemic lupus erythematosusor. Example cancers treatable by the methods herein include cancer of the colon, pancreas, breast, prostate, lung, brain, ovary, cervix, testes, renal, head and neck, lymphoma, leukemia, melanoma, and the like.

Combination Therapy

One or more additional pharmaceutical agents for treatment methods such as, for example, anti-viral agents, chemotherapeutics or other anti-cancer agents, immune enhancers, immunosuppressants, radiation, anti-tumor and anti-viral vaccines, cytokine therapy (e.g., IL2, GM-CSF, etc.), and/or tyrosine kinase inhibitors can be used in combination with the compounds and pharmaceutical compositions described herein for treatment of IDO-associated diseases, disorders or conditions (as noted above) or for enhancing the effectiveness of the treatment of a disease state or condition, such as cancer. The agents can be combined with the present compounds in a single dosage form, or the agents can be administered simultaneously or sequentially as separate dosage forms.

Suitable antiviral agents contemplated for use in combination with the compounds described herein can comprise nucleoside and nucleotide reverse transcriptase inhibitors (NRTIs), non-nucleoside reverse transcriptase inhibitors (NNRTIs), protease inhibitors and other antiviral drugs.

Example suitable NRTIs include zidovudine (AZT); didanosine (ddI); zalcitabine (ddC); stavudine (d4T); lamivudine (3TC); abacavir (1592U89); adefovir dipivoxil [bis(POM)-PMEA]; lobucavir (BMS-180194); BCH-10652; emitricitabine[(−)-FTC]; beta-L-FD4 (also called beta-L-D4C and named beta-L-2',3'-dicleoxy-5-fluoro-cytidene); DAPD, ((−)-beta-D-2,6,-diamino-purine dioxolane); and lodenosine (FddA). Typical suitable NNRTIs include nevirapine (BI-RG-587); delaviradine (BHAP, U-90152); efavirenz (DMP-266); PNU-142721; AG-1549; MKC-442 (1-(ethoxy-methyl)-5-(1-methylethyl)-6-(phenylmethyl)-(2, 4(1H,3H)-pyrimid-inedione); and (+)-calanolide A (NSC-675451) and B. Typical suitable protease inhibitors include saquinavir (Ro 31-8959); ritonavir (ABT-538); indinavir (MK-639); nelfnavir (AG-1343); amprenavir (141W94); lasinavir (BMS-234475); DMP-450; BMS-2322623; ABT-378; and AG-1549. Other antiviral agents include hydroxyurea, ribavirin, IL-2, IL-12, pentafuside and Yissum Project No. 11607.

Suitable chemotherapeutic or other anti-cancer agents include, for example, alkylating agents (including, without limitation, nitrogen mustards, ethylenimine derivatives, alkyl sulfonates, nitrosoureas and triazenes) such as uracil mustard, chlormethine, cyclophosphamide (Cytoxan™), ifosfamide, melphalan, chlorambucil, pipobroman, triethylenemelamine, triethylenethiophosphoramine, busulfan, carmustine, lomustine, streptozocin, dacarbazine, and temozolomide.

Suitable chemotherapeutic or other anti-cancer agents include, for example, antimetabolites (including, without limitation, folic acid antagonists, pyrimidine analogs, purine analogs and adenosine deaminase inhibitors) such as methotrexate, 5-fluorouracil, floxuridine, cytarabine, 6-mercaptopurine, 6-thioguanine, fludarabine phosphate, pentostatine, and gemcitabine.

Suitable chemotherapeutic or other anti-cancer agents further include, for example, certain natural products and their derivatives (for example, vinca alkaloids, antitumor antibiotics, enzymes, lymphokines and epipodophyllotoxins) such as vinblastine, vincristine, vindesine, bleomycin, dactinomycin, daunorubicin, doxorubicin, epirubicin, idarubicin, ara-C, paclitaxel (Taxol™), mithramycin, deoxyco-formycin, mitomycin-C, L-asparaginase, interferons (especially IFN-α), etoposide, and teniposide.

Other cytotoxic agents include navelbene, CPT-11, anastrazole, letrazole, capecitabine, reloxafine, cyclophosphamide, ifosamide, and droloxafine.

Also suitable are cytotoxic agents such as epidophyllotoxin; an antineoplastic enzyme; a topoisomerase inhibitor; procarbazine; mitoxantrone; platinum coordination complexes such as cis-platin and carboplatin; biological response modifiers; growth inhibitors; antihormonal therapeutic agents; leucovorin; tegafur; and haematopoietic growth factors.

Other anti-cancer agent(s) include antibody therapeutics such as trastuzumab (Herceptin), antibodies to costimulatory molecules such as CTLA-4, 4-1BB and PD-1, or antibodies to cytokines (IL-10, TGF-β, etc.).

Other anti-cancer agents also include those that block immune cell migration such as antagonists to chemokine receptors, including CCR2, CCR4 and CCR6.

Other anti-cancer agents also include those that augment the immune system such as adjuvants or adoptive T cell transfer.

Anti-cancer vaccines include dendritic cells, synthetic peptides, DNA vaccines and recombinant viruses.

Methods for the safe and effective administration of most of these chemotherapeutic agents are known to those skilled in the art. In addition, their administration is described in the standard literature. For example, the administration of many of the chemotherapeutic agents is described in the "Physicians' Desk Reference" (PDR, e.g., 1996 edition, Medical Economics Company, Montvale, N.J.), the disclosure of which is incorporated herein by reference as if set forth in its entirety.

Pharmaceutical Formulations and Dosage Forms

The pharmaceutical compositions described herein generally comprise a combination of a compound described herein and a pharmaceutically acceptable carrier, diluent, or excipient. Such compositions are substantially free of non-pharmaceutically acceptable components, i.e., contain amounts of non-pharmaceutically acceptable components lower than permitted by US regulatory requirements at the time of filing this application. In some embodiments of this aspect, if the compound is dissolved or suspended in water, the composition further optionally comprises an additional pharmaceutically acceptable carrier, diluent, or excipient. In other embodiments, the pharmaceutical compositions described herein are solid pharmaceutical compositions (e.g., tablet, capsules, etc.).

These compositions can be prepared in a manner well known in the pharmaceutical art, and can be administered by a variety of routes, depending upon whether local or systemic treatment is desired and upon the area to be treated. Administration may be topical (including ophthalmic and to mucous membranes including intranasal, vaginal and rectal delivery), pulmonary (e.g., by inhalation or insufflation of powders or aerosols, including by nebulizer; intratracheal, intranasal, epidermal and transdermal), ocular, oral or parenteral. Methods for ocular delivery can include topical administration (eye drops), subconjunctival, periocular or intravitreal injection or introduction by balloon catheter or ophthalmic inserts surgically placed in the conjunctival sac. Parenteral administration includes intravenous, intraarterial, subcutaneous, intraperitoneal or intramuscular injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Also, pharmaceutical compositions can contain, as the active ingredient, one or more of the compounds described herein above in combination with one or more pharmaceutically acceptable carriers. In making the compositions described herein, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions described herein can be formulated so as to provide quick, sustained or delayed release of the active ingredient after administration to the patient by employing procedures known in the art.

The compositions can be formulated in a unit dosage form, each dosage containing from about 5 to about 100 mg, more usually about 10 to about 30 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound described herein. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, 0.1 to about 500 mg of the active ingredient of a compound described herein.

The tablets or pills can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions in can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of the compounds can vary according to, for example, the particular use for which the treatment is made, the manner of administration of the compound, the health and condition of the patient, and the judgment of the prescribing physician. The proportion or concentration of a compound described herein in a pharmaceutical composition can vary depending upon a number of factors including dosage, chemical characteristics (e.g., hydrophobicity), and the route of administration. For example, the compounds described herein can be provided in an aqueous physiological buffer solution containing about 0.1 to about 10% w/v of the compound for parenteral adminstration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compounds described herein can also be formulated in combination with one or more additional active ingredients which can include any pharmaceutical agent such as antiviral agents, vaccines, antibodies, immune enhancers, immune suppressants, anti-inflammatory agents and the like.

Labeled Compounds and Assay Methods

Another aspect relates to fluorescent dye, spin label, heavy metal or radio-labeled derivatives of the compounds described herein that would be useful not only in imaging but also in assays, both in vitro and in vivo, for localizing and quantitating the IDO enzyme in tissue samples, including human, and for identifying IDO enzyme ligands by inhibition binding of a labeled compound. Accordingly, further provided are IDO enzyme assays that contain such labeled compounds.

Further provided are isotopically-labeled compounds of the compounds described herein. An "isotopically" or "radio-labeled" compound is a compound described herein where one or more atoms are replaced or substituted by an atom having an atomic mass or mass number different from the atomic mass or mass number typically found in nature (i.e., naturally occurring). Suitable radionuclides that may be include but are not limited to 2H (also written as D for deuterium), 3H (also written as T for tritium), $^{11}C$, $^{13}C$, $^{14}C$, $^{13}N$, $^{15}N$, $^{15}O$, $^{17}O$, $^{18}O$, $^{18}F$, $^{35}S$, $^{36}Cl$, $^{82}Br$, $^{75}Br$, $^{76}Br$, $^{77}Br$, $^{123}I$, $^{124}I$, $^{125}I$ and $^{131}I$. The radionuclide that is incorporated in the instant radio-labeled compounds will depend on the specific application of that radio-labeled compound. For example, for in vitro IDO enzyme labeling and competition assays, compounds that incorporate $^{3}H$, $^{14}C$, $^{82}Br$, $^{125}I$, $^{131}I$, $^{35}S$ or will generally be most useful. For radio-imaging applications $^{11}C$, $^{18}F$, $^{125}I$, $^{123}I$, $^{124}I$, $^{131}I$, $^{75}Br$, $^{76}Br$ or $^{77}Br$ will generally be most useful.

It is understood that a "radio-labeled" or "labeled compound" is a compound that has incorporated at least one radionuclide. In some embodiments the radionuclide is selected from the group consisting of $^{3}H$, $^{14}C$, $^{125}I$, $^{35}S$ and $^{82}Br$.

Synthetic methods for incorporating radio-isotopes into organic compounds are applicable to compounds described herein and are well known in the art.

A radio-labeled compound described herein can be used in a screening assay to identify/evaluate compounds. In general terms, a newly synthesized or identified compound (i.e., test compound) can be evaluated for its ability to reduce binding of the radio-labeled compound described herein to the IDO enzyme. Accordingly, the ability of a test compound to compete with the radio-labeled compound for binding to the IDO enzyme directly correlates to its binding affinity.

Kits

Also included are pharmaceutical kits useful, for example, in the treatment or prevention of IDO-associated diseases or disorders, obesity, diabetes and other diseases referred to herein which include one or more containers containing a pharmaceutical composition comprising a therapeutically effective amount of a compound described herein. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The following examples are offered for illustrative purposes, and are not intended to limit the disclosure in any manner. Those of skill in the art will readily recognize a variety of noncritical parameters which can be changed or modified to yield essentially the same results. The example compounds below were found to be inhibitors of IDO according to one or more of the assays described herein.

EXAMPLES

All reagents and solvents were purchased from commercial sources. All commercial reagents and solvents were used as received without further purification. The reactions were monitored using analytical thin layer chromatography (TLC) with 0.25 mm EM Science silica gel plates (60E-254). The developed TLC plates were visualized by immersion in potassium permanganate solution followed by heating on a hot plate. Flash chromatography was performed with Selecto Scientific silica gel, 32-63 µm particle sizes. All reactions were performed in flame or oven-dried glassware under a nitrogen atmosphere. All reactions were stirred magnetically at ambient temperature unless otherwise indicated. $^{1}H$ NMR spectra were obtained with a Bruker DRX400, Varian VXR400 or VXR300. $^{1}H$ NMR spectra were reported in parts per million (δ) relative to TMS (0.0), DMSO-$d_6$ (2.50) or CD$_3$OD (4.80) as an internal reference. All spectra are recorded in CDCl$_3$ unless otherwise indicated.

The following abbreviations are used in the following examples:

| | |
|---|---|
| Ac$_2$O | acetic anhydride |
| AcCl | acetyl chloride |
| AcOH | acetic acid |
| DCM | dichloromethane |
| DEAD | diethyl azodicarboxylate |
| DIBAL-H | diisobutylaluminum hydride |
| DMF | N,N-dimethylformamide |
| Et | ethyl |
| Et$_3$N | triethylamine |
| EtMgBr | ethyl magnesium bromide |
| EtOAc | ethyl acetate |
| EtOH | ethanol |
| MeOH | methanol |
| OAc | acetate |
| OMs | Mesylate |
| Ot-Bu | tert-butoxide |
| OTs | tosylate |
| rt | room temperature |
| sat'd | saturated |
| THF | tetrahydrofuran |
| TOSMIC | toluenesulfonylmethyl isocyanide |

Example 1

N-(4-Chlorobenzyl)-2-iodoaniline

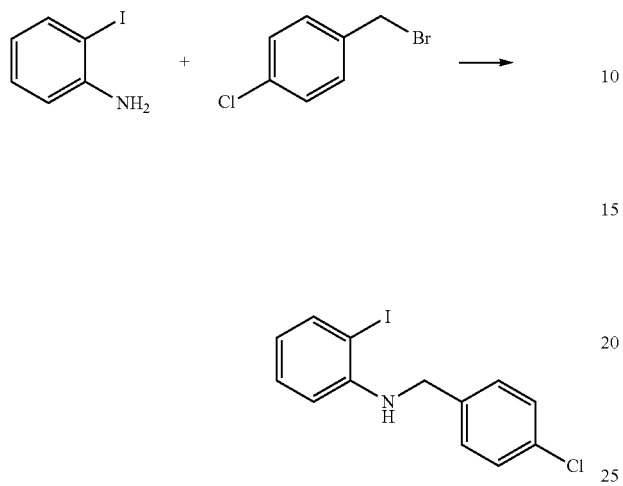

To a solution of 2-iodoaniline (280 mg, 1.82 mmol) in acetonitrile (6 mL) was added $K_2CO_3$ (212 mg, 1.54 mmol) and 4-chlorobenzyl bromide (276 mg, 1.34 mmol). After refluxing overnight under a nitrogen atmosphere, the reaction mixture was diluted with ethyl acetate and filtered. The solvent was removed under reduced pressure and the crude product was used in next step.

Example 2

Tert-Butyl 4-chlorobenzyl(2-iodophenyl)carbamate

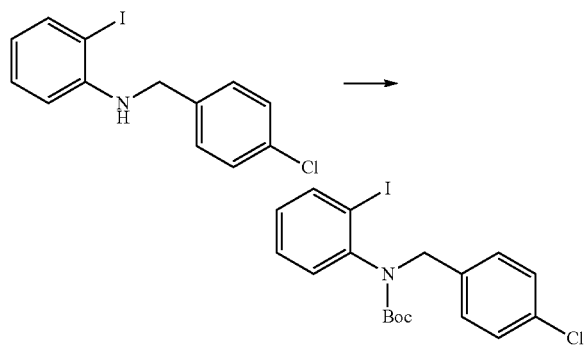

N-(4-chlorobenzyl)-2-iodoaniline (386 mg, 1.12 mmol) was dissolved in dichloromethane (6 mL) and triethylamine (0.23 mL, 1.68 mmol) was added. The mixture was stirred for 5 min and di-tert-butyl dicarbonate (257 mg, 1.18 mmol) was added. The reaction was stirred overnight and diluted with dichloromethane (30 mL). The dichloromethane solution was washed with saturated ammonium chloride (10 mL), water (10 mL) and dried over $Na_2SO_4$. The solvent was removed under reduced pressure and the crude product was used for Negishi coupling without further purification.

Example 3

(2-(1H-Imidazol-4-yl)phenyl)methanol

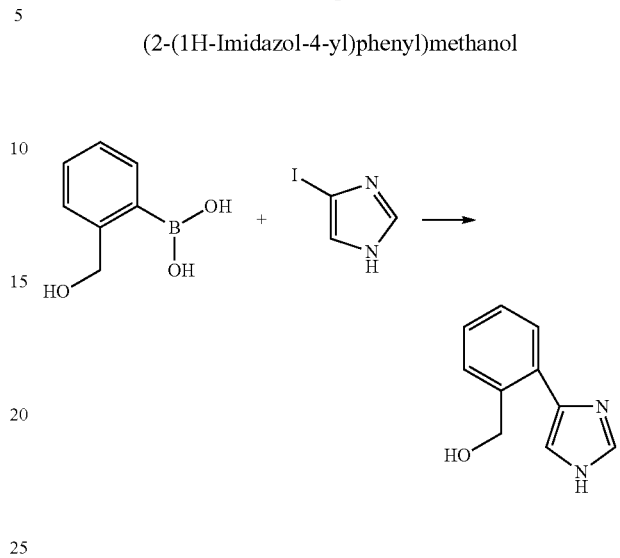

A mixture of 1-propanol (7.5 mL) and water (2.5 mL) was purged with nitrogen for 5 minutes. To the solution were added 4-bromo-1H-imidazole (146.97 mg, 1 mmol), 2-(hydroxyl-methyl)phenylboronic acid (190 mg, 1.25 mmol), $Pd(OAc)_2$ (11.2 mg, 0.05 mmol), $PPh_3$ (39.3 mg, 0.15 mmol) and potassium carbonate (276 mg, 2.0 mmol). After stirring at 85° C. for 16 h, the mixture was allowed to cool to room temperature and was partitioned between EtOAc (30 mL) and water (15 mL). The aqueous layer was extracted with EtOAc (2×20 mL) and the combined organic layers were washed with water, brine, and dried over sodium sulfate. The solvent was removed under reduced pressure and the crude product was purified by flash column chromatography on silica gel to afford the pure product (62 mg, 37% yield). $^1$H NMR: 4.48 (s, 2H), 6.25 (br s, 1H), 7.18-7.28 (m, 2H), 7.39-7.47 (m, 2H), 7.62 (d, 1H, J=7.0 Hz), 7.80 (d, 1H), 12.30 (br s, 1H).

Example 4

General Procedure for the Iodination of Phenols

To a stirred solution of the phenol (12.15 mmol) in methanol (40 mL) was dissolved sodium iodide (12.15 mmol, 1.82 g) and sodium hydroxide (12.15 mmol, 485.8 mg). The solution was cooled to 0° C. and sodium hypochlorite (6% NaOCl in water, 12.15 mmol, 14.4 mL) was added dropwise over 75 min while maintaining the temperature at 0° C. The resulting colorless slurry was allowed to stir for an additional 1 h at 0° C. The solution was treated with sat'd $Na_2S_2O_3$ (20 mL) and the pH was adjusted to <7 with 5% aqueous HCl. Most of the methanol was removed under reduced pressure and the aqueous layer was extracted with ethyl acetate (3×20 mL). The combined organic layers were washed successively with water, brine and dried (MgSO$_4$). The solvent was removed under reduced pressure to afford the crude iodo phenol, which was purified by column chromatography on silica gel using hexanes/EtOAc as the eluent.

Utilizing the appropriate starting materials, the following compounds were prepared according to Example 4:

| Compound | Name | Yield (%) | $^1$H NMR |
|---|---|---|---|
| 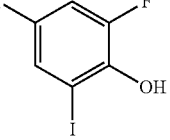 | 4-chloro-2-fluoro-6-iodophenol | 57 | 5.47(s, 1H), 7.11-7.14(d, 1H, J = 9.8 Hz), 7.47(s, 1H) |

Example 5

General Procedure for the Synthesis of Ethers by the Mitusunobu Reaction

To a stirred solution of the phenol (3.89 mmol), the primary alcohol, (3.89 mmol), and triphenyl phosphine (4.28 mmol) in anhydrous THF (15 mL) at 0° C. was added DEAD (40% in toluene, 4.28 mmol, 1.95 mL) dropwise. The yellow solution was allowed to warm to rt and stirring was continued overnight. After evaporating the solvent under reduced pressure the crude residue was dissolved in DCM (15 mL). The organic layer was washed with 10% NaOH (2×10 mL), water and brine. The organic phase was dried (Na$_2$SO$_4$), filtered and evaporated under reduced pressure. The crude residue was purified by column chromatography on silica gel using hexanes/EtOAc as the eluent.

Utilizing the appropriate starting materials, the compounds of Table A were prepared according to Example 5:

TABLE A

| Compound | Name | Yield (%) | $^1$H NMR |
|---|---|---|---|
| 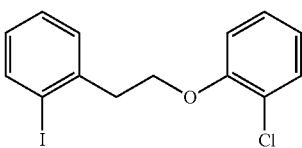 [SMILES: Clc1ccccc1OCCc1ccccc1I] | 1-chloro-2-(2-iodophenethoxy)benzene | 83 | 3.29-3.32(t, 2H, J = 6.9 Hz), 4.23-4.26(t, 2H, J = 6.9 Hz), 6.86-6.89(t, 1H, J = 7.6 Hz), 6.91-6.93(d, 1H, J = 8.2 Hz), 7.09-7.13(t, 1H, J = 7.2 Hz), 7.16-7.20(t, 1H, J = 8.1 Hz), 7.27-7.29(d, 1H, J = 7.4 Hz), 7.33-7.35(d, 1H, J = 7.9 Hz), 7.41-7.43(d, 1H, J = 7.4 Hz), 7.54-7.56(d, 1H, J = 8.0 Hz) |
| 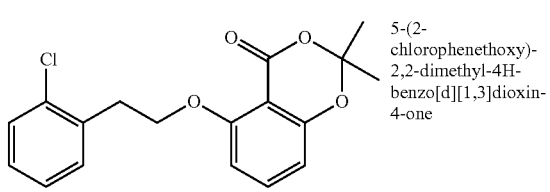 | 5-(2-chlorophenethoxy)-2,2-dimethyl-4H-benzo[d][1,3]dioxin-4-one | 85 | 1.69(s, 6H), 3.34(t, 2H, J = 6.96 Hz), 4.27(t, 2H, J = 6.96 Hz), 6.52(d, 1H, J = 8.19 Hz), 6.61(d, 1H, J = 8.55 Hz), 7.15-7.26(m, 2H), 7.33-7.42(m, 2H), 7.53(dd, 1H, J = 5.85, 1.44 Hz) |

Example 6

General Procedure for the Synthesis of 3-substituted 5-phenyl-1H-imidazoles by the Van Leusen Reaction

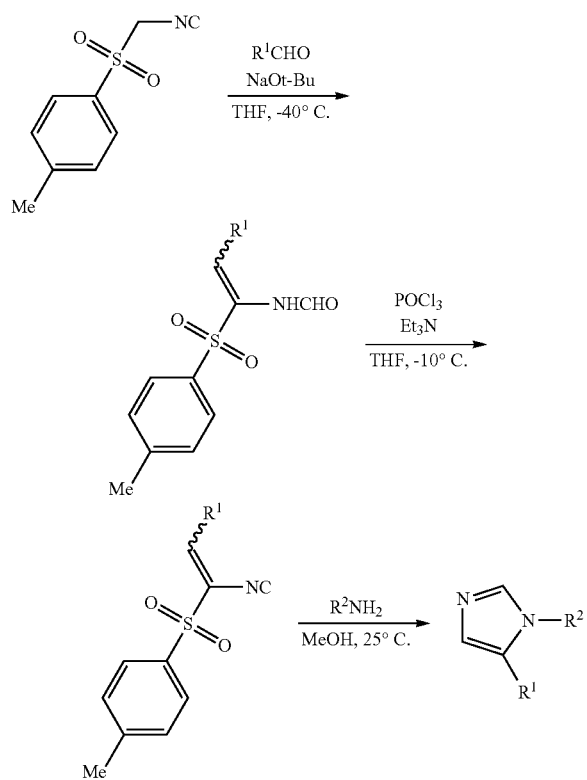

To a stirred solution of NaOt-Bu (124.0 mg, 1.3 mmol) in THF (12 mL) at −40° C., was added a solution of tosylmethyl isocyanide (390.0 mg, 2.0 mmol) in THF (6.0 mL). The solution was allowed to stir at −40° C. for 20 min and a solution of the aldehyde (1.1 mmol) in THF (6.0 mL) was added while maintaining the temperature at −40° C. The resulting mixture was allowed to stir for an additional 30 min and was poured into ice water (20 mL). The solution was neutralized with acetic acid (pH =7) and the aqueous phase was extracted with DCM (2×20 mL). The combined organic layers were dried ($Na_2SO_4$) and concentrated under reduced pressure to afford the crude product, which was filtered through a small plug of silica gel and used in next step.

To a stirred solution of the resulting crude formamide in THF (10 mL) at −5° C. was added $Et_3N$ (1.39 mL, 10.0 mmol). The reaction mixture was cooled to −10° C. and $POCl_3$ (0.27 mL, 3.0 mmol) was added after 15 min. The solution was allowed to stir at −10° C. for an additional 30 min. The reaction mixture was poured into ice water (15 mL) and the aqueous layer was extracted with DCM (2×20 mL). The combined organic layers were dried ($Na_2SO_4$) and concentrated under reduced pressure. The crude residue was dissolved in MeOH (5 mL). The appropriate amine (2.0 mmol) was added and the reaction mixture was stirred for 12 h at 25° C. The solvent was removed under reduced pressure and the resulting residue was purified by column chromatography on silica gel.

Utilizing the appropriate starting materials, the compounds of Table B were prepared according to Example 6:

TABLE B

| Compound | Name | Yield (%) | $^1$H NMR |
|---|---|---|---|
| (structure) | 1-(2-nitrobenzyl)-5-phenyl-1H-imidazole | 44 | 5.57(s, 2H), 6.68(d, 1H, J = 8.0 Hz), 7.14-7.21(m, 3H), 7.25-7.32(m, 3H), 7.42(t, 1H, J = 7.6 Hz), 7.52(t, 1H, J = 7.6 Hz), 7.58(s, 1H), 8.08(dd, 1H, J = 1.2, 8.0 Hz) |
| (structure) | 1-(4-nitrobenzyl)-5-phenyl-1H-imidazole | 43 | 5.24(s, 2H), 7.07(d, 2H, J = 5.6 Hz), 7.13(s, 1H), 7.16-7.22(m, 2H), 7.28-7.36(m, 3H), 7.6(s, 1H), 8.09(d, 2H, J = 8.4 Hz) |

TABLE B-continued

| Compound | Name | Yield (%) | $^1$H NMR |
|---|---|---|---|
| | 1-(3-nitrobenzyl)-5-phenyl-1H-imidazole | 50 | 5.24(s, 2H), 7.12(s, 1H), 7.18-7.25(m, 3H), 7.3(s, 3H), 7.44(t, 1H, J = 8.0 Hz), 7.6(s, 1H), 7.8(s, 1H) 8.09(d, 1H, J = 16.0 Hz) |
| | 2-(5-phenyl-1H-imidazole-1-yl)ethanol | 59 | 3.72(t, 2H, J = 5.2 Hz), 4.01(t, 2H, J = 5.2 Hz), 5.09(br s, 1H), 6.83(d, J = 0.8 Hz, 1H), 7.29-7.42(m, 5H), 7.51(d, 1H, J = 0.8 Hz) |
| | tert-butyl 2-(5-phenyl-1H-imidazole-1-yl)ethylcarbamate | 46 | 1.4(s, 9H), 3.22(q, 2H, J = 6.4 Hz), 4.13(t, 2H, J = 5.6 Hz), 4.77(br s, 1H), 7.05(d, 1H, J = 0.8 Hz), 7.33-7.46(m, 5H), 7.53(s, 1H). |
| | 1-phenethyl-5-phenyl-1H-imidazole | 58 | 2.83(t, 2H, J = 7.6 Hz), 4.17(t, 2H, J = 7.6 Hz), 6.91(dd, 2H, J = 1.6, 7.6 Hz), 7.02(s, 1H), 7.15-7.23(m, 3H), 7.26-7.32(m, 2H), 7.35-7.45(m, 4H) |
| | 5-phenyl-1-(3-phenylpropyl)-1H-imidazole | 55 | 1.92(m, 2H, J = 7.2 Hz), 2.49(t, 2H, J = 7.6 Hz), 3.96(t, 2H, J = 8.0 Hz), 6.98-7.09(m, 3H), 7.12-7.19(m, 1H), 7.22(t, 2H, J = 6.8 Hz), 7.28-7.33(m, 2H), 7.34-7.42(m, 3H), 7.51(s, 1H) |
| | methyl 2-(5-phenyl-1H-imidazol-1-yl)acetate | 36 | 3.7(s, 3H), 4.66(s, 2H), 7.07(d, 1H, J = 1.2 Hz), 7.26-7.3(m, 2H), 7.34-7.44(m, 3H), 7.63(d, 1H, J = 0.8 Hz) |

TABLE B-continued

| Compound | Name | Yield (%) | $^1$H NMR |
|---|---|---|---|
| | 2-(5-(2-methoxyphenyl)-1H-imidazol-1-yl)ethanol | 46 | 3.6(t, 2H, J = 5.2 Hz), 3.7(s, 3H), 3.86(t, 2H, J = 5.2 Hz), 5.93(br s, 1H), 6.79(s, 1H), 6.86-6.97(m, 2H), 7.15(d, 1H, J = 7.2 Hz), 7.33(t, 1H, J = 8.0 Hz), 7.65(s, 1H) |
| | 1-(3,3-dimethylbutyl)-5-(2-methoxyphenyl)-1H-imidazole | 45 | 0.78(s, 9H), 1.42-1.54(m, 2H), 3.75-3.85(m, 5H), 6.92-7.50(m, 3H), 7.20-7.29(m, 1H), 7.38(t, 1H, J = 7.5 Hz), 7.54(s, 1H). |
| | 1-(3-methoxybenzyl)-5-phenyl-1H-imidazole | 48 | 3.72(s, 3H), 5.12(s, 2H), 6.52(s, 1H), 6.61(d, 1H, J = 7.6 Hz), 6.79-6.81(dd, 1H, J = 2, 8 Hz), 7.14(d, 1H, J = 0.8 Hz), 7.21(t, 1H, J = 8 Hz), 7.28-7.37(m, 6H), 7.57(s, 1H) |
| | 1-(2-methoxybenzyl)-5-phenyl-1H-imidazole | 42 | 3.79(s, 3H), 5.13(s, 2H), 6.71(d, 1H, J = 7.2 Hz), 6.83-6.86(m, 2H), 7.12(s, 1H), 7.24-7.28(m, 1H), 7.32-7.38(m, 5H), 7.55(s, 1H) |
| | 3-(5-phenyl-1H-imidazol-1-yl)propan-1-amine | 51 | 1.72-1.79(m, 2H), 2.94-2.99(m, 2H), 4.01(t, 2H, J = 6.8 Hz), 5.2(br s, 2H), 7.02(s, 1H), 7.31-7.42(m, 5H), 7.54(s, 1H) |
| | 5-benzyl-4-phenyl-1H-imidazole | 62 | 4.08(s, 2H), 7.12-7.16(m, 3H), 7.19-7.24(m, 4H), 7.29-7.33(t, 2H, J = 7.5 Hz), 7.50-7.51(d, 2H, J = 7.Hz), 10.13(br s, 1H) |
| | 5-phenethyl-4-phenyl-1H-imidazole | 78 | 2.97-3.07(t, 2H, J = 7.3 Hz), 3.09-3.12(t, 2H, J = 6.8 Hz), 6.09(br s, 1H), 7.13-7.15(d, 2H, J = 7.0 Hz), 7.20-7.21(d, 1H, J = 7.24 Hz), 7.25-7.29(m, 3H), 7.36-7.39(t, 2H, J = 7.6 Hz), 7.46-7.48(d, 2H, J = 7.6 Hz), 7.51(s, 1H) |

TABLE B-continued

| Compound | Name | Yield (%) | ¹H NMR |
|---|---|---|---|
| | 1-(3,3-dimethylbutyl)-5-phenyl-1H-imidazole | 39 | 0.85(s, 9H), 1.54-1.58(m, 2H), 3.94-3.98(m, 2H), 7.05(s, 1H), 7.36-7.45(m, 5H), 7.55(s, 1H) |
| | 4-(3-(5-phenyl-1H-imidazol-1-yl)propyl)thiomorpholine | 46 | 1.67-1.74(m, 2H), 2.17-2.21(t, 2H, J = 6.6 Hz), 2.52-2.59(m, 8H), 4.05-4.07(t, 2H, J = 7.1 Hz), 7.06(s, 1H), 7.36-7.39(m, 3H), 7.42-7.45(m, 2H), 7.56(s, 1H) |
| | 1-(2-chlorobenzyl)-5-phenyl-1H-imidazole | 24 | 5.25(s, 2H), 6.72-6.74(d, 1H, 7.5 Hz), 7.17-7.29(m, 5H), 7.34-7.39(m, 4H), 7.56(s, 1H) |
| | 1-(3-chlorobenzyl)-5-phenyl-1H-imidazole | 18 | 5.13(s, 2H), 6.85-6.87(d, 1H, 6.5 Hz), 6.98 (s, 1H), 7.15(s, 1H), 7.19-7.26(m, 5H), 7.36-7.38(m, 3H), 7.57(s, 1H) |
| | 1-(4-chlorobenzyl)-5-phenyl-1H-imidazole | 31 | 5.11(s, 2H), 6.90-6.93(d, 2H, J = 8.3 Hz), 7.13(s, 1H), 7.24-7.29(m, 5H), 7.34-7.38(m, 3H), 7.55(s, 1H) |
| | 1-(4-methoxybenzyl)-5-phenyl-1H-imidazole | 28 | 3.78(s, 3H), 5.07(s, 2H), 6.81-6.83(d, 2H, J = 8.6 Hz), 6.93-6.96(d, 2H, J = 8.5 Hz), 7.12 (s, 1H), 7.29-7.38(m, 2H), 7.34-7.38(m, 3H), 7.52(s, 1H) |
| | ethyl 3-(5-phenyl-1H-imidazol-1-yl)propanoate | 30 | 1.20-1.23(t, 3H, J = 7.1 Hz), 2.56-2.59(t, 2H, J = 6.9 Hz), 4.08-4.13(q, 2H, J = 7.2 Hz), 4.29-4.32(t, 2H, J = 6.8 Hz), 7.06(s, 1H), 7.37-7.47(m, 5H), 7.61(s, 1H) |

TABLE B-continued

| Compound | Name | Yield (%) | $^1$H NMR |
|---|---|---|---|
| (structure: Boc-NH-(CH$_2$)$_4$-imidazole-Ph) | tert-butyl 4-(5-phenyl-1H-imidazol-1-yl)butylcarbamate | 52 | 1.24(m, 2H), 1.39(s, 9H), 1.58(m, 2H), 2.99 (m, 2H), 3.98(t, 2H, J = 5.4 Hz), 4.58(br s, 1H), 7.05(s, 1H), 7.31-7.42(5H, m), 7.55(s, 1H). |
| (structure: 4-cyanobenzyl-imidazole-Ph) | 4-((5-phenyl-1H-imidazol-1-yl)methyl)benzonitrile | 32 | 5.66(s, 2H), 7.19-7.41(m, 2H), 7.41-7.45(m, 5H), 7.72-7.96(m, 3H), 9.50(s, 1H) |
| (structure: EtO$_2$C-(CH$_2$)$_3$-imidazole-Ph) | ethyl 4-(5-phenyl-1H-imidazol-1-yl)butanoate | 39 | 1.26(t, 3H, J = 7.0 Hz), 1.92(m, 2H), 2.16(t, 2H, J = 7.0 Hz), 4.05(m, 4H), 7.05(s, 1H), 7.35-7.43(m, 5H), 7.55(s, 1H) |
| (structure: H$_2$N-(CH$_2$)$_4$-imidazole-Ph) | 4-(5-phenyl-1H-imidazol-1-yl)butan-1-amine | 88 | 1.39(t, 2H, 6.6 Hz), 1.66(m, 2H), 2.59-2.68 (m, 4H), 7.02(s, 1H), 7.33-7.45(m, 5H), 7.59 (s, 1H) |
| (structure: 4-methylbenzyl-imidazole-Ph) | 1-(4-methylbenzyl)-5-phenyl-1H-imidazole | 27 | 2.32(s, 3H), 5.10(s, 2H), 6.90-6.92(d, 2H, J = 8.1 Hz), 7.10-7.17(m, 5H), 7.25-7.36(m, 5H), 7.54(s, 1H) |
| (structure: 3-methylbenzyl-imidazole-Ph) | 1-(3-methylbenzyl)-5-phenyl-1H-imidazole | 26 | 2.34(s, 3H), 5.11(s, 2H), 6.83(s, 1H), 7.10-7.19(m, 5H), 7.26-7.38(m, 5H), 7.56(s, 1H) |
| (structure: 2-methylbenzyl-imidazole-Ph) | 1-(2-methylbenzyl)-5-phenyl-1H-imidazole | 22 | 2.17(s, 3H), 5.10(s, 2H), 6.83-6.85(d, 1H, J = 7.5 Hz), 7.16-7.23(m, 5H), 7.29-7.38(m, 5H), 7.44(s, 1H) |

TABLE B-continued

| Compound | Name | Yield (%) | $^1$H NMR |
|---|---|---|---|
| 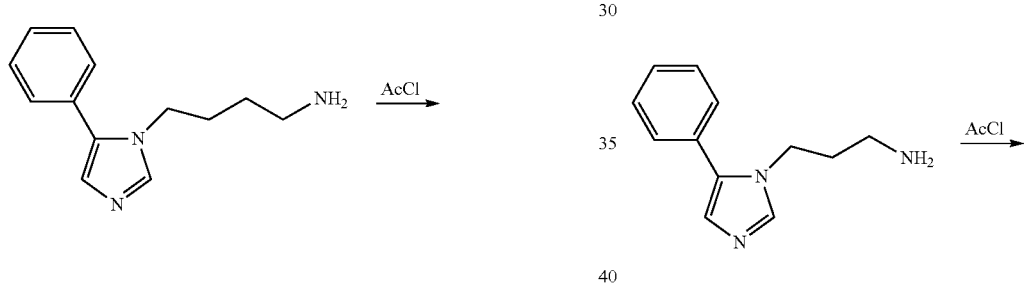 | N-(2-(5-phenyl-1H-imidazol-1-yl)ethyl)acetamide | 26 | 1.86(s, 3H), 3.33-3.36(t, 3H, J = 9.0 Hz), 4.16-4.19(t, 2H, J = 9.0 Hz), 7.03(s, 1H), 7.26-7.45(m, 5H), 7.51(s, 1H) |
| | 2-(5-phenyl-1H-imidazol-1-yl)ethanamine | 64 | 3.22(q, 2H, J = 6.4 Hz), 4.13(t, 2H, J = 5.6 Hz), 7.05(d, 1H, J = 0.8 Hz), 7.33-7.46(m, 5H), 7.53(s, 1H) |

Example 7

N-(4-(5-phenyl-1H-imidazol-1-yl)butyl)acetamide

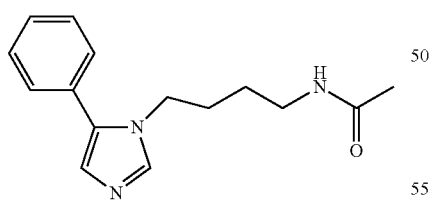

To a stirred solution of 4-(5-phenyl-1H-imidazol-1-yl)butan-1-amine (0.278 mmol) in THF (3 mL) at 0° C. was added acetyl chloride (0.306 mmol) drop wise and the resulting white suspension was allowed to warm to rt and stir for 5 h. Saturated NaHCO$_3$ (2 mL) was added and the aqueous phase was extracted with EtOAc (3×10 mL). The combined organic layers were washed with brine, dried (Na$_2$SO$_4$) and concentrated in vacuo to afford a yellowish oil. Preparative thin layer chromatography afforded the pure product as colorless oil (30 mg, 43% yield). $^1$H NMR: 1.36 (m, 2H), 1.60 (m, 2H), 1.91 (s, 3H), 2.38 (br s, 1H), 3.12 (m, 2H), 4.00 (t, 2H, J=7.1 Hz), 5.80 (br s, 1H), 7.04 (s, 1H), 7.32-7.46 (m, 5H), 7.55 (s, 1H).

Example 8

N-(3-(5-phenyl-1H-imidazol-1-yl)propyl)acetamide

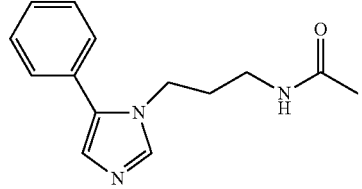

The above procedure was used to synthesize this compound. The crude product was purified by flash column chromatography (silica gel, 5%-15% MeOH/DCM gradient) to afford the desired product as a white solid (56 mg, 55%). $^1$H NMR: 1.77-1.84 (m, 2H), 1.83 (s, 3H), 3.05-3.10 (m, 2H), 4.06 (t, 2H, J=7.2 Hz), 5.68 (br s, 1H), 7.05 (s, 1H), 7.36-7.48 (m, 4 H), 7.58 (s, 1H).

Example 9

General Procedure for O-Alkylation of 5-Hydroxy-2,2-dimethyl-4H-benzo[d][1,3]dioxin-4-one

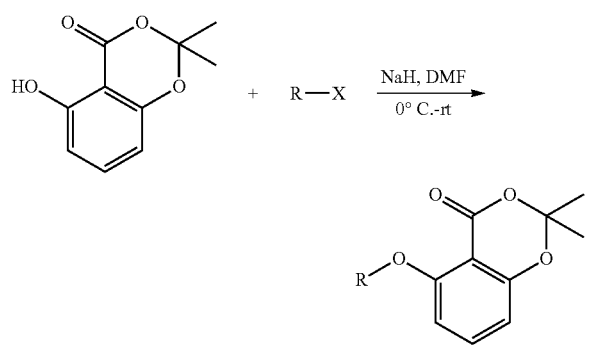

To a solution of 5-hydroxy-2,2-dimethyl-4H-benzo[d][1,3]dioxin-4-one (2.57 mmol, Alois Fulrstner, Oliver R. Thiel, and Gaetano Blanda. *Organic Letters*. 2000, 2, 3731) in anhydrous DMF (10 mL) at 0° C. was added NaH (2.83 mmol) portion wise and the suspension was allowed to stir for 0.5 h at 0° C. The alkyl halide (2.83 mmol) was added as a solution in DMF (2 mL) and the mixture was allowed to warm to rt and stir overnight. The reaction was quenched with sat'd $NH_4Cl$ (5 mL) solution and water (20 mL). The aqueous phase was extracted with $CH_2Cl_2$ (3×40 mL). The combined organic layers were dried over $Na_2SO_4$ and concentrated under reduced pressure to afford the crude product which was purified by flash column chromatography on silica gel using hexanes/EtOAc as the eleuent.

Utilizing the appropriate starting materials, the compounds of Table C were prepared according to Example 9:

TABLE C

| Compound | Name | Yield (%) | $^1$H NMR |
|---|---|---|---|
| (structure) | 5-(4-chlorobenzyloxy)-2,2-dimethyl-4H-benzo[d][1,3]dioxin-4-one | 74 | 1.71 (s, 6H), 5.20 (s, 2H), 6.50-6.67 (m, 2H), 7.29-7.40 (m, 4H), 7.50 (d, 1H, J = 8.7 Hz) |
| (structure) | 5-(3,3-dimethylbutoxy)-2,2-dimethyl-4H-benzo[d][1,3]dioxin-4-one | 53 | 0.98 (s, 9H), 1.69 (s, 6H), 1.86 (t, 2H, J = 8.1 Hz), 4.14 (t, 2H, J = 7.4 Hz), 6.52 (d, 1H, J = 8.1 Hz), 6.61 (d, 1H, J = 8.5 Hz), 7.41 (t, 1H, J = 8.4 Hz) |

Example 10

General Procedure for the Synthesis of 2-Hydroxy-1-benzaldehyde Derivatives

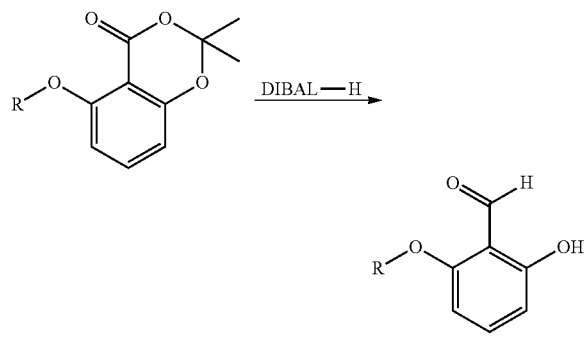

To a solution of the appropriate acetonide (0.627 mmol) in $CH_2Cl_2$ (6 mL) at −78° C. was added DIBAL-H (1.88 mmol, 1M in $CH_2Cl_2$). After stirring for 2h at −78° C. the reaction was quenched by adding 1M HCl (2 mL) and MeOH (2 mL) and the reaction was allowed to warm to rt. $H_2O$ (10 mL) was added and the aqueous phase was extracted with $CH_2Cl_2$ (3×35 mL). The combined organic layers were dried over $Na_2SO_4$ and concentrated under reduced pressure to afford the crude residue which was purified by flash column chromatography on silica gel using hexanes/EtOAc as the eleuent.

Utilizing the appropriate starting materials, the compounds of Table D were Prepared according to Example 10:

TABLE D

| Compound | Name | Yield (%) | $^1$H NMR |
|---|---|---|---|
| ![compound1] | 2-(4-chlorobenzyloxy-6-hydroxybenzaldehyde | 61 | 5.10 (s, 2H), 6.41 (d, 1H, J = 6.2 Hz), 6.55 (d, 1H, 6.3 Hz), 7.29-7.42 (m, 5H), 10.39 (s, 1H), 11.97 (s, 1H) |
| ![compound2] | 2-(3,3-dimethylbutoxy)-6-hydroxybenzaldehyde | 57 | 1.0 (s, 9H), 1.76 (t, 2H, J = 6.8 Hz), 4.10 (t, 2H, J = 6.96 Hz), 6.37 (d, 1H, J = 8.3 Hz), 6.50 (d, 1H, J = 8.6 Hz), 7.39 (t, 1H, J = 8.3 Hz), 10.34 (s, 1H), 11.97 (s, 1H). |
| ![compound3] | 2-(2-chlorophenethoxy)-6-hydroxybenzaldehyde | 34 | 3.28 (t, 2H, J = 6.60 Hz), 4.29 (t, 2H, J = 6.60 Hz), 6.37 (d, 1H, J = 8.3 Hz), 6.50 (d, 1H, J = 8.43 Hz), 7.18-7.40 (m, 5H), 10.28 (s, 1H), 11.94 (s, 1H) |

Example 11

General Procedure for the Synthesis of 3-Substituted-2-(1H-imidazol-5-yl)phenols To a stirred solution of the appropriate aldehyde (0.38 mmol) in THF (2 mL) at rt was added NH$_3$ (2.0 mL, 2.0 M in EtOH). The solution was allowed to stir overnight and 1-(isocyanomethylsulfonyl)-4-methylbenzene (0.38 mmol) and piperazine (0.57 mmol) were added. Stirring was continued for an additional 48 h. The solvent was removed under reduced pressure and the crude residue was purified by column chromatography on silica gel afford the desired product.

Utilizing the appropriate starting materials, the compounds of Table E were prepared according to Example 11:

To a stirred solution of 4-iodo-1-trityl-1H-imidazole (218.0 mg, 0.5 mmol) in anhydrous THF (4 mL) at rt was added EtMgBr (1.0 M in THF, 0.5 mmol, 0.5 mL) dropwise, under an atmosphere of N$_2$. The resulting solution was allowed to stir for 90 min and anhydrous ZnCl$_2$ (0.5 mmol, 68.2 mg) was added. The resulting white suspension was allowed to stir for 90 min and a solution of the aryl iodide (0.5 mmol) in THF (1 mL) was added followed by the immediate addition of Pd(PPh$_3$)$_4$ (56 mg, 0.05 mmol). The reaction mixture was allowed to stir at 70° C. for 12 h under an atmosphere of N$_2$. After cooling to room temperature, the solution was diluted with CH$_2$Cl$_2$ (10 mL) and the organic layer was washed with an EDTA (aq) buffer (pH=9) (2×5 mL) and brine. The organic layer was dried (Na$_2$SO$_4$) and concen-

TABLE E

| Compound | Name | Yield (%) | $^1$H NMR |
|---|---|---|---|
|  | 3-(4-chlorobenzyloxy)-2-(1H-imidazol-5-yl)phenol | 31 | 5.15 (s, 2H), 6.52 (dd, 1H, J = 7.2 Hz, 0.99 Hz), 6.56 (d, 1H, J = 8.3 Hz), 7.01 (t, 1H, J = 8.2 Hz), 7.38-7.72 (m, 5H), 7.73 (s, 1H) |
|  | 3-(2-chlorophenethoxy)-2-(1H-imidazol-5-yl)phenol | 63 | 3.30 (t, 2H, J = 6.7 Hz), 4.33 (t, 2H, J = 6.8 Hz), 6.44 (d, 1H, J = 8.2 Hz), 6.55 (d, 1H, J = 8.2 Hz), 6.99 (t, 1H, J = 8.2 Hz), 7.29 (m, 2H), 7.48 (m, 3H), 7.94 (s, 1H), 12.45 (br s, 1H) |
|  | 3-(3,3-dimethylbutoxy)-2-(1H-imidazol-5-yl)phenol | 17 | 0.91 (s, 9H), 1.73 (t, 2H, J = 6.6 Hz), 4.06 (t, 2H, J = 6.7 Hz), 6.47 (d, 1H, J = 8.1 Hz), 6.55 (dd, 1H, J = 3.3, 4.9 Hz), 7.10 (t, 1H, J = 8.0 Hz), 7.72 (s, 1H), 8.68 (d, 1H, J = 6.4 Hz) |

Example 12

General Procedure for the Palladium-Catalyzed Cross-Coupling of Aryl Iodides with 1-Trityl-1H-imidazol-4-yl)zinc(II)chloride

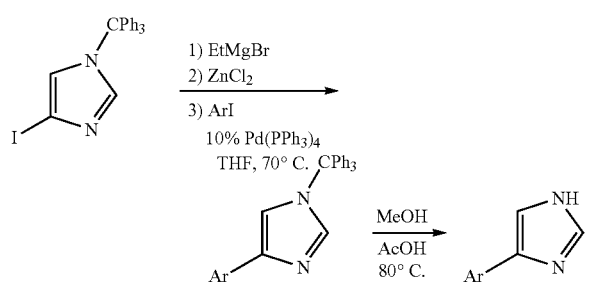

trated under reduced pressure. The crude residue was used in next step without further purification. To a solution of the crude imidazole from the previous step was added trifluoroacetic acid (1.0 mL) and MeOH (4.0 mL). The solution was stirred at 80° C. for 2 h. The reaction mixture was allowed to cool to room temperature and the pH was adjusted to ~10 with 10% NaOH (aq). The aqueous phase was extracted with EtOAc (3×20 mL). The combined organic layers were washed with water, brine, and dried. The solvent was removed in vacuo to afford the crude residue, which was purified by flash column chromatography on silica gel to afford the desired product.

Utilizing the appropriate starting materials, the compounds of Table F were prepared according to Example 12:

TABLE F

| Compound | Name | Yield (%) | ¹H NMR |
|---|---|---|---|
| | tert-butyl 2-(1H-imidazol-5-yl)phenylcarbamate | 20 | 1.53 (s, 9H), 6.98 (t, 1H, J = 7.2 Hz), 7.10-7.36 (m, 2H), 7.46 (d, 1H, J = 7.6 Hz), 7.70 (s, 1H), 8.29 (d, 1H, J = 8.0 Hz), 9.60 (br s, 1H), 10.92 (br s, 1H). |
| | ethyl 2-(1H-imidazol-5-yl)benzoate | 23 | 1.25 (t, 3H, J = 6.8 Hz), 4.26 (q, 2H, J = 6.8 Hz), 7.31-7.44 (m, 2H), 7.50 (t, 1H, J = 7.2 Hz), 7.59 (d, 1H, J = 7.6 Hz), 7.85 (d, 1H, J = 7.2 Hz), 8.04 (br s, 1H) |
| | N-(4-chlorobenzyl)-2-(1H-imidazol-5-yl)aniline | 65 | 4.37 (s, 2H), 6.57 (d, 1H, J = 8.1 Hz), 6.68 (t, 1H, J = 7.5 Hz), 7.06-7.12 (m, 1H), 7.16 (s, 1H), 7.21-7.28 (m, 4H), 7.34-7.37 (dd, 1H, J = 1.5, 7.5 Hz), 7.56 (s, 1H), 8.73 (br s, 2H) |
| | 4-(2-((2-chlorobenzyloxy)methyl)phenyl)-1H-imidazole | 49 | 4.64 (s, 2H), 4.72 (s, 2H), 7.27-7.33 (m, 3H), 7.38-7.46 (m, 4H) 7.53-7.55 (d, 1H, J = 7.1 Hz), 7.64-7.68 (m, 3H) |
| | 4-(2-(2-(2-chlorophenoxy)ethyl)phenyl)-1H-imidazole | 35 | 3.21-3.25 (t, 2H, J = 6.0 Hz), 4.36-4.40 (t, 2H, J = 5.9 Hz), 6.89-6.91 (dd, 1H, J = 1.2, 7.4 Hz), 6.94-6.96 (d, 1H, J = 7.4 Hz), 7.18-7.23 (td, 1H, J = 1.6, 8.3 Hz), 7.28-7.69 (m, 8H) |
| | 4-chloro-2-fluoro-6-(1H-imidazol-4-yl)phenol | 37 | DMSO-d₆: 7.20-7.22 (d, 1H, J = 8.0 Hz), 7.63 (s, 1H), 7.94 (s, 1H), 8.01 (s, 1H), 12.78 (br s, 1H), 12.88 (br s, 1H) |
| | 2-(3-((2-(1H-imidazol-4-yl)phenoxy)methyl)phenyl)-N-methyl-acetamide | 37 | 2.71-2.72 (d, 3H, J = 4.8 Hz), 3.51 (s, 2H), 5.10 (s, 2H), 6.09 (br s, 1H), 6.97-6.70 (d, 1H, J = 8.3 Hz), 7.02-7.04 (d, 1H, J = 7.5 Hz), 7.18-7.34 (m, 5H), 7.49 (s, 1H), 7.56 (s, 1H), 7.89-7.91 (d, 1H, J = 7.6 Hz), 9.32 (br s, 1H) |

TABLE F-continued

| Compound | Name | Yield (%) | $^1$H NMR |
|---|---|---|---|
| (F$_3$C-phenyl-OH with imidazole) | 2-(1H-imidazol-4-yl)-4-(trifluoromethyl)phenol | 10 | 7.06 (d, 1H, J = 7.07 Hz), 7.39 (d, 1H, J = 6.96 Hz), 7.44 (s, 1H), 7.71 (s, 1H), 7.76 (s, 1H) |
| (phenyl-NHSO$_2$Me with imidazole) | N-(2-(1H-imidazol-4-yl)phenyl)methane-sulfonamide | 40 | (CD$_3$OD) 7.47-7.52 (t, 3H, J = 7.5 Hz), 7.61-7.67 (m, 2H), 7.78 (s, 1H), 7.92-7.95 (d, 1H, J = 7.8 Hz), 8.05-8.08 (d, 1H, J = 8.4 Hz), 8.12 (s, 1H) |

Example 13

General Procedure For the Alkylation of 2-(1H-Imidazol-4-yl)phenols

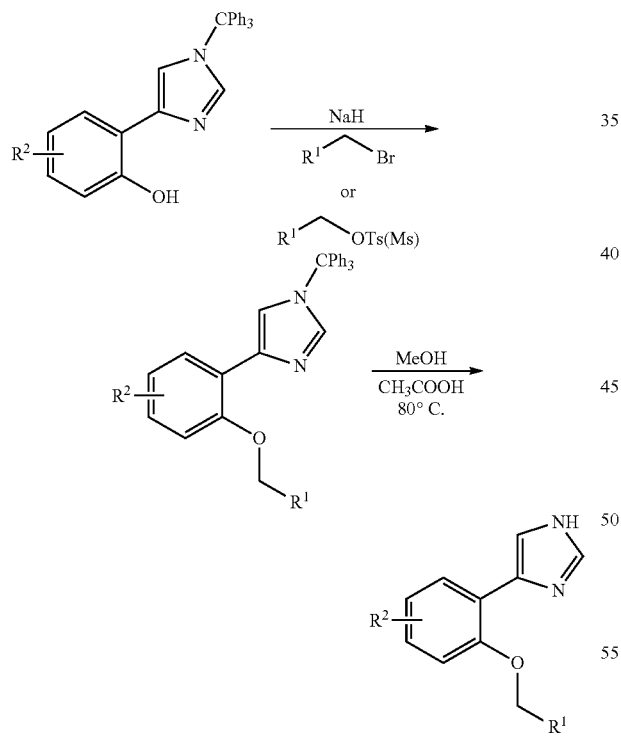

To a stirred solution of the appropriate phenol (0.5 mmol) in anhydrous DMF (3 mL) at 0° C. was added NaH (36.0 mg, 0.75 mmol). The resulting suspension was allowed to stir for 10 min. To the resulting solution was added the appropriate alkylating reagent. After stirring overnight, the reaction mixture was carefully diluted with water and extracted with ethyl acetate (2×10 mL). The combined organic layers were washed with water, brine and dried (Na$_2$SO$_4$). The solvent was removed under reduced pressure and the crude product was taken to next step without further purification. To a solution of the crude ether was added trifluoroacetic acid (1.0 mL) and MeOH (4.0 mL). The solution was stirred at 80° C. for 2 h. The solution was allowed to cool to room temperature and the pH was adjusted to ~10 with 10% NaOH (aq). The aqueous phase was extracted with EtOAc (3×20 mL). The combined organic layer were washed with water, brine, and dried. The solvent was removed in vacuo to afford the crude residue, which was purified by flash column chromatography on silica gel to afford the desired product.

Utilizing the appropriate alkyl tosylate starting materials, the compounds of Table G were prepared according to Example 13:

TABLE G

| Compound | Name | Yield (%) | $^1$H NMR |
|---|---|---|---|
| | N-(3-(2-(2-(1H-imidazol-4-yl)phenoxy)ethyl)phenyl)acetamide | 41 | 2.10 (s, 3H), 3.07 (t, 2H, J = 6.0 Hz), 4.30 (t, 2H, J = 6.4 Hz), 6.88-7.05 (m, 3H), 7.12-7.30 (m, 4H), 7.41 (s, 1H), 7.64 (s, 1H), 3.07 (dd, 1H, J = 1.2, 7.6 Hz), 8.83 (s, 1H) |
| | 1-(4-(2-(2-(1H-imidazol-4-yl)phenoxy)ethyl)piperidin-1-yl)ethanone | 28 | 1.08-1.23 (m, 2H), 1.65-1.84 (m, 4H), 2.03 (s, 3H), 2.47 (t, 1H, J = 12.8), 2.95 (t, 1H, J = 12.8 Hz), 3.49 (s, 1H), 3.73 (d, 1H, J = 13.2 Hz), 4.10 (d, 2H, J = 6.4 Hz), 5.55 (d, 1H, J = 13.2 Hz), 6.91 (d, 1H, J = 8.0 Hz), 6.97 (t, 1H, J = 7.6 Hz), 7.17 (t, 1H, J = 7.6 Hz), 7.52 (s, 1H), 7.67 (s, 1H), 7.88 (d, 1H, J = 7.6 Hz), 8.38 (br s, 1H) |
| | 4-(2-(2-cyclopentylethoxy)phenyl)-1H-imidazole | 69 | 1.10-1.25 (m, 2H), 1.47-1.70 (m, 4H), 1.75-2.00 (m, 5H), 4.09 (t, 2H, J = 6.4 Hz), 6.90-7.10 (m, 2H), 7.19 (td, 1H, J = 1.6, 7.6 Hz), 7.53 (s, 1H), 7.69 (s, 1H), 8.11 (dd, 1H, J = 1.6, 8.0 Hz), 9.54 (s, 1H) |
| | N-(4-(2-(2-(1H-imidazol-4-yl)phenoxy)ethylidene)cyclohexyl)acetamide | 15 | 0.95-2.20 (m, 12H), 3.90-4.29 (m, 3H), 5.50-5.85 (m, 1H), 6.95 (d, 1H, J = 8.0 Hz), 7.01 (t, 1H, J = 7.2 Hz), 7.21 (t, 1H, J = 7.6 Hz), 7.54 (s, 1H), 7.60-7.95 (m, 2H), 9.69 (br s, 1H) |
| | N-(4-(2-(2-(1H-imidazol-5-yl)phenoxy)ethyl)phenyl)acetamide | 25 | 2.18 (s, 3H), 3.14 (t, 2H, J = 6 Hz), 4.38 (t, 2H, J = 6 Hz), 6.89 (s, 1H), 6.98-7.02 (m, 2H), 7.19-7.27 (m, 4H), 7.49-7.52 (m, 2H), 7.76 (d, 1H, J = 7.6 Hz), 8.40 (s, 1H), 9.02 (br s, 1H) |
| | 3-((2-(1H-imidazol-5-yl)phenoxy)methyl)piperidine | 40 | 1.21-1.33 (m, 1H), 1.52-1.65 (m, 1H), 1.73-1.85 (m, 2H), 2.20 (br s, 1H), 2.55-2.71 (m, 2H), 3.01-3.05 (m, 1H), 3.31-3.36 (m, 1H), 3.82-3.95 (m, 2H), 6.85 (d, 1H, J = 8.4 Hz), 7.00 (t, 1H, J = 7.8 Hz), 7.14-7.20 (m, 1H), 7.52 (s, 1H), 7.71 (s, 1H), 7.85 (d, 1H, J = 6.9 Hz) |

TABLE G-continued

| Compound | Name | Yield (%) | $^1$H NMR |
|---|---|---|---|
| | 4-(2-(2-(1H-imidazol-5-yl)phenoxy)ethyl)phenol | 20 | (DMSO-$d_6$) 3.03 (t, 2H, J = 6.6 Hz), 4.22 (t, 2H, J = 6.6 Hz), 6.68 (d, 2H, J = 7.5 Hz), 6.89-7.02 (m, 2H), 7.09-7.15 (m, 3H), 7.42 (s, 1H), 7.64 (s, 1H), 8.06 (d, 1H, J = 7.5 Hz), 9.20 (s, 1H), 12.1 (br s, 1H) |
| | 6-(2-(1H-imidazol-4-yl)phenoxy)-N,4,4-trimethylhexanamide | 61 | 0.95 (s, 6H), 1.62-1.66 (t, 2H, J = 8.4 Hz), 1.78-1.82 (t, 2H, J = 7.1 Hz), 2.12-2.16 (t, 2H, J = 8.4 Hz), 2.75-2.78 (d, 3H, J = 4.7 Hz), 4.10-4.13 (t, 2H, J = 7.2 Hz), 6.11 (br s, 1H), 6.93-6.95 (d, 1H, J = 8.2 Hz), 6.98-7.02 (t, 1H, J = 7.5 Hz), 7.19-7.23 (t, 1H, J = 7.6 Hz), 7.53 (s, 1H), 7.70 (s, 1H), 7.84-7.86 (d, 1H, J = 7.5 Hz), 10.25 (br s, 1H) |
| | methyl 6-(2-(1H-imidazol-4-yl)phenoxy)-4,4-dimethylhexanoate | 56 | 0.99 (s, 6H), 1.66-1.70 (t, 2H, J = 8.3 Hz), 1.84-1.88 (t, 2H, J = 7.5 Hz), 2.31-2.35 (t, 2H, J = 8.3), 3.66 (s, 3H), 4.13-4.17 (t, 2H, J = 7.5 Hz), 6.96-6.98 (d, 1H, J = 8.3 Hz), 7.00-7.03 (t, 1H, J = 7.6 Hz), 7.20-7.24 (t, 1H, J = 7.5 Hz), 7.56 (s, 1H), 7.72 (s, 1H), 7.86-7.87 (d, 1H, J = 7.5 Hz), 10.11 (br s, 1H) |
| | 4-((2-(1H-imidazol-4-yl)phenoxy)methyl)piperidine | 32 | 1.60 (m, 2H), 1.92 (d, 2H, J = 9.7 Hz), 2.09 (m, 1H), 2.76 (t, 2H, J = 9.1 Hz), 3.25 (d, 2H, J = 9.3 Hz), 3.39 (s, 1H), 6.96 (d, 2H, J = 6.1 Hz), 7.03 (t, 1H, J = 5.5 Hz), 7.22 (t, 1H, J = 5.6 Hz), 7.58 (s, 1H), 7.67 (s, 1H), 7.87 (br s, 1H). |
| | 1-(4-((2-(1H-imidazol-4-yl)phenoxy)methyl)piperidin-1-yl)ethanone | 25 | 1.36 (m, 2H), 1.89 (t, 2H, J = 10.83 Hz), 2.10 (s, 3H), 2.15 (m, 1H), 2.61 (t, 1H, J = 9.33 Hz), 3.11 (t, 1H, J = 9.54 Hz), 3.85-4.03 (m, 3H), 4.69 (d, 1H, J = 9.33 Hz), 6.95 (d, 1H, J = 6.12 Hz), 7.04 (t, 1H, J = 5.49 Hz), 7.23 (t, 1H, J = 5.70 Hz), 7.54 (m, 1H), 7.76 (m, 1H), 7.87 (d, 1H, J = 5.01 Hz) |
| | 4-((2-(1H-imidazol-4-yl)phenoxy)methyl)-1-(methylsulfonyl)piperidine | 74 | 1.46 (m, 2H), 1.86 (d, 2H, J = 10.71 Hz), 1.93 (m, 1H), 2.63 (t, 2H, J = 9.00 Hz), 2.70 (s, 3H), 3.73 (d, 2H, J = 8.64 Hz), 3.89 (d, 2H, J = 4.23 Hz), 6.83 (d, 1H, J = 6.06 Hz), 6.92 (t, 1H, J = 5.55 Hz), 7.10 (t, 1H, J = 5.55 Hz), 7.38 (s, 1H), 7.53 (s, 1H), 7.92 (s, 1H) |

TABLE G-continued

| Compound | Name | Yield (%) | $^1$H NMR |
|---|---|---|---|
| 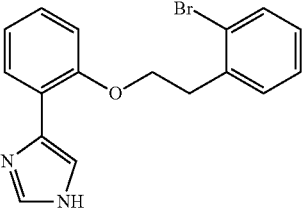 [SMILES: Brc1ccccc1CCOc1ccccc1-c1c[nH]cn1] | 4-(2-(2-bromo-phenethoxy)phenyl)-1H-imidazole | 35 | 3.46 (t, 2H, J = 6.6 Hz), 4.42 (t, 2H, J = 6.6 Hz), 6.94-7.05 (m, 2H), 7.15-7.35 (m, 4H), 7.43 (d, 1H, J = 0.6 Hz), 7.56 (d, 1H, J = 0.6 Hz), 7.61 (d, 1H, J = 7.8 Hz), 7.74 (d, 1H, J = 8.0 Hz). 9.36 (s, 1H) |
| 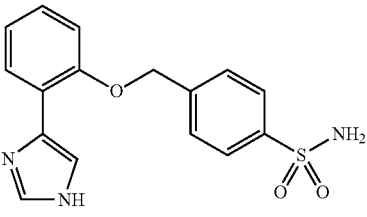 [SMILES: NS(=O)(=O)c1ccc(COc2ccccc2-c2c[nH]cn2)cc1] | 4-((2-(1H-imidazol-4-yl)phenoxy)methyl)benzenesulfonamide | 45 | (CD$_3$OD) 5.33 (s, 2H), 7.03 (ddd, 1H, J = 7.2, 6.3, 1.2 Hz), 7.10 (dd, 1H, J = 8.4, 1.2 Hz), 7.22 (ddd, 1H, J = 8.4, 7.2, 1.8 Hz), 7.52 (d, 1H, J = 1.2 Hz), 7.69 (d, 2H, J = 8.7 Hz), 7.83 (d, 1H, J = 1.2 Hz), 7.85 (dd, 1H, J = 1.8, 6.3 Hz), 7.91 (d, 2H, J = 8.7 Hz) |
| 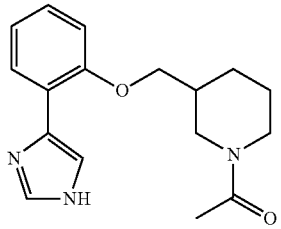 [SMILES: CC(=O)N1CCCC(COc2ccccc2-c2c[nH]cn2)C1] | 1-(3-((2-(1H-imidazol-4-yl)phenoxy)methyl)piperidin-1-yl)ethanone | 90 | 1.30-1.60 (m, 3H), 1.63-1.80 (m, 1H), 1.83-1.92 (m, 1H), 2.01 (s, 3H), 2.80-3.30 (m, 2H), 3.55-3.90 (m, 2H), 3.94-4.01 (m, 1H), 4.21-4.28 (m, 1H), 6.85-6.92 (m, 1H), 6.96-7.03 (m, 1H), 7.17-7.23 (m, 1H), 7.52-7.59 (m, 1H), 7.76-7.95 (m, 2H), 11.48 (s, 1H) |
| 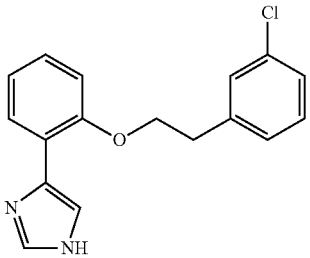 [SMILES: Clc1cccc(CCOc2ccccc2-c2c[nH]cn2)c1] | 4-(2-(3-chloro-phenethoxy)phenyl)-1H-imidazole | 11 | 3.17-3.21 (t, 2H, J = 6.3 Hz), 4.38-4.42 (t, 2H, J = 6.3 Hz), 6.97-7.02 (m, 2H), 7.20-7.38 (m, 6H), 7.51 (s, 1H), 7.75 (s, 1H) |
| 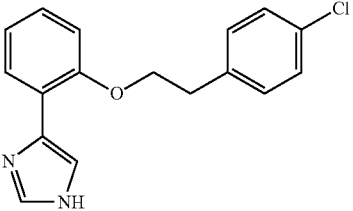 [SMILES: Clc1ccc(CCOc2ccccc2-c2c[nH]cn2)cc1] | 4-(2-(4-chloro-phenethoxy)phenyl)-1H-imidazole | 7 | 3.17-3.21 (t, 2H, J = 6.3 Hz), 4.38-4.42 (t, 2H, J = 6.3 Hz), 6.98-7.05 (m, 2H), 7.20-7.39 (m, 8H), 7.46 (s, 1H), 7.77 (s, 1H) |
| 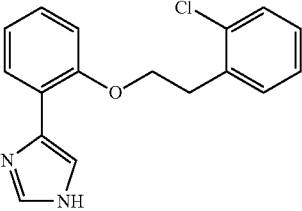 [SMILES: Clc1ccccc1CCOc1ccccc1-c1c[nH]cn1] | 4-(2-(2-chloro-phenethoxy)phenyl)-1H-imidazole | 30 | 3.31-3.38 (t, 2H, J = 6.6 Hz), 4.41-4.45 (t, 2H, J = 6.6 Hz), 6.99-7.04 (m, 2H), 7.19-7.44 (m, 6H), 7.54 (s, 1H), 7.77-7.79 (m, 1H) |

TABLE G-continued

| Compound | Name | Yield (%) | $^1$H NMR |
|---|---|---|---|
|  | 4-(2-(2-cyclopropyl-ethoxy)phenyl)-1H-imidazole | 72 | 0.13-0.19 (m, 2H), 0.50-0.57 (m, 2H), 0.84-0.89 (m, 1H), 1.77-1.84 (m, 2H), 4.16-4.20 (t, 2H, J = 6.6 Hz), 6.98-7.04 (m, 2H), 7.19-7.26 (m, 1H), 7.58 (s, 1H), 7.71 (s, 1H), 7.84-7.87 (d, 2H, J = 7.8 Hz) |
|  | 4-(2-(2-(1H-imidazol-4-yl)phenoxy)ethyl)-N-methylbenzamide | 23 | 2.93-2.94 (d, 3H, J = 4.4 Hz), 3.12-3.15 (t, 2H, J = 6 Hz), 4.31-4.34 (m, 2H), 6.85 (s, 1H), 6.91-7.00 (m, 2H), 7.15-7.20 (m, 1H), 7.26-7.37 (m, 3H), 7.54-7.59 (m, 2H), 7.74-7.77 (m, 2H), 9.53 (s, 1H) |
|  | 3-(2-(2-(1H-imidazol-4-yl)phenoxy)ethyl)-N-methylbenzamide | 90 | 2.96-2.97 (d, 3H, J = 4.8 Hz), 3.19-3.23 (t, 2H, J = 6.3 Hz), 4.38-4.43 (t, 2H, J = 6.3 Hz), 6.68-6.70 (d, 1H, J = 4.5 Hz), 6.97-7.04 (m, 2H), 7.20-7.25 (m, 2H), 7.32-7.34 (d, 1H, J = 7.8 Hz), 7.44 (s, 1H), 7.73-7.82 (m, 4H) |

Utilizing the appropriate alkyl bromide or iodide starting materials, the compounds of Table H were prepared according to Example 13:

TABLE H

| Compound | Name | Yield (%) | $^1$H NMR |
|---|---|---|---|
|  | 4-((2-(1H-imidazol-4-yl)phenoxy)methyl)benzonitrile | 25 | 5.24 (s, 2H), 6.94 (d, 1H, J = 8.2 Hz), 7.05 (t, 1H, J = 7.2 Hz), 7.18 (t, 1H, J = 6.6 Hz), 7.45-7.55 (m, 3H), 7.66 (d, 3H, J = 8.7 Hz), 7.93 (d, 1H, J = 7.8 Hz) |
|  | 3-((2-(1H-imidazol-4-yl)phenoxy)methyl)benzonitrile | 27 | 5.16 (s, 2H), 6.93 (d, 1H, J = 8.0 Hz), 7.05 (td, 1H, J = 1.2, 8.0 Hz), 7.18 (td, 1H, J = 1.6, 8.0 Hz), 7.45-7.68 (m, 5H), 7.70 (s, 1H), 7.05 (dd, 1H, J = 1.6, 7.6 Hz), 8.9 (br s, 1H) |

TABLE H-continued

| Compound | Name | Yield (%) | ¹H NMR |
|---|---|---|---|
| | 2-((2-(1H-imidazol-4-yl)phenoxy)methyl)benzonitrile | 19 | 5.37 (s, 2H), 6.99 (d, 1H, J = 8.0 Hz), 7.05 (td, 1H, J = 1.2, 7.6 Hz), 7.20 (td, 1H, J = 1.6, 8.0 Hz), 7.42-7.49 (m, 2H), 7.55-7.62 (m, 2H), 7.66 (d, 1H, J = 0.8 Hz), 7.71 (d, 1H, J = 7.2 Hz), 7.83 (dd, 1H, J = 1.6, 7.6 Hz) |
| | tert-butyl 4-(2-(2-(1H-imidazol-4-yl)phenoxy)ethyl)piperidine-1-carboxylate | 39 | 1.10-1.28 (m, 2H), 1.52 (s, 9H), 1.52-2.08 (m, 6H), 2.64 (t, 2H, J = 12.0 Hz), 3.97-4.18 (m, 4H), 6.92 (d, 1H, J = 8.0 Hz), 6.98 (t, 1H, J = 7.6 Hz), 7.10-7.25 (m, 1H), 7.52 (s, 1H), 7.68 (s, 1H), 7.80-7.87 (m, 1H), 9.21 (br s, 1H) |
| | N-(4-((2-(1H-imidazol-4-yl)phenoxy)methyl)benzyl)acetamide | 32 | 1.97 (s, 3H), 3.45 (s, 1H), 4.38 (d, 2H, J = 5.6 Hz), 5.08 (s, 2H), 6.51 (s br, 1H), 7.00 (t, 2H, J = 8.8 Hz), 7.15-7.28 (m, 3H), 7.35 (d, 2H, J = 8.0 Hz), 7.43 (s, 1H), 7.50 (s, 1H), 7.86 (d, 1H, J = 8.0 Hz) |
| | 5-(2-(benzyloxy)phenyl)-1H-imidazole | 65 | 5.14 (s, 2H), 7.00-7.03 (m, 2H), 7.17-7.21 (dt, 1H, J = 2, 8 Hz), 7.33-7.44 (m, 5H), 7.51 (s, 1H), 7.56 (s, 1H), 7.90 (d, 1H, J = 7.2 Hz) |
| | 5-(2-phenethoxy-phenyl)-1H-imidazole | 32 | 3.20 (t, 2H, J = 6.4 Hz), 4.40 (t, 2H, J = 6.4 Hz), 6.97-7.01 (m, 2H), 7.18-7.22 (m, 1H), 7.28-7.39 (m, 7H), 7.72-7.74 (dd, 1H, J = 1.6, 8.4 Hz) |
| | 5-(2-(3-phenylpropoxy)phenyl)-1H-imidazole | 59 | 2.17-2.24 (m, 2H), 2.82 (t, 2H, J = 7.6 Hz), 4.09 (t, 2H, J = 6.4 Hz), 6.90 (d, 1H, J = 8 Hz), 6.97-7.01 (m, 1H), 7.16-7.19 (m, 4H), 7.24-7.29 (m, 2H), 7.59 (s, 1H), 7.65 (s, 1H), 7.89 (s, 1H) |

TABLE H-continued

| Compound | Name | Yield (%) | ¹H NMR |
|---|---|---|---|
| | 5-(2-(neopentyloxy)phenyl-1H-imidazole | 45 | 1.11 (s, 9H), 3.77 (d, 2H), 6.95-7.04 (m, 2H), 7.19-7.26 (m, 1H), 7.60 (s, 1H), 7.70 (d, 1H, J = 0.9 Hz), 7.87 (d, 1H, J = 7.2 Hz) |
| | 5-(5-bromo-2-(4-chlorobenzyloxy)phenyl)-1H-imidazole | 57 | (DMSO-d₆) 5.22 (s, 2H), 7.06 (d, 1H, J = 8.4 Hz), 7.28 (d, 1H, J = 8.4 Hz), 7.41-7.51 (m, 5H), 7.71 (s, 1H), 8.19 (s, 1H), 12.1 (br s, 1H) |
| | 2-(2-(1H-imidazol-5-yl)phenoxy)ethanamine | 42 | 3.21 (t, 2H, J = 4.8 Hz), 4.17 (t, 2H, J = 4.8 Hz), 5.08 (br s, 2H), 6.97-7.05 (m, 2H), 7.19-7.23 (m, 1H), 7.45 (s, 1H), 7.65-7.69 (m, 2H) |
| | 5-(2-(3,3-dimethylbutoxy)phenyl)-1H-imidazole | 55 | 1.01 (s, 9H), 1.85 (t, 2H, J = 7.6 Hz), 4.15 (t, 2H, J = 7.6 Hz), 6.96-7.02 (m, 2H), 7.19-7.23 (m, 1H), 7.58 (s, 1H), 7.69 (s, 1H), 7.87 (d, 1H, J = 7.2 Hz) |
| | 5-(4-chloro-2-(4-chloro-benzyloxy)phenyl)-1H-imidazole | 61 | 5.09 (s, 2H), 6.98 (s, 1H), 7.01 (d, 1H, J = 8.8 Hz), 7.36 (s, 4H), 7.45 (s, 1H), 7.62 (s, 1H), 7.91 (d, 1H, J = 8.4 Hz), 9.98 (br s, 1H) |
| | 2-(4-((2-(1H-imidazol-5-yl)phenoxy)methyl)phenyl)-N-methylacetamide | 44 | 2.74 (d, 3H, J = 4.8 Hz), 3.53 (s, 2H), 5.10 (s, 2H), 6.20 (d, 1H, J = 3.6 Hz), 6.99-7.05 (m, 2H), 7.17-7.26 (m, 3H), 7.38 (d, 2H, J = 8.1 Hz), 7.47 (s, 1H), 7.52 (s, 1H), 7.93-7.96 (dd, 1H, J = 1.2, 7.5 Hz), 9.04 (br s, 1H) |

TABLE H-continued

| Compound | Name | Yield (%) | $^1$H NMR |
|---|---|---|---|
| | 3-(2-(1H-imidazol-4-yl)phenoxy)propan-1-amine | 56 | 1.99-2.04 (m, 2H), 3.03 (br s, 2H), 4.16-4.20 (t, 2H, J = 7.32 Hz), 5.48 (br s, 3H), 6.89-7.02 (m, 2H), 7.14-7.20 (t, 1H, J = 7.3 Hz), 7.43-7.61 (m, 3H), 7.77-7.79 (d, 2H, J = 7.7 Hz) |
| | 4-(2-(3-methylbenzyloxy)phenyl)-1H-imidazole | 18 | 2.39 (s, 3H), 2.39 (s, 2H), 7.04-7.07 (m, 2H), 7.19-7.34 (m, 5 H), 7.52 (s, 1H), 7.59 (s, 1H), 7.86 (1H) |
| | 4-(2-(2-methylbenzyloxy)phenyl)-1H-imidazole | 11 | 2.35 (s, 3H), 5.15 (s, 2H), 7.03-7.05 (d, 1H, J = 7.4 Hz), 7.07-7.09 (d, 1H, J = 7.5 Hz), 7.22-7.29 (m, 4H), 7.39-7.41 (d, 1H, J = 7.4 Hz), 7.46 (s, 1H), 7.54 (s, 1H), 7.90-7.91 (d, 1H, J = 6.7 Hz) |
| | 4-(3-bromo-2-(4-chlorobenzyloxy)phenyl)-1H-imidazole | 68 | 4.84 (s, 2H), 7.08-7.12 (t, 1H, J = 8.0 Hz), 7.35-7.42 (m, 4H), 7.49-7.52 (dd, 2H, J = 1.6, 8.0 Hz, 7.66 (s, 1H), 7.85 (br s, 1H) |
| | 4-(3-bromo-2-(3,3-dimethylbutoxy)phenyl)-1H-imidazole | 34 | 0.92 (s, 9H), 1.78-1.82 (t, 2H, J = 8.0 Hz), 3.88-3.92 (t, 2H, J = 8.0 Hz), 7.02-7.06 (t, 1H, J = 7.9 Hz), 7.46-7.48 (d, 1H, J = 7.8 Hz), 7.60 (s, 1H), 7.76 (s, 1H), 7.79-7.81 (d, 1H, J = 7.6 Hz) |
| | 2-(2-(1H-imidazol-4-yl)phenoxy)acetamide | 74 | 3.87 (s, 2H), 4.72 (s, 2H), 6.83 (d, 1H, J = 8.14 Hz), 7.06 (t, 1H, J = 6.57 Hz), 7.16-7.22 (m, 1H), 7.61 (s, 1H), 7.79 (s, 1H), 7.81 (d, 1H, J = 1.87 Hz) |

TABLE H-continued

| Compound | Name | Yield (%) | $^1$H NMR |
|---|---|---|---|
| | 4-(2-(4-chlorobenzyloxy)phenyl)-1H-imidazole | 15 | 5.14 (s, 2H), 6.99-7.08 (m, 2H), 7.19-7.24 (m, 2H), 7.38 (s, 3H), 7.49 (s, 1H), 7.63 (s, 1H), 7.90 (d, 1H, J = 6.09 Hz) |
| | 4-(2-(4-methylbenzyloxy)phenyl)-1H-imidazole | 76 | 2.38 (s, 3H), 5.13 (s, 2H), 7.04-7.36 (m, 7H), 7.50 (s, 1H), 7.57 (s, 1H), 7.88 (d, 1H, J = 7.68 Hz) |
| | 4-(2-(isopentyloxy)phenyl)-1H-imidazole | 21 | 0.99 (d, 6H, J = 6.21 Hz), 1.82 (m, 2H), 4.13 (t, 2H, J = 6.60 Hz), 6.70 (m, 2H), 7.19 (d, 1H, J = 1.59 Hz), 7.55 (s, 1H), 7.69 (s, 1H), 7.84 (d, 1H, J = 6.36 Hz) |
| | 4-(2-(2-cyclohexylethoxy)phenyl)-1H-imidazole | 73 | 1.03 (m, 2H), 1.22 (m, 3H), 1.49 (m, 1H), 1.53-1.84 (m, 7H), 4.15 (t, 2H, J = 6.84 Hz), 6.97 (d, 1H, J = 8.31 Hz), 7.02 (d, 1H, J = 7.59 Hz), 7.20 d, 1H, J = 7.24 Hz), 7.54 (s, 1H), 7.68 (s, 1H), 7.82 (s, 1H) |
| | 4-(2,5-bis(4-chlorobenzyloxy)phenyl)-1H-imidazole | 52 | (CD$_3$OD) 5.06 (s, 2H), 5.12 (s, 2H), 6.81-6.85 (m, 1H), 7.00-7.03 (d, 1H, J = 9.0 Hz), 7.35-7.45 (m, 8H), 7.51 (s, 1H), 7.56-7.57 (d, 1H, J = 3.0 Hz), 7.79 (s, 1H) |
| | 4-(2-(3-chlorobenzyloxy)phenyl)-1H-imidazole | 67 | 5.15 (s, 2H), 6.98-7.09 (m, 2H), 7.19-7.26 (m, 1H), 7.34 (m, 3H), 7.45 (s, 1H), 7.52 (s, 1H), 7.65 (s, 1H), 7.91-7.94 (d, 1H, J = 7.5 Hz) |

TABLE H-continued

| Compound | Name | Yield (%) | $^1$H NMR |
|---|---|---|---|
| | 4-(2-(2-chlorobenzyloxy)phenyl)-1H-imidazole | 86 | 5.28 (s, 2H), 6.98-7.06 (m, 2H), 7.17-7.27 (m, 3H), 7.40-7.48 (m, 2H), 7.55 (s, 1H), 7.63 (1H), 7.91-7.94 (d, 1H, J = 7.5 Hz) |
| | 4-(2-(2-(1H-imidazol-5-yl)phenoxy)ethyl)piperidine | 47 | 1.10-1.28 (m, 2H), 1.60-1.71 (m, 5H), 2.51 (t, 2H, J = 12.4 Hz), 3.28 (br s, 1H), 4.10 (t, 2H, J = 6.4 Hz), 6.90-7.02 (m, 2H), 7.11-7.20 (m, 1H), 7.51 (s, 1H), 7.68 (s, 1H), 7.79 (d, 1H, J = 7.6 Hz) |

Example 14

N-(2-(2-(1H-Imidazol-5-yl)phenoxy)ethyl)pyrimidin-2-amine

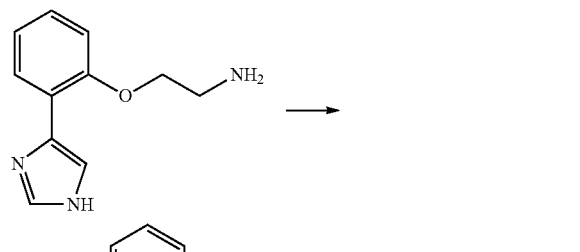

To a 20 mL vial equipped with a stirring bar was added the appropriate amine (60 mg, 0.296 mmol), 2-chloropyrimidine (34 mg, 0.296 mmol) and DMF (1 mL). The resulting mixture was heated to 100° C. for 18 h and concentrated. The crude residue was purified by flash column chromatography (silica gel; 10%-20% MeOH/DCM as eluent) to afford the desired product as a white solid (10 mg, 0.036 mmol, 12%) and some formylated side product (24 mg, 0.104 mmol, 35%). $^1$H NMR (Desired product): 3.96-4.00 (m, 2H), 4.28 (t, 2H, J=5.2 Hz), 5.81 (br s, 1H), 6.59 (t, 1H, J=4.8 Hz), 6.96-7.04 (m, 2H), 7.18-7.23 (m, 1H), 7.50 (s, 1H), 7.61 (s, 1H), 7.79 (br s, 1H), 8.31 (d, 1H, J=4.8 Hz). $^1$H NMR (Side product): 3.79-3.83 (m, 2H), 4.12 (t, 2H, J=4.8 Hz), 6.88 (d, 1H, J=8 Hz), 7.01 (t, 1H, J=7.6 Hz), 7.17-7.21 (m, 1H), 7.36-7.38 (m, 1H), 7.43 (s, 1H), 7.69 (s, 1H), 7.28-7.74 (dd, 1H, J=0.8, 7.6 Hz), 8.23 (s, 1H)

Example 15

N-(3-(2-(1H-Imidazol-4-yl)phenoxy)propyl)pyrimidin-2-amine

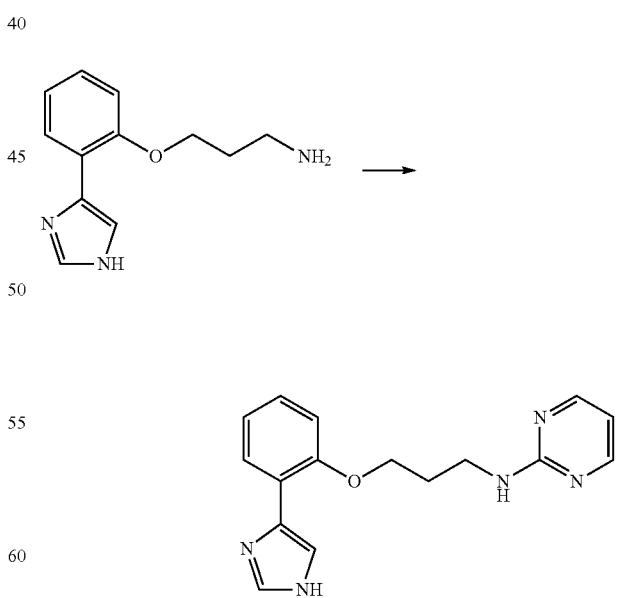

The compound was synthesized by procedure of Example 14. Yield: 43% $^1$H NMR (DMSO-d$_6$): 2.12-2.18 (m, 2H), 3.71-3.76 (q, 2H, J=6.6 Hz), 4.15-4.18 (t, 2H, J=5.6 Hz), 5.57 (br s, 1H), 6.51-6.53 (t, 1H, J=4.9 Hz), 6.92-6.94 (d, 1H, J=8.2

Hz), 6.98-7.02 (t, 1H, J=7.5 Hz), 7.19-7.23 (dt, 1H, J=1.4, 7.2 Hz), 7.49 (s, 1H), 7.70 (s, 1H), 7.73-7.75 (d, 1H, J=7.4 Hz), 8.24-8.25 (d, 2H, J=4.8 Hz)

Example 16

4-((2-(1H-Imidazol-4-yl)phenoxy)methyl)benzamide

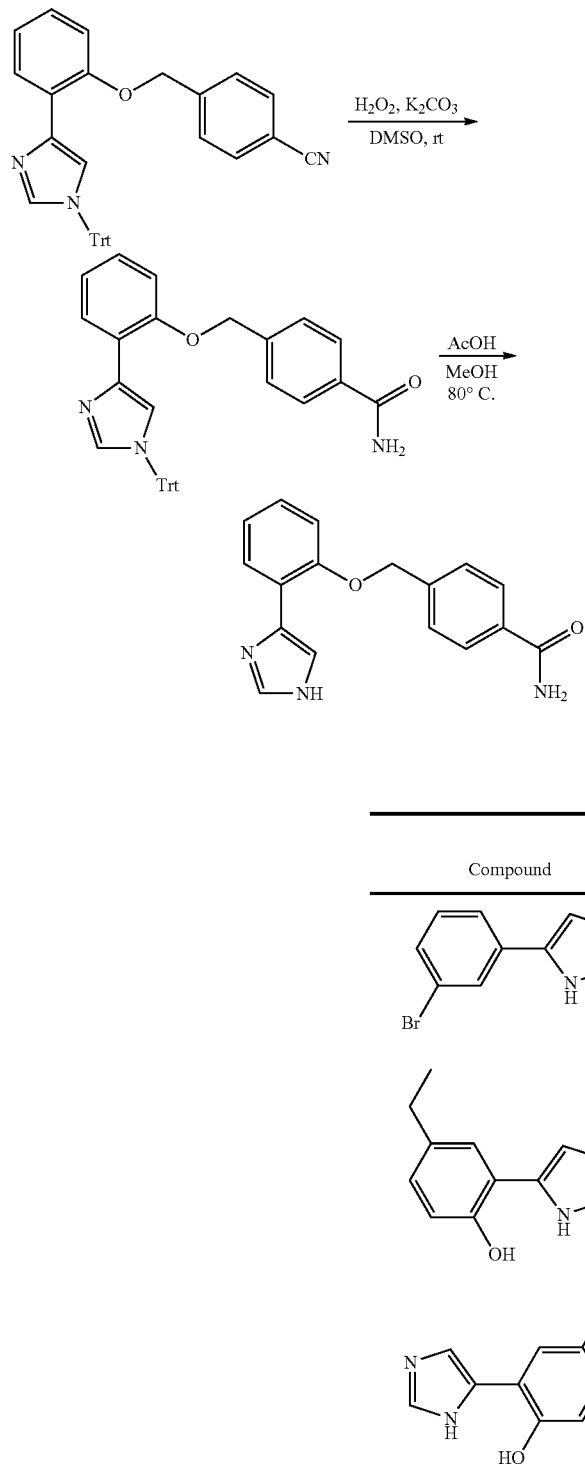

To a stirred solution of 4-((2-(1-trityl-1H-imidazol-4-yl)phenoxy)methyl)benzonitrile (0.328 mmol) in DMF (3 mL) at rt was added $K_2CO_3$ (0.164 mmol) followed by $H_2O_2$ (1.64 mmol, 30% aq. solution). After stirring for 30 min the reaction mixture was diluted with $H_2O$ (10 mL) and the aqueous phase was extracted with EtOAc (3×25 mL). The combined organic layers were dried ($Na_2SO_4$) and concentrated to afford the crude product. The crude was dissolved in a mixture of glacial acetic acid (1.0 mL) and MeOH (4.0 mL) and was heated to 80° C. for 2h. The solution was allowed to cool to room temperature and the pH was adjusted to ~10 with 10% NaOH (aq). The aqueous phase was extracted with EtOAc (3×20 mL). The combined organic layers were washed with water, brine, and dried over $Na_2SO_4$. The solvent was removed in vacuo to afford the crude residue, which was purified by flash column chromatography on silica gel to afford the desired product (58 mg, 60% yield). $^1$H NMR: 5.23 (s, 2H), 5.71 (br s, 1H), 6.24 (br s, 1H), 7.01 (d, 1H, J=8.28 Hz), 7.07 (t, 1H, J=7.44 Hz), 7.21 (m, 2H), 7.48 (s, 1H), 7.53 (d, 1H, J=8.19 Hz), 7.60 (s, 1H), 7.85 (d, 1H, J=8.19 Hz)

Example 17

General Procedure for the Condensation of α-Bromophenones with Formamide

A solution of α-bromophenone derivative (1.34 mmol) was heated (170-180° C.) in formamide (10 mL) for 5-10 h. The solution was allowed to cool to rt and the mixture was diluted with saturated $NaHCO_3$ (20 mL) and the aqueous phase was extracted with EtOAc (3×50 mL). The combined organic layers were washed with water, brine, dried ($Na_2SO_4$) and concentrated in vacuo to afford the crude residue which was purified by flash column chromatography on silica gel to yield the final product.

Utilizing the appropriate starting materials, the compounds of Table I were prepared according to Example 17:

TABLE I

| Compound | Name | Yield (%) | $^1$H NMR |
|---|---|---|---|
| | 5-(3-bromophenyl)-1H-imidazole | 53 | 7.23 (t, 1H, J = 7.6Hz), 7.33-7.41 (m, 2H), 7.66 (dd, 1H, J = 0.8, 7.6 Hz), 7.72 (s, 1H), 7.90 (t, 1H, J = 1.6 Hz) |
| | 4-ethyl-2-(1H-imidazol-5-yl)phenol | 58 | 1.19 (t, 3H, J = 7.6 Hz), 2.57 (q, 2H, J = 7.6 Hz), 6.77 (d, 1H, J = 7.6 Hz), 6.96 (dd, 1H, J = 1.6, 8.0 Hz), 7.67 (d, 1H, J = 2.0 Hz), 8.19 (s, 1H), 8.30 (s, 1H) |
| | 4-bromo-2-(1H-imidazol-5-yl)phenol | 59 | 6.85 (d, 1H, J = 8.8 Hz), 7.20-7.23 (dd, 1H, J = 2.4, 8.8 Hz), 7.34 (s, 1H), 7.56 (s, 1H), 7.71 (s, 1H), 8.87 (br s, 1H), 9.8 (br s, 1H) |

TABLE I-continued

| Compound | Name | Yield (%) | $^1$H NMR |
|---|---|---|---|
| 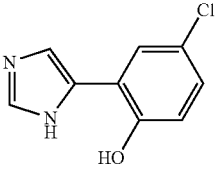 [SMILES: Oc1ccc(Cl)cc1-c1cnc[nH]1] | 4-chloro-2-(1H-imidazol-5-yl)phenol | 48 | (DMSO-d$_6$) 6.80 (d, 1H, J = 8.8 Hz), 7.02-7.04 (m, 1H), 7.72 (s, 1H), 7.81 (s, 1H), 7.89 (s, 1H) |
| 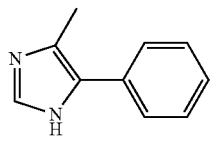 | 4-methyl-5-phenyl-1H-imidazole | 62 | 2.36 (s, 3H), 7.17-7.21 (m, 1H), 7.35-7.39 (m, 2H), 7.56-7.61 (m, 3H) |
| 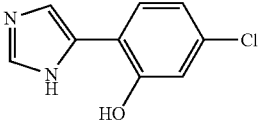 [SMILES: Oc1cc(Cl)ccc1-c1cnc[nH]1] | 5-chloro-2-(1H-imidazol-5-yl)phenol | 56 | (DMSO-d$_6$) 6.82-6.86 (m, 2H), 7.69 (d, 1H, J = 8.1 Hz), 7.75 (s, 1H), 7.91 (s, 1H), 12.6 (br s, 1H) |
| 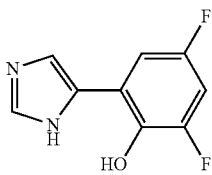 [SMILES: Oc1c(F)cc(F)cc1-c1cnc[nH]1] | 2,4-difluoro-6-(1H-imidazol-5-yl)phenol | 61 | 6.98-7.06 (m, 1H), 7.38-7.42 (m, 1H) 7.87 (s, 1H), 7.97 (s, 1H) |
| 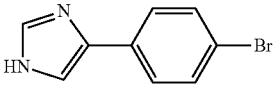 | 4-(4-bromophenyl)-1H-imidazole | 63 | 7.34 (s, 1H), 7.47-7.50 (d, 2H, J = 8.4 Hz), 7.59-7.62 (d, 2H, J = 8.6 Hz), 7.70 (s, 1H) |
| 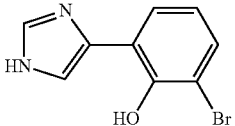 | 2-bromo-6-(1H-imidazol-4-yl)phenol | 22 | (DMSO-d$_6$) 6.74-6.78 (t, 1H, J = 7.8 Hz), 7.35-7.37 (dd, 1H, J = 1.0, 8.0 Hz), 7.65-7.67 (dd, 1H, J = 1.0, 8.0 Hz), 7.85 (s, 1H), 8.02 (s, 1H), 12.78 (br s, 1H), 13.56 (br s, 1H) |
| 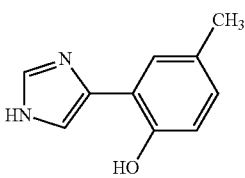 | 2-(1H-imidazol-4-yl)-4-methylphenol | 51 | 2.29 (s, 3H), 6.88-6.90 (d, 1H, J = 8.2 Hz), 6.98-6.96 (d, 1H, 8.2 Hz), 7.28 (s, 1H), 7.33 (s, 1H), 7.68 (s, 1H) |
| 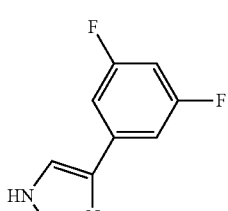 | 4-(3,5-difluorophenyl)-1H-imidazole | 18 | 7.00 (t, 1H, J = 9.39 Hz), 7.46 (m, 2H), 7.75 (s, 1H), 7.80 (s, 1H), 12.30 (br s, 1H) |
| 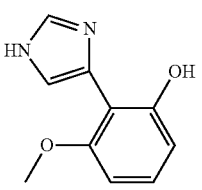 | 2-(1H-imidazol-4-yl)-3-methoxyphenol | 15 | 3.86 (s, 3H), 6.47 (dd, 2H, J = 6.4, 8.1 Hz), 7.01 (t, 1H, J = 8.1 Hz), 7.60 (s, 1H), 7.95 (s, 1H) |

TABLE I-continued

| Compound | Name | Yield (%) | ¹H NMR |
|---|---|---|---|
| (imidazole-phenyl-CN structure) | 4-(1H-imidazol-4-yl)benzonitrile | 49 | 7.75-7.83 (m, 4H), 7.93 (d, 2H, J = 8.31 Hz) |
| (imidazole-2,6-dimethoxyphenyl structure) | 5-(2,6-dimethoxyphenyl)-1H-imidazole | 51 | 3.89 (s, 6H), 6.64 (d, 2H, J = 8.4 Hz), 7.16 (t, 1H, J = 8.2 Hz), 7.63 (s, 1H), 7.74 (s, 1H) |
| (imidazole-2-nitrophenyl structure) | 5-(2-nitrophenyl)-1H-imidazole | 28 | 7.52 (t, 1H, J = 7.9 Hz), 7.66 (d, 1H, J = 8.0 Hz), 7.81 (m, 1H), 8.10 (m, 3H), 12.25 (br s, 1H) |
| (imidazole-phenyl-CN meta structure) | 3-(1H-imidazol-4-yl)benzonitrile | 43 | (CD₃OD) 7.54-7.61 (m, 3H), 7.78 (s, 1H), 8.01-8.08 (m, 2H) |
| (imidazole-benzenediol structure) | 2-(1H-imidazol-4-yl)benzene-1,4-diol | 42 | (CD₃OD) 6.55-6.57 (d, 1H, J = 8.8 Hz), 6.68-6.71 (d, 1H, J = 8.8 Hz), 7.05(s, 1H), 7.46 (s, 1H), 7.71 (s, 1H) |

Example 18

General Procedure for the Conversion of Esters to Amides

To the appropriate ester (2.0 mmol) was added the amine (2.0 M in MeOH or EtOH, 10.0 mmol, 5.0 mL). The resulting solution was allowed to stir for 24 h at rt until completion of the reaction was observed (TLC). In some cases, complete conversion required heating at 50° C. The solvent was removed under reduced pressure to afford the crude product, which was purified by column chromatography on silica gel using $CH_2Cl_2$/MeOH as the eluent.

Utilizing the appropriate starting materials, the compounds of Table J were prepared according to Example 18:

TABLE J

| Compound | Name | Yield (%) | ¹H NMR |
|---|---|---|---|
| (N-methyl-phenyl-imidazole-propanamide structure) | N-methyl-3-(5-phenyl-1H-imidazol-1-yl)propanamide | 59 | 2.39-2.44 (t, 2H, J = 6.7 Hz), 2.73-2.74 (d, 3H, J = 4.8 Hz), 4.33-4.38 (t, 2H, J = 6.7 Hz), 5.96 (br s, 1H), 7.09 (br s, 1H), 7.27-7.47 (m, 5H), 7.61 (br s, 1H) |

TABLE J-continued

| Compound | Name | Yield (%) | $^1$H NMR |
|---|---|---|---|
| (structure) | 3-(5-phenyl-(1H-imidazol-1-yl)propanamide | 15 | 2.14 (br s, 1H), 2.45-2.48 (t, 2H, J = 6.8 Hz), 4.34-4.37 (t, 2H, J = 6.8 Hz), 5.58 (s, 1H), 5.69 (s, 1H), 7.05 (s, 1H), 7.37-7.47 (m, 5H), 7.61 (s, 1H) |
| (structure) | N-methyl-4-(5-phenyl-1H-imidazol-1-yl)butanamide | 82 | 1.87-2.01 (m, 4H), 2.69 (d, 3H, J = 4.8 Hz), 4.06 (t, 2H, J = 6.2 Hz), 6.03 (br s, 1H), 7.02 (s, 1H), 7.33-7.42 (m, 5H), 7.53 (s, 1H) |
| (structure) | 4-(5-phenyl-1H-imidazol-1-yl)butanamide | 90 | 1.91 (m, 2H), 2.05 (t, 2H, J = 5.3 Hz), 4.09 (t, 2H, J = 5.0 Hz), 5.44 (br s, 1H), 5.63 (br s, 1H), 7.05 (s, 1H), 7.35-7.45 (m, 5H), 7.56 (s, 1H) |
| (structure) | N-methyl-2-(5-phenyl-1H-imidazol-1-yl)acetamide | 54 | 2.66 (s, 3H), 4.67 (s, 2H), 6.99 (s, 1H), 7.3-7.45 (m, 5H), 7.73 (s, 1H). |
| (structure) | 2-(5-phenyl-1H-imidazol-1-yl)acetamide | 37 | 2.66 (s, 3H), 4.67 (s, 2H), 6.99 (s, 1H), 7.3-7.45 (m, 5H), 7.73 (s, 1H) |

Example 19

General Procedure for the Conversion of Anisoles to Phenols using HBr

A solution of the appropriate anisole derivative (2.52 mmol) in 48% HBr (5 mL) was stirred at 110° C. for 16 h. The solution was allowed to cool to rt and was poured into saturated NaHCO$_3$ (10 mL). The aqueous phase was extracted with ethyl acetate (3×30 mL). The combined organic layers were dried over sodium sulfate and concentrated under reduced pressure to afford the crude residue, which was purified by column chromatography on silica gel to afford the desired product.

Utilizing the appropriate starting materials, the compounds of Table K were prepared according to Example 19:

TABLE K

| Compound | Name | Yield (%) | $^1$H NMR |
|---|---|---|---|
| | 4-((5-phenyl-1H-imidazol-1-yl)methyl)phenol | 24 | 5.06 (s, 2H), 6.76-6.78 (d, 2H, J = 8.5 Hz), 6.86-6.89 (d, 2H, J = 8.5 Hz), 7.14 (s, 1H), 7.32-7.34 (dd, 2H, J = 2.0, 7.9 Hz), 7.37-7.41 (t, 3H, J = 7.0 Hz), 7.52 (s, 1H) |
| | 2-(1H-imidazol-5-yl)benzene-1,3-diol | 81 | 6.30 (d, 2H, J = 8.07 Hz), 6.83 (t, 1H, J = 8.04 Hz), 7.63 (s, 1H), 7.91 (s, 1H), 11.66 (br s, 2H), 12.50 (br s, 1H) |
| | 2-(1-(3,3-dimethylbutyl)-1H-imidazol-5-yl)phenol | 77 | 1.40-1.53 (m, 2H), 3.93-4.10 (m 2H), 6.91 (t, 1H, J = 7.2 Hz), 7.02-7.15 (m, 2H), 7.27-7.45 (m 2H), 8.70(s, 1H). |
| | 2-((5-phenyl-1H-imidazol-1-yl)methyl)phenol | 45 | (DMSO-d$_6$) 5.14 (s, 2H), 6.45 (d, 1H, J = 7.8 Hz), 6.65 (t, 1H, J = 7.5 Hz), 6.78 (d, 1H, J = 8.1 Hz), 7.02-7.08 (m, 2H), 7.30-7.36 (m, 4H), 7.69 (s, 1H), 9.78 (s, 1H) |
| | 3-((5-phenyl-1H-imidazol-1-yl)methyl)phenol | 50 | 5.12 (s, 2H), 6.49 (s, 1H), 6.58(d, 1H, J = 7.6 Hz), 6.82-6.85 (dd, 1H, J = 1.5, 8 Hz), 6.97 (s, 1H), 7.16-7.21 (m, 3H), 7.28-7.33 (m, 3H), 7.57 (s, 1H) |

Example 20

4-(2-Ammoniophenyl)-1H-imidazol-1-ium Chloride

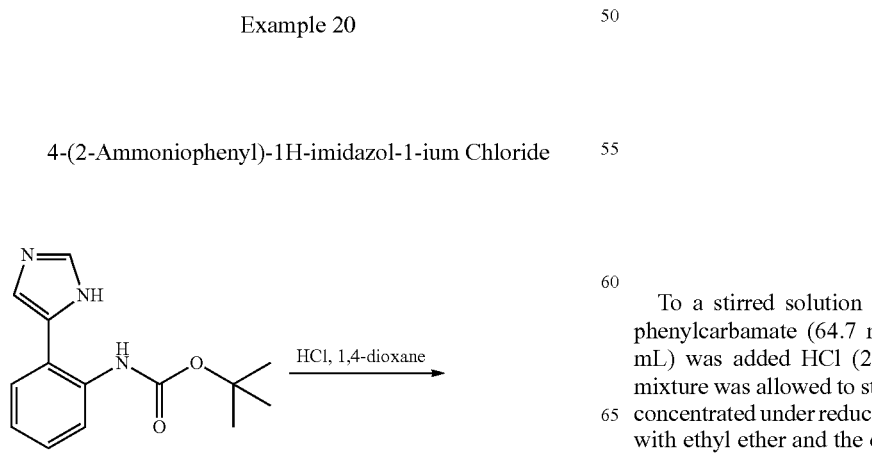

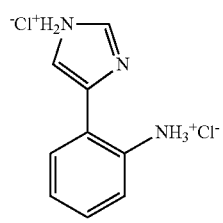

To a stirred solution of tert-butyl 2-(1H-imidazol-5-yl)phenylcarbamate (64.7 mg, 0.25 mmol) in 1,4-dioxane (2 mL) was added HCl (2 mL, 2.0 M in 1,4-dioxane). The mixture was allowed to stir at room temperature for 12 h and concentrated under reduced pressure. The residue was diluted with ethyl ether and the desired hydrochloride salt was precipitated. The colorless solid was collected by filtration, which afforded the desired product in 46% yield. ¹H NMR: 6.66-6.82 (m, 2H), 7.11-7.20 (m, 2H), 7.21-7.38 (m, 4H), 7.40-7.68 (m, 3H).

Example 21

5-(2-(2-Chlorobenzyloxy)phenyl)-1-(3,3-dimethylbutyl)-1H-imidazole

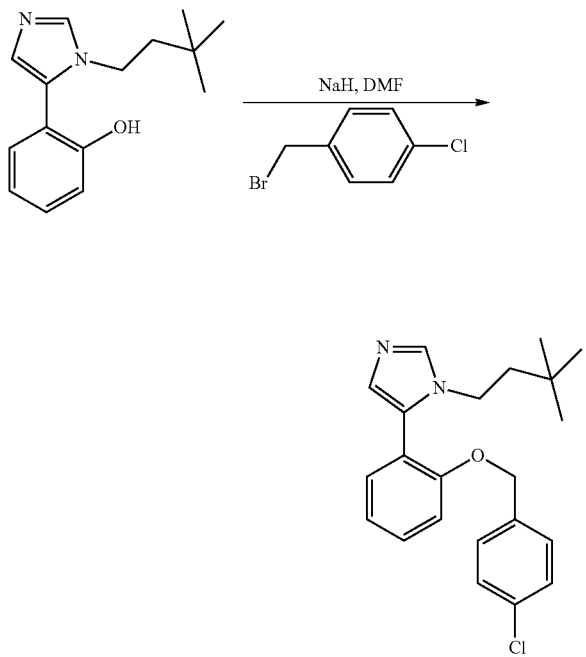

To a stirred solution of 2-(1-(3,3-dimethylbutyl)-1H-imidazol-5-yl)phenol (122.0 mg, 0.5 mmol) in DMF (3 mL) at 0° C. was added NaH (36.0 mg, 0.75 mmol) portion wise. The resulting mixture was allowed to stir for 10 min and 1-(bromomethyl)-4-chlorobenzene (123.0 mg, 0.6 mmol) was added. After stirring overnight the reaction mixture was diluted with water and the aqueous phase extracted with ethyl acetate (2×10 mL). The combined organic layers were washed with water, brine, dried (Na₂SO₄) and concentrated under reduced pressure to afford the crude residue, which was purified by column chromatography on silica gel to afford the desired product in 30% yield. ¹H NMR: 0.78 (s, 9H), 1.38-1.47 (m, 2H), 3.75-3.85 (m, 2H), 5.00 (s, 2H), 6.98-7.09 (m, 3H), 7.15 (d, 2H, J=7.6 Hz), 7.24-7.40 (m, 4H), 7.55 (s, 1H).

Example 22

2-(1-(2-Hydroxyethyl)-1H-imidazol-5-yl)phenol

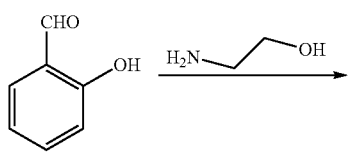

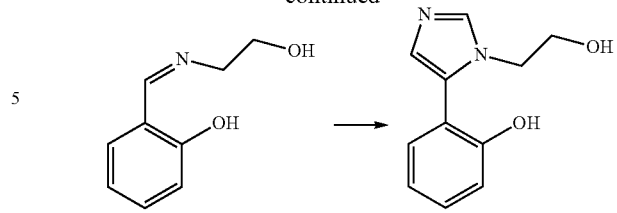

To a stirred solution of 2-amino-1-ethanol (105.0 mg, 1.0 mmol) in MeOH (1.5 mL) was added a solution of salicylaldehyde (0.10 mL, 1.0 mmol) in MeOH (1.5 mL). The reaction mixture was heated at 40° C. for 1 h and was concentrated to a give the crude amine as a yellow liquid, which was used in the next step immediately. To a solution of the crude imine in DME/MeOH (5 mL, 4:1) was added TOSMIC (2910 mg, 1.5 mmol) and K₂CO₃ (414.0 mg, 3.0 mmol). The solution was allowed to stir at room temperature for 3 days. The solvent was evaporated under reduced pressure and the crude product was absorbed on silica gel. After purification by flash column chromatography on silica gel the desired product was obtained in 46% yield. ¹H NMR: 3.32 (s, 1H), 3.57 (t, 2H, J=5.6 Hz), 4.01 (t, 2H, J=5.6 Hz), 6.86 (d, 2H, J=5.6 Hz, 2H), 6.89 (s, 1H), 7.16 (dd, 1H, J=1.6, 8.0 Hz), 7.24 (td, 1H, J=2.0, 8.0 Hz), 7.75 (1H).

Example 23

5,6-Dihydrobenzo[f]imidazo[1,5-d][1,4]oxazepine

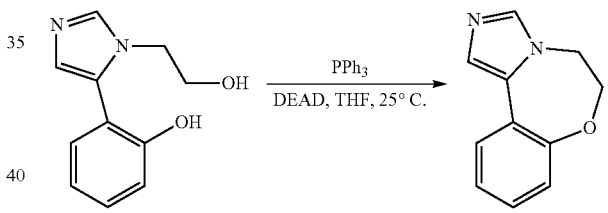

To a stirred solution of 2-(1-(2-hydroxyethyl)-1H-imidazol-5-yl)phenol (103.0 mg, 0.5 mmol) and PPh₃ (157.0 mg, 0.6 mmol) in THF (4 mL) at 0° C., was added DEAD (0.22 mL, 40% solution in toluene, 0.75 mmol). The resulting yellow solution was allowed to warm to rt and stirred overnight. The solvent was removed under reduced pressure and the crude residue was purified by flash column chromatography on silica gel to afford the desired product in 84% yield. ¹H NMR: 4.35-4.45 (m, 4H), 6.94-7.05 (m, 2H), 7.11-7.19 (m, 1H), 7.43 (d, 1H, J=0.8 Hz), 7.49 (s, 1H), 7.67 (dd, 1H, J=1.6, 8.0 Hz).

Example 24

N-(3-(2-Hydroxyethyl)phenyl)acetamide

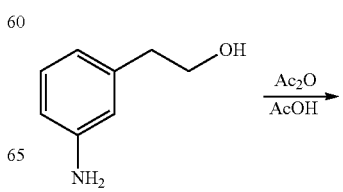

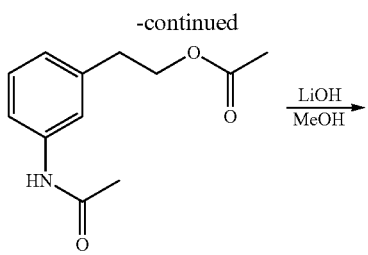

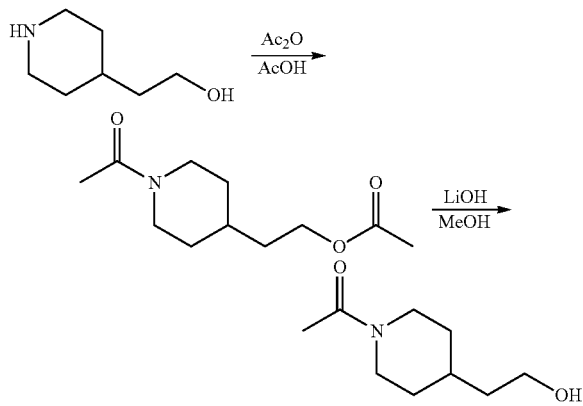

To a vial containing 2-(3-aminophenyl)ethanol (137.0 mg, 1.0 mmol) in glacial acetic acid (3 mL) was added acetic anhydride (1 mL). The reaction vial was sealed and heated at 110° C. for 6 h. The mixture was concentrated under reduced pressure. The crude product was dissolved in MeOH (3 mL) and LiOH (120.0 mg, 5.0 mmol) was added. The solution was allowed to stir overnight at rt. The solution was concentrated under reduced pressure and diluted with ethyl acetate. The organic phase was washed with water (2×5 mL), brine and dried ($Na_2SO_4$). The solvent was removed under reduced pressure and the crude mixture was purified by column chromatography to afford the desired product in 39%. $^1$H NMR: 1.65 (t, 1H, J=6.0 Hz), 2.13 (s, 3H), 2.81 (t, 2H, J=6.4 Hz), 3.81 (q, 2H, J=6.0 Hz), 6.94 (t, 1H, J=6.8 Hz), 7.22 (t, 1H, J=7.6 Hz), 7.30-7.40 (m, 3H).

Example 25

1-(4-(2-Hydroxyethyl)piperidin-1-yl)ethanone

The compound was synthesized by using the procedure of Example 24. Yield: 40% $^1$H NMR: 0.85-1.2 (m, 2H), 1.39-1.75 (m, 5H), 2.0 (s, 3H), 2.48 (t, 1H, J=9.6 Hz), 2.97 (t, 1H, J=9.6 Hz), 3.62 (t, 2H, J=6.4 Hz), 3.72 (d, 1H, J=10.0 Hz), 4.49 (d, 1H, J=10.0 Hz).

Example 26

N-(4-(hydroxymethyl)benzyl)acetamide

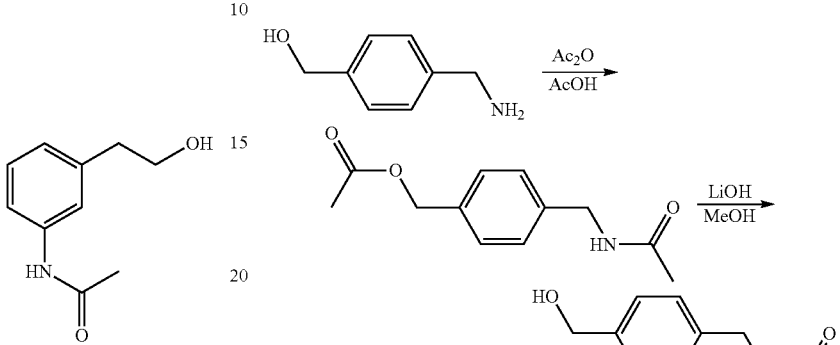

The compound was synthesized by using the procedure of Example 24. Yield: 45% $^1$H NMR: 1.94 (s, 3H), 4.30 (s, 2H), 4.54 (s, 2H), 4.88 (br s, 2H), 7.22 (d, 2H, J=8.0 Hz), 7.28 (d, 2H, J=8.0 Hz).

Example 27

N-(4-(2-Hydroxyethylidene)cyclohexyl)acetamide

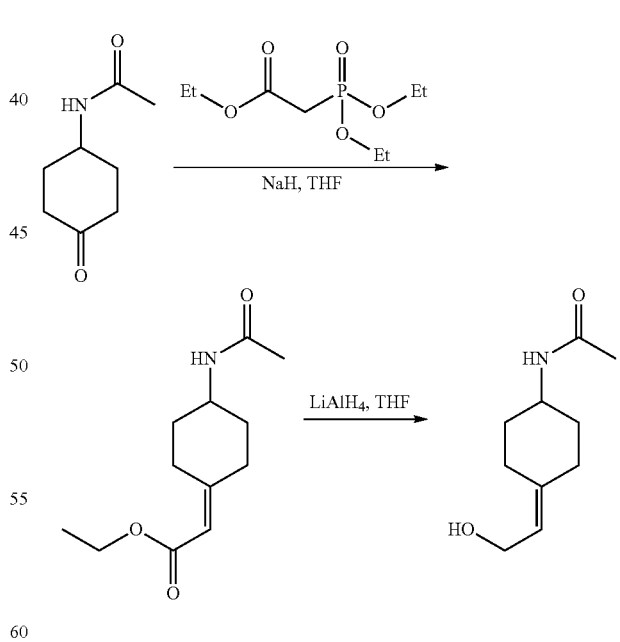

To a stirred suspension of sodium hydride (1.2 mmol) in THF was added triethyl phosphonoacetate (1.2 mmol) drop wise. The mixture was allowed to stir until it became colorless and a solution of N-(4-oxocyclohexyl)acetamide (1.0 mmol) in THF (1 mL) was added. The solution was allowed to stir at rt until the reaction was complete (by TLC). The solvent was removed under reduced pressure and the crude residue was filtered through a small plug of silica gel to afford the desired product, which was used directly in the next synthetic step.

To a stirred solution of the ester (225.6 mg, 1.0 mmol) in THF (5 mL) at 0° C. was added LiAlH$_4$ (56.9 mg, 1.5 mmol) portion wise carefully. The reaction was allowed to stir for an additional 3 h at 0° C. The excess LiAlH$_4$ was destroyed with ethyl acetate and the solvent removed under reduced pressure. The crude residue was adsorbed on silica gel and was purified by flash column chromatography on silica gel to afford the desired alcohol in 66% yield. $^1$H NMR: 1.50-1.67 (m, 2H), 1.78-2.11 (m, 4H), 1.94 (s, 3H), 2.18 (t, 2H, J=6.0 Hz), 2.34 (d, 1H, J=12.9 Hz), 3.64 (t, 2H, J=6.4 Hz), 3.78-4.09 (m, 1H), 5.39 (br s, 1H), 5.73 (d, 1H, J=6.8 Hz).

Example 28

General Procedure for the Synthesis of N-(4-(Bromomethyl)benzyl)acetamide and tent-Butyl 4-(2-bromoethyl)piperidine-1-carboxylate To a stirred solution of the alcohol (1.0 mmol) and carbon tetrabromide (364.0 mg, 1.1 mmol) in dichloromethane (5 mL) at 0° C. was added triphenyl phosphine (288.0 mg, 1.1 mmol). The reaction mixture was allowed to stir 12 h at room temperature. The mixture was concentrated under reduced pressure, adsorbed on silica gel and purified by flash column chromatography.

Utilizing the appropriate starting materials, the compounds of Table L were prepared according to Example 28:

TABLE L

| Compound | Name | Yield (%) | $^1$H NMR |
|---|---|---|---|
| ![structure] | N-(4-(bromomethyl)benzyl)acetamide | 44 | 1.96 (s, 3H), 4.33 (d, 2H, J = 6.0 Hz), 4.42 (s, 2H), 7.18 (d, 2H, J = 8.2 Hz), 7.26 (d, 2H, J = 8.2 Hz) |
| ![structure] | tert-butyl 4-(2-bromoethyl)piperidine-1-carboxylate | 69 | 0.95-1.15 (m, 2H), 1.41 (s, 9H), 1.50-1.70 (m, 3H), 1.77 (q, 2H, J = 6.6 Hz), 2.66 (t, 2H, J = 12.2 Hz), 3.41 (t, 2H, J = 7.0 Hz), 4.06 (br s, 2H) |

Example 29

Synthesis of 3,3-Dimethyl-5-(2-(1-trityl-1H-imidazol-4-yl)phenoxy)pentyl 4-methylbenzene sulfonate

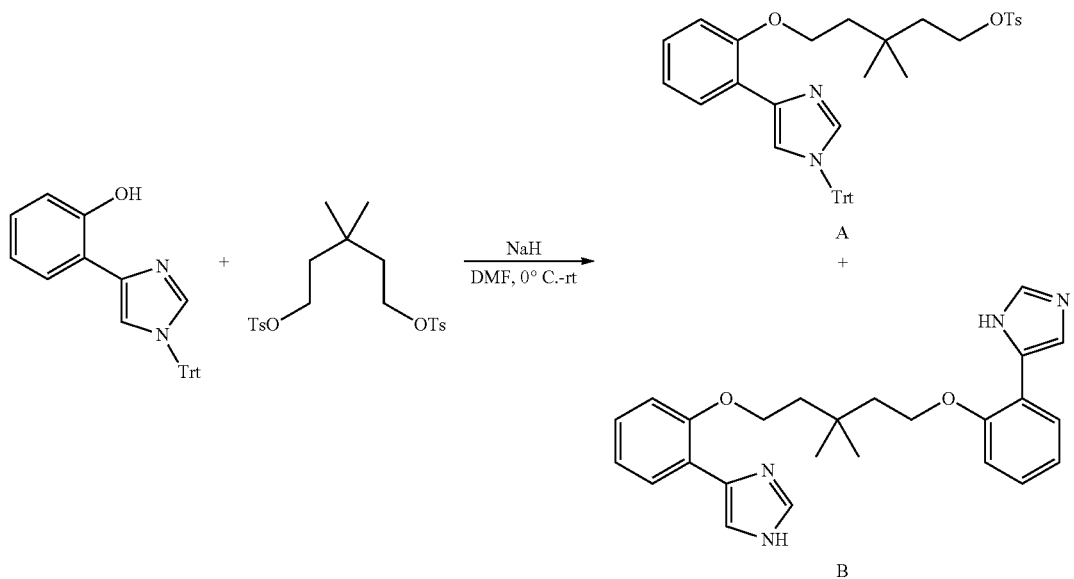

To a stirred solution of 2-(1-trityl-1H-imidazol-4-yl)phenol (1.50 g, 3.73 mmol) in anhydrous DMF (10 mL) was added NaH (4.10 mmol) portion wise at 0° C. The resulting suspension was allowed to stir for 15 min. To the resulting suspension was added a solution of 3,3-dimethylpentane-1,5-diyl bis(4-methylbenzenesulfonate) (3.28 g, 7.45 mmol) in DMF (8 mL) and the mixture was allowed to stir overnight at rt. The reaction mixture was diluted with water (50 mL) and the aqueous phase was extracted with $CH_2Cl_2$ (3×50 mL). The combined organic layers were washed with brine, dried ($Na_2SO_4$) and concentrated under reduced pressure to afford a yellow oil which was purified by flash column chromatography on silica gel to afford the desired product (1.60 g, 64% yield). $^1$H NMR (A): 0.84 (s, 6H), 1.34 (t, 2H, J=7.32 Hz), 1.52 (t, 2H, J=7.20 Hz), 2.38 (s, 3H), 3.85 (t, 2H, J=7.32 Hz), 4.02 (t, 2H, J=7.32 Hz), 6.79 (d, 1H, J=8.19 Hz), 7.03 (t, 1H, J=7.47 Hz, 7.14-7.35 (m, 18H), 7.44 (s, 1H), 7.50 (s, 1H), 7.72-7.77 (m, 2H), 8.23 (d, 1H, J=5.64 Hz). $^1$H NMR (B): 1.08 (s, 6H), 1.95 (t, 4H, J=7.08 Hz), 4.16 (t, 4H, J=6.96 Hz), 6.92-7.02 (m, 4H), 7.20 (m, 2H), 7.45 (s, 2H), 7.65 (s, 2H), 7.86 (d, 2H, J=6.12 Hz), 8.19 (br s, 2H)

Example 30

General Procedure for Reaction of 3,3-Dimethyl-5-(2-(1-trityl-1H-imidazol-4-yl)phenoxy)pentyl 4-methylbenzenesulfonate with Amines

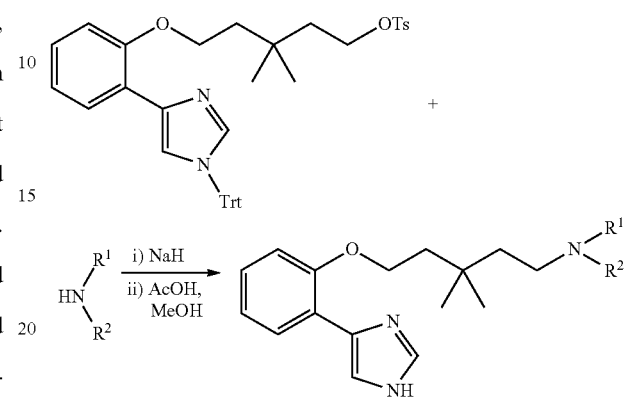

To a stirred solution of appropriate amine (0.50 mmol) in anhydrous DMF (3 mL) at 0° C. was added NaH (0.50 mmol) portion wise. The suspension was allowed to stir for 15 min at rt and a solution of the tosylate derivative (0.25 mmol) in DMF (2 mL) was added. The solution heated to 80° C. and allowed to stir overnight. The solution was allowed to cool to rt and was diluted with MeOH (2 mL), acetic acid (2 mL) and stirred at 80° C. for 3 h. The solution was allowed to cool to rt and was partitioned between EtOAc (50 mL) and 20% $NaHCO_3$ (15 mL). The organic phase was collected and the aqueous phase was extracted with EtOAc (2×40 mL). The combined organic fractions were dried ($Na_2SO_4$) and concentrated to afford the crude residue, which was purified by column chromatography on silica gel.

Utilizing the appropriate starting materials, the compounds of Table M were prepared according to Example 30:

TABLE M

| Compound | Name | Yield (%) | $^1$H NMR |
|---|---|---|---|
|  | N-(5-(2-(1H-imidazol-5-yl)phenoxy)-3,3-dimethylpentyl)pyridin-2-amine | 8 | (CDCl$_3$ + CD$_3$OD) 1.00 (s, 6H), 1.55 (t, 2H, J = 6.18 Hz), 1.86 (m, 2H), 3.09 (t, 2H, J = 6.03 Hz), 4.10 (t, 2H, J = 5.49 Hz), 6.35 (d, 2H, J = 4.80 Hz), 6.89-6.96 (m, 2H), 7.14 (m, 1H), 7.44 (s, 1H), 7.56 (s, 1H), 7.73 (d, 1H, J = 4.62 Hz), 7.90 (d, 1H, J = 4.71 Hz) |
|  | 4-(5-(2-(1H-imidazol-4-yl)phenoxy)-3,3-dimethylpentyl)morpholine | 32 | 1.02 (s, 6H), 1.54 (m, 2H), 1.88 (t, 2H, J = 5.55 Hz), 2.36-2.48 (m, 6H), 3.72 (m, 4H), 4.17 (t, 2H, J = 5.55 Hz), 6.99 (d, 1H, J = 6.33 Hz), 7.03 (d, 1H, J = 5.64 Hz), 7.23 (m, 1H), 7.42 (s, 1H), 7.54 (s, 1H), 7.67 (s, 1H), 7.83 (d, 1H, J = 5.34 Hz) |

TABLE M-continued

| Compound | Name | Yield (%) | $^1$H NMR |
|---|---|---|---|
| | 5-(2-(5-(1H-imidazol-1-yl)-3,3-dimethylpentyloxy)phenyl)-1H-imidazole | 76 | 1.05 (s, 6H), 1.80-1.90 (m, 4H), 3.98 (m, 2H), 4.12 (m, 2H), 6.88-7.22 (m, 6H), 7.45 (s, 1H), 7.50 (s, 1H), 7.68 (s, 1H) |
| | 3-(5-(2-(1H-imidazol-4-yl)phenoxy)-3,3-dimethylpentyl)-1-((2R,3R,4S,5R)-3,4-dihydroxy-5-(hydroxymethyl)tetrahydrofuran-2-yl)-5-fluoropyrimidine-2,4(1H,3H)-dione | 17 | (CDCl$_3$ + CD$_3$OD) 1.10 (s, 6H), 1.61 (t, 2H, J = 6.33 Hz), 1.95 (t, 2H, J = 5.55 Hz), 2.18 (m, 1H), 2.39 (m, 1H), 3.77 (dd, 1H, J = 7.08, 1.92 Hz), 3.87 (dd, 1H, J = 7.05, 1.92 Hz), 3.97-4.03 (m, 3H), 4.23 (t, 2H, J = 5.34 Hz), 4.43 (m, 1H), 6.32 (t, 1H, J = 4.38 Hz), 7.00 (d, 1H, J = 5.49 Hz), 7.04 (d, 1H, J = 5.64 Hz), 7.24 (t, 1H, J = 5.34 Hz ), 7.49 (s, 2H), 7.66 (s, 1H), 8.27 (d, 1H, J = 4.74 Hz) |
| | 5-(2-(1H-imidazol-5-yl)phenoxy)-N-benzyl-3,3-dimethyl-pentan-1-amine | 82 | 0.99 (s, 6H), 1.57 (t, 2H, J = 5.97 Hz), 1.84 (t, 2H, J = 5.49 Hz), 2.69 (t, 2H, J = 6.12 Hz), 3.78 (s, 2H), 4.14 (t, 2H, J = 5.49 Hz), 6.94 (d, 1H, J = 6.18 Hz), 7.01 (t, 1H, J = 5.61 Hz), 7.19-7.33 (m, 6H), 7.48 (s, 1H), 7.65 (s, 1H), 7.79 (d, 1H, J = 5.70 Hz) |
| | N-(5-(2-(1H-imidazol-4-yl)phenoxy)-3,3-dimethylpentyl)acetamide | 17 | 1.10 (s, 6H), 1.50 (m, 2H), 1.87 (t, 2H, J = 5.40 Hz), 1.94 (s, 3H), 3.26 (m, 2H), 4.16 (t, 2H, J = 5.34 Hz), 5.48 (br s, 1H), 6.96-7.03 (m, 2H), 7.22 (t, 1H, J = 6.12 Hz), 7.24 (s, 1H), 7.51 (s, 1H), 7.69 (s, 1H). |

Example 31

General Procedure for the Alkylation of Imidazole

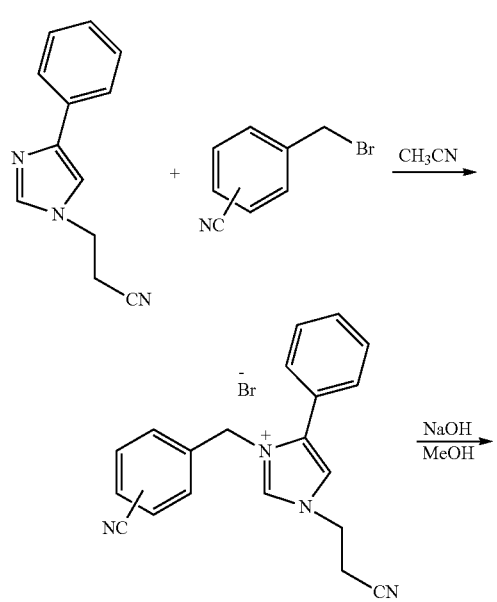

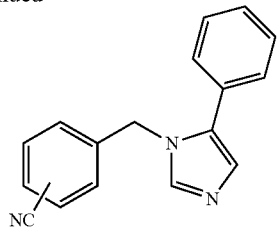

To a stirred solution of 3-(4-phenyl-1H-imidazol-1-yl)propanenitrile (0.56 mmol) in acetonitrile (4 mL) was added the appropriate cyanobenzyl bromide (0.67 mmol) and was heated at 100° C. for 24 h. After cooling to rt the solvent was removed under reduced pressure to afford an off-white solid. The solid was dissolved in MeOH (3 mL) and NaOH (41 mg in 2 mL H$_2$O) was added and stirring was continued for 90 min. The reaction mixture was diluted with water (10 mL) and the aqueous phase was extracted with CH$_2$Cl$_2$ (3×20 mL). The combined organic layers were dried (Na$_2$SO$_4$) and concentrated under reduced pressure to afford crude oil, which was purified by flash column chromatography on silica gel.

Utilizing the appropriate starting materials, the compounds of Table N were prepared according to Example 31:

TABLE N

| Compound | Name | Yield (%) | $^1$H NMR |
|---|---|---|---|
| | 3-((5-phenyl-1H-imidazol-1-yl)methyl)benzonitrile | 62 | 5.19 (s, 2H), 7.15-7.42 (m, 9H), 7.54 (d, 1H, J = 7.68 Hz), 7.60 (s, 1H) |
| | 2-((5-phenyl-1H-imidazol-1-yl)methyl)benzonitrile | 83 | 5.38 (s, 2H), 6.79 (d, 1H, J = 7.95 Hz), 7.15 (s, 1H), 7.22-7.61 (m, 9H) |

Example 32

4-(1H-Imidazol-4-yl)benzoic Acid Hydrochloride

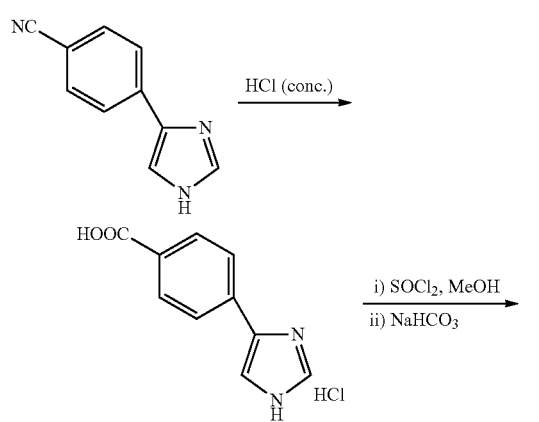

To 4-(1H-imidazol-4-yl)benzonitrile (50 mg, 0.295 mmol) was added conc. HCl (3 mL) and was stirred at 80° C. overnight. After cooling to rt the reaction mixture was concentrated under reduced pressure and the residue was diluted with MeOH/EtOAc (0.5:5, 5 mL) and the solid collected by filtration to the desired product as yellow solid (30 mg, 45% yield). $^1$H-NMR: 3.56 (br s, 1H), 7.15 (s, 1H), 7.31 (s, 1H), 7.48 (s, 1H), 8.03 (s, 2H), 8.31 (s, 1H), 9.26 (s, 1H).

Example 33

Methyl 4-(1H-imidazol-4-yl)benzoate

To a stirred solution of 4-(1H-imidazol-4-yl)benzoic acid hydrochloride (20 mg, 0.089 mmol) at 0° C. in MeOH (5 mL) was added thionyl chloride (11.6 mg, 0.097 mmol) and the solution was allowed to warm to rt. After stirring overnight the solution was concentrated under reduced pressure to dryness and the crude residue was partitioned between EtOAc (25 mL) and sat'd NaHCO$_3$ (5 mL). The organic layer was collected, dried (Na$_2$SO$_4$) and concentrated under reduced pressure to afford the desired product as a pale yellow solid (15 mg, 86% yield). $^1$H NMR: 3.92 (s, 3H), 7.41 (s, 1H), 7.67-7.77 (m, 3H), 8.03 (s, 2H).

Example 34

3-(1H-Imidazol-4-yl)benzoic Acid Hydrochloride

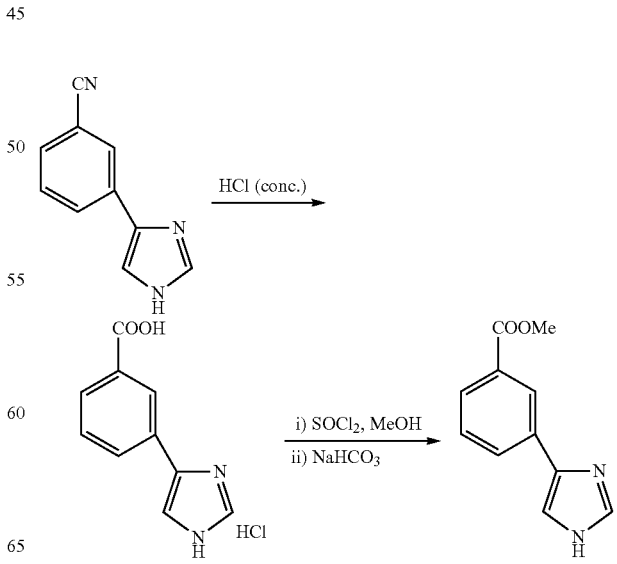

The procedure described above for Example 32 was used for this preparation. Yield: 77%. $^1$H NMR (CD$_3$OD): 7.63-7.68 (t, 1H, J=8.1 Hz), 7.97-7.80 (d, 1H, J=7.2 Hz), 8.03 (s, 1H), 8.11-8.14 (d, 1H, J=7.2 Hz), 8.42 (s, 1H), 9.05 (s, 1H)

Example 35

Methyl 3-(1H-imidazol-4-yl)benzoate

The procedure described above for Example 33 was used for this preparation. Yield: 83%. $^1$H NMR (CD$_3$OD): 3.92 (s, 1H), 7.45-7.53 (m, 2H), 7.76 (s, 1H), 7.86-7.89 (d, 1H, J=7.8 Hz), 7.93-7.96 (d, 1H, J=7.8 Hz), 8.37 (s, 1H)

Example 36

Human IDO Protein Cloning, Expression and Purification

Expression vectors for human indoleamine-2,3-dioxygenase (IDO) protein were prepared by amplification of a 1219 by fragment of the sequence present in vector phIDO6His cDNA with primers 5'-ggagcatgctaATGGCACACGCTATG-GAAAAC-3' and 5'-gagagatctACCTTCCTTCAAAAGG-GATTTC-3' and cloning the SphI-BglII 1213 bp fragment into pQE70 (Qiagen), to yield vector pQE70-hIDO. This construct adds 2 extra amino acids and a 6-Histidine tag to the C-terminus of the natural human IDO protein while preserving intact the natural start codon and N-terminus amino acid sequence. The amplified allele of human IDO shows two polymorphisms with respect to the sequence deposited in accession file P14902 of SwissProt database. These polymorphisms result in a P110S and E119G amino acid changes.

Plasmid pQE70-hIDO was transformed into M15(pREP4) cells (Qiagen) and clones were selected in LB-agar plates supplemented with carbenicillin 50 µg/mL and kanamycin 30 µg/mL. Protein expression was carried out by growing an overnight culture of the M15pREP4/pQE70-hIDO clone in 100 mL LB supplemented with 100 ug/mL carbenicillin, 50 µg/mL kanamycin and 50 µg/mL of L-tryptophan (LBCKT medium). 40 mL of this culture were inoculated into 750 mL of LBCKT for 4 hours at 37° C. This culture was diluted 1:10 into LBCKT medium and cultured for another 2 hours at 37° C. until OD600 was higher than 0.8. At this point the cultures were inoculated with Hemin to 7 µM and L-Tryptophan to 75 µg/mL and incubated at 37° C. for 2 h. Induction of protein expression was carried out by supplementing the cultures with IPTG to 1 mM, PMSF to 200 µM, EDTA to 1 mM and L-tryptophan to 50 µg/mL. Incubation was continued for additional 16 h at 25° C. Cells were collected by centrifugation, and the cell pellets were washed with PBS buffer supplemented with 200 µM PMSF and 1 mM EDTA and stored at −80° C. until protein purification.

The equivalent of 16 L of culture were processed in one batch of purification. Cell pellets were thawed, resuspended in 50 mM potassium phosphate buffer pH 7.0, 200 µM PMSF, 1 mM EDTA, 1 mg/mL lysozyme to 10 mL per liter of bacterial culture and incubated 30 minutes on ice. Cells were then lysed by sonication. Cell lysates were centrifuged 20 min at 20000 g and the supernatant was filtered through 0.45 µm filters. The filtered supernatant was loaded onto a 60 mL phosphocellulose column equilibrated with 50 mM potassium phosphate buffer pH 6.5 (KPB) at 1-3 mL/min. The column was washed with 3 volumes of 50 mM KPB, 3 volumes of 100 mM KPB and the protein was eluted with 15 volumes of a linear gradient of 100-500 mM KPB. Fractions were collected and IDO activity assay was performed by measuring kynurenine production. This was carried out by mixing 50 µL of each fraction with 100 µL of reaction mix to yield a final concentration of 50 mM KPB buffer, 20 mM ascorbic acid, 200 µg/mL catalase, 20 µM methylene blue and 400 µM L-tryptophan. Fractions demonstrating IDO activity were loaded onto a Ni-NTA purification column (15 mL). This affinity purification column was washed with 10 volumes of 250 mM KPB, 150 mM NaCl, 50 mM imidazole pH 8, and eluted with 10 volumes of buffer containing 250 mM KPB, 150 mM NaCl and a 50 to 250 mM imidazole linear gradient. Collected fractions were assayed by IDO enzymatic assay described above and the positive fractions were pooled and concentrated by ultrafiltration and dialyzed against a buffer containing 250 mM KPB, 50% glycerol. This process yields ~8-10 mg of pure protein (>98%) with a specific activity of 170 µmol/h/mg.

Example 37

Testing of IDO Inhibitory Compounds by Enzymatic IDO Assay

The IC$_{50}$ values for each compound were determined by testing the activity of IDO in a mixture containing 50 mM potassium phosphate buffer at pH 6.5; 70 nM purified human IDO protein, 200 µM L-tryptophan, 20 mM ascorbate, 20 µM methylene blue, 0.1% DMSO. The inhibitors were initially diluted in DMSO at 100 mM and were diluted in potassium phosphate 50 mM, added to the reaction mixture at final concentrations raging from 1 mM to 5 nM and preincubated with the enzyme for 5 min at 25° C. The reaction was started by addition of L-tryptophan to 200 µM and incubated 15 min at 37° C. The reaction was stopped by addition of 0.5 vol of 30% trichloroacetic acid and incubated 30 min at 60° C. to hydrolyze N-formylkynurenine to kynurenine. The reaction was centrifuged at 3400 g for 5 min to remove precipitated protein and the supernatant was reacted with 2% (w/v) of p-dimethylaminobenzaldehyde in acetic acid. The reaction was incubated 10 min at 25° C. and read at 480 nm in a spectrophotometer. Control samples with no IDO inhibitor, or with no IDO enzyme or with the reference inhibitors 1-methyl-tryptophan (200 µM) and menadione (1.2 µM) were used as controls to set the parameters for the non-linear regressions necessary for determination of the IC$_{50}$ for each compound. Nonlinear regressions and determination of the IC$_{50}$ values were performed using the GraphPad Prism 4 software. Compounds with an IC$_{50}$ of less than 500 µM were considered as active inhibitors in this assay.

Example 38

Determination of IDO Inhibitory Activity and Toxicity in Cell Based IDO/Kynurenine Assay 293-T-REx™ cells (Invitrogen) constitutively express a tet operator binding repressor protein and are maintained in DMEM, 10% FBS, 1× Penicillin+Streptomycin, 2 mM L-glutamine, 5 µg/mL blasticidin at 37° C. with a 5% CO$_2$ in air atmosphere and typically split prior to confluency. Cells were passed by splitting the culture 1/10—by removing media by aspiration, washing 1× with PBS, incubating with 0.25% trypsin/EDTA until the cells detach, disbursing the cells in fresh growth media, and plating at 1/10 dilutions in fresh growth media. For long term cryopreservation, cells are detached from the plate as described above, collected by centrifugation, resuspended in freeze medium (growth medium, 10%DMSO), stored in 1.8 mL cyropreservation vials (~2-5×106 cells per vial), in liquid nitrogen vapor storage tanks IDO1-expressing 293-T-Rex™ cell lines were generated by stable transfection of plasmid pcDNA-tetO-IDO expressing human IDO or murine IDO under the control of the doxycycline-inducible CMV-tet promoter. Transfected cells were selected in DBZ medium (DMEM, 10% FBS, 1× Penicillin+Streptomycin, 2 mM L-glutamine, 5 µg/mL blasticidin and 25 µg/ml Zeocin) at 37° C. with a 5% $CO_2$ in air atmosphere. Individual clones were isolated by limiting dilution cloning from these populations. These clones were assayed for IDO activity and the clones that showed the highest levels of IDO activity inducible by doxycycline were used for subsequent cell based IDO assays.

To setup an IDO cell based activity assay, IDO-293-T-Rex cells were harvested and resuspended in DBZ media at $10^6$ cells/mL, and split into poly-D-lysine coated 96-well plates at 100,000 cells per well. 100 µL of Neutral medium (DBZ medium, 200 µM L-tryptophan) or Induction media (Neutral medium supplemented with 5 µM doxycycline) are added to the cells and incubated 28 h at 37° C. After the IDO induction period, medium is removed and replaced with Induction or Neutral medium containing different concentrations of each inhibitor (1 mM to 0.5 nM). The cells incubated in Neutral medium serve as negative control of the assay. The cells incubated in Induction medium and without inhibitor serve as the positive control of the assay. The incubation is carried out for 16 h at 37° C. in a cell culture incubator. 200 µL of medium are transferred to U-bottom polypropylene 96-well plates containing 25 µL of 30% TCA, incubated 30 minutes at 60° C. and centrifuged at 3400 g for 5 minutes. 150 µL of the clear supernatant is transferred to a polystyrene 96-well plate containing 50 µL of 4% (w/v) of p-dimethylaminobenzaldehyde in acetic acid, incubated for 10 min. Kynurenine concentration is determined by measuring the absorbance at 480 nm.

To measure the toxicity of each compound after 16 h incubation with cells, cell viability is measured via a WST-1 assay (Roche) according to instructions from the manufacturer. Briefly, after the incubation with each compound, medium is aspirated and replaced with 100 mL of WST-1 reagent, and incubated 30 min at 37° C. Absorbance at 540 nm is correlated with the number of viable cells. Determination of $IC_{50}$ (Kynurenine assay) or $LD_{50}$ (WST-1 assay) is performed via non-linear regression analysis using GraphPad Prism software.

Example 39

Reversal of IDO-Mediated Suppression of T-Cell Proliferation by IDO Inhibitors

Human monocytes were collected from peripheral mononuclear cells by leukoapheresis and cultured overnight at $10^6$ cells/well in a 96-well plate in RPMI 1640 medium supplemented with 10% fetal calf serum and 2 mM L-glutamine. Adherent cells were retained and cultured for 7 days with 200 ng/ml IL-4, 100 ng/ml GM-CSF. Cells were matured for 2 days with a cytokine cocktail containing TNF-α, IL-1β, IL-6 and PGE2 for additional 2 days to induce dendritic cell maturation. At the end of maturation, loosely adherent cells were detached by gentle aspiration and plated in V-bottom 96 well plates, at 5000 cells/well. These cells are >80% IDO+dendritic cells. Human allogeneic T cells ($3 \times 10^5$) from normal donors were resuspended in RPMI 1640 supplemented with 100-200 U/mL IL-2 and 100 ng/mL anti-CD3 antibody and added to the wells. Serial dilutions of IDO compounds dissolved in phenol red-free RPMI was added to yield a final concentration of IDOi between 500 and 1 µM. After incubation for 2-4 days, T cell proliferation was measured by BrdU incorporation assay after an overnight pulse with BrdU labeling mix (Roche Molecular Biochemicals). At the en of the pulse, the cells were fixed and incubated with 100 µL/well anti-BrdU-POD antibody following the instructions from the manufacturer. Plates were read in a microplate reader.

Alternatively, testing of IDO inhibitors in an in vitro mouse model of IDO-mediated suppression of T cell proliferation is performed by the following procedure. C57bl6 mice are inoculated with $1 \times 10^6$ B78H1-GMCSF tumor cells in the right flank. After 10-12 days, tumor draining lymph nodes are collected and cells are stained with anti-CD11c and anti-B220 monoclonal antibodies. Cells are sorted by high-speed fluorescence activated cell sorting and the CD11c+/B220+ plasmacytoid dendritic cells are collected and seeded at 2000 cells/well in 96 well V-bottom plates. Splenocytes are collected from BM3 transgenic mice (in CBA background) and collected by nylon wool enrichment. BM3 T cells ($10^5$ cells/well) are added to each well in 200 µL of RPMI, 10% FCS, 50 µM P-mercaptoetanol. Alternatively, T cells are obtained from spleens of OT-I transgenic mice and added to the culture in combination with OVA peptide. IDO inhibitors are added dissolved in RPMI at final concentrations ranging from 1 mM to 10 nM. After 3 days of stimulation, cells are pulsed by 16 h with BrdU or $^3$H-thymidine. Cells are collected, fixed and tested for BrdU incorporation following the instructions from the BrdU labeling kit manufacturer (Roche Diagnostics). If $^3$H-tymidine is used to measure T cell proliferation, cells are harvested and dpm counts are measured in a scintillation counter following procedures widely known in the art. Control CD11c$^+$ cells taken from the contralateral lymph node or CD11c$^+$/B220$^-$ cells (IDO$^-$ population) from the TDLN are used as positive control for proliferation.

Example 40

In Vivo Testing of IDO Inhibitors for Antitumor Activity in Combination with Chemotherapeutic Agents In vivo anti-tumor efficacy can be tested using modified tumor allograft protocols. For instance, it has been described in the literature that IDO inhibition can syngerize with cytotoxic chemotherapy in immune-competent mice. Due to different susceptibilities of different tumor cell lines to chemotherapeutic drugs and to immune mediated rejection, each IDO inhibitor is tested alone and in combination with 2 different chemotherapeutic drugs in 4 different animal tumor models, represented by 4 different mouse tumor cell lines, of different tissue origin (colorectal, bladder, mammary and lung carcinoma), implanted subcutaneously in syngeneic strains of mice. These cell lines have been selected based on their known susceptibility to chemotherapeutic drugs, their partial response to IDO inhibitors as single agents, their presumed pattern of IDO expression according to their tissue of origin, and their ability to elicit an immune reaction.

For every animal tumor model, 2 different chemotherapeutic drugs are tested in separate groups of mice according to the following list: 1] LLC tumor: cyclophosphamide and paclitaxel; 2] EMT6 tumor: cyclophosphamide and paclitaxel; 3] CT26 tumor: cyclophosphamide and doxorubicin; and 4] MB49 tumor: cyclophosphamide and gemcitabine.

The following chemotherapeutic drugs are used, at the indicated doses. The maximum tolerated dose for the following chemotherapeutic agents in mice depends on the formulation, concentration, frequency of administration, route of administration and number of doses. The chemotherapeutic drugs administered in conjunction with each IDO inhibitor drug are: 1] Paclitaxel: 20 mg/kg/day i.p, every 4 days, 4 times (q4dx4) (in Cremophor); 2] Doxorubicin: 5 mg/kg, once a week for 3 weeks (q7dx3); 3] Cyclophosphamide: 100 mg/kg, I.P., every 4 days, 4 times (q4dx4); 4] Gemcitabine: 80 mg/kg every 4 days, 4 times, i.p. (q4dx4).

All animals receive a subcutaneous injection of a tumor forming dose of live tumor cells (~50000-1000000 cells) suspended in 0.1 mL of PBS or saline on day 1. Subcutaneous injection forms a localized tumor that allows monitoring tumor growth over time.

To mimic the effect of IDO inhibitor drugs as therapeutic compositions, administration of IDO inhibitor drugs begins at day 5-8 after tumor inoculation. Dosing, route of administration, dosing frequency varies depending on the toxicity and pharmacokinetics profile of each drug. Duration of the treatment is 2 weeks. Most preferably, drug is administered continuously via oral gavage or dissolution in the drinking water. Alternatively, subcutaneous slow release pellets containing 100 mg of each drug are implanted under the skin by surgical procedure. IDO inhibitor drug are administered at the maximum tolerated dose or at a concentration corresponding to the $LD_{50}$.

Example 41

Pharmacological Values

Pharmacological values for compounds tested according to one or more of the preceding examples are reported in the following table, including, Human IDO $IC_{50}$: this is the concentration of the compound at which we observe 50% of enzymatic activity using recombinant human IDO under the assay conditions described in one of the examples;

$IC_{50}$ values are reported in ranges: A: 0.5-2.5 mM; B: 0.1-0.5 mM; C: 20-100 µM; D: <20 µM.

| Cpd | $IC_{50}$ |
|---|---|
| 1 | C |
| 2 | C |
| 3 | C |
| 4 | D |
| 5 | C |
| 6 | D |
| 7 | D |
| 8 | D |
| 9 | D |
| 10 | D |
| 11 | D |
| 12 | D |
| 13 | D |
| 14 | D |
| 15 | D |
| 16 | D |
| 17 | D |
| 18 | D |
| 19 | D |
| 20 | D |
| 21 | D |
| 22 | D |
| 23 | D |
| 24 | D |
| 25 | D |
| 26 | D |
| 27 | D |
| 28 | D |
| 29 | D |
| 30 | D |
| 31 | D |
| 32 | D |
| 33 | D |
| 34 | D |
| 35 | D |
| 36 | D |
| 37 | D |
| 38 | D |
| 39 | D |
| 40 | D |
| 41 | D |
| 42 | D |
| 43 | D |
| 44 | D |
| 45 | D |
| 46 | D |
| 47 | D |
| 48 | D |
| 49 | D |
| 50 | D |
| 51 | D |
| 52 | D |
| 53 | D |
| 54 | C |
| 55 | C |
| 56 | C |
| 57 | C |
| 58 | C |
| 59 | C |
| 60 | C |
| 61 | C |
| 62 | C |
| 63 | C |
| 64 | C |
| 65 | C |
| 66 | C |
| 67 | C |
| 68 | C |
| 69 | C |
| 70 | C |
| 71 | C |
| 72 | C |
| 73 | C |
| 74 | C |
| 75 | C |
| 76 | C |
| 77 | C |
| 78 | C |
| 79 | C |
| 80 | C |
| 81 | C |
| 82 | C |
| 83 | C |
| 84 | C |
| 85 | C |
| 86 | C |
| 87 | C |
| 88 | C |
| 89 | C |
| 90 | C |
| 91 | C |
| 92 | C |
| 93 | C |
| 94 | C |
| 95 | C |
| 96 | C |
| 97 | C |
| 98 | B |
| 99 | B |
| 100 | B |
| 101 | B |
| 102 | B |
| 103 | B |
| 104 | B |
| 105 | B |
| 106 | B |

-continued

| Cpd | IC$_{50}$ |
|---|---|
| 107 | B |
| 108 | B |
| 109 | B |
| 110 | B |
| 111 | B |
| 112 | B |
| 113 | B |
| 114 | B |
| 115 | B |
| 116 | B |
| 117 | B |
| 118 | B |
| 119 | B |
| 120 | B |
| 121 | B |
| 122 | B |
| 123 | B |
| 124 | B |
| 125 | B |
| 126 | B |
| 127 | B |
| 128 | B |
| 129 | B |
| 146 | C |
| 147 | C |
| 148 | D |
| 149 | C |
| 150 | C |
| 151 | D |
| 152 | D |
| 153 | B |
| 154 | C |
| 155 | C |
| 156 | D |
| 157 | C |
| 158 | D |
| 159 | C |
| 160 | D |
| 161 | C |
| 162 | D |
| 163 | B |
| 164 | C |
| 165 | B |
| 166 | D |
| 167 | C |
| 168 | D |

We claim:

1. A pharmaceutical composition comprising a pharmaceutically acceptable excipient, diluent, or carrier, and a compound according to the formula,

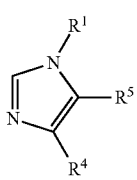

a tautomer thereof, or a pharmaceutically acceptable salt thereof, wherein $R^1$ and $R^4$ are each hydrogen
and
$R^5$ is

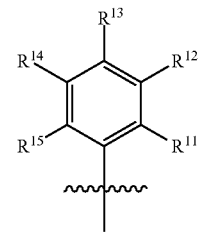

wherein
$R^{13}$ is hydrogen or —SH; and
$R^{11}$ is —C$_1$-C$_6$alkyl-R$^{A1}$, -Q-(C$_1$-C$_6$)alkyl-R$^{A1}$, —C$_1$-C$_6$alkyl-Q-R$^{A1}$, -Q-(C$_1$-C$_6$)alkyl-Q-R$^{A1}$, —C$_1$-C$_6$alkyl-Q-(C$_1$-C$_6$)alkyl-R$^{A1}$, -Q(C$_1$-C$_6$)alkyl-R$^{A1}$, or -Q(C$_1$-C$_6$)alkyl-Q-(C$_1$-C$_6$)alkyl-QR$^{A1}$;
$R^{12}$ and $R^{14}$ are each independently hydrogen or halogen; and
$R^{15}$ is hydrogen;
wherein
each Q is independently —C(R$^{A2}$)$_2$—, —O—, —N(R$^{A2}$)—, —S—, —C(O)—, —S(O)—, —S(O)$_2$—, —C(O)N(R$^{A2}$)—, —N(R$^{A2}$)C(O)—, or —CO)O—, wherein each R$^{A2}$ is independently hydrogen, C$_1$-C$_6$alkyl, or C$_1$-C$_6$haloalkyl;
$R^{A1}$ is C$_3$-C$_8$cycloalkyl, heterocyclyl, aryl, or heteroaryl, wherein the cycloalkyl, heterocyclyl, aryl, and heteroaryl groups are optionally substituted by 1, 2, 3, or 4 R$^{A3}$ groups, wherein
each R$^{A3}$ is independently halogen, cyano, nitro, —OR, —SR, —NR$_2$, —C(O)R, —C(O)OR, —C(O)NR$_2$, —S(O)R, —S(O)$_2$R, —S(O)OR, —S(O)$_2$OR, —S(O)NR$_2$, —S(O)$_2$NR$_2$, —OC(O)R, —OC(O)OR, —OC(O)NR$_2$, —N(R)C(O)R, —N(R)C(O)OR, —N(R)C(O)NR$_2$, —N(R)S(O)R, —N(R)S(O)$_2$R, C$_1$-C$_6$ alkyl, C$_1$-C$_6$ haloalkyl, C$_2$-C$_6$ alkenyl, C$_2$-C$_6$ alkynyl, C$_3$-C$_8$cycloalkyl, heterocyclyl, or aryl, wherein the cycloalkyl, heterocyclyl, aryl are each optionally substituted with 1, 2, 3, or 4 groups which are each independently R$^{30}$ or —C$_1$-C$_6$ alkyl-R$^{30}$, wherein R$^{30}$ is halogen, cyano, nitro, —OR$^{411}$, —SR$^{411}$, —N(R$^{411}$)$_2$, —C(O)OR$^{411}$, —C(O)N(R$^{411}$)$_2$, —C(O)R$^{411}$, —S(O)R$^{411}$, —S(O)$_2$R$^{411}$, —S(O)O R$^{411}$, —S(O)$_2$OR$^{411}$, —S(O)N(R$^{411}$)$_2$, —S(O)$_2$N(R$^{411}$)$_2$, OC(O)R$^{411}$, —OC(O)OR$^{411}$, —OC(O)N(R$^{411}$)$_2$, —N(R$^{411}$)C(O)R$^{411}$, —N(R$^{411}$)C(O)OR$^{411}$, —N(R$^{411}$)C(O)N(R$^{411}$)$_2$, —N(R$^{411}$)S(O)R$^{411}$, —N(R$^{411}$)S(O)$_2$R$^{411}$, C$_1$-C$_6$ alkyl, or C$_1$-C$_6$ haloalkyl, wherein each R$^{411}$ is independently hydrogen, C$_1$-C$_6$ alkyl, C$_2$-C$_6$ alkenyl, C$_2$-C$_6$ alkynyl, C$_1$-C$_6$ haloalkyl, C$_3$-C$_8$cycloalkyl, heterocyclyl, aryl, heteroaryl, C$_3$-C$_8$cycloalkyl(C$_1$-C$_6$)alkyl, heterocyclyl(C$_1$-C$_6$)alkyl, aryl(C$_1$-C$_6$)alkyl, or heteroaryl (C$_1$-C$_6$)alkyl,
or R$^{A1}$ and R$^{A2}$ taken together, when attached to the same carbon atom, form =C$_3$-C$_8$cycloalkyl, or =heterocyclyl, wherein the cycloalkyl and heterocyclyl are optionally substituted with 1, 2, 3, or 4 groups which are each independently halogen, cyano, nitro, —OR, —SR, —NR$_2$, —C(O)OR, —C(O)NR$_2$, —C(O)R, —S(O)R, —S(O)$_2$R, —S(O)OR, —S(O)$_2$OR, —S(O) NR$_2$, —S(O)$_2$NR$_2$, —OC(O)R, —OC(O)OR, —OC(O)NR$_2$, —N(R)C(O)R, —N(R)C(O)OR, —N(R)C(O)NR$_2$, —N(R)S(O)R, —N(R)S(O)$_2$R, C$_1$-C$_6$ alkyl, or C$_1$-C$_6$ haloalkyl; and each R is independently hydrogen or R$^2$, wherein R$^2$ is C$_1$-C$_6$ alkyl, C$_2$-C$_6$ alkenyl, C$_2$-C$_6$ alkynyl, C$_1$-C$_6$ haloalkyl, C$_3$-C$_8$cycloalkyl, heterocyclyl, aryl, heteroaryl, C$_3$-C$_8$cycloalkyl(C$_1$-C$_6$)alkyl, heterocyclyl(C$_1$-C$_6$)alkyl, aryl(C$_1$-C$_6$)alkyl, or heteroaryl(C$_1$-C$_6$)alkyl, wherein the alkyl, cycloalkyl, heterocyclyl, aryl, heteroaryl, cycloalkylalkyl, heterocyclylalkyl, arylalkyl, and heteroarylalkyl are each optionally substituted with 1, 2, 3, or 4 groups which are each independently halogen, cyano, nitro, —OR$^{10}$, —SR$^{10}$, —N(R$^{10}$)$_2$, —C(O)OR$^{10}$, —C(O)N(R$^{10}$)$_2$, —C(O)R$^{10}$, —S(O)R$^{10}$, —S(O)$_2$ R$^{10}$, —S(O)OR$^{10}$, —S(O)$_2$OR$^{10}$, —S(O)N(R$^{10}$)$_2$, —S(O)$_2$N(R$^{10}$)$_2$, —OC(O)R$^{10}$, —OC(O)OR$^{10}$, —OC(O)N(R$^{10}$)$_2$, —N(R$^{10}$)C(O)R$^{10}$, —N(R$^{10}$)C(O)OR$^{10}$, —N(R$^{10}$)C(O)N(R$^{10}$)$_2$, —N(R$^{10}$)S(O)R$^{10}$, —N(R$^{10}$)S(O)$_2$R$^{10}$, C$_1$-C$_6$ alkyl, C$_2$-C$_6$ alkenyl, C$_2$-C$_6$ alkynyl, C$_1$-C$_6$ haloalkyl, C$_3$-C$_8$cycloalkyl, heterocyclyl, aryl, or heteroaryl, wherein each R$^{10}$ is independently hydrogen, C$_1$-C$_6$ alkyl, C$_2$-C$_6$ alkenyl, C$_2$-C$_6$ alkynyl, C$_1$-C$_6$ haloalkyl, C$_3$-C$_8$cycloalkyl, heterocyclyl, aryl, heteroaryl, C$_3$-C$_8$cycloalkyl(C$_1$-C$_6$)alkyl, heterocyclyl(C$_1$-C$_6$)alkyl, aryl(C$_1$-C$_6$)alkyl, or heteroaryl (C$_1$-C$_6$)alkyl, wherein C$_3$-C$_8$cycloalkyl is cyclopentyl, cyclopentenyl, cyclohexyl, cyclohexenyl, cycloheptyl, cyclooctyl, bicyclo[3.1.1]heptane, bicyclo[2.2.1]heptane, bicyclo[2.2.2]octane, bicyclo[3.2.2]nonane, bicyclo[3.3.1]nonane or bicyclo[4.2.1]nonane.

2. A pharmaceutical composition wherein the compound is
4-(4-chloro-2-(4-chlorobenzyloxy)phenyl)-1H-imidazole;
4-(2-(2-bromophenethoxy)phenyl)-1H-imidazole;
4-(2-(2-(2-chlorophenoxy)ethyl)phenyl)-1H-imidazole;
3-(2-chlorophenethoxy)-2-(1H-imidazol-5-yl)phenol;
5-(2-(4-chlorobenzyloxy)phenyl)-1H-imidazole;
4-(2-(2-chlorophenethoxy)phenyl)-1H-imidazole;
4-(2-(2-cyclohexylethoxy)phenyl)-1H-imidazole;
5,5'-(2,2'-(3,3-dimethylpentane-1,5-diyl)bis(oxy)bis(2,1-phenylene))bis(1H-imidazole);
5-(2-(2-cyclopentylethoxy)phenyl)-1H-imidazole;
4-(2-phenethoxyphenyl)-1H-imidazole;
5-(2-(3-chlorobenzyloxy)phenyl)-1H-imidazole;
N-(2-(1H-imidazol-4-yl)benzyl)-2-chlorobenzamide;
4-(2-(3-chlorophenethoxy)phenyl)-1H-imidazole;
N-(4-(2-(2-(1H-imidazol-4-yl)phenoxy)ethyl)phenyl)acetamide;
4-(2-(2-methylbenzyloxy)phenyl)-1H-imidazole;
N-(3-(2-(2-(1H-imidazol-4-yl)phenoxy)ethyl)phenyl)acetamide;
4-(2-((2-chlorobenzyloxy)methyl)phenyl)-1H-imidazole;
5-(2-(3-phenylpropoxy)phenyl)-1H-imidazole;
4-(2-(2-(1H-imidazol-4-yl)phenoxy)ethyl)-N-methylbenzamide;
4-((2-(1H-imidazol-4-yl)phenoxy)methyl)benzenesulfonamide;
4-(2-(benzyloxy)phenyl)-1H-imidazole;
5-(2-(3-methylbenzyloxy)phenyl)-1H-imidazole;
4-(5-bromo-2-(4-chlorobenzyloxy)phenyl)-1H-imidazole;
3-(2-(2-(1H-imidazol-4-yl)phenoxy)ethyl)-N-methylbenzamide;
4-((2-(1H-imidazol-4-yl)phenoxy)methyl)benzonitrile;
4-(3-bromo-2-(4-chlorobenzyloxy)phenyl)-1H-imidazole;
4-(2-(4-chlorophenethoxy)phenyl)-1H-imidazole;
N-(4-chlorobenzyl)-2-(1H-imidazol-4-yl)aniline;
4-(2-(4-methylbenzyloxy)phenyl)-1H-imidazole;
3-(4-chlorobenzyloxy)-2-(1H-imidazol-5-yl)phenol;
3-((2-(1H-imidazol-4-yl)phenoxy)methyl)benzonitrile;
4-(2-(2-chlorobenzyloxy)phenyl)-1H-imidazole;
3-((2-(1H-imidazol-4-yl)phenoxy)methyl)piperidine;
4-((2-(1H-imidazol-4-yl)phenoxy)methyl)-1-(methylsulfonyl)piperidine;
4-((2-(1H-imidazol-4-yl)phenoxy)methyl)benzamide ;
N-(3-(2-(1H-imidazol-5-yl)phenoxy)propyl)pyrimidin-2-amine;
2-((2-(1H-imidazol-4-yl)phenoxy)methyl)benzonitrile ;
1-(4-((2-(1H-imidazol-4-yl)phenoxy)methyl)piperidin-1-yl)ethanone;
N-(2-(2-(1H-imidazol-5-yl)phenoxy)ethyl)pyrimidin-2-amine;
1-(3-((2-(1H-imidazol-4-yl)phenoxy)methyl)piperidin-1-yl)ethanone;
4-((2-(1H-imidazol-4-yl)phenoxy)methyl)benzamide;
4-(4-chloro-2-(4-chlorobenzyloxy)phenyl)-1H-imidazole;
4-(2-(2-bromophenethoxy)phenyl)-1H-imidazole;
4-(2-(2-(2-chlorophenoxy)ethyl)phenyl)-1H-imidazole;
tert-butyl 4-(2-(2-(1H-imidazol-4-yl)phenoxy)ethyl)piperidine-1-carboxylate;
1-(4-(2-(2-(1H-imidazol-4-yl)phenoxy)ethyl)piperidin-1-yl)ethanone;
tert-butyl 2-(1H-imidazol-4-yl)phenylcarbamate;
N-(4-((2-(1H-imidazol-4-yl)phenoxy)methyl)benzyl)acetamide;
4-((2-(1H-imidazol-4-yl)phenoxy)methyl)piperidine;
4-(2-(2-(1H-imidazol-4-yl)phenoxy)ethyl)phenol;
2-(2-(1H-imidazol-4-yl)phenoxy)-2,3-dihydro-1H-inden-1-one;
4-(5-(2-(1H-imidazol-4-yl)phenoxy)-3,3-dimethylpentyl)morpholine;
3-(5-(2-(1H-imidazol-4-yl)phenoxy)-3,3-dimethylpentyl)-1-((2R,3R,4S,5R)-3,4-dihydroxy-5-(hydroxymethyl)tetrahydrofuran-2-yl)-5-fluoropyrimidine-2,4 (1H,3H)-dione;
5-(2-(5-(1H-imidazol-1-yl)-3,3-dimethylpentyloxy)phenyl)-1H-imidazole;
N-(5-(2-(1H-imidazol-5-yl)phenoxy)-3,3-dimethylpentyl)pyridin-4-amine;
N-(2-(2-(2-(1H-imidazol-4-yl)phenoxy)ethyl)phenyl)acetamide;
5-(2-(1H-imidazol-4-yl)phenoxy)-N-benzyl-3,3-dimethylpentan-1-amine;
4-(2-(2-(1H-imidazol-4-yl)phenoxy)ethylidene)cyclohexanecarboxamide;
4-((2-(1H-imidazol-5-yl)phenoxy)methyl)-7-methoxy-2H-chromen-2-one;
3-(2-(2-(1H-imidazol-5-yl)phenoxy)ethyl)-1H-indole;
2-(2-(1H-imidazol-5-yl)phenoxy)-N-(5,7-difluorobenzo[d]thiazol-2-yl)acetamide;
2-(2-(1H-imidazol-5-yl)phenoxy)-1-(4-(pyrrolidin-1-yl)phenyl)ethanone;
2-(2-(1H-imidazol-5-yl)phenoxy)-N-(2-chlorophenyl)acetamide;
2-(2-(1H-imidazol-5-yl)phenoxy)-1-(benzofuran-2-yl)ethanone;
2-(2-(1H-imidazol-5-yl)phenoxy)-1-(thiazol-2-yl)ethanone;
2-(2-(1H-imidazol-5-yl)phenoxy)-1-(benzofuran-5-yl)ethanone;

2-(3-(2-(1H-imidazol-5-yl)phenoxy)propyl)isoindoline-1,3-dione;
2-(2-(1H-imidazol-5-yl)phenoxy)-1-(4-(diethylamino)phenyl)ethanone;
2-(2-(1H-imidazol-5-yl)phenoxy)-1-(thiophen-3-yl)ethanone;
2-(2-(1H-imidazol-5-yl)phenoxy)-1-(thiophen-2-yl)ethanone;
2-(2-(1H-imidazol-5-yl)phenoxy)-1-(benzofuran-3-yl)ethanone;
2-(2-(1H-imidazol-5-yl)phenoxy)-1-(pyridin-2-yl)ethanone;
2-(2-(1H-imidazol-5-yl)phenoxy)-1-(pyridin-4-yl)ethanone;
1-(2-(2-(1H-imidazol-5-yl)phenoxy)ethyl)-1H-pyrazole;
2-(2-(1H-imidazol-5-yl)phenoxy)-N-(thiophen-2-ylmethyl)acetamide;
2-(2-(1H-imidazol-5-yl)phenoxy)-1-(benzo[b]thiophen-5-yl)ethanone;
2-(4-(2-(1H-imidazol-5-yl)phenoxy)butyl)isoindoline-1,3-dione;
2-(2-(2-(1H-imidazol-5-yl)phenoxy)ethyl)isoindoline-1,3-dione;
2-(2-(1H-imidazol-5-yl)phenoxy)-1-(3-phenylisoxazol-5-yl)ethanone;
5-(2-(phenylsulfonylmethoxy)phenyl)-1H-imidazole;
5-(2-(2-(2,3-dihydrobenzofuran-5-yl)ethoxy)phenyl)-1H-imidazole;
2-(2-(1H-imidazol-5-yl)phenoxy)-N-(furan-2-ylmethyl)acetamide;
5-(2-(1-phenylpropan-2-yloxy)phenyl)-1H-imidazole;
2-(2-(1H-imidazol-5-yl)phenoxy)-1-(4-(methylsulfonyl)phenyl)ethanone;
3-(2-(1H-imidazol-5-yl)phenoxy)-1-phenylpyrrolidin-2-one;
2-(2-(1H-imidazol-5-yl)phenoxy)-1-(2,4-dihydroxyphenyl)ethanone;
2-(2-(1H-imidazol-5-yl)phenoxy)-N-phenylpropanamide;
4-(2-(2-(1H-imidazol-5-yl)phenoxy)ethyl)-3,5-dimethyl-1H-pyrazole;
3-(2-(2-(1H-imidazol-5-yl)phenoxy)acetyl)-2H-chromen-2-one;
2-(2-(1H-imidazol-5-yl)phenoxy)-1-(2-hydroxyphenyl)ethanone;
2-(2-(1H-imidazol-5-yl)phenoxy)-2,3-dihydro-1H-inden-1-one;
5-(2-((2,3-dihydrobenzo[b][1,4]dioxin-2-yl)methoxy)phenyl)-1H-imidazole;
2-(2-(1H-imidazol-5-yl)phenoxy)-1-(4-(difluoromethoxy)phenyl)ethanone;
5-(2-(1H-imidazol-5-yl)phenoxy)-6,7-dihydrobenzo[c][1,2,5]oxadiazol-4(5H)-one;
5-(2-(2-(1H-pyrrol-1-yl)ethoxy)phenyl)-1H-imidazole;
3-(2-(2-(1H-imidazol-5-yl)phenoxy)acetyl)benzoic acid;
2-((2-(1H-imidazol-5-yl)phenoxy)methyl)-1H-benzo[d]imidazole;
6-(2-(2-(1H-imidazol-5-yl)phenoxy)acetyl)-2H-benzo[b][1,4]oxazin-3(4H)-one;
6-(2-(2-(1H-imidazol-5-yl)phenoxy)acetyl)benzo[d]oxazol-2(3H)-one;
1-(3-(2-(1H-imidazol-5-yl)phenoxy)propyl)-4-(3-chlorophenyl)piperazine;
2-((2-(1H-imidazol-5-yl)phenoxy)methyl)pyridine;
5-((2-(1H-imidazol-5-yl)phenoxy)methyl)-2-chloropyridine;
4-((2-(1H-imidazol-5-yl)phenoxy)methyl)pyridine;
2-((2-(1H-imidazol-5-yl)phenoxy)methyl)quinazolin-4(3H)-one;
2-((2-(1H-imidazol-5-yl)phenoxy)methyl)quinoline;
3-((2-(1H-imidazol-5-yl)phenoxy)methyl)quinoxalin-2(1H)-one;
3-((2-(1H-imidazol-5-yl)phenoxy)methyl)benzo[d]thiazol-2(3H)-one;
ethyl 2-(2-(2-(2-(1H-imidazol-5-yl)phenoxy)acetamido)thiazol-4-yl)acetate;
5-(2-(naphthalen-2-ylmethoxy)phenyl)-1H-imidazole;
5-(2-(2-(naphthalen-1-yl)ethoxy)phenyl)-1H-imidazole;
or a pharmaceutically acceptable salt thereof.

3. The pharmaceutical composition of claim 1, wherein
(i) $R^{11}$ is —$C_6$alkyl-$R^{A1}$, -Q-($C_1$-$C_6$)alkyl-$R^{A1}$, —$C_1$-$C_6$alkyl-Q-$R^{A1}$, -Q-($C_1$-$C_6$)alkyl-Q-$R^{A1}$, $C_1$-$C_6$-alkyl-Q-($C_1$-$C_6$)alkyl-$R^{A1}$, -Q($C_1$-$C_6$)alkyl-Q-($C_1$-$C_6$)alkyl-$R^{A1}$, or -Q($C_1$-$C_6$)alkyl-Q-($C_1$-$C_6$)alkyl-Q$R^{A1}$,
or
and $R^{12}$ and $R^{14}$ is halogen,
and
(ii) $R^{13}$ is hydrogen or —SH.

4. The pharmaceutical composition of claim 3, wherein $R^{11}$ is —$C_1$-$C_6$alkyl-$R^{A1}$, -Q-($C_1$-$C_6$)alkyl-$R^{A1}$, —$C_1$-$C_6$alkyl-Q-$R^{A1}$, -Q-($C_1$-$C_6$)alkyl-Q-$R^{A1}$, —$C_1$-$C_6$alkyl-Q-($C_1$-$C_6$)alkyl-$R^{A1}$, -Q($C_1$-$C_6$)alkyl-Q-($C_1$-$C_6$)alkyl-$R^{A1}$, or -Q($C_1$-$C_6$)alkyl-Q-($C_1$-$C_6$)alkyl-Q$R^{A1}$.

5. The pharmaceutical composition of claim 3, wherein $R^{11}$ is —$C_1$-$C_6$alkyl-$R^{A1}$, -Q-($C_1$-$C_6$)alkyl-$R^{A1}$, —$C_1$-$C_6$alkyl-Q-$R^{A1}$, -Q-($C_1$-$C_6$)alkyl-C($R^{A2}$)$_2$—$R^{A1}$, or —($C_1$-$C_6$)alkyl-Q-$C_1$-$C_6$ alkyl-$R^{A1}$, or -Q($C_1$-$C_6$)alkyl-C($R^{A2}$)$_2$—($C_1$-$C_6$)alkyl-Q-$R^{A1}$, wherein each is Q is independently —O—, —N($R^{A2}$)—, or —S—.

6. The pharmaceutical composition of claim 3, wherein $R^{12}$ and $R^{14}$ are halogen
and
$R^{13}$ is hydrogen or —SH.

7. The pharmaceutical composition of claim 3, wherein $R^{13}$ is hydrogen or —SH, and at least one of $R^{12}$ and $R^{14}$ is fluoro, chloro, bromo, methyl, or ethyl.

* * * * *